United States Patent
Pandit et al.

(10) Patent No.: US 11,208,485 B2
(45) Date of Patent: Dec. 28, 2021

(54) PD-1 SINGLE DOMAIN ANTIBODIES AND THERAPEUTIC COMPOSITIONS THEREOF

(71) Applicant: InhibRx, Inc., La Jolla, CA (US)

(72) Inventors: Rajay A. Pandit, La Jolla, CA (US); John C. Timmer, La Jolla, CA (US); Angelica N. Sanabria, La Jolla, CA (US); Florian Sulzmaier, La Jolla, CA (US); Brendan P. Eckelman, La Jolla, CA (US)

(73) Assignee: InhibRx, Inc., La Jolla, CA (US)

( * ) Notice: Subject to any disclaimer, the term of this patent is extended or adjusted under 35 U.S.C. 154(b) by 0 days.

(21) Appl. No.: 16/600,298

(22) Filed: Oct. 11, 2019

(65) Prior Publication Data

US 2020/0190193 A1    Jun. 18, 2020

Related U.S. Application Data

(60) Provisional application No. 62/791,152, filed on Jan. 11, 2019, provisional application No. 62/744,615, filed on Oct. 11, 2018.

(51) Int. Cl.
*C07K 16/28* (2006.01)
*C07K 16/30* (2006.01)

(52) U.S. Cl.
CPC ...... *C07K 16/2818* (2013.01); *C07K 16/2812* (2013.01); *C07K 16/2815* (2013.01); *C07K 16/2866* (2013.01); *C07K 16/30* (2013.01); *C07K 2317/24* (2013.01); *C07K 2317/31* (2013.01); *C07K 2317/565* (2013.01); *C07K 2317/76* (2013.01)

(58) Field of Classification Search
CPC ............ C07K 16/2818; C07K 16/2812; C07K 16/2815; C07K 16/2866; C07K 16/30
See application file for complete search history.

(56) References Cited

U.S. PATENT DOCUMENTS

| | | |
|---|---|---|
| 4,522,811 A | 6/1985 | Eppstein et al. |
| 4,816,567 A | 3/1989 | Cabilly et al. |
| 4,832,959 A | 5/1989 | Engels et al. |
| 5,258,498 A | 11/1993 | Huston et al. |
| 5,500,362 A | 3/1996 | Robinson et al. |
| 5,525,491 A | 6/1996 | Huston et al. |
| 5,731,168 A | 3/1998 | Carter et al. |
| 5,821,337 A | 10/1998 | Carter et al. |
| 5,834,597 A | 11/1998 | Tso et al. |
| 6,054,297 A | 4/2000 | Carter et al. |
| 6,120,762 A | 9/2000 | Johnson et al. |
| 6,132,992 A | 10/2000 | Ledbetter et al. |
| 6,982,321 B2 | 1/2006 | Winter |
| 7,087,409 B2 | 8/2006 | Barbas, III et al. |
| 7,183,076 B2 | 2/2007 | Arathoon et al. |
| 7,381,803 B1 | 6/2008 | Weiner et al. |
| 7,527,791 B2 | 5/2009 | Adams et al. |
| 7,635,475 B2 | 12/2009 | Kumagai et al. |
| 7,728,114 B2 | 7/2010 | Mach et al. |
| 7,959,925 B2 | 6/2011 | Weinberg et al. |
| 7,994,289 B2 | 8/2011 | Waldmann et al. |
| 7,998,469 B2 | 8/2011 | Gantier et al. |
| 8,044,178 B2 | 10/2011 | Boghaert et al. |
| 8,052,964 B2 | 11/2011 | Gantier et al. |
| 9,006,399 B2 | 4/2015 | Liu et al. |
| 9,035,026 B2 | 5/2015 | Hoffman et al. |
| 9,605,084 B2 | 3/2017 | Moore et al. |
| 9,644,016 B2 | 5/2017 | Stagliano et al. |
| 9,650,446 B2 | 5/2017 | Moore et al. |
| 9,701,750 B2 | 7/2017 | Hoffman et al. |
| 9,701,759 B2 | 7/2017 | Desjarlais et al. |
| 9,803,021 B2 | 10/2017 | Morrison |
| 10,544,222 B2* | 1/2020 | Punnonen ............... A61P 31/12 |
| 2005/0123546 A1 | 6/2005 | Umana et al. |
| 2006/0270045 A1 | 11/2006 | Cregg et al. |
| 2011/0274685 A1 | 11/2011 | Keler et al. |
| 2011/0275787 A1 | 11/2011 | Kufer et al. |
| 2012/0237498 A1 | 9/2012 | Ahrens et al. |
| 2013/0183321 A1 | 7/2013 | Smith et al. |
| 2014/0322129 A1 | 10/2014 | Leong et al. |

(Continued)

FOREIGN PATENT DOCUMENTS

| | | |
|---|---|---|
| CN | 107474135 A | 12/2017 |
| EP | 219781 A2 | 10/1985 |

(Continued)

OTHER PUBLICATIONS

Zhao et al. "BTLA identifies dysfunctional PD-1-expressing CD4C T cells in human hepatocellular carcinoma", Oncoimmunology, 5:12 e1254855 (Year: 2016).*

(Continued)

*Primary Examiner* — Sharon X Wen
*Assistant Examiner* — Peter Johansen
(74) *Attorney, Agent, or Firm* — Cooley LLP; Ivor R. Elrifi; Cynthia A. Kozakiewicz

(57) ABSTRACT

Provided herein are binding polypeptides that specifically bind PD-1. More specifically, provided herein are fusion proteins, including multivalent and/or multispecific constructs and chimeric antigen receptors, that bind PD-1. Also provided are pharmaceutical compositions containing the polypeptides, nucleic acid molecules encoding the polypeptides and vectors and cells thereof, and methods of use and uses of the provided PD-1 binding polypeptides for treating diseases and conditions, such as cancer.

28 Claims, 8 Drawing Sheets

Specification includes a Sequence Listing.

(56) References Cited

U.S. PATENT DOCUMENTS

| | | |
|---|---|---|
| 2014/0348841 A1 | 11/2014 | Schebye et al. |
| 2014/0363426 A1 | 12/2014 | Moore et al. |
| 2015/0064204 A1 | 3/2015 | Beers et al. |
| 2015/0079088 A1 | 3/2015 | Lowman et al. |
| 2015/0087810 A1 | 3/2015 | Moore et al. |
| 2015/0239991 A1 | 8/2015 | Blein et al. |
| 2015/0307617 A1 | 10/2015 | Du et al. |
| 2015/0307628 A1 | 10/2015 | Kim et al. |
| 2016/0122425 A1 | 5/2016 | Daugherty et al. |
| 2016/0194399 A1 | 7/2016 | Irving et al. |
| 2016/0207981 A1 | 7/2016 | Eckelman et al. |
| 2016/0280795 A1 | 9/2016 | Wang |
| 2016/0289324 A1 | 10/2016 | Moore et al. |
| 2017/0022284 A1 | 1/2017 | Timmer et al. |
| 2017/0037130 A1 | 2/2017 | Raum et al. |
| 2017/0000813 A1 | 3/2017 | Stagliano et al. |
| 2017/0020413 A1 | 7/2017 | Moore et al. |
| 2017/0198050 A1 | 7/2017 | Eckelman et al. |
| 2017/0226215 A1 | 8/2017 | Gray et al. |
| 2017/0369563 A1 | 12/2017 | Dubridge et al. |
| 2018/0016354 A1 | 1/2018 | Wozniak-Knopp et al. |
| 2018/0194842 A1 | 7/2018 | Mach et al. |
| 2018/0355038 A1 | 12/2018 | Smith et al. |

FOREIGN PATENT DOCUMENTS

| | | | |
|---|---|---|---|
| EP | | 1391213 A1 | 8/2002 |
| WO | WO 1992/008737 A1 | | 5/1992 |
| WO | WO 1994/04679 A1 | | 3/1994 |
| WO | WO 1998/050431 A2 | | 11/1998 |
| WO | WO 2000/24884 A2 | | 5/2000 |
| WO | WO 2000/041474 A2 | | 7/2000 |
| WO | WO 2002/079249 A2 | | 10/2002 |
| WO | WO 2002/083733 A2 | | 10/2002 |
| WO | WO 2002/086156 A2 | | 10/2002 |
| WO | WO 2002/095067 A2 | | 11/2002 |
| WO | WO 2002/101048 A2 | | 12/2002 |
| WO | WO 2003/000896 A2 | | 1/2003 |
| WO | WO 2003/023032 A2 | | 3/2003 |
| WO | WO 2004/022593 A2 | | 3/2004 |
| WO | WO 2004/022747 A1 | | 3/2004 |
| WO | WO 2004/92219 A2 | | 10/2004 |
| WO | WO 2005/035584 A1 | | 4/2005 |
| WO | WO 2005/040220 A1 | | 5/2005 |
| WO | WO 2005/063816 A2 | | 7/2005 |
| WO | WO 2005/100402 A1 | | 10/2005 |
| WO | WO 2006/029879 A2 | | 3/2006 |
| WO | WO 2007/033230 A2 | | 3/2007 |
| WO | WO 2008/119567 A2 | | 10/2008 |
| WO | WO 2009/067800 A1 | | 6/2009 |
| WO | WO 2009/089004 A1 | | 7/2009 |
| WO | WO 2010/151792 A1 | | 12/2010 |
| WO | WO 2011/056983 A1 | | 5/2011 |
| WO | WO 2011/133886 A2 | | 10/2011 |
| WO | WO 2011/143545 A1 | | 11/2011 |
| WO | WO 2012/058768 A1 | | 5/2012 |
| WO | WO 2013/026837 A1 | | 12/2013 |
| WO | WO 2014/067011 A1 | | 5/2014 |
| WO | WO 2014/099997 A1 | | 6/2014 |
| WO | WO 2014/194100 A1 | | 12/2014 |
| WO | WO 2015/001085 A1 | | 1/2015 |
| WO | WO 2015/095392 A1 | | 6/2015 |
| WO | WO 2016/177762 A1 | | 11/2016 |
| WO | WO 2016/179517 A1 | | 11/2016 |
| WO | WO 2016/204966 A1 | | 12/2016 |
| WO | WO 2017/015623 A2 | | 1/2017 |
| WO | WO 2017/030926 A1 | | 2/2017 |
| WO | WO 2017/123650 A2 | | 7/2017 |
| WO | WO 2017/123673 A2 | | 7/2017 |
| WO | WO 2017/134440 A2 | | 8/2017 |
| WO | WO 2017/167672 A1 | | 10/2017 |
| WO | WO 2018/027025 A1 | | 2/2018 |
| WO | WO 2019/133761 A1 | | 7/2019 |
| WO | WO 2020/077257 A1 | | 4/2020 |

OTHER PUBLICATIONS

Lamminmaki et al. "Crystal structure of a recombinant anti-estradiol Fab fragment in complex with 17beta-estradiol", JBC 2001, 276:36687-36694 (Year: 2001).*

Rudikoff et al . "Single amino acid altering antigen-binding specificity", Proc Natl Acad Sci USA 1982 vol. 79 p. 1979 (Year: 1982).*

MacCallum et al. "Antibody-antigen Interactions: Contact Analysis and Binding Site Topography", J. Mol. Biol. (1996) 262, 732-745 (Year: 1996).*

Pascalis et al. "Grafting of "Abbreviated" Complementarity-Determining Regions Containing Specificity-Determining Residues Essential for Ligand Contact to Engineer a Less Immunogenic Humanized Monoclonal Antibody", The Journal of Immunology (2002) 169, 3076-3084 (Year: 2002).*

Casset et al. "A peptide mimetic of an anti-CD4 monoclonal antibody by rational design", BBRC 2003, 307:198-205 (Year: 2003).*

Vajdos et al. "Comprehensive functional maps of the antigen-binding site of an anti-ErbB2 antibody obtained with shotgun scanning mutagenesis", J. Mol. Biol. (2002) 320, 415-428 (Year: 2002).*

Chen et al. "Selection and analysis of an optimized anti-VEGF antibody: crystal structure of an affinity-matured Fab in complex with antigen", J. Mol. Bio. (1999) 293, 865-881 (Year: 1999).*

Wu et al. "Humanization of a murine monoclonal antibody by simultaneous optimization of framework and CDR residues", J. Mol. Biol. (1999) 294, 151-162 (Year: 1999).*

Padlan et al. "Structure of an antibody-antigen complex: crystal structure of the HyHEL-10 Fab-lysozyme complex", PNAS 1989, 86: 5938-5942 (Year: 1989).*

Ackerman, et al. "Biologic activity in a fragment of recombinant human interferon alpha." Proc Natl Acad Sci USA. Feb. 1984;81(4):1045-7.

Al-Lazikani, et al. "Standard conformations for the canonical structures of immunoglobulins." J Mol Biol. Nov. 7, 1997;273(4):927-48.

Almagro, JC and Fransson, J. "Humanization of antibodies." Front Biosci. Jan. 1, 2008;13:1619-33.

Alegre, et al. "Effect of a single amino acid mutation on the activating and immunosuppressive properties of a "humanized" OKT3 monoclonal antibody." J Immunol. Jun. 1, 1992;148(11):3461-8.

Anasetti, et al. "Treatment of acute graft-versus-host disease with a nonmitogenic anti-CD3 monoclonal antibody." Transplantation, Nov. 1992;54(5):844-51.

Anderson, et al. "Fc gamma receptor type III (CD16) is included in the zeta NK receptor complex expressed by human natural killer cells." Proc Natl Acad Sci U S A. Mar. 1990;87(6):2274-8.

Arndt, et al. "A bispecific diabody that mediates natural killer cell cytotoxicity against xenotransplantated human Hodgkin's tumors." Blood. Oct. 15, 1999;94(8):2562-8.

Baca, et al. "Antibody humanization using monovalent phage display." J Biol Chem. Apr. 18, 1997;272(16):10678-84.

Behar, et al. "Isolation and characterization of anti-FcgammaRIII (CD 16) llama single-domain antibodies that activate natural killer cells." Protein Eng Des Sel. Jan. 2008;21(1):1-10.

Beliveau, et al. "Probing the substrate specificities of matriptase, matriptase-2, hepsin and DESC1 with internally quenched fluorescent peptides." FEBS J. Apr. 2009;276(8):2213-26. doi: 10.1111/j.1742-4658.2009.06950.x.

Bruggemann, et al. "Comparison of the effector functions of human immunoglobulins using a matched set of chimeric antibodies." J Exp Med. Nov. 1, 1987;166(5):1351-61.

Capel, et al. "Heterogeneity of human IgG Fc receptors." Immunomethods. Feb. 1994;4(1):25-34.

Carter, P. "Bispecific human IgG by design." J Immunol Methods. Feb. 1, 2001;248(1-2):7-15.

Carter, et al. "Humanization of an anti-p185HER2 antibody for human cancer therapy." Proc Natl Acad Sci U S A, May 15, 1992;89(10):4285-9.

(56) References Cited

OTHER PUBLICATIONS

Carter, et al. "PD-1:PD-L inhibitory pathway affects both CD4(+) and CD8(+) T cells and is overcome by IL-2," Eur J Immunol, Mar. 2002;32(3):634-43.
Chen, et al. "Fusion protein linkers: property, design and functionality." Adv Drug Deliv Rev. Oct. 2013;65(10):1357-69, doi: 10.1016/j.addr.2012.09.039.
Clackson, et al. "Making antibody fragments using phage display libraries." Nature. Aug. 15, 1991;352(6336):624-8.
Clynes, et al. "Fc receptors are required in passive and active immunity to melanoma." Proc Natl Acad Sci U S A. Jan. 20, 1998;95(2):652-6.
Cragg, M.S. and Glennie, M.J. "Antibody specificity controls in vivo effector mechanisms of anti-CD20 reagents." Blood. Apr. 1, 2004;103(7):2738-43.
Cragg, M.S. "Complement-mediated lysis by anti-CD20 mAb correlates with segregation into lipid rafts." Blood. Feb. 1, 2003; 101(3): 1045-52.
Daeron, et al. "Fc receptor biology." Annu Rev Immunol. 1997;15:203-34.
Dall'Acqua, et al. "Antibody humanization by framework shuffling." Methods. May 2005;36(1):43-60.
Dall'Acqua, et al. "Properties of human IgG1s engineered for enhanced binding to the neonatal Fc receptor (FcRn)," J Biol Chem. Aug. 18, 2006;281(33):23514-24.
Davis, et al. "SEEDbodies: fusion proteins based on strand-exchange engineered domain (SEED) CH3 heterodimers in an Fc analogue platform for asymmetric binders or immunofusions and bispecific antibodies." Protein Eng Des Sel. Apr. 2010;23(4):195-202, doi: 10.1093/protein/gzp094.
De Haas, et al. "Fc gamma receptors of phagocytes." J Lab Clin Med. Oct. 1995;126(4):330-41.
Diaz, et al. "Structure of the human type-I interferon gene cluster determined from a YAC clone contig." Genomics. Aug. 1994;22(3):540-52.
Deisenhofer, J. "Crystallographic refinement and atomic models of a human Fc fragment and its complex with fragment B of protein A from *Staphylococcus aureus* at 2.9- and 2.8-A resolution." Biochemistry. Apr. 28, 1981;20(9):2361-70.
Dotti, et al. "Design and development of therapies using chimeric antigen receptor-expressing T cells." Immunol Rev. Jan. 2014;257(1):107-26. doi: 10.1111/imr.12131.
Endo, Y. and Sawasaki, T. "High-throughput, genome-scale protein production method based on the wheat germ cell-free expression system," Biotechnol Adv. Nov. 2003;21(8):695-713.
Freeman, et al. "Engagement of the PD-1 immunoinhibitory receptor by a novel B7 family member leads to negative regulation of lymphocyte activation," J Exp Med. Oct. 2, 2000;192(7):1027-34.
Gazzano-Santoro, et al. "A non-radioactive complement-dependent cytotoxicity assay for anti-CD20 monoclonal antibody." J Immunol Methods. Mar. 28, 1997;202(2):163-71.
Ghetie, et al. "Increasing the serum persistence of an IgG fragment by random mutagenesis." Nat Biotechnol. Jul. 1997;15(7):637-40.
Ghetie, V and Ward, ES. "FcRn: the MHC class I-related receptor that is more than an IgG transporter," Immunol Today. Dec. 1997;18(12):592-8.
Gunasekaran, et al. "Enhancing antibody Fc heterodimer formation through electrostatic steering effects: applications to bispecific molecules and monovalent IgG." J Biol Chem. Jun. 18, 2010;285(25):19637-46, doi: 10.1074/jbc.M110.117382.
Golovleva, et al. "Ethnic differences in interferon-alpha allele frequencies." Hum Hered. Jul.-Aug. 1997;47(4): 185-8.
Golovleva, et al. "Novel variants of human IFN-alpha detected in tumor cell lines and biopsy specimens." J Interferon Cytokine Res. Oct. 1997;17(10):637-45.
Golovleva, et al. "Polymorphism in the interferon-alpha gene family." Am J Hum Genet. Sep. 1996;59(3):570-8.
Guyer, et al. "Immunoglobulin binding by mouse intestinal epithelial cell receptors." J Immunol. Aug. 1976;117(2):587-93.

Ha, et al. "Immunoglobulin Fc Heterodimer Platform Technology: From Design to Applications in Therapeutic Antibodies and Proteins." Front Immunol, Oct. 6, 2016;7:394, eCollection 2016.
Hermanson, GT. "Amine-Reactive and Sulfhydryl-Reactive Cross-linkers" Bioconjugate Techniques; Academic Press: New York (1996), pp. 234-242.
Hayward, et al. "Lysis of CD3 hybridoma targets by cloned human CD4 lymphocytes." Immunology, May 1988;64(1):87-92.
Hawkins, et al. "Phase I evaluation of a synthetic mutant of beta-interferon." Cancer Res. Nov. 1985;45(11 Pt 2):5914-20.
Hellstrom, et al. "Antitumor effects of L6, an IgG2a antibody that reacts with most human carcinomas." Proc Natl Acad Sci U S A. Sep. 1986;83(18):7059-63.
Hellstrom, et al. "Strong antitumor activities of IgG3 antibodies to a human melanoma-associated ganglioside." Proc Natl Acad Sci U S A. Mar. 1985;82(5): 1499-502.
Hinton, et al. "Engineered human IgG antibodies with longer serum half-lives in primates." J Biol Chem. Feb. 20, 2004;279(8):6213-6.
Hinman, et al. "Preparation and characterization of monoclonal antibody conjugates of the calicheamicins: a novel and potent family of antitumor antibiotics." Cancer Res. Jul. 15, 1993;53(14):3336-42.
Holliger, et al. "Specific killing of lymphoma cells by cytotoxic T-cells mediated by a bispecific diabody." Protein Eng. Mar. 1996;9(3):299-305.
Honegger, et al. "Yet another numbering scheme for immunoglobulin variable domains: an automatic modeling and analysis tool." J Mol Biol. Jun. 8, 2001;309(3):657-70.
Husain, B. and Ellerman, D. "Expanding the Boundaries of Biotherapeutics with Bispecific Antibodies." BioDrugs. Oct. 2018;32(5):441-464, doi: 10.1007/s40259-018-0299-9.
Hussain, et al. "A new allele of interferon-alpha17 gene encoding IFN-alpha17b is the major variant in human population," J Interferon Cytokine Res. Jul. 1998;18(7):469-77.
Hussain, et al. "Both variant forms of interferon-alpha4 gene (IFNA4a and IFNA4b) are present in the human population," J Interferon Cytokine Res. Sep. 1997;17(9):559-66.
Hussain, et al. "IFN-alpha1a gene is the major variant in the North American population." J Interferon Cytokine Res. Sep. 2000;20(9):763-8.
Hussain, et al. "Interferon-alpha 8b is the only variant of interferon-alpha 8 identified in a large human population," J Interferon Cytokine Res. Jul. 1996;16(7):523-9.
Idusogie, et al. "Engineered antibodies with increased activity to recmit complement." J Immunol. Feb. 15, 2001;166(4):2571-5.
IMGT Scientific Chart (IMGT®, the international ImMunoGeneTics information system®, http://www.imgt.org/IMGTScientificChart/Numbering/Hu_IGHGnber.html (created: May 17, 2001, last updated: Jan. 10, 2013).
Ishida, et al. "Induced expression of PD-1, a novel member of the immunoglobulin gene superfamily, upon programmed cell death," EMBO J. Nov. 1992;11(11):3887-95.
Jaitin, et al. "Inquiring into the differential action of interferons (IFNs): an IFN-alpha2 mutant with enhanced affinity to IFNAR1 is functionally similar to IFN-beta." Mol Cell Biol. Mar. 2006;26(5):1888-97.
Jendeberg, et al. "Engineering of Fc(1) and Fc(3) from human immunoglobulin G to analyse subclass specificity for staphylococcal protein A." J Immunol Methods. Feb. 14, 1997;201(1):25-34.
Kalie, et al. "An interferon alpha2 mutant optimized by phage display for IFNAR1 binding confers specifically enhanced antitumor activities." JBiol Chem, Apr. 13, 2007;282(15):11602-11.
Kaneko, et al. "Optimizing therapeutic antibody function: progress with Fc domain engineering." BioDrugs. Feb. 1, 2011;25(1):1-11. doi: 10.2165/11537830-000000000-00000.
Kashmiri, et al. "SDR grafting—a new approach to antibody humanization." Methods. May 2005;36(1):25-34.
Kipriyanov, et al. "Bispecific tandem diabody for tumor therapy with improved antigen binding and pharmacokinetics." J Mol Biol. Oct. 15, 1999;293(1):41-56.
Kim, et al. "Interferon, alpha 17 (IFNA17) Ile184Arg polymorphism and cervical cancer risk." Cancer Lett. Jan. 28, 2003;189(2):183-8.

(56) References Cited

OTHER PUBLICATIONS

Kita, et al. "Determination of interferon-alpha2 allele composition in the genomic DNA from healthy volunteers and leukemic patients in Japan," J Interferon Cytokine Res. Mar. 1997;17(3):135-40.
Kohler, et al. "Continuous cultures of fused cells secreting antibody of predefined specificity." Nature. Aug. 7, 1975;256(5517):495-7.
Klimka, et al. "Human anti-CD30 recombinant antibodies by guided phage antibody selection using cell panning," Br J Cancer, Jul. 2000;83(2):252-60.
Krause, et al. "Signaling by covalent heterodimers of interferon-gamma. Evidence for one-sided signaling in the active tetrameric receptor complex," J Biol Chem, Jul. 28, 2000;275(30):22995-3004.
Latchman, et al. "PD-L2 is a second ligand for PD-1 and inhibits T cell activation." Nat Immunol. Mar. 2001;2(3):261-8.
Ledbetter, et al. "Valency of CD3 binding and internalization of the CD3 cell-surface complex control T cell responses to second signals: distinction between effects on protein kinase C, cytoplasmic free calcium, and proliferation," J Immunol. Jun. 1, 1986;136(11):3945-52.
Lazar, et al. "Engineered antibody Fc variants with enhanced effector function." Proc Natl Acad Sci U S A. Mar. 14, 2006;103(11):4005-10.
Leaver-Fay, et al. "Computationally Designed Bispecific Antibodies using Negative State Repertoires." Structure. Apr. 5, 2016;24(4):641-651. doi: 10.1016/j.str.2016.02.013.
Lefranc, et al. "IMGT unique numbering for immunoglobulin and T cell receptor variable domains and Ig superfamily V-like domains." Dev Comp Immunol. Jan. 2003;27(1):55-77.
Linge, et al. "Transcription of interferon-alpha 2 alleles from virus-induced human leucocytes and lymphoblastoid cells of African origin," Biochim Biophys Acta. Dec. 27, 1995;1264(3):363-8.
Liu, et al. "Eradication of large colon tumor xenografts by targeted delivery of maytansinoids." Proc Natl Acad Sci U S A. Aug. 6, 1996;93(16):8618-23.
Lundell, et al. "The carboxyl-terminal region of human interferon gamma is important for biological activity: mutagenic and NMR analysis." Protein Eng. Feb. 1991;4(3):335-41.
Lode, et al. "Targeted therapy with a novel enediyene antibiotic calicheamicin theta(I)1 effectively suppresses growth and dissemination of liver metastases in a syngeneic model of murine neuroblastoma." Cancer Res. Jul. 15, 1998;58(14):2925-8.
MacCallum, et al. "Antibody-antigen interactions: contact analysis and binding site topography." J Mol Biol. Oct. 11, 1996;262(5):732-45.
Mandelboim, et al. "Human CD 16 as a lysis receptor mediating direct natural killer cell cytotoxicity." Proc Natl Acad Sci U S A. May 11, 1999;96(10):5640-4.
Mandler, et al. "Immunoconjugates of geldanamycin and anti-HER2 monoclonal antibodies: antiproliferative activity on human breast carcinoma cell lines." J Natl Cancer Inst. Oct. 4, 2000;92(19):1573-81.
Mandler, et al. "Modifications in synthesis strategy improve the yield and efficacy of geldanamycin-herceptin immunoconjugates." Bioconjug Chem. Jul.-Aug. 2002;13(4):786-91.
Mandler, et al. "Synthesis and evaluation of antiproliferative activity of a geldanamycin-Herceptin immunoconjugate." Bioorg Med Chem Lett. May 15, 2000;10(10):1025-8.
Martin, et al. "Modeling antibody hypervariable loops: a combined algorithm." Proc Natl Acad Sci U S A. Dec. 1989;86(23):9268-72.
McCafferty, et al. "Phage antibodies: filamentous phage displaying antibody variable domains." Nature. Dec. 6, 1990;348(6301):552-4.
McCall, et al. "Isolation and characterization of an anti-CD16 single-chain Fv fragment and construction of an anti-HER2/neu/anti-CD16 bispecific scFv that triggers CD16-dependent tumor cytolysis." Mol Immunol. May 1999;36(7):433-45.
Merchant, et al. "An efficient route to human bispecific IgG." Nat Biotechnol. Jul. 1998;16(7):677-81.

Miller, S. "Protein-protein recognition and the association of immunoglobulin constant domains." J Mol Biol. Dec. 20, 1990;216(4):965-73.
Moore, et al. "A novel bispecific antibody format enables simultaneous bivalent and monovalent co-engagement of distinct target antigens." MAbs. Nov.-Dec. 2011;3(6):546-57. doi: 10.4161/mabs.3.6.18123.
Moore, et al. "Engineered Fc variant antibodies with enhanced ability to recruit complement and mediate effector functions." MAbs. Mar.-Apr. 2010;2(2):181-9.
Nagorsen, et al. "Immunomodulatory therapy of cancer with T cell-engaging BiTE antibody blinatumomab." Exp Cell Res. May 15, 2011;317(9):1255-60, doi: 10.1016/j.yexcr.2011.03.010.
Natsume, et al. "Engineered antibodies of IgG1/IgG3 mixed isotype with enhanced cytotoxic activities." Cancer Res. May 15, 2008;68(10):3863-72, doi: 10.1158/0008-5472.CAN-07-6297.
Nicolaou, et al. "Calicheamicin θ : A Rationally Designed Molecule with Extremely Potent and Selective DNA Cleaving Properties and Apoptosis Inducing Activity." Agnew, Chem Inti. Ed. Engl, 33: 183-186 (1994).
Nyman, et al. "Identification of nine interferon-alpha subtypes produced by Sendai virus-induced human peripheral blood leucocytes." Biochem J. Jan. 15, 1998;329 ( Pt 2):295-302.
Ohigashi, et al. "Clinical significance of programmed death-1 ligand-1 and programmed death-1 ligand-2 expression in human esophageal cancer," Clin Cancer Res. Apr. 15, 2005;11(8):2947-53.
Osbourn, et al. "From rodent reagents to human therapeutics using antibody guided selection." Methods. May 2005;36(1):61-8.
Padlan, E.A. "A possible procedure for reducing the immunogenicity of antibody variable domains while preserving their ligand-binding properties." Mol Immunol. Apr.-May 1991;28(4-5):489-98.
Pan, et al. "Site-specific PEGylation of an anti-CEA/CD3 bispecific antibody improves its antitumor efficacy." Int J Nanomedicine. May 29, 2018;13:3189-3201. doi: 10.2147/IJN.S164542. eCollection 2018.
Pan, et al. "Structural characterization of human interferon gamma. Heterogeneity of the carboxyl terminus." Eur J Biochem. Jul. 1, 1987;166(1):145-9.
Petkova, et al. "Enhanced half-life of genetically engineered human IgG1 antibodies in a humanized FcRn mouse model: potential application in humorally mediated autoimmune disease." Int Immunol. Dec. 2006;18(12):1759-69.
Pessano, et al. "The T3/T cell receptor complex: antigenic distinction between the two 20-kd T3 (T3-delta and T3-epsilon) subunits." EMBO J. Feb. 1985;4(2):337-44.
Pestka, S. "Interferon from 1981 to 1986." Methods Enzymol. 1986;119:3-14.
Pestka, S. "The human interferons—from protein purification and sequence to cloning and expression in bacteria: before, between, and beyond." Arch Biochem Biophys. Feb. 15, 1983;221(1):1-37.
Pollard, et al. "Fixation, processing, and immunochemical reagent effects on preservation of T-lymphocyte surface membrane antigens in paraffin-embedded tissue." J Histochem Cytochem. Nov. 1987;35(11):1329-38.
Portolano, et al. "Lack of promiscuity in autoantigen-specific H and L chain combinations as revealed by human H and L chain "roulette"." J Immunol. Feb. 1, 1993;150(3):880-7.
Presta, et al. "Humanization of an antibody directed against IgE." J Immunol. Sep. 1, 1993;151(5):2623-32.
Queen, et al. "A humanized antibody that binds to the interleukin 2 receptor." Proc Natl Acad Sci U S A. Dec. 1989;86(24):10029-33.
Ravetch, JV and Kinet, JP. "Fc receptors." Annu Rev Immunol. 1991;9:457-92.
Reusch, et al. "A novel tetravalent bispecific TandAb (CD30/CD16A) efficiently recruits NK cells for the lysis of CD30+ tumor cells." MAbs. May-Jun. 2014;6(3):728-39, doi: 10.4161/mabs.28591.
Riechmann, et al. "Reshaping human antibodies for therapy." Nature. Mar. 24, 1988;332(6162):323-7.
Ridgway, et al. "'Knobs-into-holes' engineering of antibody CH3 domains for heavy chain heterodimerization." Protein Eng. Jul. 1996;9(7):617-21.

(56) References Cited

OTHER PUBLICATIONS

Rocca, et al. "Zymographic detection and clinical correlations of MMP-2 and MMP-9 in breast cancer sera." Br J Cancer, Apr. 5, 2004;90(7):1414-21.

Rodrigues, et al. "Engineering a humanized bispecific F(ab')2 fragment for improved binding to T cells." Int J Cancer Suppl. 1992;7:45-50.

Rohrlich, et al. "HLA-B*0702 transgenic, H-2KbDb double-knockout mice: phenotypical and functional characterization in response to influenza virus." Int Immunol. Jun. 2003;15(6):765-72.

Rosenberg, et al. "Use of tumor-infiltrating lymphocytes and interleukin-2 in the immunotherapy of patients with metastatic melanoma. A preliminary report." N Engl J Med. Dec. 22, 1988;319(25):1676-80.

Rosok, et al. "A combinatorial library strategy for the rapid humanization of anticarcinoma BR96 Fab." J Biol Chem. Sep. 13, 1996;271(37):22611-8.

Rowland, et al. "Drug localisation and growth inhibition studies of vindesine-monoclonal anti-CEA conjugates in a human tumour xenograft." Cancer Immunol Immunother. 1986;21(3):183-7.

Running Deer, et al. "High-level expression of proteins in mammalian cells using transcription regulatory sequences from the Chinese hamster EF-1alpha gene." Biotechnol Prog. May-Jun. 2004;20(3):880-9.

Sadelain, et al. "The basic principles of chimeric antigen receptor design." Cancer Discov. Apr. 2013;3(4):388-98, doi: 10.1158/2159-8290.CD-12-0548.

Sadelain, et al. "The promise and potential pitfalls of chimeric antigen receptors." Curr Opin Immunol. Apr. 2009;21(2):215-23, doi: 10.1016/j.coi.2009.02.009.

Seimetz, et al. "Development and approval of the trifunctional antibody catumaxomab (anti-EpCAM x anti-CD3) as a targeted cancer immunotherapy." Cancer Treat Rev. Oct. 2010;36(6):458-67. doi: 10.1016/j.ctrv.2010.03.001.

Sims, et al. "A humanized CD 18 antibody can block function without cell destruction." J Immunol. Aug. 15, 1993;151(4):2296-308.

Sitaraman, K. and Chatterjee, DK. "High-throughput protein expression using cell-free system," Methods Mol Biol. 2009;498:229-44. doi: 10.1007/978-1-59745-196-3_15.

Shields, et al. "High resolution mapping of the binding site on human IgG1 for Fc gamma RI, Fc gamma RII, Fc gamma RIII, and FcRn and design of IgG1 variants with improved binding to the Fc gamma R," J Biol Chem. Mar. 2, 2001;276(9):6591-604.

Spirin, et al. "High-throughput cell-free systems for synthesis of functionally active proteins." Trends Biotechnol. Oct. 2004;22(10):538-45.

Stavenhagen, et al. "Enhancing the potency of therapeutic monoclonal antibodies via Fc optimization," Adv Enzyme Regul. 2008;48:152-64, doi: 10.1016/j.advenzreg.2007.11.011.

Stavenhagen, et al. "Fc optimization of therapeutic antibodies enhances their ability to kill tumor cells in vitro and controls tumor expansion in vivo via low-affinity activating Fcgamma receptors." Cancer Res. Sep. 15, 2007;67(18):8882-90.

UniProt Accession No. P41273: "RecName: Full=Tumor necrosis factor ligand superfamily member 9; AltName: Full-4-1BB ligand; Short-4-1BBL" Oct. 16, 2019 <https://www.ncbi.nlm.nih.gov/protein/P41273>.

UniProt Accession No. P23510: "RecName: Full=Tumor necrosis factor ligand superfamily member 4; AltName: Full=Glycoprotein Gp34; AltName: Full=OX40 ligand; Short=OX40L; AltName: Full= TAX transcriptionally-activated glycoprotein 1; AltName: CD_antigen= CD252" Oct. 16, 2019 <https://www.ncbi.nlm.nih.gov/protein/P23510>.

UniProt Accession No. Q9UNG2: "RecName: Full=Tumor necrosis factor ligand superfamily member 18; AltName: Full=Activation-inducible TNF-related ligand; Short=AITRL; AltName: Full-Glucocorticoid-induced TNF-related ligand; Short-hGITRL" Oct. 16, 2019 <https://www.ncbi.nlm.nih.gov/protein/Q9UNG2>.

UniProt Accession No. P32970: "RecName: Full=CD70 antigen; AltName: Full=CD27 ligand; Short=CD27-L; AltName: Full= Tumor necrosis factor ligand superfamily member 7; AltName: CD antigen=CD70" Nov. 13, 2019 <https://www.ncbi.nlm.nih.gov/protein/P32970>.

Van De Winkel, et al. "Human IgG Fc receptor heterogeneity: molecular aspects and clinical implications." Immunol Today. May 1993;14(5):215-21.

Valedkarimi, et al. "Antibody-cytokine fusion proteins for improving efficacy and safety of cancer therapy." Biomed Pharmacother. Nov. 2017;95:731-742, doi: 10.1016/j.biopha.2017.07.160.

Vivier, et al. "Structure and function of the CD16:zeta:gamma complex expressed on human natural-killer cells." Int J Cancer Suppl. 1992;7:11-4.

Von Kreudenstein, et al. "Improving biophysical properties of a bispecific antibody scaffold to aid developability: quality by molecular design." MAbs. Sep.-Oct. 2013;5(5):646-54. doi: 10.4161/mabs.25632.

Wirthmueller, et al. "Signal transduction by Fc gamma RIII (CD16) is mediated through the gamma chain," J Exp Med. May 1, 1992;175(5):1381-90.

Yang, et al. "A common pathway for T lymphocyte activation involving both the CD3-Ti complex and CD2 sheep erythrocyte receptor determinants." J Immunol. Aug. 15, 1986; 137(4):1097-100.

Yamamoto, et al. "Creation of interferon-alpha8 mutants with amino acid substitutions against interferon-alpha receptor-2 binding sites using phage display system and evaluation of their biologic properties." J Interferon Cytokine Res. Mar. 2009;29(3):161-70, doi: 10.1089/jir.2008.0038.

Yokoyama, et al. "How do natural killer cells find self to achieve tolerance?" Immunity. Mar. 2006;24(3):249-57.

Young, et al. "Antibody-cytokine fusion proteins for treatment of cancer: engineering cytokines for improved efficacy and safety." Semin Oncol. Oct. 2014;41(5):623-36. doi: 10.1053/j.seminoncol.2014.08.002.

Zalevsky, et al. "Enhanced antibody half-life improves in vivo activity." Nat Biotechnol. Feb. 2010;28(2):157-9. doi: 10.1038/nbt.1601.

* cited by examiner

SEQUENCE LISTING

<160> NUMBER OF SEQ ID NOS: 323

<210> SEQ ID NO 1
<211> LENGTH: 6
<212> TYPE: PRT
<213> ORGANISM: Artificial Sequence
<220> FEATURE:
<223> OTHER INFORMATION: GS linker

<400> SEQUENCE: 1

Gly Gly Ser Gly Gly Ser
1               5

<210> SEQ ID NO 2
<211> LENGTH: 9
<212> TYPE: PRT
<213> ORGANISM: Artificial Sequence
<220> FEATURE:
<223> OTHER INFORMATION: GS linker

<400> SEQUENCE: 2

Gly Gly Ser Gly Gly Ser Gly Gly Ser
1               5

<210> SEQ ID NO 3
<211> LENGTH: 12
<212> TYPE: PRT
<213> ORGANISM: Artificial Sequence
<220> FEATURE:
<223> OTHER INFORMATION: GS linker

<400> SEQUENCE: 3

```
Gly Gly Ser Gly Gly Ser Gly Gly Ser
1               5                  10

<210> SEQ ID NO 4
<211> LENGTH: 15
<212> TYPE: PRT
<213> ORGANISM: Artificial Sequence
<220> FEATURE:
<223> OTHER INFORMATION: GS linker

<400> SEQUENCE: 4

Gly Gly Ser Gly Gly Ser Gly Gly Ser Gly Gly Ser Gly Gly Ser
1               5                  10                  15

<210> SEQ ID NO 5
<211> LENGTH: 4
<212> TYPE: PRT
<213> ORGANISM: Artificial Sequence
<220> FEATURE:
<223> OTHER INFORMATION: Glycine linker

<400> SEQUENCE: 5

Gly Gly Gly Gly
1

<210> SEQ ID NO 6
<211> LENGTH: 5
<212> TYPE: PRT
<213> ORGANISM: Artificial Sequence
<220> FEATURE:
<223> OTHER INFORMATION: Glycine linker

<400> SEQUENCE: 6

Gly Gly Gly Gly Gly
1               5

<210> SEQ ID NO 7
<211> LENGTH: 6
<212> TYPE: PRT
<213> ORGANISM: Artificial Sequence
<220> FEATURE:
<223> OTHER INFORMATION: Glycine linker

<400> SEQUENCE: 7

Gly Gly Gly Gly Gly Gly
1               5

<210> SEQ ID NO 8
<211> LENGTH: 218
<212> TYPE: PRT
<213> ORGANISM: Homo sapiens

<400> SEQUENCE: 8

Pro Ala Pro Glu Leu Leu Gly Gly Pro Ser Val Phe Leu Phe Pro Pro
1               5                  10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80
```

-continued

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 9
<211> LENGTH: 215
<212> TYPE: PRT
<213> ORGANISM: Artificial Sequence
<220> FEATURE:
<223> OTHER INFORMATION: Fc xELL Fc region

<400> SEQUENCE: 9

Pro Ala Pro Gly Gly Pro Ser Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser His Glu Asp Pro Glu Val Lys Phe Asn Trp Tyr Val Asp
        35                  40                  45

Gly Val Glu Val His Asn Ala Lys Thr Lys Pro Arg Glu Glu Gln Tyr
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Ala Leu
                85                  90                  95

Pro Ala Pro Ile Glu Lys Thr Ile Ser Lys Ala Lys Gly Gln Pro Arg
            100                 105                 110

Glu Pro Gln Val Tyr Thr Leu Pro Pro Ser Arg Asp Glu Leu Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Lys Leu Thr Val Asp Lys Ser Arg Trp Gln Gln Gly Asn Val Phe Ser
            180                 185                 190

Cys Ser Val Met His Glu Ala Leu His Asn His Tyr Thr Gln Lys Ser
        195                 200                 205

Leu Ser Leu Ser Pro Gly Lys
    210                 215

<210> SEQ ID NO 10
<211> LENGTH: 217
<212> TYPE: PRT
<213> ORGANISM: Homo sapiens

<400> SEQUENCE: 10

Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Lys Val Ser Asn Lys
                85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 11
<211> LENGTH: 218
<212> TYPE: PRT
<213> ORGANISM: Homo sapiens

<400> SEQUENCE: 11

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Thr Lys Gly
            100                 105                 110

```
Gln Pro Arg Glu Pro Gln Val Tyr Thr Leu Pro Pro Ser Arg Glu Glu
            115                 120                 125

Met Thr Lys Asn Gln Val Ser Leu Thr Cys Leu Val Lys Gly Phe Tyr
130                 135                 140

Pro Ser Asp Ile Ala Val Glu Trp Glu Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
        195                 200                 205

Gln Lys Ser Leu Ser Leu Ser Pro Gly Lys
    210                 215
```

<210> SEQ ID NO 12
<211> LENGTH: 218
<212> TYPE: PRT
<213> ORGANISM: Homo sapiens

<400> SEQUENCE: 12

```
Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215
```

<210> SEQ ID NO 13
<211> LENGTH: 218
<212> TYPE: PRT
<213> ORGANISM: Homo sapiens

<400> SEQUENCE: 13

```
Pro Ala Pro Glu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
                35                  40                  45

Tyr Val Asp Gly Val Glu Val His Asn Ala Lys Thr Lys Pro Arg Glu
            50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
                100                 105                 110

Gln Pro Arg Glu Pro Gln Val Tyr Thr Leu Pro Pro Ser Gln Glu Glu
            115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
            195                 200                 205

Gln Lys Ser Leu Ser Leu Ser Leu Gly Lys
    210                 215

<210> SEQ ID NO 14
<211> LENGTH: 14
<212> TYPE: PRT
<213> ORGANISM: Artificial Sequence
<220> FEATURE:
<223> OTHER INFORMATION: modified IgG1 hinge

<400> SEQUENCE: 14

Glu Pro Lys Ser Ser Asp Lys Thr His Thr Cys Pro Pro Cys
1               5                   10

<210> SEQ ID NO 15
<211> LENGTH: 9
<212> TYPE: PRT
<213> ORGANISM: Artificial Sequence
<220> FEATURE:
<223> OTHER INFORMATION: truncated IgG1 hinge

<400> SEQUENCE: 15

Asp Lys Thr His Thr Cys Pro Pro Cys
1               5

<210> SEQ ID NO 16
<211> LENGTH: 11
<212> TYPE: PRT
<213> ORGANISM: Artificial Sequence
<220> FEATURE:
<223> OTHER INFORMATION: modified IgG4 hinge

<400> SEQUENCE: 16

Glu Ser Lys Tyr Gly Pro Pro Cys Pro Pro Cys
```

<210> SEQ ID NO 17
<211> LENGTH: 12
<212> TYPE: PRT
<213> ORGANISM: Artificial Sequence
<220> FEATURE:
<223> OTHER INFORMATION: carboxy-terminal sequence

<400> SEQUENCE: 17

Gly Gln Gly Thr Leu Val Thr Val Lys Pro Gly Gly
1               5                   10

<210> SEQ ID NO 18
<211> LENGTH: 12
<212> TYPE: PRT
<213> ORGANISM: Artificial Sequence
<220> FEATURE:
<223> OTHER INFORMATION: carboxy-terminal sequence

<400> SEQUENCE: 18

Gly Gln Gly Thr Leu Val Thr Val Glu Pro Gly Gly
1               5                   10

<210> SEQ ID NO 19
<211> LENGTH: 119
<212> TYPE: PRT
<213> ORGANISM: Artificial Sequence
<220> FEATURE:
<223> OTHER INFORMATION: OKT3 VH

<400> SEQUENCE: 19

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
                20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Asn Tyr Asn Gln Lys Val
        50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser
        115

<210> SEQ ID NO 20
<211> LENGTH: 106
<212> TYPE: PRT
<213> ORGANISM: Artificial Sequence
<220> FEATURE:
<223> OTHER INFORMATION: OKT3 VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

Asn Trp Tyr Gln Gln Thr Pro Gly Lys Ala Pro Lys Arg Trp Ile Tyr

```
                    35                  40                  45
Asp Thr Ser Lys Leu Ala Ser Gly Val Pro Ser Arg Phe Ser Gly Ser
 50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gln Gly Thr Lys Leu Gln Ile Thr
                100                 105

<210> SEQ ID NO 21
<211> LENGTH: 119
<212> TYPE: PRT
<213> ORGANISM: Artificial Sequence
<220> FEATURE:
<223> OTHER INFORMATION: OKT3 humanized VH

<400> SEQUENCE: 21

Gln Val Gln Leu Val Gln Ser Gly Gly Gly Val Gln Pro Gly Arg
 1               5                  10                  15

Ser Leu Arg Leu Ser Cys Lys Ala Ser Gly Tyr Thr Phe Thr Arg Tyr
                 20                  25                  30

Thr Met His Trp Val Arg Gln Ala Pro Gly Lys Gly Leu Glu Trp Ile
             35                  40                  45

Gly Tyr Ile Asn Pro Ser Arg Gly Tyr Thr Asn Tyr Asn Gln Lys Val
 50                  55                  60

Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Ser Leu Asp Tyr Trp Gly Gln Gly
                100                 105                 110

Thr Pro Val Thr Val Ser Ser
        115

<210> SEQ ID NO 22
<211> LENGTH: 119
<212> TYPE: PRT
<213> ORGANISM: Artificial Sequence
<220> FEATURE:
<223> OTHER INFORMATION: OKT3 humanized VH

<400> SEQUENCE: 22

Asp Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Arg Tyr
                 20                  25                  30

Thr Met His Trp Val Arg Gln Ala Pro Gly Gln Gly Leu Glu Trp Ile
             35                  40                  45

Gly Tyr Ile Asn Pro Ser Arg Gly Tyr Thr Asn Tyr Ala Asp Ser Val
 50                  55                  60

Lys Gly Arg Phe Thr Ile Thr Thr Asp Lys Ser Thr Ser Thr Ala Tyr
 65                  70                  75                  80

Met Glu Leu Ser Ser Leu Arg Ser Glu Asp Thr Ala Thr Tyr Tyr Cys
                 85                  90                  95

Ala Arg Tyr Tyr Asp Asp His Tyr Cys Leu Asp Tyr Trp Gly Gln Gly
                100                 105                 110
```

```
Thr Thr Val Thr Val Ser Ser
        115

<210> SEQ ID NO 23
<211> LENGTH: 119
<212> TYPE: PRT
<213> ORGANISM: Artificial Sequence
<220> FEATURE:
<223> OTHER INFORMATION: OKT3 humanized VH

<400> SEQUENCE: 23

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser Ser
        115

<210> SEQ ID NO 24
<211> LENGTH: 106
<212> TYPE: PRT
<213> ORGANISM: Artificial Sequence
<220> FEATURE:
<223> OTHER INFORMATION: OKT3 humanized VL

<400> SEQUENCE: 24

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 25
<211> LENGTH: 106
<212> TYPE: PRT
<213> ORGANISM: Artificial Sequence
<220> FEATURE:
<223> OTHER INFORMATION: OKT3 humanized VL

<400> SEQUENCE: 25

Asp Ile Gln Met Thr Gln Ser Pro Ser Ser Leu Ser Ala Ser Val Gly
```

```
                1               5                   10                  15
Asp Arg Val Thr Ile Thr Cys Arg Ala Ser Gln Ser Val Ser Tyr Met
                    20                  25                  30

Asn Trp Tyr Gln Gln Lys Pro Gly Lys Ala Pro Lys Arg Trp Ile Tyr
                    35                  40                  45

Asp Thr Ser Lys Val Ala Ser Gly Val Pro Ala Arg Phe Ser Gly Ser
                50                  55                  60

Gly Ser Gly Thr Asp Tyr Ser Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                    85                  90                  95

Phe Gly Gly Gly Thr Lys Val Glu Ile Lys
                100                 105

<210> SEQ ID NO 26
<211> LENGTH: 108
<212> TYPE: PRT
<213> ORGANISM: Artificial Sequence
<220> FEATURE:
<223> OTHER INFORMATION: OKT3 humanized VL

<400> SEQUENCE: 26

Asp Ile Gln Leu Thr Gln Ser Pro Ser Ile Leu Ser Ala Ser Val Gly
1               5                   10                  15

Asp Arg Val Thr Ile Thr Cys Arg Ala Ser Ser Ser Val Ser Tyr Met
                    20                  25                  30

Asn Trp Tyr Gln Gln Lys Pro Gly Lys Ala Pro Lys Arg Trp Ile Tyr
                    35                  40                  45

Asp Thr Ser Lys Val Ala Ser Gly Val Pro Tyr Arg Phe Ser Gly Ser
                50                  55                  60

Gly Ser Gly Thr Glu Tyr Thr Leu Thr Ile Ser Ser Met Gln Pro Glu
65                  70                  75                  80

Asp Phe Ala Thr Tyr Tyr Cys Gln Gln Trp Ser Ser Asn Pro Leu Thr
                    85                  90                  95

Phe Gly Cys Gly Thr Lys Val Glu Ile Lys Arg Thr
                100                 105

<210> SEQ ID NO 27
<211> LENGTH: 125
<212> TYPE: PRT
<213> ORGANISM: Artificial Sequence
<220> FEATURE:
<223> OTHER INFORMATION: anti-CD3 Hv

<400> SEQUENCE: 27

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                    20                  25                  30

Ala Met Asn Trp Val Arg Gln Ala Pro Gly Lys Gly Leu Glu Trp Val
                    35                  40                  45

Ala Arg Ile Arg Ser Lys Tyr Asn Asn Tyr Ala Thr Tyr Tyr Ala Asp
                50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                    85                  90                  95
```

Tyr Cys Val Arg His Gly Asn Phe Gly Asn Ser Tyr Val Ser Trp Phe
            100                 105                 110
Ala Tyr Trp Gly Gln Gly Thr Leu Val Thr Val Ser Ala
        115                 120                 125

<210> SEQ ID NO 28
<211> LENGTH: 109
<212> TYPE: PRT
<213> ORGANISM: Artificial Sequence
<220> FEATURE:
<223> OTHER INFORMATION: anti-CD3 Lv

<400> SEQUENCE: 28

Gln Ala Val Val Thr Gln Glu Ser Ala Leu Thr Thr Ser Pro Gly Glu
1               5                   10                  15
Thr Val Thr Leu Thr Cys Arg Ser Ser Thr Gly Ala Val Thr Thr Ser
            20                  25                  30
Asn Tyr Ala Asn Trp Val Gln Glu Lys Pro Asp His Leu Phe Thr Gly
        35                  40                  45
Leu Ile Gly Gly Thr Asn Lys Arg Ala Pro Gly Val Pro Ala Arg Phe
    50                  55                  60
Ser Gly Ser Leu Ile Gly Asp Lys Ala Ala Leu Thr Ile Thr Gly Ala
65                  70                  75                  80
Gln Thr Glu Asp Glu Ala Ile Tyr Phe Cys Ala Leu Trp Tyr Ser Asn
                85                  90                  95
Leu Trp Val Phe Gly Gly Gly Thr Lys Leu Thr Val Leu
            100                 105

<210> SEQ ID NO 29
<211> LENGTH: 5
<212> TYPE: PRT
<213> ORGANISM: Artificial Sequence
<220> FEATURE:
<223> OTHER INFORMATION: anti-CD3 VH CDR1

<400> SEQUENCE: 29

Thr Tyr Ala Met Asn
1               5

<210> SEQ ID NO 30
<211> LENGTH: 19
<212> TYPE: PRT
<213> ORGANISM: Artificial Sequence
<220> FEATURE:
<223> OTHER INFORMATION: anti-CD3 VH CDR2

<400> SEQUENCE: 30

Arg Ile Arg Ser Lys Tyr Asn Asn Tyr Ala Thr Tyr Tyr Ala Asp Ser
1               5                   10                  15
Val Lys Asp

<210> SEQ ID NO 31
<211> LENGTH: 14
<212> TYPE: PRT
<213> ORGANISM: Artificial Sequence
<220> FEATURE:
<223> OTHER INFORMATION: anti-CD3 VH CDR3

<400> SEQUENCE: 31

His Gly Asn Phe Gly Asn Ser Tyr Val Ser Trp Phe Ala Tyr
1               5                   10

```
<210> SEQ ID NO 32
<211> LENGTH: 14
<212> TYPE: PRT
<213> ORGANISM: Artificial Sequence
<220> FEATURE:
<223> OTHER INFORMATION: anti-CD3 VL CDR1

<400> SEQUENCE: 32

Arg Ser Ser Thr Gly Ala Val Thr Thr Ser Asn Tyr Ala Asn
1               5                   10

<210> SEQ ID NO 33
<211> LENGTH: 7
<212> TYPE: PRT
<213> ORGANISM: Artificial Sequence
<220> FEATURE:
<223> OTHER INFORMATION: anti-CD3 VL CDR2

<400> SEQUENCE: 33

Gly Thr Asn Lys Arg Ala Pro
1               5

<210> SEQ ID NO 34
<211> LENGTH: 9
<212> TYPE: PRT
<213> ORGANISM: Artificial Sequence
<220> FEATURE:
<223> OTHER INFORMATION: anti-CD3 VL CDR3

<400> SEQUENCE: 34

Ala Leu Trp Tyr Ser Asn Leu Trp Val
1               5

<210> SEQ ID NO 35
<211> LENGTH: 125
<212> TYPE: PRT
<213> ORGANISM: Artificial Sequence
<220> FEATURE:
<223> OTHER INFORMATION: anti-CD3 VH1

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 36
<211> LENGTH: 125
<212> TYPE: PRT
<213> ORGANISM: Artificial Sequence
<220> FEATURE:
<223> OTHER INFORMATION: anti-CD3 VH2
```

<400> SEQUENCE: 36

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 37
<211> LENGTH: 125
<212> TYPE: PRT
<213> ORGANISM: Artificial Sequence
<220> FEATURE:
<223> OTHER INFORMATION: anti-CD3 VH3

<400> SEQUENCE: 37

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 38
<211> LENGTH: 125
<212> TYPE: PRT
<213> ORGANISM: Artificial Sequence
<220> FEATURE:
<223> OTHER INFORMATION: anti-CD3 VH4

<400> SEQUENCE: 38

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

```
Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 39
<211> LENGTH: 125
<212> TYPE: PRT
<213> ORGANISM: Artificial Sequence
<220> FEATURE:
<223> OTHER INFORMATION: anti-CD3 VH5

<400> SEQUENCE: 39

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 40
<211> LENGTH: 125
<212> TYPE: PRT
<213> ORGANISM: Artificial Sequence
<220> FEATURE:
<223> OTHER INFORMATION: anti-CD3 VH6

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
```

-continued

```
                    100                 105                 110
Ala Tyr Trp Gly Gln Gly Thr Leu Val Thr Val Ser Ser
            115                 120                 125

<210> SEQ ID NO 41
<211> LENGTH: 125
<212> TYPE: PRT
<213> ORGANISM: Artificial Sequence
<220> FEATURE:
<223> OTHER INFORMATION: anti-CD3 VH7

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 42
<211> LENGTH: 124
<212> TYPE: PRT
<213> ORGANISM: Artificial Sequence
<220> FEATURE:
<223> OTHER INFORMATION: anti-CD3 VH8

<400> SEQUENCE: 42

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser
        115                 120

<210> SEQ ID NO 43
<211> LENGTH: 125
<212> TYPE: PRT
<213> ORGANISM: Artificial Sequence
<220> FEATURE:
```

<223> OTHER INFORMATION: anti-CD3 VH9

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Thr Val Thr Val Ser Ser
        115                 120                 125

<210> SEQ ID NO 44
<211> LENGTH: 125
<212> TYPE: PRT
<213> ORGANISM: Artificial Sequence
<220> FEATURE:
<223> OTHER INFORMATION: anti-CD3 VH10

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser
        115                 120                 125

<210> SEQ ID NO 45
<211> LENGTH: 125
<212> TYPE: PRT
<213> ORGANISM: Artificial Sequence
<220> FEATURE:
<223> OTHER INFORMATION: anti-CD3 VH11

<400> SEQUENCE: 45

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val

-continued

```
                35                  40                  45

Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Gln Ser Ile
 65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 46
<211> LENGTH: 125
<212> TYPE: PRT
<213> ORGANISM: Artificial Sequence
<220> FEATURE:
<223> OTHER INFORMATION: anti-CD3 VH12

<400> SEQUENCE: 46

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
            50                  55                  60

Ser Val Lys Gly Arg Phe Thr Ile Ser Arg Asp Asp Ala Lys Asn Thr
 65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Lys Pro
            115                 120                 125

<210> SEQ ID NO 47
<211> LENGTH: 125
<212> TYPE: PRT
<213> ORGANISM: Artificial Sequence
<220> FEATURE:
<223> OTHER INFORMATION: anti-CD3 VH13

<400> SEQUENCE: 47

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Cys Leu Glu Trp Val
                35                  40                  45

Ala Arg Ile Arg Ser Lys Tyr Asn Asn Tyr Ala Thr Tyr Tyr Ala Asp
            50                  55                  60

Ser Val Lys Gly Arg Phe Thr Ile Ser Arg Asp Asp Ala Lys Asn Thr
 65                  70                  75                  80

Leu Tyr Leu Gln Met Ser Ser Leu Arg Ala Glu Asp Thr Ala Val Tyr
                85                  90                  95
```

Tyr Cys Val Arg His Gly Asn Phe Gly Asn Ser Tyr Val Ser Trp Phe
              100                 105                 110

Ala Tyr Trp Gly Gln Gly Thr Leu Val Thr Val Lys Pro
        115                 120                 125

<210> SEQ ID NO 48
<211> LENGTH: 125
<212> TYPE: PRT
<213> ORGANISM: Artificial Sequence
<220> FEATURE:
<223> OTHER INFORMATION: anti-CD3 VH14

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
              100                 105                 110

Ala Tyr Trp Gly Cys Gly Thr Leu Val Thr Val Lys Pro
        115                 120                 125

<210> SEQ ID NO 49
<211> LENGTH: 125
<212> TYPE: PRT
<213> ORGANISM: Artificial Sequence
<220> FEATURE:
<223> OTHER INFORMATION: anti-CD3 VH15

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
              100                 105                 110

Ala Tyr Trp Gly Gln Gly Thr Leu Val Thr Val Ser Ser
        115                 120                 125

<210> SEQ ID NO 50
<211> LENGTH: 125
<212> TYPE: PRT
<213> ORGANISM: Artificial Sequence

```
<220> FEATURE:
<223> OTHER INFORMATION: anti-CD3 VH16

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 51
<211> LENGTH: 125
<212> TYPE: PRT
<213> ORGANISM: Artificial Sequence
<220> FEATURE:
<223> OTHER INFORMATION: anti-CD3 VH17

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 52
<211> LENGTH: 125
<212> TYPE: PRT
<213> ORGANISM: Artificial Sequence
<220> FEATURE:
<223> OTHER INFORMATION: anti-CD3 VH18

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Ser Thr Tyr
            20                  25                  30
```

Ala Met Asn Trp Val Arg Gln Ala Pro Gly Lys Cys Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 53
<211> LENGTH: 125
<212> TYPE: PRT
<213> ORGANISM: Artificial Sequence
<220> FEATURE:
<223> OTHER INFORMATION: anti-CD3 VH19

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
            35                  40                  45

Ser Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 54
<211> LENGTH: 125
<212> TYPE: PRT
<213> ORGANISM: Artificial Sequence
<220> FEATURE:
<223> OTHER INFORMATION: anti-CD3 VH20

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Ser Thr Tyr
            20                  25                  30

Ala Met Asn Trp Val Arg Gln Ala Pro Gly Lys Cys Leu Glu Trp Val
            35                  40                  45

Ser Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 55
<211> LENGTH: 125
<212> TYPE: PRT
<213> ORGANISM: Artificial Sequence
<220> FEATURE:
<223> OTHER INFORMATION: anti-CD3 VH21

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 56
<211> LENGTH: 125
<212> TYPE: PRT
<213> ORGANISM: Artificial Sequence
<220> FEATURE:
<223> OTHER INFORMATION: anti-CD3 VH22

<400> SEQUENCE: 56

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 57
<211> LENGTH: 125
<212> TYPE: PRT

<213> ORGANISM: Artificial Sequence
<220> FEATURE:
<223> OTHER INFORMATION: anti-CD3 VH23

<400> SEQUENCE: 57

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 58
<211> LENGTH: 125
<212> TYPE: PRT
<213> ORGANISM: Artificial Sequence
<220> FEATURE:
<223> OTHER INFORMATION: anti-CD3 VH24

<400> SEQUENCE: 58

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 59
<211> LENGTH: 125
<212> TYPE: PRT
<213> ORGANISM: Artificial Sequence
<220> FEATURE:
<223> OTHER INFORMATION: anti-CD3 VH25

<400> SEQUENCE: 59

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
                    100                 105                 110

Ala Tyr Trp Gly Gln Gly Thr Leu Val Thr Val Ser Ser
            115                 120                 125

<210> SEQ ID NO 60
<211> LENGTH: 125
<212> TYPE: PRT
<213> ORGANISM: Artificial Sequence
<220> FEATURE:
<223> OTHER INFORMATION: anti-CD3 VH26

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
            35                  40                  45

Ser Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
                    100                 105                 110

Ala Tyr Trp Gly Gln Gly Thr Leu Val Thr Val Ser Ser
            115                 120                 125

<210> SEQ ID NO 61
<211> LENGTH: 125
<212> TYPE: PRT
<213> ORGANISM: Artificial Sequence
<220> FEATURE:
<223> OTHER INFORMATION: anti-CD3 VH27

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Cys Leu Glu Trp Val
            35                  40                  45

Gly Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr 85                  90                  95
Tyr Cys Val Arg His Gly Asn Phe Gly Asp Ser Tyr Val Ser Trp Phe
                100                 105                 110

Ala Tyr Trp Gly Gln Gly Thr Leu Val Thr Val Ser Ser
        115                 120                 125

<210> SEQ ID NO 62
<211> LENGTH: 124
<212> TYPE: PRT
<213> ORGANISM: Artificial Sequence
<220> FEATURE:
<223> OTHER INFORMATION: anti-CD3 VH28

<400> SEQUENCE: 62

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser
        115                 120

<210> SEQ ID NO 63
<211> LENGTH: 125
<212> TYPE: PRT
<213> ORGANISM: Artificial Sequence
<220> FEATURE:
<223> OTHER INFORMATION: anti-CD3 VH29

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Thr Val Thr Val Ser Ser
        115                 120                 125

<210> SEQ ID NO 64
<211> LENGTH: 125

```
<212> TYPE: PRT
<213> ORGANISM: Artificial Sequence
<220> FEATURE:
<223> OTHER INFORMATION: anti-CD3 VH30

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser
        115                 120                 125

<210> SEQ ID NO 65
<211> LENGTH: 125
<212> TYPE: PRT
<213> ORGANISM: Artificial Sequence
<220> FEATURE:
<223> OTHER INFORMATION: anti-CD3 VH31

<400> SEQUENCE: 65

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
            85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 66
<211> LENGTH: 109
<212> TYPE: PRT
<213> ORGANISM: Artificial Sequence
<220> FEATURE:
<223> OTHER INFORMATION: anti-CD3 VL1

<400> SEQUENCE: 66

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
```

```
                20                  25                  30

Asn Tyr Ala Asn Trp Val Gln Glu Lys Pro Asp His Leu Phe Thr Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 67
<211> LENGTH: 109
<212> TYPE: PRT
<213> ORGANISM: Artificial Sequence
<220> FEATURE:
<223> OTHER INFORMATION: anti-CD3 VL2

<400> SEQUENCE: 67

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Gln Lys Pro Gly Lys Ser Pro Arg Gly
            35                  40                  45

Leu Ile Gly Gly Thr Asn Lys Arg Ala Pro Gly Val Pro Ala Arg Phe
        50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Glu Ile Lys
            100                 105

<210> SEQ ID NO 68
<211> LENGTH: 109
<212> TYPE: PRT
<213> ORGANISM: Artificial Sequence
<220> FEATURE:
<223> OTHER INFORMATION: anti-CD3 VL3

<400> SEQUENCE: 68

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 69
<211> LENGTH: 109
<212> TYPE: PRT
<213> ORGANISM: Artificial Sequence
<220> FEATURE:
<223> OTHER INFORMATION: anti-CD3 VL4

<400> SEQUENCE: 69

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 70
<211> LENGTH: 109
<212> TYPE: PRT
<213> ORGANISM: Artificial Sequence
<220> FEATURE:
<223> OTHER INFORMATION: anti-CD3 VL5

<400> SEQUENCE: 70

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 71
<211> LENGTH: 109
<212> TYPE: PRT
<213> ORGANISM: Artificial Sequence
<220> FEATURE:
<223> OTHER INFORMATION: anti-CD3 VL6

<400> SEQUENCE: 71

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly

```
                35                  40                  45
Leu Ile Gly Gly Thr Asn Lys Arg Ala Pro Gly Val Pro Ala Arg Phe
 50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Ala Leu Trp Tyr Ser Asn
                 85                  90                  95

Leu Trp Val Phe Gly Gly Gly Thr Lys Leu Thr Val Leu
                100                 105
```

<210> SEQ ID NO 72
<211> LENGTH: 109
<212> TYPE: PRT
<213> ORGANISM: Artificial Sequence
<220> FEATURE:
<223> OTHER INFORMATION: anti-CD3 VL7

<400> SEQUENCE: 72

```
Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
                35                  40                  45

Leu Ile Gly Gly Thr Asn Lys Arg Ala Pro Gly Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu
                100                 105
```

<210> SEQ ID NO 73
<211> LENGTH: 109
<212> TYPE: PRT
<213> ORGANISM: Artificial Sequence
<220> FEATURE:
<223> OTHER INFORMATION: anti-CD3 VL8

<400> SEQUENCE: 73

```
Gln Thr Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Ser Gly
                20                  25                  30

Asn Tyr Pro Asn Trp Val Gln Gln Lys Pro Gly Gln Ala Pro Arg Gly
                35                  40                  45

Leu Ile Gly Gly Thr Lys Phe Leu Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Val Leu Trp Tyr Ser Asn
                 85                  90                  95

Arg Trp Val Phe Gly Gly Gly Thr Lys Leu Thr Val Leu
                100                 105
```

<210> SEQ ID NO 74
<211> LENGTH: 109

```
<212> TYPE: PRT
<213> ORGANISM: Artificial Sequence
<220> FEATURE:
<223> OTHER INFORMATION: anti-CD3 VL9

<400> SEQUENCE: 74

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Glu Ile Lys
            100                 105

<210> SEQ ID NO 75
<211> LENGTH: 109
<212> TYPE: PRT
<213> ORGANISM: Artificial Sequence
<220> FEATURE:
<223> OTHER INFORMATION: anti-CD3 VL10

<400> SEQUENCE: 75

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Glu Ile Lys
            100                 105

<210> SEQ ID NO 76
<211> LENGTH: 109
<212> TYPE: PRT
<213> ORGANISM: Artificial Sequence
<220> FEATURE:
<223> OTHER INFORMATION: anti-CD3 VL11

<400> SEQUENCE: 76

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Cys Phe Arg Gly
        35                  40                  45

Leu Ile Gly Gly Thr Asn Lys Arg Ala Pro Gly Val Pro Ala Arg Phe
```

```
                 50                  55                  60

Ser Gly Ser Leu Leu Gly Gly Lys Ala Ala Leu Thr Ile Ser Gly Ala
 65                  70                  75                  80

Gln Pro Glu Asp Glu Ala Asp Tyr Tyr Cys Ala Leu Trp Tyr Ser Asn
                 85                  90                  95

His Trp Val Phe Gly Gly Gly Thr Lys Leu Glu Ile Lys
            100                 105

<210> SEQ ID NO 77
<211> LENGTH: 109
<212> TYPE: PRT
<213> ORGANISM: Artificial Sequence
<220> FEATURE:
<223> OTHER INFORMATION: anti-CD3 VL12

<400> SEQUENCE: 77

Gln Ala Val Val Thr Gln Glu Ser Ala Leu Thr Thr Ser Pro Gly Glu
  1               5                  10                  15

Thr Val Thr Leu Thr Cys Arg Ser Ser Thr Gly Ala Val Thr Thr Ser
                 20                  25                  30

Asn Tyr Ala Asn Trp Val Gln Glu Lys Pro Asp His Leu Phe Thr Gly
             35                  40                  45

Leu Ile Gly Gly Thr Asn Lys Arg Ala Pro Gly Val Pro Ala Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

Leu Trp Val Phe Gly Cys Gly Thr Lys Leu Thr Val Leu
            100                 105

<210> SEQ ID NO 78
<211> LENGTH: 109
<212> TYPE: PRT
<213> ORGANISM: Artificial Sequence
<220> FEATURE:
<223> OTHER INFORMATION: anti-CD3 VL13

<400> SEQUENCE: 78

Gln Ala Val Val Thr Gln Glu Pro Ser Leu Thr Val Ser Pro Gly Gly
  1               5                  10                  15

Thr Val Thr Leu Thr Cys Gly Ser Ser Thr Gly Ala Val Thr Thr Ser
                 20                  25                  30

Asn Tyr Ala Asn Trp Val Gln Gln Lys Pro Gly Lys Ser Pro Arg Gly
             35                  40                  45

Leu Ile Gly Gly Thr Asn Lys Arg Ala Pro Gly Val Pro Ala Arg Phe
 50                  55                  60

Ser Gly Ser Leu Leu Gly Gly Lys Ala Ala Leu Thr Ile Ser Gly Ala
 65                  70                  75                  80

Gln Pro Glu Asp Glu Ala Asp Tyr Tyr Cys Ala Leu Trp Tyr Ser Asn
                 85                  90                  95

His Trp Val Phe Gly Gly Gly Thr Lys Leu Glu Ile Lys
            100                 105

<210> SEQ ID NO 79
<211> LENGTH: 109
<212> TYPE: PRT
<213> ORGANISM: Artificial Sequence
<220> FEATURE:
```

<223> OTHER INFORMATION: anti-CD3 VL14

<400> SEQUENCE: 79

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Cys Gly Thr Lys Leu Thr Val Leu
            100                 105

<210> SEQ ID NO 80
<211> LENGTH: 109
<212> TYPE: PRT
<213> ORGANISM: Artificial Sequence
<220> FEATURE:
<223> OTHER INFORMATION: anti-CD3 VL15

<400> SEQUENCE: 80

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 81
<211> LENGTH: 109
<212> TYPE: PRT
<213> ORGANISM: Artificial Sequence
<220> FEATURE:
<223> OTHER INFORMATION: anti-CD3 VL16

<400> SEQUENCE: 81

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala

Gln Ala Asp Asp Glu Ser Ile Tyr Phe Cys Ala Leu Trp Tyr Ser Asn
                85                  90                  95

Leu Trp Val Phe Gly Cys Gly Thr Lys Leu Thr Val Leu
            100                 105

<210> SEQ ID NO 82
<211> LENGTH: 109
<212> TYPE: PRT
<213> ORGANISM: Artificial Sequence
<220> FEATURE:
<223> OTHER INFORMATION: anti-CD3 VL17

<400> SEQUENCE: 82

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Cys Gly Thr Lys Leu Thr Val Leu
            100                 105

<210> SEQ ID NO 83
<211> LENGTH: 109
<212> TYPE: PRT
<213> ORGANISM: Artificial Sequence
<220> FEATURE:
<223> OTHER INFORMATION: anti-CD3 VL18

<400> SEQUENCE: 83

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Cys Gly Thr Lys Leu Thr Val Leu
            100                 105

<210> SEQ ID NO 84
<211> LENGTH: 109
<212> TYPE: PRT
<213> ORGANISM: Artificial Sequence
<220> FEATURE:
<223> OTHER INFORMATION: anti-CD3 VL19

<400> SEQUENCE: 84

-continued

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Cys Gly Thr Lys Leu Thr Val Leu
            100                 105

<210> SEQ ID NO 85
<211> LENGTH: 129
<212> TYPE: PRT
<213> ORGANISM: Artificial Sequence
<220> FEATURE:
<223> OTHER INFORMATION: anti-CD3 VHH

<400> SEQUENCE: 85

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

His Met Gly Trp Phe Arg Gln Ala Pro Gly Lys Glu Arg Glu Leu Val
        35                  40                  45

Ala Ala Ile Ser Gly Ser Gly Ser Thr Tyr Tyr Thr Asp Ser Val
    50                  55                  60

Lys Gly Arg Phe Thr Ile Ser Arg Asn Asn Ala Lys Asn Thr Met Ser
65                  70                  75                  80

Leu Gln Met Ser Asn Leu Lys Pro Glu Asp Thr Gly Val Tyr Tyr Cys
                85                  90                  95

Thr Thr Pro Thr Glu Lys Gly Ser Ser Ile Asp Tyr Trp Gly Gln Gly
            100                 105                 110

Thr Gln Val Thr Val Ser Ser Gly Arg Tyr Pro Tyr Asp Val Pro Asp
            115                 120                 125

Tyr

<210> SEQ ID NO 86
<211> LENGTH: 129
<212> TYPE: PRT
<213> ORGANISM: Artificial Sequence
<220> FEATURE:
<223> OTHER INFORMATION: FR alpha sdAb

<400> SEQUENCE: 86

Gln Leu Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Asn Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

```
Lys Gly Arg Phe Thr Ile Ser Arg Asn Asn Ala Lys Gly Thr Val Tyr
 65                  70                  75                  80

Leu Leu Met Asn Ser Leu Lys Pro Glu Asp Thr Ala Val Tyr Tyr Cys
                 85                  90                  95

Ala Thr Glu Leu Val Pro Ala Cys Thr Tyr Ser Asn Gly Arg Gly Pro
            100                 105                 110

Leu Asp Gly Met Asp Tyr Trp Gly Lys Gly Thr Gln Val Thr Val Lys
        115                 120                 125

Pro

<210> SEQ ID NO 87
<211> LENGTH: 119
<212> TYPE: PRT
<213> ORGANISM: Artificial Sequence
<220> FEATURE:
<223> OTHER INFORMATION: FR alpha sdAb

<400> SEQUENCE: 87

Glu Val Gln Leu Leu Glu Ser Gly Gly Gly Val Gln Pro Gly Gly
 1               5                  10                  15

Ser Leu Arg Leu Ser Cys Ala Ala Ser Gly Ser Ile Phe Ser Ile Asp
            20                  25                  30

Ala Thr Ala Trp Tyr Arg Gln Ala Pro Gly Lys Gln Arg Glu Leu Val
        35                  40                  45

Ala Ile Ile Thr Ser Ser Gly Ser Thr Asn Tyr Pro Glu Ser Val Lys
    50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Asn
                 85                  90                  95

Ala Ile Thr Arg Tyr Gly Gly Ser Thr Tyr Asp Phe Trp Gly Gln Gly
            100                 105                 110

Thr Leu Val Thr Val Lys Pro
        115

<210> SEQ ID NO 88
<211> LENGTH: 101
<212> TYPE: PRT
<213> ORGANISM: Artificial Sequence
<220> FEATURE:
<223> OTHER INFORMATION: FR alpha sdAb

<400> SEQUENCE: 88

Glu Val Gln Pro Gly Gly Ser Leu Arg Leu Ser Cys Ala Ala Ser Glu
 1               5                  10                  15

Thr Phe Gly Val Val Phe Thr Leu Gly Trp Tyr Arg Gln Ala Pro Gly
            20                  25                  30

Lys Gly Arg Glu Phe Val Ala Arg Val Thr Gly Thr Asp Thr Val Asp
        35                  40                  45

Tyr Ala Glu Ser Val Lys Gly Arg Phe Thr Ile Ser Ser Asp Phe Ala
    50                  55                  60

Arg Asn Thr Val Tyr Leu Gln Met Asn Ser Leu Arg Ala Glu Asp Thr
 65                  70                  75                  80

Ala Val Tyr Tyr Cys Asn Thr Gly Ala Tyr Trp Gly Gln Gly Thr Leu
                 85                  90                  95

Val Thr Val Lys Pro
            100
```

<210> SEQ ID NO 89
<211> LENGTH: 125
<212> TYPE: PRT
<213> ORGANISM: Artificial Sequence
<220> FEATURE:
<223> OTHER INFORMATION: cMET sdAb

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Ser Cys Leu Leu Glu Tyr Asp Tyr
            100                 105                 110

Asp Tyr Trp Gly Gln Gly Thr Leu Val Thr Val Lys Pro
        115                 120                 125

<210> SEQ ID NO 90
<211> LENGTH: 247
<212> TYPE: PRT
<213> ORGANISM: Artificial Sequence
<220> FEATURE:
<223> OTHER INFORMATION: CD20 scFv

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Gly Gly Gly Gly Ser Gly Gly Gly
        115                 120                 125

Gly Thr Gly Gly Gly Gly Ser Asp Ile Val Met Thr Gln Thr Pro Leu
    130                 135                 140

Ser Leu Pro Val Thr Pro Gly Glu Pro Ala Ser Ile Ser Cys Arg Ser
145                 150                 155                 160

Ser Lys Ser Leu Leu His Ser Asn Gly Ile Thr Tyr Leu Tyr Trp Tyr
                165                 170                 175

Leu Gln Lys Pro Gly Gln Ser Pro Gln Leu Leu Ile Tyr Gln Met Ser

```
                180                 185                 190
Asn Leu Val Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Ala Gln Asn Leu Glu Leu Pro Tyr Thr Phe Gly Gly
225                 230                 235                 240

Gly Thr Lys Val Glu Ile Lys
            245

<210> SEQ ID NO 91
<211> LENGTH: 119
<212> TYPE: PRT
<213> ORGANISM: Artificial Sequence
<220> FEATURE:
<223> OTHER INFORMATION: CD20 VH

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 92
<211> LENGTH: 115
<212> TYPE: PRT
<213> ORGANISM: Artificial Sequence
<220> FEATURE:
<223> OTHER INFORMATION: CD20 VL

<400> SEQUENCE: 92

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110
```

Arg Thr Val
        115

<210> SEQ ID NO 93
<211> LENGTH: 241
<212> TYPE: PRT
<213> ORGANISM: Artificial Sequence
<220> FEATURE:
<223> OTHER INFORMATION: DLL3 scFv

<400> SEQUENCE: 93

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Val Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ile Ala Val Thr Gly Phe Tyr Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

Ser Leu Ser Pro Gly Glu Arg Val Thr Leu Ser Cys Arg Ala Ser Gln
145                 150                 155                 160

Arg Val Asn Asn Asn Tyr Leu Ala Trp Tyr Gln Gln Arg Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu Pro Glu Asp Phe Ala Val Tyr Tyr Cys Gln Gln
    210                 215                 220

Tyr Asp Arg Ser Pro Leu Thr Phe Gly Gly Gly Thr Lys Leu Glu Ile
225                 230                 235                 240

Lys

<210> SEQ ID NO 94
<211> LENGTH: 241
<212> TYPE: PRT
<213> ORGANISM: Artificial Sequence
<220> FEATURE:
<223> OTHER INFORMATION: DLL3 scFv

<400> SEQUENCE: 94

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

```
Gly Tyr Val Tyr Tyr Ser Gly Thr Thr Asn Tyr Asn Pro Ser Leu Lys
        50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Ser Ile Ala Val Thr Gly Phe Tyr Phe Asp Tyr Trp Gly Gln Gly Thr
                100                 105                 110

Leu Val Thr Val Ser Ser Gly Gly Gly Gly Ser Gly Gly Gly Gly Ser
            115                 120                 125

Gly Gly Gly Gly Ser Glu Ile Val Leu Thr Gln Ser Pro Gly Thr Leu
        130                 135                 140

Ser Leu Ser Pro Gly Glu Arg Val Thr Leu Ser Cys Arg Ala Ser Gln
145                 150                 155                 160

Arg Val Asn Asn Asn Tyr Leu Ala Trp Tyr Gln Gln Arg Pro Gly Gln
                165                 170                 175

Ala Pro Arg Leu Leu Ile Tyr Gly Ala Ser Ser Arg Ala Thr Gly Ile
                180                 185                 190

Pro Asp Arg Phe Ser Gly Ser Gly Ser Gly Thr Asp Phe Thr Leu Thr
                195                 200                 205

Ile Ser Arg Leu Glu Pro Glu Asp Phe Ala Val Tyr Tyr Cys Gln Gln
            210                 215                 220

Tyr Asp Arg Ser Pro Leu Thr Phe Gly Gly Gly Thr Lys Leu Glu Ile
225                 230                 235                 240

Lys

<210> SEQ ID NO 95
<211> LENGTH: 223
<212> TYPE: PRT
<213> ORGANISM: Artificial Sequence
<220> FEATURE:
<223> OTHER INFORMATION: DLL3 Fd

<400> SEQUENCE: 95

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
                 20                  25                  30

Gly Met Asn Trp Val Lys Gln Ala Pro Gly Lys Gly Leu Lys Trp Met
             35                  40                  45

Ala Trp Ile Asn Thr Tyr Thr Gly Glu Pro Thr Tyr Ala Asp Asp Phe
 50                  55                  60

Lys Gly Arg Phe Ala Phe Ser Leu Glu Thr Ser Ala Ser Thr Ala Ser
 65                  70                  75                  80

Leu Gln Ile Ile Asn Leu Lys Asn Glu Asp Thr Ala Thr Tyr Phe Cys
                 85                  90                  95

Ala Arg Ile Gly Asp Ser Ser Pro Ser Asp Tyr Trp Gly Gln Gly Thr
                100                 105                 110

Thr Leu Thr Val Ser Ser Ser Ala Ser Thr Lys Gly Pro Ser Val
            115                 120                 125

Phe Pro Leu Ala Pro Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 96
<211> LENGTH: 214
<212> TYPE: PRT
<213> ORGANISM: Artificial Sequence
<220> FEATURE:
<223> OTHER INFORMATION: DLL3 LC

<400> SEQUENCE: 96

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Val Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ala Gly
50                  55                  60

Ser Gly Tyr Gly Thr Asp Phe Ser Phe Thr Ile Ser Thr Val Gln Ala
65                  70                  75                  80

Glu Asp Leu Ala Val Tyr Phe Cys Gln Gln Asp Tyr Thr Ser Pro Trp
                85                  90                  95

Thr Phe Gly Gly Gly Thr Lys Leu Glu Ile Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 97
<211> LENGTH: 225
<212> TYPE: PRT
<213> ORGANISM: Artificial Sequence
<220> FEATURE:
<223> OTHER INFORMATION: 5T4 Fd

<400> SEQUENCE: 97

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gln Trp Asp Tyr Asp Val Arg Ala Met Asn Tyr Trp
            100                 105                 110

Gly Gln Gly Thr Ser Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
210                 215                 220

Cys
225

<210> SEQ ID NO 98
<211> LENGTH: 214
<212> TYPE: PRT
<213> ORGANISM: Artificial Sequence
<220> FEATURE:
<223> OTHER INFORMATION: 5T4 LC

<400> SEQUENCE: 98

Asp Ile Val Met Thr Gln Ser His Ile Phe Met Ser Thr Ser Val Gly
1               5                   10                  15

Asp Arg Val Ser Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
            35                  40                  45

Tyr Trp Ala Ser Thr Arg Leu Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 99
<211> LENGTH: 122
<212> TYPE: PRT
<213> ORGANISM: Artificial Sequence
<220> FEATURE:
<223> OTHER INFORMATION: anti-5T4 VH
<220> FEATURE:
<221> NAME/KEY: misc_feature
<222> LOCATION: (97)..(97)
<223> OTHER INFORMATION: Xaa can be any amino acid

<400> SEQUENCE: 99

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Xaa Cys Val Arg Gln Trp Asp Tyr Asp Val Arg Ala Met Asn Tyr Trp
            100                 105                 110

Gly Gln Gly Thr Ser Val Thr Val Ser Ser
        115                 120

<210> SEQ ID NO 100
<211> LENGTH: 107
<212> TYPE: PRT
<213> ORGANISM: Artificial Sequence
<220> FEATURE:
<223> OTHER INFORMATION: anti-5T4 VL

<400> SEQUENCE: 100

Asp Ile Val Met Thr Gln Ser His Ile Phe Met Ser Thr Ser Val Gly
1               5                   10                  15

Asp Arg Val Ser Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg Leu Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
```

<210> SEQ ID NO 101
<211> LENGTH: 222
<212> TYPE: PRT
<213> ORGANISM: Artificial Sequence
<220> FEATURE:
<223> OTHER INFORMATION: gpNMB Fd

<400> SEQUENCE: 101

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Phe
            20                  25                  30

Asn Tyr Tyr Trp Ser Trp Ile Arg His His Pro Gly Lys Gly Leu Glu
        35                  40                  45

Trp Ile Gly Tyr Ile Tyr Tyr Ser Gly Ser Thr Tyr Ser Asn Pro Ser
    50                  55                  60

Leu Lys Ser Arg Val Thr Ile Ser Val Asp Thr Ser Lys Asn Gln Phe
65                  70                  75                  80

Ser Leu Thr Leu Ser Ser Val Thr Ala Ala Asp Thr Ala Val Tyr Tyr
                85                  90                  95

Cys Ala Arg Gly Tyr Asn Trp Asn Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 102
<211> LENGTH: 215
<212> TYPE: PRT
<213> ORGANISM: Artificial Sequence
<220> FEATURE:
<223> OTHER INFORMATION: gpNMB LC

<400> SEQUENCE: 102

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Asn Asn
            20                  25                  30

Leu Val Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

-continued

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 103
<211> LENGTH: 226
<212> TYPE: PRT
<213> ORGANISM: Artificial Sequence
<220> FEATURE:
<223> OTHER INFORMATION: Knob Fc

<400> SEQUENCE: 103

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Thr
225

<210> SEQ ID NO 104
<211> LENGTH: 226
<212> TYPE: PRT
<213> ORGANISM: Artificial Sequence
<220> FEATURE:
<223> OTHER INFORMATION: Hole Fc

<400> SEQUENCE: 104

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Thr
225

<210> SEQ ID NO 105
<211> LENGTH: 223
<212> TYPE: PRT
<213> ORGANISM: Artificial Sequence
<220> FEATURE:
<223> OTHER INFORMATION: Knob Fc

<400> SEQUENCE: 105

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

```
Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Thr
    210                 215                 220

<210> SEQ ID NO 106
<211> LENGTH: 223
<212> TYPE: PRT
<213> ORGANISM: Artificial Sequence
<220> FEATURE:
<223> OTHER INFORMATION: Hole Fc

<400> SEQUENCE: 106

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205
```

Leu His Asn His Tyr Thr Gln Lys Ser Leu Ser Leu Ser Pro Thr
    210                 215                 220

<210> SEQ ID NO 107
<211> LENGTH: 226
<212> TYPE: PRT
<213> ORGANISM: Artificial Sequence
<220> FEATURE:
<223> OTHER INFORMATION: Knob Fc

<400> SEQUENCE: 107

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 108
<211> LENGTH: 226
<212> TYPE: PRT
<213> ORGANISM: Artificial Sequence
<220> FEATURE:
<223> OTHER INFORMATION: Hole Fc

<400> SEQUENCE: 108

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val

```
                50                  55                  60
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly
225

<210> SEQ ID NO 109
<211> LENGTH: 223
<212> TYPE: PRT
<213> ORGANISM: Artificial Sequence
<220> FEATURE:
<223> OTHER INFORMATION: Knob Fc

<400> SEQUENCE: 109

Asp Lys Thr His Thr Cys Pro Pro Cys Pro Ala Pro Gly Gly Pro Ser
 1               5                  10                  15

Val Phe Leu Phe Pro Pro Lys Pro Lys Asp Thr Leu Met Ile Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
 50                  55                  60

Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
            115                 120                 125

Pro Pro Cys Arg Asp Glu Leu Thr Lys Asn Gln Val Ser Leu Trp Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
```

Arg Trp Gln Gln Gly Asn Val Phe Ser Cys Ser Val Met His Glu Ala
            180             185                 190

Leu His Asn His Tyr Thr Gln Lys Ser Leu Ser Leu Ser Pro Gly
    195                 200                 205

210                 215                 220

<210> SEQ ID NO 110
<211> LENGTH: 223
<212> TYPE: PRT
<213> ORGANISM: Artificial Sequence
<220> FEATURE:
<223> OTHER INFORMATION: Hole Fc

<400> SEQUENCE: 110

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly
    210                 215                 220

<210> SEQ ID NO 111
<211> LENGTH: 226
<212> TYPE: PRT
<213> ORGANISM: Artificial Sequence
<220> FEATURE:
<223> OTHER INFORMATION: Hole Fc

<400> SEQUENCE: 111

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
210                 215                 220

Pro Thr
225

<210> SEQ ID NO 112
<211> LENGTH: 223
<212> TYPE: PRT
<213> ORGANISM: Artificial Sequence
<220> FEATURE:
<223> OTHER INFORMATION: Hole Fc

<400> SEQUENCE: 112

Asp Lys Thr His Thr Cys Pro Pro Cys Pro Ala Pro Gly Gly Pro Ser
 1               5                  10                  15

Val Phe Leu Phe Pro Pro Lys Pro Lys Asp Thr Leu Met Ile Ser Arg
                 20                  25                  30

Thr Pro Glu Val Thr Cys Val Val Val Asp Val Ser His Glu Asp Pro
             35                  40                  45

Glu Val Lys Phe Asn Trp Tyr Val Asp Gly Val Glu Val His Asn Ala
 50                  55                  60

Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

```
Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn Arg Tyr Thr Gln Lys Ser Leu Ser Leu Ser Pro Thr
    210                 215                 220

<210> SEQ ID NO 113
<211> LENGTH: 226
<212> TYPE: PRT
<213> ORGANISM: Artificial Sequence
<220> FEATURE:
<223> OTHER INFORMATION: Hole Fc

<400> SEQUENCE: 113

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly
225

<210> SEQ ID NO 114
<211> LENGTH: 223
<212> TYPE: PRT
<213> ORGANISM: Artificial Sequence
<220> FEATURE:
<223> OTHER INFORMATION: Hole Fc

<400> SEQUENCE: 114

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30
```

```
Thr Pro Glu Val Thr Cys Val Val Asp Val Ser His Glu Asp Pro
        35                  40                  45

Glu Val Lys Phe Asn Trp Tyr Val Asp Gly Val Glu Val His Asn Ala
 50                  55                  60

Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Cys Thr Leu
            115                 120                 125

Pro Pro Ser Arg Asp Glu Leu Thr Lys Asn Gln Val Ser Leu Ser Cys
130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn Arg Tyr Thr Gln Lys Ser Leu Ser Leu Ser Pro Gly
    210                 215                 220

<210> SEQ ID NO 115
<211> LENGTH: 226
<212> TYPE: PRT
<213> ORGANISM: Artificial Sequence
<220> FEATURE:
<223> OTHER INFORMATION: Knob Fc

<400> SEQUENCE: 115

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Tyr
                20                  25                  30

Ile Ser Arg Thr Pro Glu Val Thr Cys Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn His Tyr Thr Gln Lys Ser Leu Ser Leu Ser
    210                 215                 220

Pro Thr
225

<210> SEQ ID NO 116
<211> LENGTH: 223
<212> TYPE: PRT
<213> ORGANISM: Artificial Sequence
<220> FEATURE:
<223> OTHER INFORMATION: Knob Fc

<400> SEQUENCE: 116

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn His Tyr Thr Gln Lys Ser Leu Ser Leu Ser Pro Thr
    210                 215                 220

<210> SEQ ID NO 117
<211> LENGTH: 226
<212> TYPE: PRT
<213> ORGANISM: Artificial Sequence
<220> FEATURE:
<223> OTHER INFORMATION: Knob Fc

<400> SEQUENCE: 117

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
```

```
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Cys Arg Asp Glu Leu Thr Lys Asn Gln Val Ser
    130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Val
        195                 200                 205
His Glu Ala Leu His Asn His Tyr Thr Gln Lys Ser Leu Ser Leu Ser
    210                 215                 220
Pro Gly
225

<210> SEQ ID NO 118
<211> LENGTH: 223
<212> TYPE: PRT
<213> ORGANISM: Artificial Sequence
<220> FEATURE:
<223> OTHER INFORMATION: Knob Fc

<400> SEQUENCE: 118

Asp Lys Thr His Thr Cys Pro Pro Cys Pro Ala Pro Gly Gly Pro Ser
1               5                   10                  15
Val Phe Leu Phe Pro Pro Lys Pro Lys Asp Thr Leu Tyr Ile Ser Arg
            20                  25                  30
Thr Pro Glu Val Thr Cys Val Val Val Asp Val Ser His Glu Asp Pro
        35                  40                  45
Glu Val Lys Phe Asn Trp Tyr Val Asp Gly Val Glu Val His Asn Ala
    50                  55                  60
Lys Thr Lys Pro Arg Glu Glu Gln Tyr Asn Ser Thr Tyr Arg Val Val
65                  70                  75                  80
Ser Val Leu Thr Val Leu His Gln Asp Trp Leu Asn Gly Lys Glu Tyr
                85                  90                  95
Lys Cys Lys Val Ser Asn Lys Ala Leu Pro Ala Pro Ile Glu Lys Thr
            100                 105                 110
Ile Ser Lys Ala Lys Gly Gln Pro Arg Glu Pro Gln Val Tyr Thr Leu
        115                 120                 125
Pro Pro Cys Arg Asp Glu Leu Thr Lys Asn Gln Val Ser Leu Trp Cys
    130                 135                 140
Leu Val Lys Gly Phe Tyr Pro Ser Asp Ile Ala Val Glu Trp Glu Ser
```

```
145                 150                 155                 160
Asn Gly Gln Pro Glu Asn Asn Tyr Lys Thr Thr Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val His Glu Ala
            195                 200                 205

Leu His Asn His Tyr Thr Gln Lys Ser Leu Ser Leu Ser Pro Gly
        210                 215                 220
```

<210> SEQ ID NO 119
<211> LENGTH: 226
<212> TYPE: PRT
<213> ORGANISM: Artificial Sequence
<220> FEATURE:
<223> OTHER INFORMATION: Hole Fc

<400> SEQUENCE: 119

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65              70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn Arg Tyr Thr Gln Lys Ser Leu Ser Leu Ser
    210                 215                 220

Pro Thr
225
```

<210> SEQ ID NO 120
<211> LENGTH: 223
<212> TYPE: PRT
<213> ORGANISM: Artificial Sequence
<220> FEATURE:
<223> OTHER INFORMATION: Hole Fc

<400> SEQUENCE: 120

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
        50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
            115                 120                 125

Pro Pro Ser Arg Asp Glu Leu Thr Lys Asn Gln Val Ser Leu Ser Cys
130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Val His Glu Ala
            195                 200                 205

Leu His Asn Arg Tyr Thr Gln Lys Ser Leu Ser Leu Ser Pro Thr
210                 215                 220

<210> SEQ ID NO 121
<211> LENGTH: 226
<212> TYPE: PRT
<213> ORGANISM: Artificial Sequence
<220> FEATURE:
<223> OTHER INFORMATION: Hole Fc

<400> SEQUENCE: 121

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

```
Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn Arg Tyr Thr Gln Lys Ser Leu Ser Leu Ser
    210                 215                 220

Pro Gly
225

<210> SEQ ID NO 122
<211> LENGTH: 223
<212> TYPE: PRT
<213> ORGANISM: Artificial Sequence
<220> FEATURE:
<223> OTHER INFORMATION: Hole Fc

<400> SEQUENCE: 122

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn Arg Tyr Thr Gln Lys Ser Leu Ser Leu Ser Pro Gly
    210                 215                 220

<210> SEQ ID NO 123
<211> LENGTH: 33
<212> TYPE: PRT
<213> ORGANISM: Artificial Sequence
<220> FEATURE:
<223> OTHER INFORMATION: GS linker
<220> FEATURE:
<221> NAME/KEY: MISC_FEATURE
```

```
<222> LOCATION: (4)..(6)
<223> OTHER INFORMATION: May be present or absent
<220> FEATURE:
<221> NAME/KEY: MISC_FEATURE
<222> LOCATION: (7)..(9)
<223> OTHER INFORMATION: May be present or absent
<220> FEATURE:
<221> NAME/KEY: MISC_FEATURE
<222> LOCATION: (10)..(12)
<223> OTHER INFORMATION: May be present or absent
<220> FEATURE:
<221> NAME/KEY: MISC_FEATURE
<222> LOCATION: (13)..(15)
<223> OTHER INFORMATION: May be present or absent
<220> FEATURE:
<221> NAME/KEY: MISC_FEATURE
<222> LOCATION: (16)..(18)
<223> OTHER INFORMATION: May be present or absent
<220> FEATURE:
<221> NAME/KEY: MISC_FEATURE
<222> LOCATION: (19)..(21)
<223> OTHER INFORMATION: May be present or absent
<220> FEATURE:
<221> NAME/KEY: MISC_FEATURE
<222> LOCATION: (22)..(24)
<223> OTHER INFORMATION: May be present or absent
<220> FEATURE:
<221> NAME/KEY: MISC_FEATURE
<222> LOCATION: (25)..(27)
<223> OTHER INFORMATION: May be present or absent
<220> FEATURE:
<221> NAME/KEY: MISC_FEATURE
<222> LOCATION: (28)..(30)
<223> OTHER INFORMATION: May be present or absent
<220> FEATURE:
<221> NAME/KEY: MISC_FEATURE
<222> LOCATION: (31)..(33)
<223> OTHER INFORMATION: May be present or absent

<400> SEQUENCE: 123

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
                20                  25                  30

Ser

<210> SEQ ID NO 124
<211> LENGTH: 24
<212> TYPE: PRT
<213> ORGANISM: Artificial Sequence
<220> FEATURE:
<223> OTHER INFORMATION: GS linker
<220> FEATURE:
<221> NAME/KEY: MISC_FEATURE
<222> LOCATION: (7)..(12)
<223> OTHER INFORMATION: May be present or absent
<220> FEATURE:
<221> NAME/KEY: MISC_FEATURE
<222> LOCATION: (13)..(18)
<223> OTHER INFORMATION: May be present or absent
<220> FEATURE:
<221> NAME/KEY: MISC_FEATURE
<222> LOCATION: (19)..(24)
<223> OTHER INFORMATION: May be present or absent

<400> SEQUENCE: 124

Gly Gly Gly Gly Gly Ser Gly Gly Gly Gly Ser Gly Gly Gly Gly Gly
1               5                   10                  15

Gly Ser Gly Gly Gly Gly Gly Ser
                20

<210> SEQ ID NO 125
```

```
<211> LENGTH: 5
<212> TYPE: PRT
<213> ORGANISM: Artificial Sequence
<220> FEATURE:
<223> OTHER INFORMATION: GS linker

<400> SEQUENCE: 125

Gly Gly Gly Gly Ser
1               5

<210> SEQ ID NO 126
<211> LENGTH: 6
<212> TYPE: PRT
<213> ORGANISM: Artificial Sequence
<220> FEATURE:
<223> OTHER INFORMATION: GS linker

<400> SEQUENCE: 126

Gly Gly Gly Gly Gly Ser
1               5

<210> SEQ ID NO 127
<211> LENGTH: 18
<212> TYPE: PRT
<213> ORGANISM: Artificial Sequence
<220> FEATURE:
<223> OTHER INFORMATION: GS linker

<400> SEQUENCE: 127

Gly Gly Gly Gly Gly Ser Gly Gly Gly Gly Ser Gly Gly Gly Gly
1               5                   10                  15

Gly Ser

<210> SEQ ID NO 128
<211> LENGTH: 15
<212> TYPE: PRT
<213> ORGANISM: Artificial Sequence
<220> FEATURE:
<223> OTHER INFORMATION: GS linker

<400> SEQUENCE: 128

Gly Gly Gly Gly Ser Gly Gly Gly Gly Ser Gly Gly Gly Gly Ser
1               5                   10                  15

<210> SEQ ID NO 129
<211> LENGTH: 18
<212> TYPE: PRT
<213> ORGANISM: Artificial Sequence
<220> FEATURE:
<223> OTHER INFORMATION: GS linker

<400> SEQUENCE: 129

Gly Gly Ser Gly Gly Gly Gly Ser Gly Gly Gly Gly Ser Gly Gly
1               5                   10                  15

Gly Ser

<210> SEQ ID NO 130
<211> LENGTH: 17
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (2)..(5)
<223> OTHER INFORMATION: up to 4 of the amino acids may be absent
<220> FEATURE:
```

```
<221> NAME/KEY: MISC_FEATURE
<222> LOCATION: (6)..(6)
<223> OTHER INFORMATION: Xaa is independently selected from Ala, Val,
      Leu, Ile, Met, Phe, Trp, Pro, Gly, Ser, Thr, Cys, Tyr, Asn, Gln,
      Lys, Arg, His, Asp and Glu
<220> FEATURE:
<221> NAME/KEY: MISC_FEATURE
<222> LOCATION: (7)..(11)
<223> OTHER INFORMATION: up to 4 of the amino acids may be absent
<220> FEATURE:
<221> NAME/KEY: MISC_FEATURE
<222> LOCATION: (12)..(12)
<223> OTHER INFORMATION: Xaa is independently selected from Ala, Val,
      Leu, Ile, Met, Phe, Trp, Pro, Gly, Ser, Thr, Cys, Tyr, Asn, Gln,
      Lys, Arg, His, Asp and Glu
<220> FEATURE:
<221> NAME/KEY: MISC_FEATURE
<222> LOCATION: (13)..(17)
<223> OTHER INFORMATION: up to 4 of the amino acids may be absent

<400> SEQUENCE: 130

Gly Gly Gly Gly Gly Xaa Gly Gly Gly Gly Gly Xaa Gly Gly Gly Gly
1               5                   10                  15

Gly

<210> SEQ ID NO 131
<211> LENGTH: 11
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (4)..(4)
<223> OTHER INFORMATION: Xaa is independently selected from Ala, Val,
      Leu, Ile, Met, Phe, Trp, Pro, Gly, Ser, Thr, Cys, Tyr, Asn, Gln,
      Lys, Arg, His, Asp and Glu
<220> FEATURE:
<221> NAME/KEY: MISC_FEATURE
<222> LOCATION: (8)..(8)
<223> OTHER INFORMATION: Xaa is independently selected from Ala, Val,
      Leu, Ile, Met, Phe, Trp, Pro, Gly, Ser, Thr, Cys, Tyr, Asn, Gln,
      Lys, Arg, His, Asp and Glu

<400> SEQUENCE: 131

Gly Gly Gly Xaa Gly Gly Gly Xaa Gly Gly Gly
1               5                   10

<210> SEQ ID NO 132
<211> LENGTH: 45
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (6)..(10)
<223> OTHER INFORMATION: May be present or absent
<220> FEATURE:
<221> NAME/KEY: MISC_FEATURE
<222> LOCATION: (11)..(15)
<223> OTHER INFORMATION: May be present or absent
<220> FEATURE:
<221> NAME/KEY: MISC_FEATURE
<222> LOCATION: (16)..(20)
<223> OTHER INFORMATION: May be present or absent
<220> FEATURE:
<221> NAME/KEY: MISC_FEATURE
<222> LOCATION: (21)..(25)
<223> OTHER INFORMATION: May be present or absent
<220> FEATURE:
<221> NAME/KEY: MISC_FEATURE
<222> LOCATION: (26)..(30)
<223> OTHER INFORMATION: May be present or absent
```

```
<220> FEATURE:
<221> NAME/KEY: MISC_FEATURE
<222> LOCATION: (31)..(35)
<223> OTHER INFORMATION: May be present or absent
<220> FEATURE:
<221> NAME/KEY: MISC_FEATURE
<222> LOCATION: (36)..(40)
<223> OTHER INFORMATION: May be present or absent
<220> FEATURE:
<221> NAME/KEY: MISC_FEATURE
<222> LOCATION: (41)..(45)
<223> OTHER INFORMATION: May be present or absent

<400> SEQUENCE: 132

Ser Ser Ser Ser Gly Ser Ser Ser Gly Ser Ser Ser Gly Ser
1               5                   10                  15

Ser Ser Ser Gly Ser Ser Ser Gly Ser Ser Ser Gly Ser Ser
            20                  25                  30

Ser Ser Gly Ser Ser Ser Ser Gly Ser Ser Ser Ser Gly
        35                  40                  45

<210> SEQ ID NO 133
<211> LENGTH: 11
<212> TYPE: PRT
<213> ORGANISM: Artificial Sequence
<220> FEATURE:
<223> OTHER INFORMATION: peptide linker

<400> SEQUENCE: 133

Gly Gly Gly Gly Gly Cys Gly Gly Gly Gly Gly
1               5                   10

<210> SEQ ID NO 134
<211> LENGTH: 100
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (11)..(15)
<223> OTHER INFORMATION: May be present or absent
<220> FEATURE:
<221> NAME/KEY: MISC_FEATURE
<222> LOCATION: (16)..(20)
<223> OTHER INFORMATION: May be present or absent
<220> FEATURE:
<221> NAME/KEY: MISC_FEATURE
<222> LOCATION: (21)..(25)
<223> OTHER INFORMATION: May be present or absent
<220> FEATURE:
<221> NAME/KEY: MISC_FEATURE
<222> LOCATION: (26)..(30)
<223> OTHER INFORMATION: May be present or absent
<220> FEATURE:
<221> NAME/KEY: MISC_FEATURE
<222> LOCATION: (31)..(35)
<223> OTHER INFORMATION: May be present or absent
<220> FEATURE:
<221> NAME/KEY: MISC_FEATURE
<222> LOCATION: (36)..(40)
<223> OTHER INFORMATION: May be present or absent
<220> FEATURE:
<221> NAME/KEY: MISC_FEATURE
<222> LOCATION: (41)..(45)
<223> OTHER INFORMATION: May be present or absent
<220> FEATURE:
<221> NAME/KEY: MISC_FEATURE
<222> LOCATION: (46)..(50)
<223> OTHER INFORMATION: May be present or absent
<220> FEATURE:
<221> NAME/KEY: MISC_FEATURE
<222> LOCATION: (51)..(55)
```

<220> FEATURE:
<221> NAME/KEY: MISC_FEATURE
<222> LOCATION: (56)..(60)
<223> OTHER INFORMATION: May be present or absent
<220> FEATURE:
<221> NAME/KEY: MISC_FEATURE
<222> LOCATION: (61)..(65)
<223> OTHER INFORMATION: May be present or absent
<220> FEATURE:
<221> NAME/KEY: MISC_FEATURE
<222> LOCATION: (66)..(70)
<223> OTHER INFORMATION: May be present or absent
<220> FEATURE:
<221> NAME/KEY: MISC_FEATURE
<222> LOCATION: (71)..(75)
<223> OTHER INFORMATION: May be present or absent
<220> FEATURE:
<221> NAME/KEY: MISC_FEATURE
<222> LOCATION: (76)..(80)
<223> OTHER INFORMATION: May be present or absent
<220> FEATURE:
<221> NAME/KEY: MISC_FEATURE
<222> LOCATION: (81)..(85)
<223> OTHER INFORMATION: May be present or absent
<220> FEATURE:
<221> NAME/KEY: MISC_FEATURE
<222> LOCATION: (86)..(90)
<223> OTHER INFORMATION: May be present or absent
<220> FEATURE:
<221> NAME/KEY: MISC_FEATURE
<222> LOCATION: (91)..(95)
<223> OTHER INFORMATION: May be present or absent
<220> FEATURE:
<221> NAME/KEY: MISC_FEATURE
<222> LOCATION: (96)..(100)
<223> OTHER INFORMATION: May be present or absent

<400> SEQUENCE: 134

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
                20                  25                  30

Ala Ala Lys Glu Ala Ala Ala Lys Glu Ala Ala Ala Lys Glu Ala Ala
            35                  40                  45

Ala Lys Glu Ala Ala Ala Lys Glu Ala Ala Ala Lys Glu Ala Ala Ala
        50                  55                  60

Lys Glu Ala Ala Ala Lys Glu Ala Ala Ala Lys Glu Ala Ala Ala Lys
65                  70                  75                  80

Glu Ala Ala Ala Lys Glu Ala Ala Lys Glu Ala Ala Ala Lys Glu
                85                  90                  95

Ala Ala Ala Lys
            100

<210> SEQ ID NO 135
<211> LENGTH: 44
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (7)..(8)
<223> OTHER INFORMATION: May be present or absent
<220> FEATURE:
<221> NAME/KEY: MISC_FEATURE
<222> LOCATION: (9)..(10)
<223> OTHER INFORMATION: May be present or absent
<220> FEATURE:
<221> NAME/KEY: MISC_FEATURE
<222> LOCATION: (11)..(12)

```
<223> OTHER INFORMATION: May be present or absent
<220> FEATURE:
<221> NAME/KEY: MISC_FEATURE
<222> LOCATION: (13)..(14)
<223> OTHER INFORMATION: May be present or absent
<220> FEATURE:
<221> NAME/KEY: MISC_FEATURE
<222> LOCATION: (15)..(16)
<223> OTHER INFORMATION: May be present or absent
<220> FEATURE:
<221> NAME/KEY: MISC_FEATURE
<222> LOCATION: (17)..(18)
<223> OTHER INFORMATION: May be present or absent
<220> FEATURE:
<221> NAME/KEY: MISC_FEATURE
<222> LOCATION: (19)..(20)
<223> OTHER INFORMATION: May be present or absent
<220> FEATURE:
<221> NAME/KEY: MISC_FEATURE
<222> LOCATION: (21)..(22)
<223> OTHER INFORMATION: May be present or absent
<220> FEATURE:
<221> NAME/KEY: MISC_FEATURE
<222> LOCATION: (23)..(24)
<223> OTHER INFORMATION: May be present or absent
<220> FEATURE:
<221> NAME/KEY: MISC_FEATURE
<222> LOCATION: (25)..(26)
<223> OTHER INFORMATION: May be present or absent
<220> FEATURE:
<221> NAME/KEY: MISC_FEATURE
<222> LOCATION: (27)..(28)
<223> OTHER INFORMATION: May be present or absent
<220> FEATURE:
<221> NAME/KEY: MISC_FEATURE
<222> LOCATION: (29)..(30)
<223> OTHER INFORMATION: May be present or absent
<220> FEATURE:
<221> NAME/KEY: MISC_FEATURE
<222> LOCATION: (31)..(32)
<223> OTHER INFORMATION: May be present or absent
<220> FEATURE:
<221> NAME/KEY: MISC_FEATURE
<222> LOCATION: (33)..(34)
<223> OTHER INFORMATION: May be present or absent
<220> FEATURE:
<221> NAME/KEY: MISC_FEATURE
<222> LOCATION: (35)..(36)
<223> OTHER INFORMATION: May be present or absent
<220> FEATURE:
<221> NAME/KEY: MISC_FEATURE
<222> LOCATION: (37)..(38)
<223> OTHER INFORMATION: May be present or absent
<220> FEATURE:
<221> NAME/KEY: MISC_FEATURE
<222> LOCATION: (39)..(40)
<223> OTHER INFORMATION: May be present or absent
<220> FEATURE:
<221> NAME/KEY: MISC_FEATURE
<222> LOCATION: (41)..(42)
<223> OTHER INFORMATION: May be present or absent

<400> SEQUENCE: 135

Ala Ser Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro Ala Pro Gly Thr
        35                  40

<210> SEQ ID NO 136
<211> LENGTH: 104
<212> TYPE: PRT
<213> ORGANISM: Artificial Sequence
<220> FEATURE:
```

```
<223> OTHER INFORMATION: peptide linker
<220> FEATURE:
<221> NAME/KEY: MISC_FEATURE
<222> LOCATION: (13)..(17)
<223> OTHER INFORMATION: May be present or absent
<220> FEATURE:
<221> NAME/KEY: MISC_FEATURE
<222> LOCATION: (18)..(22)
<223> OTHER INFORMATION: May be present or absent
<220> FEATURE:
<221> NAME/KEY: MISC_FEATURE
<222> LOCATION: (23)..(27)
<223> OTHER INFORMATION: May be present or absent
<220> FEATURE:
<221> NAME/KEY: MISC_FEATURE
<222> LOCATION: (28)..(32)
<223> OTHER INFORMATION: May be present or absent
<220> FEATURE:
<221> NAME/KEY: MISC_FEATURE
<222> LOCATION: (33)..(37)
<223> OTHER INFORMATION: May be present or absent
<220> FEATURE:
<221> NAME/KEY: MISC_FEATURE
<222> LOCATION: (38)..(42)
<223> OTHER INFORMATION: May be present or absent
<220> FEATURE:
<221> NAME/KEY: MISC_FEATURE
<222> LOCATION: (43)..(47)
<223> OTHER INFORMATION: May be present or absent
<220> FEATURE:
<221> NAME/KEY: MISC_FEATURE
<222> LOCATION: (48)..(52)
<223> OTHER INFORMATION: May be present or absent
<220> FEATURE:
<221> NAME/KEY: MISC_FEATURE
<222> LOCATION: (53)..(57)
<223> OTHER INFORMATION: May be present or absent
<220> FEATURE:
<221> NAME/KEY: MISC_FEATURE
<222> LOCATION: (58)..(62)
<223> OTHER INFORMATION: May be present or absent
<220> FEATURE:
<221> NAME/KEY: MISC_FEATURE
<222> LOCATION: (63)..(67)
<223> OTHER INFORMATION: May be present or absent
<220> FEATURE:
<221> NAME/KEY: MISC_FEATURE
<222> LOCATION: (68)..(72)
<223> OTHER INFORMATION: May be present or absent
<220> FEATURE:
<221> NAME/KEY: MISC_FEATURE
<222> LOCATION: (73)..(77)
<223> OTHER INFORMATION: May be present or absent
<220> FEATURE:
<221> NAME/KEY: MISC_FEATURE
<222> LOCATION: (78)..(82)
<223> OTHER INFORMATION: May be present or absent
<220> FEATURE:
<221> NAME/KEY: MISC_FEATURE
<222> LOCATION: (83)..(87)
<223> OTHER INFORMATION: May be present or absent
<220> FEATURE:
<221> NAME/KEY: MISC_FEATURE
<222> LOCATION: (88)..(92)
<223> OTHER INFORMATION: May be present or absent
<220> FEATURE:
<221> NAME/KEY: MISC_FEATURE
<222> LOCATION: (93)..(97)
<223> OTHER INFORMATION: May be present or absent
<220> FEATURE:
<221> NAME/KEY: MISC_FEATURE
<222> LOCATION: (98)..(102)
<223> OTHER INFORMATION: May be present or absent

<400> SEQUENCE: 136

Ala Ser Glu Ala Ala Ala Lys Glu Ala Ala Lys Glu Ala Ala Ala
1               5                   10                  15
```

```
Lys Glu Ala Ala Ala Lys Glu Ala Ala Ala Lys Glu Ala Ala Lys
            20                  25                  30

Glu Ala Ala Ala Lys Glu Ala Ala Lys Glu Ala Ala Ala Lys Glu
        35                  40                  45

Ala Ala Ala Lys Glu Ala Ala Lys Glu Ala Ala Lys Glu Ala
    50                  55                  60

Ala Ala Lys Glu Ala Ala Lys Glu Ala Ala Lys Glu Ala Ala
65                  70                  75                  80

Ala Lys Glu Ala Ala Lys Glu Ala Ala Lys Glu Ala Ala Ala
                85                  90                  95

Lys Glu Ala Ala Ala Lys Gly Thr
            100

<210> SEQ ID NO 137
<211> LENGTH: 100
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (11)..(15)
<223> OTHER INFORMATION: May be present or absent
<220> FEATURE:
<221> NAME/KEY: MISC_FEATURE
<222> LOCATION: (16)..(20)
<223> OTHER INFORMATION: May be present or absent
<220> FEATURE:
<221> NAME/KEY: MISC_FEATURE
<222> LOCATION: (21)..(25)
<223> OTHER INFORMATION: May be present or absent
<220> FEATURE:
<221> NAME/KEY: MISC_FEATURE
<222> LOCATION: (26)..(30)
<223> OTHER INFORMATION: May be present or absent
<220> FEATURE:
<221> NAME/KEY: MISC_FEATURE
<222> LOCATION: (31)..(35)
<223> OTHER INFORMATION: May be present or absent
<220> FEATURE:
<221> NAME/KEY: MISC_FEATURE
<222> LOCATION: (36)..(40)
<223> OTHER INFORMATION: May be present or absent
<220> FEATURE:
<221> NAME/KEY: MISC_FEATURE
<222> LOCATION: (41)..(45)
<223> OTHER INFORMATION: May be present or absent
<220> FEATURE:
<221> NAME/KEY: MISC_FEATURE
<222> LOCATION: (46)..(50)
<223> OTHER INFORMATION: May be present or absent
<220> FEATURE:
<221> NAME/KEY: MISC_FEATURE
<222> LOCATION: (51)..(55)
<223> OTHER INFORMATION: May be present or absent
<220> FEATURE:
<221> NAME/KEY: MISC_FEATURE
<222> LOCATION: (56)..(60)
<223> OTHER INFORMATION: May be present or absent
<220> FEATURE:
<221> NAME/KEY: MISC_FEATURE
<222> LOCATION: (61)..(65)
<223> OTHER INFORMATION: May be present or absent
<220> FEATURE:
<221> NAME/KEY: MISC_FEATURE
<222> LOCATION: (66)..(70)
<223> OTHER INFORMATION: May be present or absent
<220> FEATURE:
<221> NAME/KEY: MISC_FEATURE
<222> LOCATION: (71)..(75)
<223> OTHER INFORMATION: May be present or absent
<220> FEATURE:
<221> NAME/KEY: MISC_FEATURE
```

```
<222> LOCATION: (76)..(80)
<223> OTHER INFORMATION: May be present or absent
<220> FEATURE:
<221> NAME/KEY: MISC_FEATURE
<222> LOCATION: (81)..(85)
<223> OTHER INFORMATION: May be present or absent
<220> FEATURE:
<221> NAME/KEY: MISC_FEATURE
<222> LOCATION: (86)..(90)
<223> OTHER INFORMATION: May be present or absent
<220> FEATURE:
<221> NAME/KEY: MISC_FEATURE
<222> LOCATION: (91)..(95)
<223> OTHER INFORMATION: May be present or absent
<220> FEATURE:
<221> NAME/KEY: MISC_FEATURE
<222> LOCATION: (96)..(100)
<223> OTHER INFORMATION: May be present or absent

<400> SEQUENCE: 137

Gly Gly Gly Gly Ala Gly Gly Gly Ala Gly Gly Gly Ala Gly
1               5                   10                  15

Gly Gly Gly Ala Gly Gly Gly Ala Gly Gly Gly Ala Gly Gly
            20                  25                  30

Gly Gly Ala Gly Gly Gly Ala Gly Gly Gly Ala Gly Gly Gly
        35                  40                  45

Gly Ala Gly Gly Gly Ala Gly Gly Gly Ala Gly Gly Gly Gly
    50                  55                  60

Ala Gly Gly Gly Gly Ala Gly Gly Gly Ala Gly Gly Gly Ala
65                  70                  75                  80

Gly Gly Gly Gly Ala Gly Gly Gly Ala Gly Gly Gly Ala Gly
                85                  90                  95

Gly Gly Gly Ala
            100

<210> SEQ ID NO 138
<211> LENGTH: 100
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (11)..(15)
<223> OTHER INFORMATION: May be present or absent
<220> FEATURE:
<221> NAME/KEY: MISC_FEATURE
<222> LOCATION: (16)..(20)
<223> OTHER INFORMATION: May be present or absent
<220> FEATURE:
<221> NAME/KEY: MISC_FEATURE
<222> LOCATION: (21)..(25)
<223> OTHER INFORMATION: May be present or absent
<220> FEATURE:
<221> NAME/KEY: MISC_FEATURE
<222> LOCATION: (26)..(30)
<223> OTHER INFORMATION: May be present or absent
<220> FEATURE:
<221> NAME/KEY: MISC_FEATURE
<222> LOCATION: (31)..(35)
<223> OTHER INFORMATION: May be present or absent
<220> FEATURE:
<221> NAME/KEY: MISC_FEATURE
<222> LOCATION: (36)..(40)
<223> OTHER INFORMATION: May be present or absent
<220> FEATURE:
<221> NAME/KEY: MISC_FEATURE
<222> LOCATION: (41)..(45)
<223> OTHER INFORMATION: May be present or absent
<220> FEATURE:
<221> NAME/KEY: MISC_FEATURE
```

```
<222> LOCATION: (46)..(50)
<223> OTHER INFORMATION: May be present or absent
<220> FEATURE:
<221> NAME/KEY: MISC_FEATURE
<222> LOCATION: (51)..(55)
<223> OTHER INFORMATION: May be present or absent
<220> FEATURE:
<221> NAME/KEY: MISC_FEATURE
<222> LOCATION: (56)..(60)
<223> OTHER INFORMATION: May be present or absent
<220> FEATURE:
<221> NAME/KEY: MISC_FEATURE
<222> LOCATION: (61)..(65)
<223> OTHER INFORMATION: May be present or absent
<220> FEATURE:
<221> NAME/KEY: MISC_FEATURE
<222> LOCATION: (66)..(70)
<223> OTHER INFORMATION: May be present or absent
<220> FEATURE:
<221> NAME/KEY: MISC_FEATURE
<222> LOCATION: (71)..(75)
<223> OTHER INFORMATION: May be present or absent
<220> FEATURE:
<221> NAME/KEY: MISC_FEATURE
<222> LOCATION: (76)..(80)
<223> OTHER INFORMATION: May be present or absent
<220> FEATURE:
<221> NAME/KEY: MISC_FEATURE
<222> LOCATION: (81)..(85)
<223> OTHER INFORMATION: May be present or absent
<220> FEATURE:
<221> NAME/KEY: MISC_FEATURE
<222> LOCATION: (86)..(90)
<223> OTHER INFORMATION: May be present or absent
<220> FEATURE:
<221> NAME/KEY: MISC_FEATURE
<222> LOCATION: (91)..(95)
<223> OTHER INFORMATION: May be present or absent
<220> FEATURE:
<221> NAME/KEY: MISC_FEATURE
<222> LOCATION: (96)..(100)
<223> OTHER INFORMATION: May be present or absent

<400> SEQUENCE: 138

Pro Gly Gly Gly Ser Pro Gly Gly Gly Ser Pro Gly Gly Gly Ser Pro
1               5                   10                  15

Gly Gly Gly Ser Pro Gly Gly Gly Ser Pro Gly Gly Gly Ser Pro Gly
            20                  25                  30

Gly Gly Ser Pro Gly Gly Gly Ser Pro Gly Gly Gly Ser Pro Gly Gly
        35                  40                  45

Gly Ser Pro Gly Gly Gly Ser Pro Gly Gly Gly Ser Pro Gly Gly Gly
    50                  55                  60

Ser Pro Gly Gly Gly Ser Pro Gly Gly Gly Ser Pro Gly Gly Gly Ser
65                  70                  75                  80

Pro Gly Gly Gly Ser Pro Gly Gly Gly Ser Pro Gly Gly Gly Ser Pro
                85                  90                  95

Gly Gly Gly Ser
            100

<210> SEQ ID NO 139
<211> LENGTH: 100
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (11)..(15)
<223> OTHER INFORMATION: May be present or absent
<220> FEATURE:
<221> NAME/KEY: MISC_FEATURE
```

```
<222> LOCATION: (16)..(20)
<223> OTHER INFORMATION: May be present or absent
<220> FEATURE:
<221> NAME/KEY: MISC_FEATURE
<222> LOCATION: (21)..(25)
<223> OTHER INFORMATION: May be present or absent
<220> FEATURE:
<221> NAME/KEY: MISC_FEATURE
<222> LOCATION: (26)..(30)
<223> OTHER INFORMATION: May be present or absent
<220> FEATURE:
<221> NAME/KEY: MISC_FEATURE
<222> LOCATION: (31)..(35)
<223> OTHER INFORMATION: May be present or absent
<220> FEATURE:
<221> NAME/KEY: MISC_FEATURE
<222> LOCATION: (36)..(40)
<223> OTHER INFORMATION: May be present or absent
<220> FEATURE:
<221> NAME/KEY: MISC_FEATURE
<222> LOCATION: (41)..(45)
<223> OTHER INFORMATION: May be present or absent
<220> FEATURE:
<221> NAME/KEY: MISC_FEATURE
<222> LOCATION: (46)..(50)
<223> OTHER INFORMATION: May be present or absent
<220> FEATURE:
<221> NAME/KEY: MISC_FEATURE
<222> LOCATION: (51)..(55)
<223> OTHER INFORMATION: May be present or absent
<220> FEATURE:
<221> NAME/KEY: MISC_FEATURE
<222> LOCATION: (56)..(60)
<223> OTHER INFORMATION: May be present or absent
<220> FEATURE:
<221> NAME/KEY: MISC_FEATURE
<222> LOCATION: (61)..(65)
<223> OTHER INFORMATION: May be present or absent
<220> FEATURE:
<221> NAME/KEY: MISC_FEATURE
<222> LOCATION: (66)..(70)
<223> OTHER INFORMATION: May be present or absent
<220> FEATURE:
<221> NAME/KEY: MISC_FEATURE
<222> LOCATION: (71)..(75)
<223> OTHER INFORMATION: May be present or absent
<220> FEATURE:
<221> NAME/KEY: MISC_FEATURE
<222> LOCATION: (76)..(80)
<223> OTHER INFORMATION: May be present or absent
<220> FEATURE:
<221> NAME/KEY: MISC_FEATURE
<222> LOCATION: (81)..(85)
<223> OTHER INFORMATION: May be present or absent
<220> FEATURE:
<221> NAME/KEY: MISC_FEATURE
<222> LOCATION: (86)..(90)
<223> OTHER INFORMATION: May be present or absent
<220> FEATURE:
<221> NAME/KEY: MISC_FEATURE
<222> LOCATION: (91)..(95)
<223> OTHER INFORMATION: May be present or absent
<220> FEATURE:
<221> NAME/KEY: MISC_FEATURE
<222> LOCATION: (96)..(100)
<223> OTHER INFORMATION: May be present or absent

<400> SEQUENCE: 139

Ala Gly Gly Gly Ser Ala Gly Gly Gly Ser Ala Gly Gly Gly Ser Ala
1               5                   10                  15

Gly Gly Gly Ser Ala Gly Gly Gly Ser Ala Gly Gly Gly Ser Ala Gly
                20                  25                  30

Gly Gly Ser Ala Gly Gly Gly Ser Ala Gly Gly Gly Ser Ala Gly Gly
            35                  40                  45

Gly Ser Ala Gly Gly Gly Ser Ala Gly Gly Gly Ser Ala Gly Gly Gly
```

```
                50                  55                  60
Ser Ala Gly Gly Gly Ser Ala Gly Gly Gly Ser Ala Gly Gly Gly Ser
 65                  70                  75                  80

Ala Gly Gly Gly Ser Ala Gly Gly Gly Ser Ala Gly Gly Gly Ser Ala
                 85                  90                  95

Gly Gly Gly Ser
            100

<210> SEQ ID NO 140
<211> LENGTH: 286
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (32)..(45)
<223> OTHER INFORMATION: May be present or absent
<220> FEATURE:
<221> NAME/KEY: MISC_FEATURE
<222> LOCATION: (46)..(59)
<223> OTHER INFORMATION: May be present or absent
<220> FEATURE:
<221> NAME/KEY: MISC_FEATURE
<222> LOCATION: (60)..(73)
<223> OTHER INFORMATION: May be present or absent
<220> FEATURE:
<221> NAME/KEY: MISC_FEATURE
<222> LOCATION: (74)..(87)
<223> OTHER INFORMATION: May be present or absent
<220> FEATURE:
<221> NAME/KEY: MISC_FEATURE
<222> LOCATION: (88)..(101)
<223> OTHER INFORMATION: May be present or absent
<220> FEATURE:
<221> NAME/KEY: MISC_FEATURE
<222> LOCATION: (102)..(115)
<223> OTHER INFORMATION: May be present or absent
<220> FEATURE:
<221> NAME/KEY: MISC_FEATURE
<222> LOCATION: (116)..(129)
<223> OTHER INFORMATION: May be present or absent
<220> FEATURE:
<221> NAME/KEY: MISC_FEATURE
<222> LOCATION: (130)..(143)
<223> OTHER INFORMATION: May be present or absent
<220> FEATURE:
<221> NAME/KEY: MISC_FEATURE
<222> LOCATION: (144)..(157)
<223> OTHER INFORMATION: May be present or absent
<220> FEATURE:
<221> NAME/KEY: MISC_FEATURE
<222> LOCATION: (158)..(171)
<223> OTHER INFORMATION: May be present or absent
<220> FEATURE:
<221> NAME/KEY: MISC_FEATURE
<222> LOCATION: (172)..(185)
<223> OTHER INFORMATION: May be present or absent
<220> FEATURE:
<221> NAME/KEY: MISC_FEATURE
<222> LOCATION: (186)..(199)
<223> OTHER INFORMATION: May be present or absent
<220> FEATURE:
<221> NAME/KEY: MISC_FEATURE
<222> LOCATION: (200)..(213)
<223> OTHER INFORMATION: May be present or absent
<220> FEATURE:
<221> NAME/KEY: MISC_FEATURE
<222> LOCATION: (214)..(227)
<223> OTHER INFORMATION: May be present or absent
<220> FEATURE:
<221> NAME/KEY: MISC_FEATURE
<222> LOCATION: (228)..(241)
<223> OTHER INFORMATION: May be present or absent
<220> FEATURE:
```

<220> FEATURE:
<221> NAME/KEY: MISC_FEATURE
<222> LOCATION: (242)..(255)
<223> OTHER INFORMATION: May be present or absent
<220> FEATURE:
<221> NAME/KEY: MISC_FEATURE
<222> LOCATION: (256)..(269)
<223> OTHER INFORMATION: May be present or absent
<220> FEATURE:
<221> NAME/KEY: MISC_FEATURE
<222> LOCATION: (270)..(283)
<223> OTHER INFORMATION: May be present or absent

<400> SEQUENCE: 140

```
Gly Gly Ser Glu Gly Lys Ser Gly Ser Gly Ser Glu Ser Lys Ser
1               5                   10                  15
Thr Glu Gly Lys Ser Gly Ser Gly Ser Glu Ser Lys Ser Thr Glu
                20                  25                  30
Gly Lys Ser Ser Gly Ser Gly Ser Glu Ser Lys Ser Thr Glu Gly Lys
                35                  40                  45
Ser Ser Gly Ser Gly Ser Glu Ser Lys Ser Thr Glu Gly Lys Ser Ser
            50                  55                  60
Gly Ser Gly Ser Glu Ser Lys Ser Thr Glu Gly Lys Ser Ser Gly Ser
65                  70                  75                  80
Gly Ser Glu Ser Lys Ser Thr Glu Gly Lys Ser Ser Gly Ser Gly Ser
                85                  90                  95
Glu Ser Lys Ser Thr Glu Gly Lys Ser Ser Gly Ser Gly Ser Glu Ser
                100                 105                 110
Lys Ser Thr Glu Gly Lys Ser Ser Gly Ser Gly Ser Glu Ser Lys Ser
            115                 120                 125
Thr Glu Gly Lys Ser Ser Gly Ser Gly Ser Glu Ser Lys Ser Thr Glu
        130                 135                 140
Gly Lys Ser Ser Gly Ser Gly Ser Glu Ser Lys Ser Thr Glu Gly Lys
145                 150                 155                 160
Ser Ser Gly Ser Gly Ser Glu Ser Lys Ser Thr Glu Gly Lys Ser Ser
                165                 170                 175
Gly Ser Gly Ser Glu Ser Lys Ser Thr Glu Gly Lys Ser Ser Gly Ser
                180                 185                 190
Gly Ser Glu Ser Lys Ser Thr Glu Gly Lys Ser Ser Gly Ser Gly Ser
            195                 200                 205
Glu Ser Lys Ser Thr Glu Gly Lys Ser Ser Gly Ser Gly Ser Glu Ser
        210                 215                 220
Lys Ser Thr Glu Gly Lys Ser Ser Gly Ser Gly Ser Glu Ser Lys Ser
225                 230                 235                 240
Thr Glu Gly Lys Ser Ser Gly Ser Gly Ser Glu Ser Lys Ser Thr Glu
                245                 250                 255
Gly Lys Ser Ser Gly Ser Gly Ser Glu Ser Lys Ser Thr Glu Gly Lys
                260                 265                 270
Ser Ser Gly Ser Gly Ser Glu Ser Lys Ser Thr Gly Gly Ser
            275                 280                 285
```

<210> SEQ ID NO 141
<211> LENGTH: 9
<212> TYPE: PRT
<213> ORGANISM: Artificial Sequence
<220> FEATURE:
<223> OTHER INFORMATION: peptide linker

<400> SEQUENCE: 141

Ser Ser Ser Ala Ser Ala Ser Ser Ala

```
1               5

<210> SEQ ID NO 142
<211> LENGTH: 7
<212> TYPE: PRT
<213> ORGANISM: Artificial Sequence
<220> FEATURE:
<223> OTHER INFORMATION: peptide linker

<400> SEQUENCE: 142

Gly Ser Pro Gly Ser Pro Gly
1               5

<210> SEQ ID NO 143
<211> LENGTH: 11
<212> TYPE: PRT
<213> ORGANISM: Artificial Sequence
<220> FEATURE:
<223> OTHER INFORMATION: peptide linker

<400> SEQUENCE: 143

Ala Thr Thr Thr Gly Ser Ser Pro Gly Pro Thr
1               5                   10

<210> SEQ ID NO 144
<211> LENGTH: 5
<212> TYPE: PRT
<213> ORGANISM: Artificial Sequence
<220> FEATURE:
<223> OTHER INFORMATION: cleavable linker
<220> FEATURE:
<221> NAME/KEY: misc_feature
<222> LOCATION: (1)..(1)
<223> OTHER INFORMATION: Xaa is Ile, Leu, Tyr, Met, Phe, Val or Ala
<220> FEATURE:
<221> NAME/KEY: misc_feature
<222> LOCATION: (2)..(2)
<223> OTHER INFORMATION: Xaa is Ala, Gly, Ser, Val, Glu, Asp, Gln, Asn
      or Tyr
<220> FEATURE:
<221> NAME/KEY: misc_feature
<222> LOCATION: (3)..(3)
<223> OTHER INFORMATION: Xaa is His, Pro, Ala, Val, Gly, Ser or Thr
<220> FEATURE:
<221> NAME/KEY: misc_feature
<222> LOCATION: (4)..(4)
<223> OTHER INFORMATION: Xaa is Asp or Glu
<220> FEATURE:
<221> NAME/KEY: misc_feature
<222> LOCATION: (5)..(5)
<223> OTHER INFORMATION: Xaa is Ile, Leu, Tyr, Met, Phe, Val, Thr, Ser,
      Gly or Ala

<400> SEQUENCE: 144

Xaa Xaa Xaa Xaa Xaa
1               5

<210> SEQ ID NO 145
<211> LENGTH: 5
<212> TYPE: PRT
<213> ORGANISM: Artificial Sequence
<220> FEATURE:
<223> OTHER INFORMATION: cleavable linker
<220> FEATURE:
<221> NAME/KEY: misc_feature
<222> LOCATION: (1)..(1)
<223> OTHER INFORMATION: Xaa is Ile or Leu
<220> FEATURE:
<221> NAME/KEY: misc_feature
<222> LOCATION: (3)..(3)
<223> OTHER INFORMATION: Xaa is Pro or Ala
<220> FEATURE:
```

```
<221> NAME/KEY: misc_feature
<222> LOCATION: (5)..(5)
<223> OTHER INFORMATION: Xaa is Ile, Val, Thr, Ser, or Gly

<400> SEQUENCE: 145

Xaa Glu Xaa Asp Xaa
1               5

<210> SEQ ID NO 146
<211> LENGTH: 4
<212> TYPE: PRT
<213> ORGANISM: Artificial Sequence
<220> FEATURE:
<223> OTHER INFORMATION: substrate for granzyme B

<400> SEQUENCE: 146

Leu Glu Ala Asp
1

<210> SEQ ID NO 147
<211> LENGTH: 4
<212> TYPE: PRT
<213> ORGANISM: Artificial Sequence
<220> FEATURE:
<223> OTHER INFORMATION: substrate for granzyme B

<400> SEQUENCE: 147

Leu Glu Pro Asp
1

<210> SEQ ID NO 148
<211> LENGTH: 4
<212> TYPE: PRT
<213> ORGANISM: Artificial Sequence
<220> FEATURE:
<223> OTHER INFORMATION: substrate for granzyme B

<400> SEQUENCE: 148

Leu Glu Ala Glu
1

<210> SEQ ID NO 149
<211> LENGTH: 5
<212> TYPE: PRT
<213> ORGANISM: Artificial Sequence
<220> FEATURE:
<223> OTHER INFORMATION: cleavable linker

<400> SEQUENCE: 149

Ile Glu Pro Asp Ile
1               5

<210> SEQ ID NO 150
<211> LENGTH: 5
<212> TYPE: PRT
<213> ORGANISM: Artificial Sequence
<220> FEATURE:
<223> OTHER INFORMATION: cleavable linker

<400> SEQUENCE: 150

Leu Glu Pro Asp Gly
1               5

<210> SEQ ID NO 151
<211> LENGTH: 5
<212> TYPE: PRT
<213> ORGANISM: Artificial Sequence
```

```
<220> FEATURE:
<223> OTHER INFORMATION: cleavable linker

<400> SEQUENCE: 151

Leu Glu Ala Asp Thr
1               5

<210> SEQ ID NO 152
<211> LENGTH: 5
<212> TYPE: PRT
<213> ORGANISM: Artificial Sequence
<220> FEATURE:
<223> OTHER INFORMATION: cleavable linker

<400> SEQUENCE: 152

Ile Glu Pro Asp Gly
1               5

<210> SEQ ID NO 153
<211> LENGTH: 5
<212> TYPE: PRT
<213> ORGANISM: Artificial Sequence
<220> FEATURE:
<223> OTHER INFORMATION: cleavable linker

<400> SEQUENCE: 153

Ile Glu Pro Asp Val
1               5

<210> SEQ ID NO 154
<211> LENGTH: 5
<212> TYPE: PRT
<213> ORGANISM: Artificial Sequence
<220> FEATURE:
<223> OTHER INFORMATION: cleavable linker

<400> SEQUENCE: 154

Ile Glu Pro Asp Ser
1               5

<210> SEQ ID NO 155
<211> LENGTH: 5
<212> TYPE: PRT
<213> ORGANISM: Artificial Sequence
<220> FEATURE:
<223> OTHER INFORMATION: cleavable linker

<400> SEQUENCE: 155

Ile Glu Pro Asp Thr
1               5

<210> SEQ ID NO 156
<211> LENGTH: 5
<212> TYPE: PRT
<213> ORGANISM: Artificial Sequence
<220> FEATURE:
<223> OTHER INFORMATION: cleavable linker
<220> FEATURE:
<221> NAME/KEY: misc_feature
<222> LOCATION: (1)..(1)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa is Ala or Val

<400> SEQUENCE: 156

Xaa Gln Ala Arg Xaa
```

```
1               5
```

```
<210> SEQ ID NO 157
<211> LENGTH: 5
<212> TYPE: PRT
<213> ORGANISM: Artificial Sequence
<220> FEATURE:
<223> OTHER INFORMATION: cleavable linker
<220> FEATURE:
<221> NAME/KEY: misc_feature
<222> LOCATION: (5)..(5)
<223> OTHER INFORMATION: Xaa is Ala or Val

<400> SEQUENCE: 157

Arg Gln Ala Arg Xaa
1               5

<210> SEQ ID NO 158
<211> LENGTH: 4
<212> TYPE: PRT
<213> ORGANISM: Artificial Sequence
<220> FEATURE:
<223> OTHER INFORMATION: substrate for matriptase

<400> SEQUENCE: 158

Arg Gln Ala Arg
1

<210> SEQ ID NO 159
<211> LENGTH: 5
<212> TYPE: PRT
<213> ORGANISM: Artificial Sequence
<220> FEATURE:
<223> OTHER INFORMATION: cleavable linker

<400> SEQUENCE: 159

Arg Gln Ala Arg Val
1               5

<210> SEQ ID NO 160
<211> LENGTH: 4
<212> TYPE: PRT
<213> ORGANISM: Artificial Sequence
<220> FEATURE:
<223> OTHER INFORMATION: cleavable linker
<220> FEATURE:
<221> NAME/KEY: misc_feature
<222> LOCATION: (1)..(1)
<223> OTHER INFORMATION: Xaa is Pro, Val or Ala
<220> FEATURE:
<221> NAME/KEY: misc_feature
<222> LOCATION: (2)..(2)
<223> OTHER INFORMATION: Xaa is Gln or Asp
<220> FEATURE:
<221> NAME/KEY: misc_feature
<222> LOCATION: (3)..(3)
<223> OTHER INFORMATION: Xaa is Ala or Asn
<220> FEATURE:
<221> NAME/KEY: misc_feature
<222> LOCATION: (4)..(4)
<223> OTHER INFORMATION: Xaa is Leu, Ile or Met

<400> SEQUENCE: 160

Xaa Xaa Xaa Xaa
1

<210> SEQ ID NO 161
<211> LENGTH: 4
<212> TYPE: PRT
<213> ORGANISM: Artificial Sequence
```

```
<220> FEATURE:
<223> OTHER INFORMATION: cleavable linker
<220> FEATURE:
<221> NAME/KEY: misc_feature
<222> LOCATION: (2)..(2)
<223> OTHER INFORMATION: Xaa is Gln or Asp
<220> FEATURE:
<221> NAME/KEY: misc_feature
<222> LOCATION: (3)..(3)
<223> OTHER INFORMATION: Xaa is Ala or Asn
<220> FEATURE:
<221> NAME/KEY: misc_feature
<222> LOCATION: (4)..(4)
<223> OTHER INFORMATION: Xaa is Leu or Ile

<400> SEQUENCE: 161

Pro Xaa Xaa Xaa
1

<210> SEQ ID NO 162
<211> LENGTH: 4
<212> TYPE: PRT
<213> ORGANISM: Artificial Sequence
<220> FEATURE:
<223> OTHER INFORMATION: substrate for MMP

<400> SEQUENCE: 162

Pro Ala Gly Leu
1

<210> SEQ ID NO 163
<211> LENGTH: 19
<212> TYPE: PRT
<213> ORGANISM: Artificial Sequence
<220> FEATURE:
<223> OTHER INFORMATION: cleavable linker

<400> SEQUENCE: 163

Thr Gly Leu Glu Ala Asp Gly Ser Pro Ala Gly Leu Gly Arg Gln Ala
1               5                   10                  15

Arg Val Gly

<210> SEQ ID NO 164
<211> LENGTH: 19
<212> TYPE: PRT
<213> ORGANISM: Artificial Sequence
<220> FEATURE:
<223> OTHER INFORMATION: cleavable linker

<400> SEQUENCE: 164

Thr Gly Leu Glu Ala Asp Gly Ser Arg Gln Ala Arg Val Gly Pro Ala
1               5                   10                  15

Gly Leu Gly

<210> SEQ ID NO 165
<211> LENGTH: 19
<212> TYPE: PRT
<213> ORGANISM: Artificial Sequence
<220> FEATURE:
<223> OTHER INFORMATION: cleavable linker

<400> SEQUENCE: 165

Thr Gly Ser Pro Ala Gly Leu Glu Ala Asp Gly Ser Arg Gln Ala Arg
1               5                   10                  15

Val Gly Ser
```

```
<210> SEQ ID NO 166
<211> LENGTH: 19
<212> TYPE: PRT
<213> ORGANISM: Artificial Sequence
<220> FEATURE:
<223> OTHER INFORMATION: cleavable linker

<400> SEQUENCE: 166

Thr Gly Pro Ala Gly Leu Gly Leu Glu Ala Asp Gly Ser Arg Gln Ala
1               5                   10                  15

Arg Val Gly

<210> SEQ ID NO 167
<211> LENGTH: 19
<212> TYPE: PRT
<213> ORGANISM: Artificial Sequence
<220> FEATURE:
<223> OTHER INFORMATION: cleavable linker

<400> SEQUENCE: 167

Thr Gly Arg Gln Ala Arg Val Gly Leu Glu Ala Asp Gly Ser Pro Ala
1               5                   10                  15

Gly Leu Gly

<210> SEQ ID NO 168
<211> LENGTH: 18
<212> TYPE: PRT
<213> ORGANISM: Artificial Sequence
<220> FEATURE:
<223> OTHER INFORMATION: cleavable linker

<400> SEQUENCE: 168

Thr Gly Ser Arg Gln Ala Arg Val Gly Pro Ala Gly Leu Glu Ala Asp
1               5                   10                  15

Gly Ser

<210> SEQ ID NO 169
<211> LENGTH: 20
<212> TYPE: PRT
<213> ORGANISM: Artificial Sequence
<220> FEATURE:
<223> OTHER INFORMATION: cleavable linker

<400> SEQUENCE: 169

Thr Gly Pro Ala Gly Leu Gly Ser Arg Gln Ala Arg Val Gly Leu Glu
1               5                   10                  15

Ala Asp Gly Ser
            20

<210> SEQ ID NO 170
<211> LENGTH: 18
<212> TYPE: PRT
<213> ORGANISM: Artificial Sequence
<220> FEATURE:
<223> OTHER INFORMATION: cleavable linker

<400> SEQUENCE: 170

Gly Pro Ala Gly Leu Gly Leu Glu Pro Asp Gly Ser Arg Gln Ala Arg
1               5                   10                  15

Val Gly

<210> SEQ ID NO 171
<211> LENGTH: 18
<212> TYPE: PRT
```

```
<213> ORGANISM: Artificial Sequence
<220> FEATURE:
<223> OTHER INFORMATION: cleavable linker

<400> SEQUENCE: 171

Gly Gly Ser Gly Gly Gly Gly Ile Glu Pro Asp Ile Gly Gly Ser Gly
1               5                   10                  15

Gly Ser

<210> SEQ ID NO 172
<211> LENGTH: 18
<212> TYPE: PRT
<213> ORGANISM: Artificial Sequence
<220> FEATURE:
<223> OTHER INFORMATION: cleavable linker

<400> SEQUENCE: 172

Gly Gly Ser Gly Gly Gly Gly Leu Glu Ala Asp Thr Gly Gly Ser Gly
1               5                   10                  15

Gly Ser

<210> SEQ ID NO 173
<211> LENGTH: 9
<212> TYPE: PRT
<213> ORGANISM: Artificial Sequence
<220> FEATURE:
<223> OTHER INFORMATION: cleavable linker

<400> SEQUENCE: 173

Gly Ser Ile Glu Pro Asp Ile Gly Ser
1               5

<210> SEQ ID NO 174
<211> LENGTH: 9
<212> TYPE: PRT
<213> ORGANISM: Artificial Sequence
<220> FEATURE:
<223> OTHER INFORMATION: cleavable linker

<400> SEQUENCE: 174

Gly Ser Leu Glu Ala Asp Thr Gly Ser
1               5

<210> SEQ ID NO 175
<211> LENGTH: 18
<212> TYPE: PRT
<213> ORGANISM: Artificial Sequence
<220> FEATURE:
<223> OTHER INFORMATION: cleavable linker

<400> SEQUENCE: 175

Gly Gly Ser Gly Gly Gly Gly Ile Glu Pro Asp Gly Gly Gly Ser Gly
1               5                   10                  15

Gly Ser

<210> SEQ ID NO 176
<211> LENGTH: 18
<212> TYPE: PRT
<213> ORGANISM: Artificial Sequence
<220> FEATURE:
<223> OTHER INFORMATION: cleavable linker

<400> SEQUENCE: 176

Gly Gly Ser Gly Gly Gly Gly Ile Glu Pro Asp Val Gly Gly Ser Gly
1               5                   10                  15
```

Gly Ser

<210> SEQ ID NO 177
<211> LENGTH: 18
<212> TYPE: PRT
<213> ORGANISM: Artificial Sequence
<220> FEATURE:
<223> OTHER INFORMATION: cleavable linker

<400> SEQUENCE: 177

Gly Gly Ser Gly Gly Gly Gly Ile Glu Pro Asp Ser Gly Gly Ser Gly
1               5                   10                  15

Gly Ser

<210> SEQ ID NO 178
<211> LENGTH: 18
<212> TYPE: PRT
<213> ORGANISM: Artificial Sequence
<220> FEATURE:
<223> OTHER INFORMATION: cleavable linker

<400> SEQUENCE: 178

Gly Gly Ser Gly Gly Gly Gly Ile Glu Pro Asp Thr Gly Gly Ser Gly
1               5                   10                  15

Gly Ser

<210> SEQ ID NO 179
<211> LENGTH: 12
<212> TYPE: PRT
<213> ORGANISM: Artificial Sequence
<220> FEATURE:
<223> OTHER INFORMATION: cleavable linker

<400> SEQUENCE: 179

Gly Gly Gly Ser Leu Glu Pro Asp Gly Ser Gly Ser
1               5                   10

<210> SEQ ID NO 180
<211> LENGTH: 18
<212> TYPE: PRT
<213> ORGANISM: Artificial Sequence
<220> FEATURE:
<223> OTHER INFORMATION: cleavable linker

<400> SEQUENCE: 180

Gly Pro Ala Gly Leu Gly Leu Glu Ala Asp Gly Ser Arg Gln Ala Arg
1               5                   10                  15

Val Gly

<210> SEQ ID NO 181
<211> LENGTH: 15
<212> TYPE: PRT
<213> ORGANISM: Artificial Sequence
<220> FEATURE:
<223> OTHER INFORMATION: cleavable linker

<400> SEQUENCE: 181

Gly Gly Glu Gly Gly Gly Gly Ser Gly Gly Ser Gly Gly Gly Ser
1               5                   10                  15

<210> SEQ ID NO 182
<211> LENGTH: 18
<212> TYPE: PRT
<213> ORGANISM: Artificial Sequence
<220> FEATURE:
<223> OTHER INFORMATION: cleavable linker

<400> SEQUENCE: 182

Gly Ser Ser Ala Gly Ser Glu Ala Gly Gly Ser Gly Gln Ala Gly Val
1               5                   10                  15

Gly Ser

<210> SEQ ID NO 183
<211> LENGTH: 18
<212> TYPE: PRT
<213> ORGANISM: Artificial Sequence
<220> FEATURE:
<223> OTHER INFORMATION: cleavable linker

<400> SEQUENCE: 183

Gly Gly Ser Gly Gly Gly Gly Leu Glu Ala Glu Gly Ser Gly Gly Gly
1               5                   10                  15

Gly Ser

<210> SEQ ID NO 184
<211> LENGTH: 18
<212> TYPE: PRT
<213> ORGANISM: Artificial Sequence
<220> FEATURE:
<223> OTHER INFORMATION: cleavable linker

<400> SEQUENCE: 184

Gly Gly Ser Gly Gly Gly Gly Ile Glu Pro Asp Pro Gly Gly Ser Gly
1               5                   10                  15

Gly Ser

<210> SEQ ID NO 185
<211> LENGTH: 19
<212> TYPE: PRT
<213> ORGANISM: Artificial Sequence
<220> FEATURE:
<223> OTHER INFORMATION: cleavable linker

<400> SEQUENCE: 185

Thr Gly Gly Ser Gly Gly Gly Gly Ile Glu Pro Asp Ile Gly Gly Ser
1               5                   10                  15

Gly Gly Ser

<210> SEQ ID NO 186
<211> LENGTH: 204
<212> TYPE: PRT
<213> ORGANISM: Artificial Sequence
<220> FEATURE:
<223> OTHER INFORMATION: 41BBL

<400> SEQUENCE: 186

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
                20                  25                  30

Ala Gly Leu Leu Asp Leu Arg Gln Gly Met Phe Ala Gln Leu Val Ala
            35                  40                  45

Gln Asn Val Leu Leu Ile Asp Gly Pro Leu Ser Trp Tyr Ser Asp Pro
        50                  55                  60

Gly Leu Ala Gly Val Ser Leu Thr Gly Gly Leu Ser Tyr Lys Glu Asp
65                  70                  75                  80

```
Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Asn
    130                 135                 140

Ser Ala Phe Gly Phe Gln Gly Arg Leu Leu His Leu Ser Ala Gly Gln
145                 150                 155                 160

Arg Leu Gly Val His Leu His Thr Glu Ala Arg Ala Arg His Ala Trp
                165                 170                 175

Gln Leu Thr Gln Gly Ala Thr Val Leu Gly Leu Phe Arg Val Thr Pro
            180                 185                 190

Glu Ile Pro Ala Gly Leu Pro Ser Pro Arg Ser Glu
        195                 200

<210> SEQ ID NO 187
<211> LENGTH: 116
<212> TYPE: PRT
<213> ORGANISM: Artificial Sequence
<220> FEATURE:
<223> OTHER INFORMATION: 41BB VH

<400> SEQUENCE: 187

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 188
<211> LENGTH: 108
<212> TYPE: PRT
<213> ORGANISM: Artificial Sequence
<220> FEATURE:
<223> OTHER INFORMATION: 41BB VL

<400> SEQUENCE: 188

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
```

```
                    50                  55                  60
Asn Ser Gly Asn Thr Ala Thr Leu Thr Ile Ser Gly Thr Gln Ala Met
 65                  70                  75                  80

Asp Glu Ala Asp Tyr Tyr Cys Ala Thr Tyr Thr Gly Phe Gly Ser Leu
                 85                  90                  95

Ala Val Phe Gly Gly Gly Thr Lys Leu Thr Val Leu
            100                 105
```

<210> SEQ ID NO 189
<211> LENGTH: 121
<212> TYPE: PRT
<213> ORGANISM: Artificial Sequence
<220> FEATURE:
<223> OTHER INFORMATION: 41BB VH

<400> SEQUENCE: 189

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Ser Pro Glu Lys Gly Leu Glu Trp Ile
             35                  40                  45

Gly Glu Ile Asn His Gly Gly Tyr Val Thr Tyr Asn Pro Ser Leu Glu
         50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
            115                 120
```

<210> SEQ ID NO 190
<211> LENGTH: 109
<212> TYPE: PRT
<213> ORGANISM: Artificial Sequence
<220> FEATURE:
<223> OTHER INFORMATION: 41BB VL

<400> SEQUENCE: 190

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Ala Leu Thr Phe Gly Gly Gly Thr Lys Val Glu Ile Lys
            100                 105
```

<210> SEQ ID NO 191
<211> LENGTH: 120

```
<212> TYPE: PRT
<213> ORGANISM: Artificial Sequence
<220> FEATURE:
<223> OTHER INFORMATION: 41BB VH

<400> SEQUENCE: 191

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
            20                  25                  30

Tyr Met His Trp Val Arg Gln Ala Pro Gly Gln Gly Leu Glu Trp Met
        35                  40                  45

Gly Trp Val Asn Pro Met Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Met Ala Met Arg Leu Glu Leu Asp Lys Trp Gly Gln
            100                 105                 110

Gly Thr Leu Val Thr Val Ser Ser
        115                 120

<210> SEQ ID NO 192
<211> LENGTH: 106
<212> TYPE: PRT
<213> ORGANISM: Artificial Sequence
<220> FEATURE:
<223> OTHER INFORMATION: 41BB VL

<400> SEQUENCE: 192

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Val Val
                85                  90                  95

Phe Gly Gly Gly Thr Gln Leu Thr Val Leu
            100                 105

<210> SEQ ID NO 193
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 193

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
```

```
                  35                  40                  45
Asn Lys Met Met Ala Thr Ile Tyr Glu Leu Lys Glu Asp Lys Ser Tyr
 50                  55                  60
Asn Val Thr Gly Val Thr Phe Asp Asp Lys Lys Cys Thr Tyr Ala Ile
 65                  70                  75                  80
Ser Thr Phe Val Pro Gly Ser Gln Pro Gly Glu Phe Thr Leu Gly Lys
                 85                  90                  95
Ile Lys Ser Phe Pro Gly His Thr Ser Ser Leu Val Arg Val Val Ser
                100                 105                 110
Thr Asn Tyr Asn Gln His Ala Met Val Phe Phe Lys Phe Val Phe Gln
                115                 120                 125
Asn Arg Glu Glu Phe Tyr Ile Thr Leu Tyr Gly Arg Thr Lys Glu Leu
                130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 194
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 194

```
Gln Asp Ser Thr Ser Asp Leu Ile Pro Ala Pro Pro Leu Ser Lys Val
 1                   5                  10                  15
Pro Leu Gln Gln Asn Phe Gln Asp Asn Gln Phe His Gly Lys Trp Tyr
                 20                  25                  30
Val Val Gly Gln Ala Gly Asn Ile Arg Leu Arg Glu Asp Lys Asp Pro
                 35                  40                  45
Ile Lys Met Met Ala Thr Ile Tyr Glu Leu Lys Glu Asp Lys Ser Tyr
 50                  55                  60
Asp Val Thr Met Val Lys Phe Asp Asp Lys Lys Cys Met Tyr Asp Ile
 65                  70                  75                  80
Trp Thr Phe Val Pro Gly Ser Gln Pro Gly Glu Phe Thr Leu Gly Lys
                 85                  90                  95
Ile Lys Ser Phe Pro Gly His Thr Ser Ser Leu Val Arg Val Val Ser
                100                 105                 110
Thr Asn Tyr Asn Gln His Ala Met Val Phe Phe Lys Phe Val Phe Gln
                115                 120                 125
Asn Arg Glu Glu Phe Tyr Ile Thr Leu Tyr Gly Arg Thr Lys Glu Leu
                130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 195
<211> LENGTH: 178
<212> TYPE: PRT
<213> ORGANISM: Artificial Sequence
<220> FEATURE:

<223> OTHER INFORMATION: 41BB Anticalin

<400> SEQUENCE: 195

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
        35                  40                  45

Asn Lys Met Met Ala Thr Ile Tyr Glu Leu Lys Glu Asp Lys Ser Tyr
    50                  55                  60

Asp Val Thr Ala Val Ala Phe Asp Lys Lys Cys Thr Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 196
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 196

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
        35                  40                  45

Asn Lys Met Met Ala Thr Ile Tyr Glu Leu Lys Glu Asp Lys Ser Tyr
    50                  55                  60

Asp Val Thr Ala Val Ala Phe Asp Lys Lys Cys Thr Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 197
<211> LENGTH: 175
<212> TYPE: PRT
<213> ORGANISM: Artificial Sequence
<220> FEATURE:
<223> OTHER INFORMATION: 41BB Anticalin

<400> SEQUENCE: 197

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Ser Lys Met
        35                  40                  45

Met Ala Thr Ile Tyr Glu Leu Lys Glu Asp Lys Ser Tyr Asp Val Thr
    50                  55                  60

Gly Val Ser Phe Asp Asp Lys Lys Cys Thr Tyr Ala Ile Met Thr Phe
65                  70                  75                  80

Val Pro Gly Ser Gln Pro Gly Glu Phe Thr Leu Gly Lys Ile Lys Ser
                85                  90                  95

Phe Pro Gly His Thr Ser Ser Leu Val Arg Val Val Ser Thr Asn Tyr
            100                 105                 110

Asn Gln His Ala Met Val Phe Phe Lys Phe Val Phe Gln Asn Arg Glu
        115                 120                 125

Glu Phe Tyr Ile Thr Leu Tyr Gly Arg Thr Lys Glu Leu Thr Ser Glu
    130                 135                 140

Leu Lys Glu Asn Phe Ile Arg Phe Ser Lys Ser Leu Gly Leu Pro Glu
145                 150                 155                 160

Asn His Ile Val Phe Pro Val Pro Ile Asp Gln Cys Ile Asp Gly
                165                 170                 175

<210> SEQ ID NO 198
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 198

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
        35                  40                  45

Val Lys Met Met Ala Thr Ile Tyr Glu Leu Lys Glu Asp Lys Ser Tyr
    50                  55                  60

Asp Val Thr Gly Val Thr Phe Asp Asp Lys Lys Cys Arg Tyr Asp Ile
65                  70                  75                  80

Ser Thr Phe Val Pro Gly Ser Gln Pro Gly Glu Phe Thr Phe Gly Lys
                85                  90                  95

Ile Lys Ser Phe Pro Gly His Thr Ser Ser Leu Val Arg Val Val Ser
            100                 105                 110

```
Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 199
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 199

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
        35                  40                  45

His Lys Met Met Ala Thr Ile Tyr Glu Leu Lys Glu Asp Lys Ser Tyr
    50                  55                  60

Asp Val Thr Gly Val Thr Phe Asp Asp Lys Lys Cys Thr Tyr Ala Ile
65                  70                  75                  80

Ser Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 200
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 200

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
        35                  40                  45

Asn Lys Met Met Ala Thr Ile Tyr Glu Leu Lys Glu Asp Lys Ser Tyr
```

```
                    50                  55                  60
Asp Val Thr Gly Val Thr Phe Asp Asp Lys Lys Cys Thr Tyr Ala Ile
 65                  70                  75                  80

Ser Thr Leu Val Pro Gly Ser Gln Pro Gly Glu Phe Thr Phe Gly Lys
                    85                  90                  95

Ile Lys Ser Phe Pro Gly His Thr Ser Ser Leu Val Arg Val Val Ser
                   100                 105                 110

Thr Asn Tyr Asn Gln His Ala Met Val Phe Phe Lys Phe Val Phe Gln
                   115                 120                 125

Asn Arg Glu Glu Phe Tyr Ile Thr Leu Tyr Gly Arg Thr Lys Glu Leu
                   130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                   165                 170                 175

Asp Gly
```

<210> SEQ ID NO 201
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 201

```
Gln Asp Ser Thr Ser Asp Leu Ile Pro Ala Pro Pro Leu Ser Lys Val
 1                   5                  10                  15

Pro Leu Gln Gln Asn Phe Gln Asp Asn Gln Phe His Gly Lys Trp Tyr
                    20                  25                  30

Val Val Gly Gln Ala Gly Asn Ile Arg Leu Arg Glu Asp Lys Asp Pro
                    35                  40                  45

Ser Lys Met Met Ala Thr Ile Tyr Glu Leu Lys Glu Asp Lys Ser Tyr
 50                  55                  60

Asp Val Thr Ala Val Thr Phe Asp Asp Lys Lys Cys Asn Tyr Ala Ile
 65                  70                  75                  80

Ser Thr Phe Val Pro Gly Ser Gln Pro Gly Glu Phe Thr Leu Gly Lys
                    85                  90                  95

Ile Lys Ser Phe Pro Gly His Thr Ser Ser Leu Val Arg Val Val Ser
                   100                 105                 110

Thr Asn Tyr Asn Gln His Ala Met Val Phe Phe Lys Phe Val Phe Gln
                   115                 120                 125

Asn Arg Glu Glu Phe Tyr Ile Thr Leu Tyr Gly Arg Thr Lys Glu Leu
                   130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                   165                 170                 175

Asp Gly
```

<210> SEQ ID NO 202
<211> LENGTH: 184
<212> TYPE: PRT
<213> ORGANISM: Homo sapiens

<400> SEQUENCE: 202

Arg Glu Gly Pro Glu Leu Ser Pro Asp Asp Pro Ala Gly Leu Leu Asp

```
          1               5                   10                  15
Leu Arg Gln Gly Met Phe Ala Gln Leu Val Ala Gln Asn Val Leu Leu
            20                  25                  30
Ile Asp Gly Pro Leu Ser Trp Tyr Ser Asp Pro Gly Leu Ala Gly Val
            35                  40                  45
Ser Leu Thr Gly Gly Leu Ser Tyr Lys Glu Asp Thr Lys Glu Leu Val
 50                  55                  60
Val Ala Lys Ala Gly Val Tyr Tyr Val Phe Phe Gln Leu Glu Leu Arg
 65                  70                  75                  80
Arg Val Val Ala Gly Glu Gly Ser Gly Ser Val Ser Leu Ala Leu His
                85                  90                  95
Leu Gln Pro Leu Arg Ser Ala Ala Gly Ala Ala Leu Ala Leu Thr
                100                 105                 110
Val Asp Leu Pro Pro Ala Ser Ser Glu Ala Arg Asn Ser Ala Phe Gly
                115                 120                 125
Phe Gln Gly Arg Leu Leu His Leu Ser Ala Gly Gln Arg Leu Gly Val
                130                 135                 140
His Leu His Thr Glu Ala Arg Ala Arg His Ala Trp Gln Leu Thr Gln
145                 150                 155                 160
Gly Ala Thr Val Leu Gly Leu Phe Arg Val Thr Pro Glu Ile Pro Ala
                165                 170                 175
Gly Leu Pro Ser Pro Arg Ser Glu
                180

<210> SEQ ID NO 203
<211> LENGTH: 170
<212> TYPE: PRT
<213> ORGANISM: Homo sapiens

<400> SEQUENCE: 203

Leu Asp Leu Arg Gln Gly Met Phe Ala Gln Leu Val Ala Gln Asn Val
 1               5                   10                  15
Leu Leu Ile Asp Gly Pro Leu Ser Trp Tyr Ser Asp Pro Gly Leu Ala
                20                  25                  30
Gly Val Ser Leu Thr Gly Gly Leu Ser Tyr Lys Glu Asp Thr Lys Glu
                35                  40                  45
Leu Val Val Ala Lys Ala Gly Val Tyr Tyr Val Phe Phe Gln Leu Glu
 50                  55                  60
Leu Arg Arg Val Val Ala Gly Glu Gly Ser Gly Ser Val Ser Leu Ala
 65                  70                  75                  80
Leu His Leu Gln Pro Leu Arg Ser Ala Ala Gly Ala Ala Leu Ala
                85                  90                  95
Leu Thr Val Asp Leu Pro Pro Ala Ser Ser Glu Ala Arg Asn Ser Ala
                100                 105                 110
Phe Gly Phe Gln Gly Arg Leu Leu His Leu Ser Ala Gly Gln Arg Leu
                115                 120                 125
Gly Val His Leu His Thr Glu Ala Arg Ala Arg His Ala Trp Gln Leu
                130                 135                 140
Thr Gln Gly Ala Thr Val Leu Gly Leu Phe Arg Val Thr Pro Glu Ile
145                 150                 155                 160
Pro Ala Gly Leu Pro Ser Pro Arg Ser Glu
                165                 170

<210> SEQ ID NO 204
<211> LENGTH: 175
```

```
<212> TYPE: PRT
<213> ORGANISM: Homo sapiens

<400> SEQUENCE: 204

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
                20                  25                  30

Asp Pro Gly Leu Ala Gly Val Ser Leu Thr Gly Gly Leu Ser Tyr Lys
            35                  40                  45

Glu Asp Thr Lys Glu Leu Val Ala Lys Ala Gly Val Tyr Tyr Val
    50                  55                  60

Phe Phe Gln Leu Glu Leu Arg Arg Val Val Ala Gly Glu Gly Ser Gly
65              70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145             150                 155                 160

Val Thr Pro Glu Ile Pro Ala Gly Leu Pro Ser Pro Arg Ser Glu
                165                 170                 175

<210> SEQ ID NO 205
<211> LENGTH: 203
<212> TYPE: PRT
<213> ORGANISM: Homo sapiens

<400> SEQUENCE: 205

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
                20                  25                  30

Leu Leu Asp Leu Arg Gln Gly Met Phe Ala Gln Leu Val Ala Gln Asn
            35                  40                  45

Val Leu Leu Ile Asp Gly Pro Leu Ser Trp Tyr Ser Asp Pro Gly Leu
    50                  55                  60

Ala Gly Val Ser Leu Thr Gly Gly Leu Ser Tyr Lys Glu Asp Thr Lys
65              70                  75                  80

Glu Leu Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
        115                 120                 125

Ala Leu Thr Val Asp Leu Pro Pro Ala Ser Ser Glu Ala Arg Asn Ser
    130                 135                 140

Ala Phe Gly Phe Gln Gly Arg Leu Leu His Leu Ser Ala Gly Gln Arg
145             150                 155                 160

Leu Gly Val His Leu His Thr Glu Ala Arg Ala Arg His Ala Trp Gln
                165                 170                 175
```

Leu Thr Gln Gly Ala Thr Val Leu Gly Leu Phe Arg Val Thr Pro Glu
        180                 185                 190

Ile Pro Ala Gly Leu Pro Ser Pro Arg Ser Glu
        195                 200

<210> SEQ ID NO 206
<211> LENGTH: 178
<212> TYPE: PRT
<213> ORGANISM: Homo sapiens

<400> SEQUENCE: 206

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu

<210> SEQ ID NO 207
<211> LENGTH: 164
<212> TYPE: PRT
<213> ORGANISM: Homo sapiens

<400> SEQUENCE: 207

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu

```
            115                 120                 125
Gly Val His Leu His Thr Glu Ala Arg Ala Arg His Ala Trp Gln Leu
        130                 135                 140

Thr Gln Gly Ala Thr Val Leu Gly Leu Phe Arg Val Thr Pro Glu Ile
145                 150                 155                 160

Pro Ala Gly Leu

<210> SEQ ID NO 208
<211> LENGTH: 169
<212> TYPE: PRT
<213> ORGANISM: Homo sapiens

<400> SEQUENCE: 208

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu
                165

<210> SEQ ID NO 209
<211> LENGTH: 197
<212> TYPE: PRT
<213> ORGANISM: Homo sapiens

<400> SEQUENCE: 209

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
        35                  40                  45

Val Leu Leu Ile Asp Gly Pro Leu Ser Trp Tyr Ser Asp Pro Gly Leu
    50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110
```

Ala Leu His Leu Gln Pro Leu Arg Ser Ala Gly Ala Ala Leu
            115                 120                 125

Ala Leu Thr Val Asp Leu Pro Pro Ala Ser Ser Glu Ala Arg Asn Ser
            130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu
        195

<210> SEQ ID NO 210
<211> LENGTH: 121
<212> TYPE: PRT
<213> ORGANISM: Artificial Sequence
<220> FEATURE:
<223> OTHER INFORMATION: 41BB sdAb

<400> SEQUENCE: 210

Glu Val Gln Leu Leu Glu Ser Gly Gly Gly Val Gln Pro Gly Gly
1               5                   10                  15

Ser Leu Arg Leu Ser Cys Ala Ser Gly Phe Ser Phe Ser Ile Asn
            20                  25                  30

Ala Met Gly Trp Tyr Arg Gln Ala Pro Gly Lys Arg Arg Glu Phe Val
            35                  40                  45

Ala Ala Ile Glu Ser Gly Arg Asn Thr Val Tyr Ala Glu Ser Val Lys
50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
            115                 120

<210> SEQ ID NO 211
<211> LENGTH: 133
<212> TYPE: PRT
<213> ORGANISM: Artificial Sequence
<220> FEATURE:
<223> OTHER INFORMATION: OX40 ligand

<400> SEQUENCE: 211

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
            35                  40                  45

Gly Phe Tyr Leu Ile Ser Leu Lys Gly Tyr Phe Ser Gln Glu Val Asn
            50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys

```
                85                  90                  95
Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 212
<211> LENGTH: 133
<212> TYPE: PRT
<213> ORGANISM: Artificial Sequence
<220> FEATURE:
<223> OTHER INFORMATION: OX40 ligand

<400> SEQUENCE: 212

Gln Val Ser His Arg Tyr Pro Arg Phe Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 213
<211> LENGTH: 133
<212> TYPE: PRT
<213> ORGANISM: Artificial Sequence
<220> FEATURE:
<223> OTHER INFORMATION: OX40 ligand

<400> SEQUENCE: 213

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110
```

```
Phe His Val Asn Gly Gly Glu Leu Ile Leu Ile His Gln Asn Pro Gly
        115                 120                 125

Glu Phe Cys Val Leu
    130

<210> SEQ ID NO 214
<211> LENGTH: 133
<212> TYPE: PRT
<213> ORGANISM: Artificial Sequence
<220> FEATURE:
<223> OTHER INFORMATION: OX40 ligand

<400> SEQUENCE: 214

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 215
<211> LENGTH: 132
<212> TYPE: PRT
<213> ORGANISM: Artificial Sequence
<220> FEATURE:
<223> OTHER INFORMATION: OX40 ligand

<400> SEQUENCE: 215

Val Ser His Arg Tyr Pro Arg Ile Gln Ser Ile Lys Val Gln Phe Thr
1               5                   10                  15

Glu Tyr Lys Lys Glu Lys Gly Phe Ile Leu Thr Ser Gln Lys Glu Asp
            20                  25                  30

Glu Ile Met Lys Val Gln Asn Asn Ser Val Ile Ile Asn Cys Asp Gly
        35                  40                  45

Phe Tyr Leu Ile Ser Leu Lys Gly Tyr Phe Ser Gln Glu Val Asn Ile
    50                  55                  60

Ser Leu His Tyr Gln Lys Asp Glu Glu Pro Leu Phe Gln Leu Lys Lys
65                  70                  75                  80

Val Arg Ser Val Asn Ser Leu Met Val Ala Ser Leu Thr Tyr Lys Asp
                85                  90                  95

Lys Val Tyr Leu Asn Val Thr Thr Asp Asn Thr Ser Leu Asp Asp Phe
            100                 105                 110

His Val Asn Gly Gly Glu Leu Ile Leu Ile His Gln Asn Pro Gly Glu
        115                 120                 125

Phe Cys Val Leu
    130
```

<210> SEQ ID NO 216
<211> LENGTH: 117
<212> TYPE: PRT
<213> ORGANISM: Artificial Sequence
<220> FEATURE:
<223> OTHER INFORMATION: OX40 VH

<400> SEQUENCE: 216

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115
```

<210> SEQ ID NO 217
<211> LENGTH: 109
<212> TYPE: PRT
<213> ORGANISM: Artificial Sequence
<220> FEATURE:
<223> OTHER INFORMATION: OX40 VL

<400> SEQUENCE: 217

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg Thr
            100                 105
```

<210> SEQ ID NO 218
<211> LENGTH: 121
<212> TYPE: PRT
<213> ORGANISM: Artificial Sequence
<220> FEATURE:
<223> OTHER INFORMATION: OX40 VH

<400> SEQUENCE: 218

```
Glu Val Gln Leu Val Glu Ser Gly Gly Gly Leu Val Gln Pro Gly Gly
1               5                   10                  15
```

```
Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
            35                  40                  45

Gly Arg Ile Arg Ser Lys Ala Asn Ser Tyr Ala Thr Ala Tyr Ala Ala
 50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Ser Gly Ile Tyr Asp Ser Ser Gly Tyr Asp Tyr Trp Gly
                100                 105                 110

Gln Gly Thr Leu Val Thr Val Ser Ser
            115                 120

<210> SEQ ID NO 219
<211> LENGTH: 112
<212> TYPE: PRT
<213> ORGANISM: Artificial Sequence
<220> FEATURE:
<223> OTHER INFORMATION: OX40 VL

<400> SEQUENCE: 219

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
                100                 105                 110

<210> SEQ ID NO 220
<211> LENGTH: 115
<212> TYPE: PRT
<213> ORGANISM: Artificial Sequence
<220> FEATURE:
<223> OTHER INFORMATION: OX40 sdAb

<400> SEQUENCE: 220

Glu Val Gln Leu Leu Glu Ser Gly Gly Gly Val Gln Pro Gly Gly
1               5                   10                  15

Ser Leu Arg Leu Ser Cys Ala Ala Ser Gly Phe Thr Phe Ser Asp Ala
            20                  25                  30

Phe Met Tyr Trp Val Arg Gln Ala Pro Gly Lys Gly Leu Glu Trp Val
            35                  40                  45

Ser Ser Ile Ser Asn Arg Gly Leu Lys Thr Ala Tyr Ala Glu Ser Val
 50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95
```

-continued

Ser Arg Asp Val Asp Gly Asp Phe Arg Gly Gln Gly Thr Leu Val Thr
            100                 105                 110

Val Lys Pro
        115

<210> SEQ ID NO 221
<211> LENGTH: 128
<212> TYPE: PRT
<213> ORGANISM: Artificial Sequence
<220> FEATURE:
<223> OTHER INFORMATION: GITR ligand

<400> SEQUENCE: 221

Gln Leu Glu Thr Ala Lys Glu Pro Cys Met Ala Lys Phe Gly Pro Leu
1               5                   10                  15

Pro Ser Lys Trp Gln Met Ala Ser Glu Pro Cys Val Asn Lys
            20                  25                  30

Val Ser Asp Trp Lys Leu Glu Ile Leu Gln Asn Gly Leu Tyr Leu Ile
            35                  40                  45

Tyr Gly Gln Val Ala Pro Asn Ala Asn Tyr Asn Asp Val Ala Pro Phe
    50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                85                  90                  95

Asp Thr Ile Asp Leu Ile Phe Asn Ser Glu His Gln Val Leu Lys Asn
            100                 105                 110

Asn Thr Tyr Trp Gly Ile Ile Leu Leu Ala Asn Pro Gln Phe Ile Ser
        115                 120                 125

<210> SEQ ID NO 222
<211> LENGTH: 118
<212> TYPE: PRT
<213> ORGANISM: Artificial Sequence
<220> FEATURE:
<223> OTHER INFORMATION: GITR VH

<400> SEQUENCE: 222

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Thr Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Gly Gly Tyr Tyr Asp Ser Met Asp Tyr Trp Gly Gln Gly Thr
            100                 105                 110

Leu Val Thr Val Ser Ser
        115

<210> SEQ ID NO 223
<211> LENGTH: 111
<212> TYPE: PRT

<213> ORGANISM: Artificial Sequence
<220> FEATURE:
<223> OTHER INFORMATION: GITR VL

<400> SEQUENCE: 223

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Val Ser Phe Met Asn Trp Tyr Gln Gln Lys Pro Gly Gln Ala Pro
        35                  40                  45

Arg Leu Leu Ile Tyr Ala Ala Ser Asn Gln Gly Ser Gly Ile Pro Asp
50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Thr Lys
                85                  90                  95

Glu Val Thr Trp Thr Phe Gly Gln Gly Thr Lys Val Glu Ile Lys
            100                 105                 110

<210> SEQ ID NO 224
<211> LENGTH: 119
<212> TYPE: PRT
<213> ORGANISM: Artificial Sequence
<220> FEATURE:
<223> OTHER INFORMATION: GITR VH

<400> SEQUENCE: 224

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Gln Pro Ser
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser Ser
        115

<210> SEQ ID NO 225
<211> LENGTH: 107
<212> TYPE: PRT
<213> ORGANISM: Artificial Sequence
<220> FEATURE:
<223> OTHER INFORMATION: GITR VL

<400> SEQUENCE: 225

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Gly Thr Asn
            20                  25                  30

Val Ala Trp Tyr Gln Gln Lys Pro Gly Gln Ala Pro Arg Leu Leu Ile
        35                  40                  45

```
Tyr Ser Ala Ser Tyr Arg Tyr Ser Gly Ile Pro Ala Arg Phe Ser Gly
        50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Thr Asp Pro Leu
                85                  90                  95

Thr Phe Gly Gly Gly Thr Lys Val Glu Ile Lys
                100                 105

<210> SEQ ID NO 226
<211> LENGTH: 125
<212> TYPE: PRT
<213> ORGANISM: Artificial Sequence
<220> FEATURE:
<223> OTHER INFORMATION: GITR VH

<400> SEQUENCE: 226

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Gly
                20                  25                  30

Gly Tyr Phe Trp Ser Trp Ile Arg Gln Pro Pro Gly Lys Gly Leu Glu
            35                  40                  45

Trp Ile Gly Tyr Ile Tyr Tyr Ser Gly Thr Thr Tyr Tyr Asn Pro Ser
 50                  55                  60

Leu Lys Ser Arg Val Thr Ile Ser Ile Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Asp Leu Phe Tyr Tyr Asp Thr Ser Gly Pro Arg Gly Phe
            100                 105                 110

Asp Pro Trp Gly Gln Gly Thr Leu Val Thr Val Ser Ser
        115                 120                 125

<210> SEQ ID NO 227
<211> LENGTH: 108
<212> TYPE: PRT
<213> ORGANISM: Artificial Sequence
<220> FEATURE:
<223> OTHER INFORMATION: GITR VL

<400> SEQUENCE: 227

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Thr Val Ser Ser Asn
                20                  25                  30

Tyr Leu Ala Trp Tyr Gln Gln Lys Pro Gly Gln Ala Pro Arg Leu Leu
            35                  40                  45

Ile Tyr Gly Ser Ser Thr Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Asp Ser Ser Pro
                85                  90                  95

Trp Thr Phe Gly Gln Gly Thr Lys Val Glu Ile Lys
            100                 105
```

```
<210> SEQ ID NO 228
<211> LENGTH: 123
<212> TYPE: PRT
<213> ORGANISM: Artificial Sequence
<220> FEATURE:
<223> OTHER INFORMATION: GITR VH

<400> SEQUENCE: 228

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Pro Gly Ser Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Leu Gly Arg Tyr Tyr Tyr Tyr Gly Met Asp Val
            100                 105                 110

Trp Gly Gln Gly Thr Thr Val Thr Val Ser Ser
        115                 120

<210> SEQ ID NO 229
<211> LENGTH: 107
<212> TYPE: PRT
<213> ORGANISM: Artificial Sequence
<220> FEATURE:
<223> OTHER INFORMATION: GITR VL

<400> SEQUENCE: 229

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Trp
                85                  90                  95

Thr Phe Gly Gln Gly Thr Lys Val Asp Ile Lys
            100                 105

<210> SEQ ID NO 230
<211> LENGTH: 119
<212> TYPE: PRT
<213> ORGANISM: Artificial Sequence
<220> FEATURE:
<223> OTHER INFORMATION: GITR sdAb

<400> SEQUENCE: 230

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30
```

```
Ala Met Gly Trp Tyr Arg Gln Ala Pro Gly Lys Gln Arg Glu Leu Val
            35                  40                  45

Ala Val Leu Ser Gly Ile Ser Ser Ala Lys Tyr Ala Ala Ser Ala Pro
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
            115
```

```
<210> SEQ ID NO 231
<211> LENGTH: 193
<212> TYPE: PRT
<213> ORGANISM: Homo sapiens

<400> SEQUENCE: 231
```

```
Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro
```

```
<210> SEQ ID NO 232
<211> LENGTH: 119
<212> TYPE: PRT
<213> ORGANISM: Artificial Sequence
<220> FEATURE:
<223> OTHER INFORMATION: CD70 VH

<400> SEQUENCE: 232
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

```
                    20                  25                  30
Asp Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Ser Gly Asn Trp Gly Phe Phe Asp Tyr Trp Gly Gln Gly
            100                 105                 110

Thr Leu Val Thr Val Ser Ser
            115

<210> SEQ ID NO 233
<211> LENGTH: 107
<212> TYPE: PRT
<213> ORGANISM: Artificial Sequence
<220> FEATURE:
<223> OTHER INFORMATION: CD70 VL

<400> SEQUENCE: 233

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Arg Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Thr Tyr Pro Arg
                85                  90                  95

Thr Phe Gly Gln Gly Thr Lys Val Glu Ile Lys
            100                 105

<210> SEQ ID NO 234
<211> LENGTH: 124
<212> TYPE: PRT
<213> ORGANISM: Artificial Sequence
<220> FEATURE:
<223> OTHER INFORMATION: ICOS sdAb

<400> SEQUENCE: 234

Gln Val Gln Leu Gln Gln Ser Gly Gly Gly Leu Val Gln Pro Gly Gly
 1               5                  10                  15

Ser Leu Arg Leu Ser Cys Ala Ala Ser Gly Ser Ile Phe Ser Ile Asn
            20                  25                  30

Gly Met Gly Trp Tyr Arg Gln Ala Pro Gly Lys Glu Arg Glu Leu Val
        35                  40                  45

Ala Gly Leu Thr Ser Gly Gly Ser Val Thr Asn Tyr Ala Asp Ser Val
    50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95
```

```
Arg Ala Glu Ile Phe Thr Arg Thr Gly Glu Asn Tyr Tyr Gly Met Asp
                100                 105                 110

Tyr Trp Gly Lys Gly Thr Gln Val Thr Val Lys Pro
        115                 120

<210> SEQ ID NO 235
<211> LENGTH: 124
<212> TYPE: PRT
<213> ORGANISM: Artificial Sequence
<220> FEATURE:
<223> OTHER INFORMATION: CD28 sdAb

<400> SEQUENCE: 235

Glu Val Gln Leu Val Glu Ser Gly Gly Gly Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ala Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
                100                 105                 110

Tyr Trp Gly Gln Gly Thr Leu Val Thr Val Lys Pro
        115                 120

<210> SEQ ID NO 236
<211> LENGTH: 112
<212> TYPE: PRT
<213> ORGANISM: Artificial Sequence
<220> FEATURE:
<223> OTHER INFORMATION: CD3zeta signaling domain

<400> SEQUENCE: 236

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 237
<211> LENGTH: 42
<212> TYPE: PRT
<213> ORGANISM: Artificial Sequence
<220> FEATURE:
<223> OTHER INFORMATION: 4-1BB-derived costimulatory domain
```

-continued

```
<400> SEQUENCE: 237

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 238
<211> LENGTH: 40
<212> TYPE: PRT
<213> ORGANISM: Artificial Sequence
<220> FEATURE:
<223> OTHER INFORMATION: CD28-derived costimulatory domain

<400> SEQUENCE: 238

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 239
<211> LENGTH: 41
<212> TYPE: PRT
<213> ORGANISM: Artificial Sequence
<220> FEATURE:
<223> OTHER INFORMATION: CD28-derived costimulatory domain 2

<400> SEQUENCE: 239

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 240
<211> LENGTH: 44
<212> TYPE: PRT
<213> ORGANISM: Artificial Sequence
<220> FEATURE:
<223> OTHER INFORMATION: CD28-derived costimulatory domain 3

<400> SEQUENCE: 240

Phe Trp Val Arg Ser Lys Arg Ser Arg Leu Leu His Ser Asp Tyr Met
1               5                   10                  15

Asn Met Thr Pro Arg Arg Pro Gly Pro Thr Arg Lys His Tyr Gln Pro
            20                  25                  30

Tyr Ala Pro Pro Arg Asp Phe Ala Ala Tyr Arg Ser
        35                  40

<210> SEQ ID NO 241
<211> LENGTH: 71
<212> TYPE: PRT
<213> ORGANISM: Artificial Sequence
<220> FEATURE:
<223> OTHER INFORMATION: CD8-derived hinge and transmembrane domain

<400> SEQUENCE: 241

Lys Pro Thr Thr Thr Pro Ala Pro Arg Pro Pro Thr Pro Ala Pro Thr
```

```
                  1               5                  10                  15
Ile Ala Ser Gln Pro Leu Ser Leu Arg Pro Glu Ala Ser Arg Pro Ala
              20                  25                  30

Ala Gly Gly Ala Val His Thr Arg Gly Leu Asp Phe Ala Ser Asp Ile
          35                  40                  45

Tyr Ile Trp Ala Pro Leu Ala Gly Thr Cys Gly Val Leu Leu Leu Ser
 50                  55                  60

Leu Val Ile Thr Leu Tyr Cys
 65                  70
```

<210> SEQ ID NO 242
<211> LENGTH: 69
<212> TYPE: PRT
<213> ORGANISM: Artificial Sequence
<220> FEATURE:
<223> OTHER INFORMATION: CD8-derived hinge and transmembrane domain

<400> SEQUENCE: 242

```
Ala Lys Pro Thr Thr Thr Pro Ala Pro Arg Pro Pro Thr Pro Ala Pro
 1               5                  10                  15

Thr Ile Ala Ser Gln Pro Leu Ser Leu Arg Pro Glu Ala Cys Arg Pro
              20                  25                  30

Ala Ala Gly Gly Ala Val His Thr Arg Gly Leu Asp Phe Ala Cys Asp
          35                  40                  45

Ile Tyr Ile Trp Ala Pro Leu Ala Gly Thr Cys Gly Val Leu Leu Leu
 50                  55                  60

Ser Leu Val Ile Thr
 65
```

<210> SEQ ID NO 243
<211> LENGTH: 68
<212> TYPE: PRT
<213> ORGANISM: Artificial Sequence
<220> FEATURE:
<223> OTHER INFORMATION: CD8 hinge and transmembrane domain

<400> SEQUENCE: 243

```
Lys Pro Thr Thr Thr Pro Ala Pro Arg Pro Pro Thr Pro Ala Pro Thr
 1               5                  10                  15

Ile Ala Ser Gln Pro Leu Ser Leu Arg Pro Glu Ala Cys Arg Pro Ala
              20                  25                  30

Ala Gly Gly Ala Val His Thr Arg Gly Leu Asp Phe Ala Cys Asp Ile
          35                  40                  45

Tyr Ile Trp Ala Pro Leu Ala Gly Thr Cys Gly Val Leu Leu Leu Ser
 50                  55                  60

Leu Val Ile Thr
 65
```

<210> SEQ ID NO 244
<211> LENGTH: 6
<212> TYPE: PRT
<213> ORGANISM: Artificial Sequence
<220> FEATURE:
<223> OTHER INFORMATION: (GGS)2 linker

<400> SEQUENCE: 244

```
Gly Gly Ser Gly Gly Ser
 1               5
```

<210> SEQ ID NO 245

```
<211> LENGTH: 9
<212> TYPE: PRT
<213> ORGANISM: Artificial Sequence
<220> FEATURE:
<223> OTHER INFORMATION: (GGS)3 linker

<400> SEQUENCE: 245

Gly Gly Ser Gly Gly Ser Gly Gly Ser
1               5

<210> SEQ ID NO 246
<211> LENGTH: 12
<212> TYPE: PRT
<213> ORGANISM: Artificial Sequence
<220> FEATURE:
<223> OTHER INFORMATION: (GGS)4 linker

<400> SEQUENCE: 246

Gly Gly Ser Gly Gly Ser Gly Gly Ser Gly Gly Ser
1               5                   10

<210> SEQ ID NO 247
<211> LENGTH: 15
<212> TYPE: PRT
<213> ORGANISM: Artificial Sequence
<220> FEATURE:
<223> OTHER INFORMATION: (GGS)5 linker

<400> SEQUENCE: 247

Gly Gly Ser Gly Gly Ser Gly Gly Ser Gly Gly Ser Gly Gly Ser
1               5                   10                  15

<210> SEQ ID NO 248
<211> LENGTH: 4
<212> TYPE: PRT
<213> ORGANISM: Artificial Sequence
<220> FEATURE:
<223> OTHER INFORMATION: glycine linker

<400> SEQUENCE: 248

Gly Gly Gly Gly
1

<210> SEQ ID NO 249
<211> LENGTH: 5
<212> TYPE: PRT
<213> ORGANISM: Artificial Sequence
<220> FEATURE:
<223> OTHER INFORMATION: glycine linker

<400> SEQUENCE: 249

Gly Gly Gly Gly Gly
1               5

<210> SEQ ID NO 250
<211> LENGTH: 6
<212> TYPE: PRT
<213> ORGANISM: Artificial Sequence
<220> FEATURE:
<223> OTHER INFORMATION: (GGS)2 linker

<400> SEQUENCE: 250

Gly Gly Ser Gly Gly Ser
1               5

<210> SEQ ID NO 251
<211> LENGTH: 115
```

```
<212> TYPE: PRT
<213> ORGANISM: Artificial Sequence
<220> FEATURE:
<223> OTHER INFORMATION: hz18H10v1

<400> SEQUENCE: 251

Glu Val Gln Leu Val Glu Ser Gly Gly Gly Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gly Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro
        115

<210> SEQ ID NO 252
<211> LENGTH: 115
<212> TYPE: PRT
<213> ORGANISM: Artificial Sequence
<220> FEATURE:
<223> OTHER INFORMATION: hz18H10v2

<400> SEQUENCE: 252

Glu Val Gln Leu Val Glu Ser Gly Gly Gly Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro
        115

<210> SEQ ID NO 253
<211> LENGTH: 115
<212> TYPE: PRT
<213> ORGANISM: Artificial Sequence
<220> FEATURE:
<223> OTHER INFORMATION: hz18H10v3

<400> SEQUENCE: 253

Glu Val Gln Leu Val Glu Ser Gly Gly Gly Val Gln Pro Gly Gly
1               5                   10                  15

Ser Leu Arg Leu Ser Cys Ala Ala Ser Gly Ser Met Thr Gly Ala Asn
```

```
                 20                  25                  30
Thr Met Gly Trp Tyr Arg Gln Ala Pro Gly Lys Gln Arg Asp Leu Val
            35                  40                  45

Ser Leu Ile Gly Asn Tyr Val Thr His Tyr Ala Glu Ser Val Lys Gly
 50                  55                  60

Arg Phe Thr Ile Ser Arg Asp Asn Ala Lys Asn Thr Val Tyr Leu Gln
 65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro
        115

<210> SEQ ID NO 254
<211> LENGTH: 115
<212> TYPE: PRT
<213> ORGANISM: Artificial Sequence
<220> FEATURE:
<223> OTHER INFORMATION: hz18H10v4

<400> SEQUENCE: 254

Glu Val Gln Leu Val Glu Ser Gly Gly Gly Glu Val Gln Pro Gly Gly
 1               5                  10                  15

Ser Leu Arg Leu Ser Cys Ala Ala Ser Gly Ser Met Thr Gly Ala Asn
                20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
 50                  55                  60

Arg Phe Thr Ile Ser Arg Asp Asn Ala Lys Asn Thr Val Tyr Leu Gln
 65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro
        115

<210> SEQ ID NO 255
<211> LENGTH: 115
<212> TYPE: PRT
<213> ORGANISM: Artificial Sequence
<220> FEATURE:
<223> OTHER INFORMATION: hz18H10v5

<400> SEQUENCE: 255

Glu Val Gln Leu Val Glu Ser Gly Gly Gly Glu Val Gln Pro Gly Gly
 1               5                  10                  15

Ser Leu Arg Leu Ser Cys Ala Ala Ser Gly Ser Met Thr Gly Ala Asn
                20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
 50                  55                  60

Arg Phe Thr Ile Ser Arg Glu Asn Ala Lys Asn Thr Val Tyr Leu Gln
 65                  70                  75                  80
```

```
Met Ser Ser Leu Arg Ala Glu Asp Thr Ala Val Tyr Tyr Cys Tyr Leu
             85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 256
<211> LENGTH: 115
<212> TYPE: PRT
<213> ORGANISM: Artificial Sequence
<220> FEATURE:
<223> OTHER INFORMATION: hz18H10v6

<400> SEQUENCE: 256

Glu Val Gln Leu Val Glu Ser Gly Gly Gly Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
             85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 257
<211> LENGTH: 115
<212> TYPE: PRT
<213> ORGANISM: Artificial Sequence
<220> FEATURE:
<223> OTHER INFORMATION: hz18H10v7

<400> SEQUENCE: 257

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
             85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 258
```

```
<211> LENGTH: 115
<212> TYPE: PRT
<213> ORGANISM: Artificial Sequence
<220> FEATURE:
<223> OTHER INFORMATION: hz18H10v8

<400> SEQUENCE: 258

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 259
<211> LENGTH: 115
<212> TYPE: PRT
<213> ORGANISM: Artificial Sequence
<220> FEATURE:
<223> OTHER INFORMATION: hz18H10v9

<400> SEQUENCE: 259

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 260
<211> LENGTH: 115
<212> TYPE: PRT
<213> ORGANISM: Artificial Sequence
<220> FEATURE:
<223> OTHER INFORMATION: hz18H10v10

<400> SEQUENCE: 260

Glu Val Gln Leu Val Glu Ser Gly Gly Gly Glu Val Gln Pro Gly Gly
1               5                   10                  15
```

```
Ser Leu Arg Leu Ser Cys Ala Ala Ser Gly Ser Met Thr Gly Ala Asn
             20                  25                  30

Thr Met Gly Trp Tyr Arg Gln Ala Pro Gly Lys Gln Arg Asp Leu Val
         35                  40                  45

Ser Leu Ile Gly Asn Tyr Val Thr His Tyr Ala Glu Ser Val Lys Gly
     50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 261
<211> LENGTH: 115
<212> TYPE: PRT
<213> ORGANISM: Artificial Sequence
<220> FEATURE:
<223> OTHER INFORMATION: hz18H10v11

<400> SEQUENCE: 261

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
             20                  25                  30

Thr Met Gly Trp Tyr Arg Gln Ala Pro Gly Lys Gln Arg Asp Leu Val
         35                  40                  45

Ser Leu Ile Gly Asn Tyr Val Thr His Tyr Ala Glu Ser Val Lys Gly
     50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 262
<211> LENGTH: 115
<212> TYPE: PRT
<213> ORGANISM: Artificial Sequence
<220> FEATURE:
<223> OTHER INFORMATION: hz18H10v12

<400> SEQUENCE: 262

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
             20                  25                  30

Thr Met Gly Trp Tyr Arg Gln Ala Pro Gly Lys Gln Arg Asp Leu Val
         35                  40                  45

Ala Leu Ile Gly Asn Tyr Val Thr His Tyr Ala Glu Ser Val Lys Gly
     50                  55                  60

Arg Phe Thr Ile Ser Arg Glu Asn Ala Lys Asn Thr Val Tyr Leu Gln
65                  70                  75                  80
```

```
Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 263
<211> LENGTH: 115
<212> TYPE: PRT
<213> ORGANISM: Artificial Sequence
<220> FEATURE:
<223> OTHER INFORMATION: hz18H10v13

<400> SEQUENCE: 263

Glu Val Gln Leu Val Glu Ser Gly Gly Gly Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Glu Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 264
<211> LENGTH: 115
<212> TYPE: PRT
<213> ORGANISM: Artificial Sequence
<220> FEATURE:
<223> OTHER INFORMATION: hz18H10v14

<400> SEQUENCE: 264

Glu Val Gln Leu Val Glu Ser Gly Gly Gly Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115
```

```
<210> SEQ ID NO 265
<211> LENGTH: 115
<212> TYPE: PRT
<213> ORGANISM: Artificial Sequence
<220> FEATURE:
<223> OTHER INFORMATION: hz18H10v15

<400> SEQUENCE: 265
```

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

```
<210> SEQ ID NO 266
<211> LENGTH: 115
<212> TYPE: PRT
<213> ORGANISM: Artificial Sequence
<220> FEATURE:
<223> OTHER INFORMATION: hz18H10v16

<400> SEQUENCE: 266
```

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

```
<210> SEQ ID NO 267
<211> LENGTH: 115
<212> TYPE: PRT
<213> ORGANISM: Artificial Sequence
<220> FEATURE:
<223> OTHER INFORMATION: hz18H10v17

<400> SEQUENCE: 267
```

Glu Val Gln Leu Val Glu Ser Gly Gly Gly Glu Val Gln Pro Gly Gly
1               5                   10                  15

-continued

```
Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Asn Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 268
<211> LENGTH: 10
<212> TYPE: PRT
<213> ORGANISM: Artificial Sequence
<220> FEATURE:
<223> OTHER INFORMATION: CDR1

<400> SEQUENCE: 268

Gly Ser Met Thr Gly Ala Asn Thr Met Gly
1               5                   10

<210> SEQ ID NO 269
<211> LENGTH: 9
<212> TYPE: PRT
<213> ORGANISM: Artificial Sequence
<220> FEATURE:
<223> OTHER INFORMATION: (GGS)3 linker

<400> SEQUENCE: 269

Gly Gly Ser Gly Gly Ser Gly Gly Ser
1               5

<210> SEQ ID NO 270
<211> LENGTH: 12
<212> TYPE: PRT
<213> ORGANISM: Artificial Sequence
<220> FEATURE:
<223> OTHER INFORMATION: (GGS)4 linker

<400> SEQUENCE: 270

Gly Gly Ser Gly Gly Ser Gly Gly Ser Gly Gly Ser
1               5                   10

<210> SEQ ID NO 271
<211> LENGTH: 15
<212> TYPE: PRT
<213> ORGANISM: Artificial Sequence
<220> FEATURE:
<223> OTHER INFORMATION: (GGS)5 linker

<400> SEQUENCE: 271

Gly Gly Ser Gly Gly Ser Gly Gly Ser Gly Gly Ser Gly Gly Ser
1               5                   10                  15

<210> SEQ ID NO 272
<211> LENGTH: 10
<212> TYPE: PRT
<213> ORGANISM: Artificial Sequence
```

```
<220> FEATURE:
<223> OTHER INFORMATION: CDR1

<400> SEQUENCE: 272

Gly Ser Val Thr Gly Ala Asn Thr Met Gly
1               5                   10

<210> SEQ ID NO 273
<211> LENGTH: 10
<212> TYPE: PRT
<213> ORGANISM: Artificial Sequence
<220> FEATURE:
<223> OTHER INFORMATION: CDR1

<400> SEQUENCE: 273

Gly Ser Ile Thr Gly Ala Asn Thr Met Gly
1               5                   10

<210> SEQ ID NO 274
<211> LENGTH: 6
<212> TYPE: PRT
<213> ORGANISM: Artificial Sequence
<220> FEATURE:
<223> OTHER INFORMATION: (GGS)2 linker

<400> SEQUENCE: 274

Gly Gly Ser Gly Gly Ser
1               5

<210> SEQ ID NO 275
<211> LENGTH: 9
<212> TYPE: PRT
<213> ORGANISM: Artificial Sequence
<220> FEATURE:
<223> OTHER INFORMATION: (GGS)3 linker

<400> SEQUENCE: 275

Gly Gly Ser Gly Gly Ser Gly Gly Ser
1               5

<210> SEQ ID NO 276
<211> LENGTH: 12
<212> TYPE: PRT
<213> ORGANISM: Artificial Sequence
<220> FEATURE:
<223> OTHER INFORMATION: (GGS)4 linker

<400> SEQUENCE: 276

Gly Gly Ser Gly Gly Ser Gly Gly Ser Gly Gly Ser
1               5                   10

<210> SEQ ID NO 277
<211> LENGTH: 15
<212> TYPE: PRT
<213> ORGANISM: Artificial Sequence
<220> FEATURE:
<223> OTHER INFORMATION: (GGS)5 linker

<400> SEQUENCE: 277

Gly Gly Ser Gly Gly Ser Gly Gly Ser Gly Gly Ser Gly Gly Ser
1               5                   10                  15

<210> SEQ ID NO 278
<211> LENGTH: 8
<212> TYPE: PRT
<213> ORGANISM: Artificial Sequence
<220> FEATURE:
```

```
<223> OTHER INFORMATION: CDR2

<400> SEQUENCE: 278

Leu Ile Gly Asn Tyr Val Thr His
1               5

<210> SEQ ID NO 279
<211> LENGTH: 6
<212> TYPE: PRT
<213> ORGANISM: Artificial Sequence
<220> FEATURE:
<223> OTHER INFORMATION: (GGS)2 linker

<400> SEQUENCE: 279

Gly Gly Ser Gly Gly Ser
1               5

<210> SEQ ID NO 280
<211> LENGTH: 9
<212> TYPE: PRT
<213> ORGANISM: Artificial Sequence
<220> FEATURE:
<223> OTHER INFORMATION: (GGS)3 linker

<400> SEQUENCE: 280

Gly Gly Ser Gly Gly Ser Gly Gly Ser
1               5

<210> SEQ ID NO 281
<211> LENGTH: 12
<212> TYPE: PRT
<213> ORGANISM: Artificial Sequence
<220> FEATURE:
<223> OTHER INFORMATION: (GGS)4 linker

<400> SEQUENCE: 281

Gly Gly Ser Gly Gly Ser Gly Gly Ser Gly Gly Ser
1               5                   10

<210> SEQ ID NO 282
<211> LENGTH: 15
<212> TYPE: PRT
<213> ORGANISM: Artificial Sequence
<220> FEATURE:
<223> OTHER INFORMATION: (GGS)5 linker

<400> SEQUENCE: 282

Gly Gly Ser Gly Gly Ser Gly Gly Ser Gly Gly Ser Gly Gly Ser
1               5                   10                  15

<210> SEQ ID NO 283
<211> LENGTH: 8
<212> TYPE: PRT
<213> ORGANISM: Artificial Sequence
<220> FEATURE:
<223> OTHER INFORMATION: CDR3

<400> SEQUENCE: 283

Tyr Thr Asp Asn Leu Gly Thr Ser
1               5

<210> SEQ ID NO 284
<211> LENGTH: 113
<212> TYPE: PRT
<213> ORGANISM: Artificial Sequence
<220> FEATURE:
<223> OTHER INFORMATION: 18H10
```

<400> SEQUENCE: 284

| Gln | Val | Gln | Leu | Val | Gln | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Val | Ala | Ser | Gly | Ser | Met | Thr | Gly | Ala | Asn |
| | | | 20 | | | | | 25 | | | | | 30 | | |

| Thr | Met | Gly | Trp | Tyr | Arg | Gln | Ala | Pro | Gly | Lys | Gln | Arg | Asp | Leu | Val |
| | | | 35 | | | | | 40 | | | | | 45 | | |

| Ala | Leu | Ile | Gly | Asn | Tyr | His | Tyr | Ala | Asp | Ser | Val | Lys | Gly | Arg | Phe |
| | 50 | | | | | 55 | | | | | 60 | | | | |

| Thr | Ile | Ser | Arg | Glu | Asn | Ala | Lys | Asn | Thr | Val | Ile | Leu | Gln | Met | Asn |
| 65 | | | | | 70 | | | | | 75 | | | | | 80 |

| Ser | Leu | Asn | Pro | Glu | Asp | Thr | Ala | Val | Tyr | Tyr | Cys | Tyr | Leu | Tyr | Thr |
| | | | | 85 | | | | | 90 | | | | | 95 | |

| Asp | Asn | Leu | Gly | Thr | Ser | Trp | Gly | Gln | Gly | Thr | Leu | Val | Thr | Val | Lys |
| | | | 100 | | | | | 105 | | | | | 110 | | |

Pro

<210> SEQ ID NO 285
<211> LENGTH: 109
<212> TYPE: PRT
<213> ORGANISM: Artificial Sequence
<220> FEATURE:
<223> OTHER INFORMATION: anti-CD3 VL (CON)

<400> SEQUENCE: 285

| Gln | Ala | Val | Val | Thr | Gln | Glu | Pro | Ser | Leu | Thr | Val | Ser | Pro | Gly | Gly |
|---|---|---|---|---|---|---|---|---|---|---|---|---|---|---|---|
| 1 | | | | 5 | | | | | 10 | | | | | 15 | |

| Thr | Val | Thr | Leu | Thr | Cys | Gly | Ser | Ser | Thr | Gly | Ala | Val | Thr | Thr | Ser |
| | | | 20 | | | | | 25 | | | | | 30 | | |

| Asn | Tyr | Ala | Asn | Trp | Val | Gln | Gln | Lys | Pro | Gly | Gln | Ala | Phe | Arg | Gly |
| | | | 35 | | | | | 40 | | | | | 45 | | |

| Leu | Ile | Gly | Gly | Thr | Asn | Lys | Arg | Ala | Pro | Gly | Val | Pro | Ala | Arg | Phe |
| | 50 | | | | | 55 | | | | | 60 | | | | |

| Ser | Gly | Ser | Leu | Leu | Gly | Gly | Lys | Ala | Ala | Leu | Thr | Ile | Ser | Gly | Ala |
| 65 | | | | | 70 | | | | | 75 | | | | | 80 |

| Gln | Pro | Glu | Asp | Glu | Ala | Asp | Tyr | Tyr | Cys | Ala | Leu | Trp | Tyr | Ser | Asn |
| | | | | 85 | | | | | 90 | | | | | 95 | |

| His | Trp | Val | Phe | Gly | Cys | Gly | Thr | Lys | Leu | Thr | Val | Leu |
| | | | 100 | | | | | 105 | | | | |

<210> SEQ ID NO 286
<211> LENGTH: 288
<212> TYPE: PRT
<213> ORGANISM: Artificial Sequence
<220> FEATURE:
<223> OTHER INFORMATION: Homo sapiens

<400> SEQUENCE: 286

| Met | Gln | Ile | Pro | Gln | Ala | Pro | Trp | Pro | Val | Val | Trp | Ala | Val | Leu | Gln |
|---|---|---|---|---|---|---|---|---|---|---|---|---|---|---|---|
| 1 | | | | 5 | | | | | 10 | | | | | 15 | |

| Leu | Gly | Trp | Arg | Pro | Gly | Trp | Phe | Leu | Asp | Ser | Pro | Asp | Arg | Pro | Trp |
| | | | 20 | | | | | 25 | | | | | 30 | | |

| Asn | Pro | Pro | Thr | Phe | Ser | Pro | Ala | Leu | Leu | Val | Val | Thr | Glu | Gly | Asp |
| | | | 35 | | | | | 40 | | | | | 45 | | |

| Asn | Ala | Thr | Phe | Thr | Cys | Ser | Phe | Ser | Asn | Thr | Ser | Glu | Ser | Phe | Val |
| | 50 | | | | | 55 | | | | | 60 | | | | |

```
Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 287
<211> LENGTH: 5
<212> TYPE: PRT
<213> ORGANISM: Artificial Sequence
<220> FEATURE:
<223> OTHER INFORMATION: peptide linker

<400> SEQUENCE: 287

Gly Gly Gly Gly Ala
1               5

<210> SEQ ID NO 288
<211> LENGTH: 4
<212> TYPE: PRT
<213> ORGANISM: Artificial Sequence
<220> FEATURE:
<223> OTHER INFORMATION: peptide linker

<400> SEQUENCE: 288

Gly Gly Gly Ala
1

<210> SEQ ID NO 289
<211> LENGTH: 25
<212> TYPE: PRT
<213> ORGANISM: Artificial Sequence
<220> FEATURE:
<223> OTHER INFORMATION: GS linker
<220> FEATURE:
<221> NAME/KEY: MISC_FEATURE
<222> LOCATION: (6)..(10)
<223> OTHER INFORMATION: May be present or absent
```

<220> FEATURE:
<221> NAME/KEY: MISC_FEATURE
<222> LOCATION: (11)..(15)
<223> OTHER INFORMATION: May be present or absent
<220> FEATURE:
<221> NAME/KEY: MISC_FEATURE
<222> LOCATION: (16)..(20)
<223> OTHER INFORMATION: May be present or absent
<220> FEATURE:
<221> NAME/KEY: MISC_FEATURE
<222> LOCATION: (21)..(25)
<223> OTHER INFORMATION: May be present or absent

<400> SEQUENCE: 289

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 290
<211> LENGTH: 25
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(12)
<223> OTHER INFORMATION: up to 11 amino acids may be absent
<220> FEATURE:
<221> NAME/KEY: MISC_FEATURE
<222> LOCATION: (14)..(25)
<223> OTHER INFORMATION: up to 11 amino acids may be absent

<400> SEQUENCE: 290

Gly Gly Gly Gly Gly Gly Gly Gly Gly Gly Gly Cys Gly Gly Gly
1               5                   10                  15

Gly Gly Gly Gly Gly Gly Gly Gly Gly
            20                  25

<210> SEQ ID NO 291
<211> LENGTH: 40
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(6)
<223> OTHER INFORMATION: May be present or absent
<220> FEATURE:
<221> NAME/KEY: MISC_FEATURE
<222> LOCATION: (7)..(8)
<223> OTHER INFORMATION: May be present or absent
<220> FEATURE:
<221> NAME/KEY: MISC_FEATURE
<222> LOCATION: (9)..(10)
<223> OTHER INFORMATION: May be present or absent
<220> FEATURE:
<221> NAME/KEY: MISC_FEATURE
<222> LOCATION: (11)..(12)
<223> OTHER INFORMATION: May be present or absent
<220> FEATURE:
<221> NAME/KEY: MISC_FEATURE
<222> LOCATION: (13)..(14)
<223> OTHER INFORMATION: May be present or absent
<220> FEATURE:
<221> NAME/KEY: MISC_FEATURE
<222> LOCATION: (15)..(16)
<223> OTHER INFORMATION: May be present or absent
<220> FEATURE:
<221> NAME/KEY: MISC_FEATURE
<222> LOCATION: (17)..(18)

<223> OTHER INFORMATION: May be present or absent
<220> FEATURE:
<221> NAME/KEY: MISC_FEATURE
<222> LOCATION: (19)..(20)
<223> OTHER INFORMATION: May be present or absent
<220> FEATURE:
<221> NAME/KEY: MISC_FEATURE
<222> LOCATION: (21)..(22)
<223> OTHER INFORMATION: May be present or absent
<220> FEATURE:
<221> NAME/KEY: MISC_FEATURE
<222> LOCATION: (23)..(24)
<223> OTHER INFORMATION: May be present or absent
<220> FEATURE:
<221> NAME/KEY: MISC_FEATURE
<222> LOCATION: (25)..(26)
<223> OTHER INFORMATION: May be present or absent
<220> FEATURE:
<221> NAME/KEY: MISC_FEATURE
<222> LOCATION: (27)..(28)
<223> OTHER INFORMATION: May be present or absent
<220> FEATURE:
<221> NAME/KEY: MISC_FEATURE
<222> LOCATION: (29)..(30)
<223> OTHER INFORMATION: May be present or absent
<220> FEATURE:
<221> NAME/KEY: MISC_FEATURE
<222> LOCATION: (31)..(32)
<223> OTHER INFORMATION: May be present or absent
<220> FEATURE:
<221> NAME/KEY: MISC_FEATURE
<222> LOCATION: (33)..(34)
<223> OTHER INFORMATION: May be present or absent
<220> FEATURE:
<221> NAME/KEY: MISC_FEATURE
<222> LOCATION: (35)..(36)
<223> OTHER INFORMATION: May be present or absent
<220> FEATURE:
<221> NAME/KEY: MISC_FEATURE
<222> LOCATION: (37)..(38)
<223> OTHER INFORMATION: May be present or absent
<220> FEATURE:
<221> NAME/KEY: MISC_FEATURE
<222> LOCATION: (39)..(40)
<223> OTHER INFORMATION: May be present or absent

<400> SEQUENCE: 291

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
        35                  40

<210> SEQ ID NO 292
<211> LENGTH: 5
<212> TYPE: PRT
<213> ORGANISM: Artificial Sequence
<220> FEATURE:
<223> OTHER INFORMATION: cleavable linker

<400> SEQUENCE: 292

Ile Glu Pro Asp Pro
1               5

<210> SEQ ID NO 293
<211> LENGTH: 5
<212> TYPE: PRT
<213> ORGANISM: Artificial Sequence
<220> FEATURE:
<223> OTHER INFORMATION: cleavable linker

<400> SEQUENCE: 293

<210> SEQ ID NO 294
<211> LENGTH: 4
<212> TYPE: PRT
<213> ORGANISM: Artificial Sequence
<220> FEATURE:
<223> OTHER INFORMATION: substrate for granzyme B

<400> SEQUENCE: 294

```
Leu Glu Pro Gly
1
```

<210> SEQ ID NO 295
<211> LENGTH: 143
<212> TYPE: PRT
<213> ORGANISM: Artificial Sequence
<220> FEATURE:
<223> OTHER INFORMATION: recombinant version of the human PD-1
      extracellular domain

<400> SEQUENCE: 295

```
Leu Asp Ser Pro Asp Arg Pro Trp Asn Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Ser Ala Gly Gln Phe Gln
    130                 135                 140
```

<210> SEQ ID NO 296
<211> LENGTH: 123
<212> TYPE: PRT
<213> ORGANISM: Artificial Sequence
<220> FEATURE:
<223> OTHER INFORMATION: cPD1-8

<400> SEQUENCE: 296

```
Gln Val Gln Leu Gln Gln Ser Gly Gly Gly Leu Val Gln Ala Gly Gly
1               5                   10                  15

Ser Leu Arg Val Ser Cys Ala Ala Ser Gly Arg Thr Phe Ser Ser Tyr
            20                  25                  30

Gly Met Gly Trp Phe Arg Gln Ala Pro Gly Lys Glu Arg Glu Phe Val
        35                  40                  45

Ala Ala Ile Ser Trp Ser Gly Gly Thr Gln Tyr Tyr Ala Asp Ser Ala
    50                  55                  60

Lys Gly Arg Phe Thr Ile Ser Arg Asp Asn Ala Lys Asn Thr Val Tyr
65                  70                  75                  80
```

Leu Gln Met Asn Ser Leu Lys Pro Glu Asp Thr Ala Val Tyr Tyr Cys
                85                  90                  95

Ala Asp Tyr Thr Asp Tyr Val Val Tyr Arg Pro Gln Glu Ile Gly Tyr
            100                 105                 110

Trp Gly Gln Gly Thr Gln Val Thr Val Lys Pro
        115                 120

<210> SEQ ID NO 297
<211> LENGTH: 120
<212> TYPE: PRT
<213> ORGANISM: Artificial Sequence
<220> FEATURE:
<223> OTHER INFORMATION: cPD1-14

<400> SEQUENCE: 297

Gln Leu Gln Leu Gln Ser Gly Gly Gly Leu Ala Gln Ala Gly Gly
1               5                   10                  15

Ser Leu Arg Leu Ser Cys Ala Ala Ser Gly Arg Thr Val Ser Ile Tyr
            20                  25                  30

Ala Met Gly Trp Phe Arg Gln Ala Pro Gly Lys Glu Arg Glu Phe Val
        35                  40                  45

Ala Gly Ile Gly Trp Asn Gly Gly Thr Thr Tyr Tyr Ala Asp Ser Val
    50                  55                  60

Glu Gly Arg Phe Thr Ile Ser Arg Asp His Ala Lys Asn Thr Ala Tyr
65                  70                  75                  80

Leu Gln Met Asn Ser Leu Lys Pro Glu Asp Thr Ala Val Tyr Tyr Cys
                85                  90                  95

Ala Ala Gln Glu Ser Ala Ala Gly Thr Leu Gly Asp Tyr Trp Gly Arg
            100                 105                 110

Gly Thr Gln Val Thr Val Lys Pro
        115                 120

<210> SEQ ID NO 298
<211> LENGTH: 120
<212> TYPE: PRT
<213> ORGANISM: Artificial Sequence
<220> FEATURE:
<223> OTHER INFORMATION: cPD1-13

<400> SEQUENCE: 298

Gln Val Thr Leu Lys Glu Ser Gly Gly Gly Leu Val Gln Ala Gly Gly
1               5                   10                  15

Ser Leu Arg Leu Ser Cys Ala Ala Ser Gly Arg Thr Glu Ile Ile Tyr
            20                  25                  30

Ala Met Gly Trp Phe Arg Gln Ala Pro Gly Lys Glu Arg Glu Phe Val
        35                  40                  45

Ala Gly Ile Gly Trp Ser Gly Gly Thr Thr Tyr Tyr Ala Asp Ser Val
    50                  55                  60

Glu Gly Arg Phe Thr Ile Ser Arg Asp Ser Ala Lys Asn Thr Val Tyr
65                  70                  75                  80

Leu Gln Met Arg Ser Leu Lys Pro Glu Asp Thr Ala Val Tyr Tyr Cys
                85                  90                  95

Ala Ala Gln Asp Ser Val Ala Gly Thr Leu Gly Asp Tyr Trp Gly Gln
            100                 105                 110

Gly Thr Gln Val Thr Val Lys Pro
        115                 120

```
<210> SEQ ID NO 299
<211> LENGTH: 127
<212> TYPE: PRT
<213> ORGANISM: Artificial Sequence
<220> FEATURE:
<223> OTHER INFORMATION: cPD1-5

<400> SEQUENCE: 299

Gln Val Thr Leu Arg Glu Ser Gly Gly Gly Leu Val Gln Pro Gly Gly
1               5                   10                  15

Ser Leu Arg Leu Ser Cys Ala Ala Ser Gly Leu Thr Phe Gly Leu Tyr
            20                  25                  30

Ala Met Thr Trp Phe Arg Gln Ala Pro Gly Lys Asp Arg Glu Gly Ile
        35                  40                  45

Ser Cys Ile Ser Ser Ser Asp Gly Ser Thr Ile Tyr Ala Asp Ser Val
    50                  55                  60

Lys Gly Arg Phe Thr Ala Ser Arg Asp Asn Ala Lys Asp Thr Met Tyr
65                  70                  75                  80

Leu Gln Met Asn Asn Leu Asn Pro Glu Asp Thr Ala Val Tyr Tyr Cys
                85                  90                  95

Ala Thr Asp Tyr Glu Thr Arg Cys Asp Tyr Gly Leu Arg Leu Arg Asp
            100                 105                 110

Arg Thr Ala Tyr Trp Gly Pro Gly Thr Gln Val Thr Val Lys Pro
        115                 120                 125

<210> SEQ ID NO 300
<211> LENGTH: 7
<212> TYPE: PRT
<213> ORGANISM: Artificial Sequence
<220> FEATURE:
<223> OTHER INFORMATION: cPD1-8 CDR1

<400> SEQUENCE: 300

Gly Arg Thr Phe Ser Ser Tyr
1               5

<210> SEQ ID NO 301
<211> LENGTH: 7
<212> TYPE: PRT
<213> ORGANISM: Artificial Sequence
<220> FEATURE:
<223> OTHER INFORMATION: cPD1-14 CDR1

<400> SEQUENCE: 301

Gly Arg Thr Val Ser Ile Tyr
1               5

<210> SEQ ID NO 302
<211> LENGTH: 7
<212> TYPE: PRT
<213> ORGANISM: Artificial Sequence
<220> FEATURE:
<223> OTHER INFORMATION: cPD1-13 CDR2

<400> SEQUENCE: 302

Gly Arg Thr Glu Ile Ile Tyr
1               5

<210> SEQ ID NO 303
<211> LENGTH: 7
<212> TYPE: PRT
<213> ORGANISM: Artificial Sequence
<220> FEATURE:
<223> OTHER INFORMATION: cPD1-5 CDR1
```

<400> SEQUENCE: 303

Gly Leu Thr Phe Gly Leu Tyr
1               5

<210> SEQ ID NO 304
<211> LENGTH: 6
<212> TYPE: PRT
<213> ORGANISM: Artificial Sequence
<220> FEATURE:
<223> OTHER INFORMATION: cPD1-8 CDR2

<400> SEQUENCE: 304

Ser Trp Ser Gly Gly Thr
1               5

<210> SEQ ID NO 305
<211> LENGTH: 6
<212> TYPE: PRT
<213> ORGANISM: Artificial Sequence
<220> FEATURE:
<223> OTHER INFORMATION: cPD1-14 CDR2

<400> SEQUENCE: 305

Gly Trp Asn Gly Gly Thr
1               5

<210> SEQ ID NO 306
<211> LENGTH: 6
<212> TYPE: PRT
<213> ORGANISM: Artificial Sequence
<220> FEATURE:
<223> OTHER INFORMATION: cPD1-13 CDR2

<400> SEQUENCE: 306

Gly Trp Ser Gly Gly Thr
1               5

<210> SEQ ID NO 307
<211> LENGTH: 5
<212> TYPE: PRT
<213> ORGANISM: Artificial Sequence
<220> FEATURE:
<223> OTHER INFORMATION: cPD1-5 CDR2

<400> SEQUENCE: 307

Ser Asp Gly Ser Thr
1               5

<210> SEQ ID NO 308
<211> LENGTH: 14
<212> TYPE: PRT
<213> ORGANISM: Artificial Sequence
<220> FEATURE:
<223> OTHER INFORMATION: cPD1-8 CDR3

<400> SEQUENCE: 308

Tyr Thr Asp Tyr Val Val Tyr Arg Pro Gln Glu Ile Gly Tyr
1               5                   10

<210> SEQ ID NO 309
<211> LENGTH: 11
<212> TYPE: PRT
<213> ORGANISM: Artificial Sequence
<220> FEATURE:
<223> OTHER INFORMATION: cPD1-14 CDR3

<400> SEQUENCE: 309

Gln Glu Ser Ala Ala Gly Thr Leu Gly Asp Tyr
1               5                   10

<210> SEQ ID NO 310
<211> LENGTH: 11
<212> TYPE: PRT
<213> ORGANISM: Artificial Sequence
<220> FEATURE:
<223> OTHER INFORMATION: cPD1-13 CDR3

<400> SEQUENCE: 310

Gln Asp Ser Val Ala Gly Thr Leu Gly Asp Tyr
1               5                   10

<210> SEQ ID NO 311
<211> LENGTH: 18
<212> TYPE: PRT
<213> ORGANISM: Artificial Sequence
<220> FEATURE:
<223> OTHER INFORMATION: cPD1-5 CDR3

<400> SEQUENCE: 311

Asp Tyr Glu Thr Arg Cys Asp Tyr Gly Leu Arg Leu Arg Asp Arg Thr
1               5                   10                  15

Ala Tyr

<210> SEQ ID NO 312
<211> LENGTH: 122
<212> TYPE: PRT
<213> ORGANISM: Artificial Sequence
<220> FEATURE:
<223> OTHER INFORMATION: PD1 single domain antibody (PD-1 sdAb)

<400> SEQUENCE: 312

Gln Val Gln Leu Gln Gln Ser Gly Gly Gly Leu Ala Gln Ala Gly Gly
1               5                   10                  15

Ser Leu Arg Leu Ser Cys Ala Ala Ser Gly Arg Thr Val Ser Ile Tyr
            20                  25                  30

Ala Met Gly Trp Phe Arg Gln Ala Pro Gly Lys Glu Arg Glu Phe Val
        35                  40                  45

Ala Gly Ile Gly Trp Asn Gly Gly Thr Thr Tyr Tyr Ala Asp Ser Val
    50                  55                  60

Glu Gly Arg Phe Thr Ile Ser Arg Asp His Ala Lys Asn Thr Ala Tyr
65                  70                  75                  80

Leu Gln Met Asn Ser Leu Lys Pro Glu Asp Thr Ala Val Tyr Tyr Cys
                85                  90                  95

Ala Ala Gln Glu Ser Ala Ala Gly Thr Leu Gly Asp Tyr Trp Gly Arg
            100                 105                 110

Gly Thr Gln Val Thr Val Lys Pro Gly Gly
        115                 120

<210> SEQ ID NO 313
<211> LENGTH: 10
<212> TYPE: PRT
<213> ORGANISM: Artificial Sequence
<220> FEATURE:
<223> OTHER INFORMATION: PD-1 sdAb CDR1

<400> SEQUENCE: 313

Gly Arg Thr Val Ser Ile Tyr Ala Met Gly
1               5                   10

<210> SEQ ID NO 314
<211> LENGTH: 10
<212> TYPE: PRT
<213> ORGANISM: Artificial Sequence
<220> FEATURE:
<223> OTHER INFORMATION: PD-1 sdAb CDR2

<400> SEQUENCE: 314

Gly Ile Gly Trp Asn Gly Gly Thr Thr Tyr
1               5                   10

<210> SEQ ID NO 315
<211> LENGTH: 10
<212> TYPE: PRT
<213> ORGANISM: Artificial Sequence
<220> FEATURE:
<223> OTHER INFORMATION: PD-1 sdAb CDR3

<400> SEQUENCE: 315

Glu Ser Ala Ala Gly Thr Leu Gly Asp Tyr
1               5                   10

<210> SEQ ID NO 316
<211> LENGTH: 122
<212> TYPE: PRT
<213> ORGANISM: Artificial Sequence
<220> FEATURE:
<223> OTHER INFORMATION: Anti-CD3 VH 312557

<400> SEQUENCE: 316

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Phe Thr Ile Ser Arg Asp Asn Ala Lys Asn Ser Leu Tyr Leu
65                  70                  75                  80

Gln Met Asn Ser Leu Arg Ala Glu Asp Thr Ala Leu Tyr Tyr Cys Ala
                85                  90                  95

Lys Asp Ser Arg Gly Tyr Gly Asp Tyr Arg Leu Gly Gly Ala Tyr Trp
            100                 105                 110

Gly Gln Gly Thr Leu Val Thr Val Ser Ser
        115                 120

<210> SEQ ID NO 317
<211> LENGTH: 122
<212> TYPE: PRT
<213> ORGANISM: Artificial Sequence
<220> FEATURE:
<223> OTHER INFORMATION: Anti-CD3 VH 312557 G44C

<400> SEQUENCE: 317

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Cys Leu Glu Trp Val
        35                  40                  45

```
Ser Gly Ile Ser Trp Asn Ser Gly Ser Ile Gly Tyr Ala Asp Ser Val
    50                  55                  60

Lys Gly Phe Thr Ile Ser Arg Asp Asn Ala Lys Asn Ser Leu Tyr Leu
65                  70                  75                  80

Gln Met Asn Ser Leu Arg Ala Glu Asp Thr Ala Leu Tyr Tyr Cys Ala
                85                  90                  95

Lys Asp Ser Arg Gly Tyr Gly Asp Tyr Arg Leu Gly Gly Ala Tyr Trp
            100                 105                 110

Gly Gln Gly Thr Leu Val Thr Val Ser Ser
            115                 120
```

<210> SEQ ID NO 318
<211> LENGTH: 107
<212> TYPE: PRT
<213> ORGANISM: Artificial Sequence
<220> FEATURE:
<223> OTHER INFORMATION: Anti-CD3 VL 312557

<400> SEQUENCE: 318

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105
```

<210> SEQ ID NO 319
<211> LENGTH: 107
<212> TYPE: PRT
<213> ORGANISM: Artificial Sequence
<220> FEATURE:
<223> OTHER INFORMATION: Anti-CD3 VL 312557 Q100C

<400> SEQUENCE: 319

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Cys Gly Thr Lys Val Glu Ile Lys
            100                 105
```

```
<210> SEQ ID NO 320
<211> LENGTH: 124
<212> TYPE: PRT
<213> ORGANISM: Artificial Sequence
<220> FEATURE:
<223> OTHER INFORMATION: CD3-VH-G

<400> SEQUENCE: 320
```

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120

```
<210> SEQ ID NO 321
<211> LENGTH: 124
<212> TYPE: PRT
<213> ORGANISM: Artificial Sequence
<220> FEATURE:
<223> OTHER INFORMATION: CD3-VH-G G44C

<400> SEQUENCE: 321
```

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asp Tyr
            20                  25                  30

Ser Met His Trp Val Arg Gln Ala Pro Gly Lys Cys Leu Glu Trp Val
        35                  40                  45

Ser Gly Ile Ser Trp Asn Ser Gly Ser Lys Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120

```
<210> SEQ ID NO 322
<211> LENGTH: 108
<212> TYPE: PRT
<213> ORGANISM: Artificial Sequence
<220> FEATURE:
<223> OTHER INFORMATION: VK1-39Jkappa5

<400> SEQUENCE: 322
```

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 323
<211> LENGTH: 108
<212> TYPE: PRT
<213> ORGANISM: Artificial Sequence
<220> FEATURE:
<223> OTHER INFORMATION: VK1-39Jkappa5 Q100C

<400> SEQUENCE: 323

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Cys Gly Thr Arg Leu Glu Ile Lys
            100                 105
```

PD-1 SINGLE DOMAIN ANTIBODIES AND THERAPEUTIC COMPOSITIONS THEREOF

RELATED APPLICATIONS

This application claims the benefit of U.S. Provisional Application No. 62/744,615 filed on Oct. 11, 2018, and U.S. Provisional Application No. 62/791,152 filed on Jan. 11, 2019, the contents of which are incorporated herein by reference in their entirety.

INCORPORATION-BY-REFERENCE OF SEQUENCE LISTING

The contents of the text file submitted electronically herewith are incorporated herein by reference in their entirety: A computer readable format copy of the Sequence Listing (filename: INHI-041_001US_SeqList_ST25, date recorded: Jan. 24, 2020; 301 kilobytes).

FIELD

This disclosure generally provides binding polypeptides that specifically bind PD-1. More specifically, the disclosure relates to fusion protein, including multivalent and/or multispecific constructs and chimeric molecules, that bind at least PD-1. The disclosure also provides nucleic acid molecules encoding the polypeptides and vectors and cells thereof, and methods of use and uses of the provided PD-1 binding polypeptides for treating diseases and conditions, such as cancer.

BACKGROUND

PD-1 is a member of the immunoglobulin superfamily of immune cell modulating molecules. It is expressed on the surface of a activated T-cells. The expression of PD-1 on activated T-cells is targeted by PD-L1 by tumor cells and stromal cells in the tumor microenvironment to suppress immune responses, thereby making agents that block or target PD-1 a desirable therapeutic target. Improved therapeutic molecules and agents targeting PD-1 are needed. Provided herein are embodiments that meet such needs.

BRIEF DESCRIPTION OF THE DRAWINGS

FIG. 3 is a graph depicting the ability of 18H10, its humanized variant hz18H10v7 or 1-14 to block PD1/PDL1-mediated suppression of T cell receptor (TCR) signaling in a Jurkat reporter luciferase assay system. FIG. 3A depicts the PD1 blockade by 18H10 and hz18H10v7, while

DETAILED DESCRIPTION

Figure 1A:
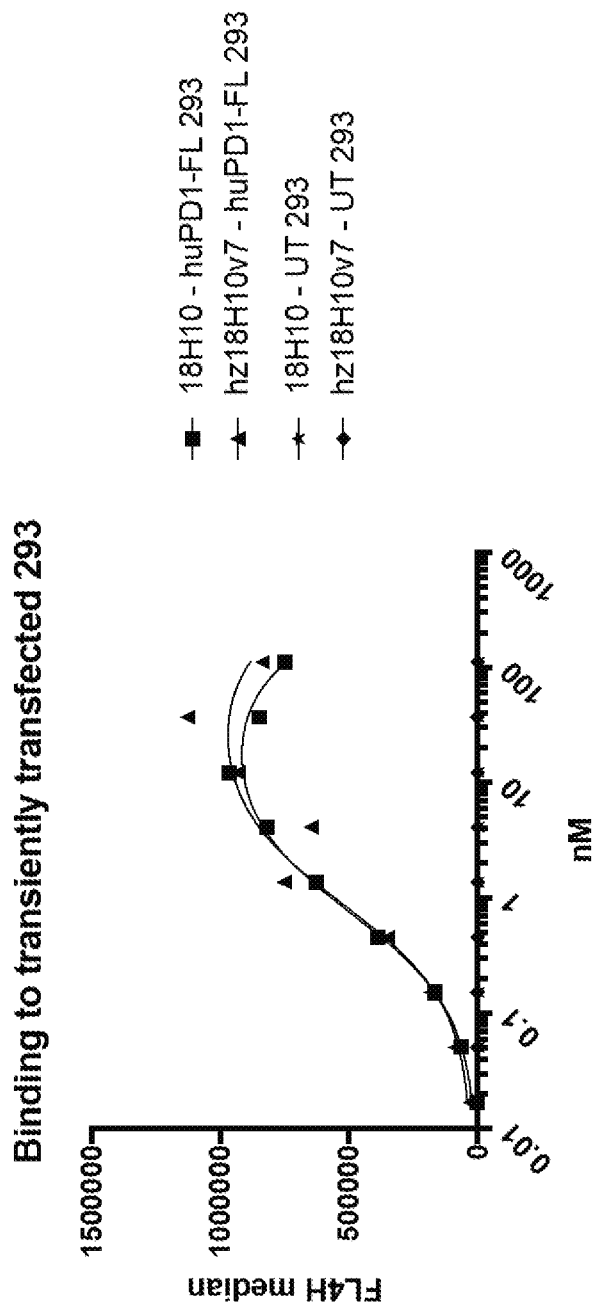
FIG. 1A-1G depict the binding of 18H10 and its humanized variant hz18H10, or 1-14 to FreeStyle 293 cells expressing human PD-1 (FIG. 1A, 1D, 1E, 1F, 1G), cynomolgus PD-1 (FIG. 1B) or mouse PD-1 (FIG. 1C). Binding to untransfected (293) cells also was assessed and is shown.
Figure 1B:
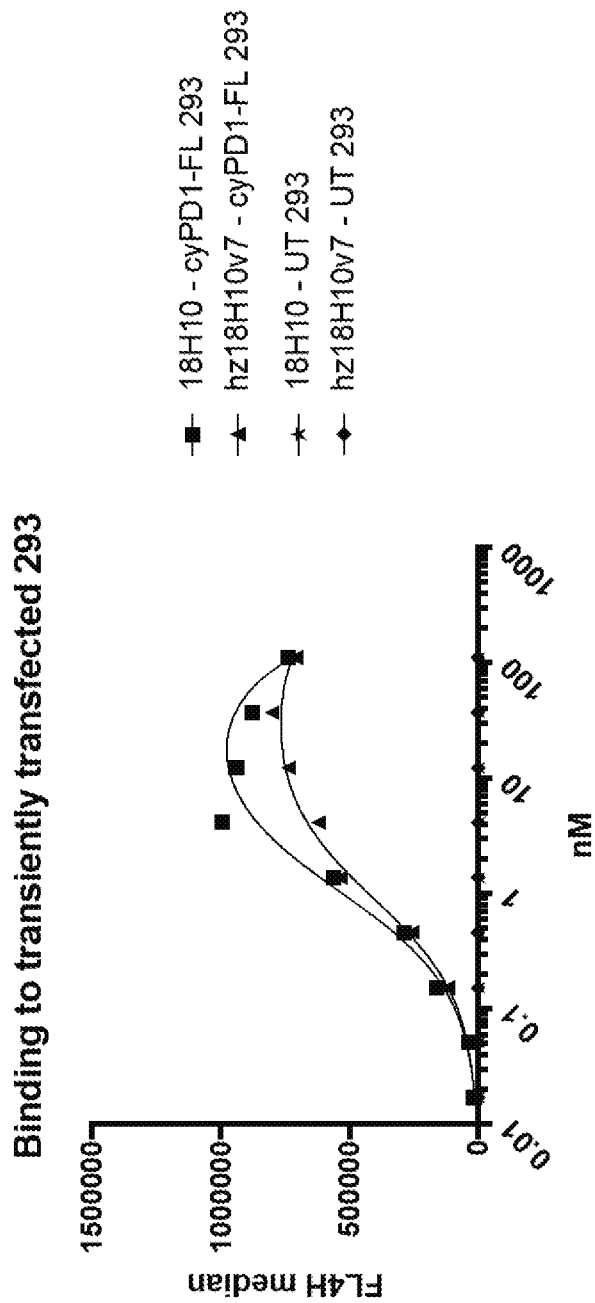
Figure 1C:
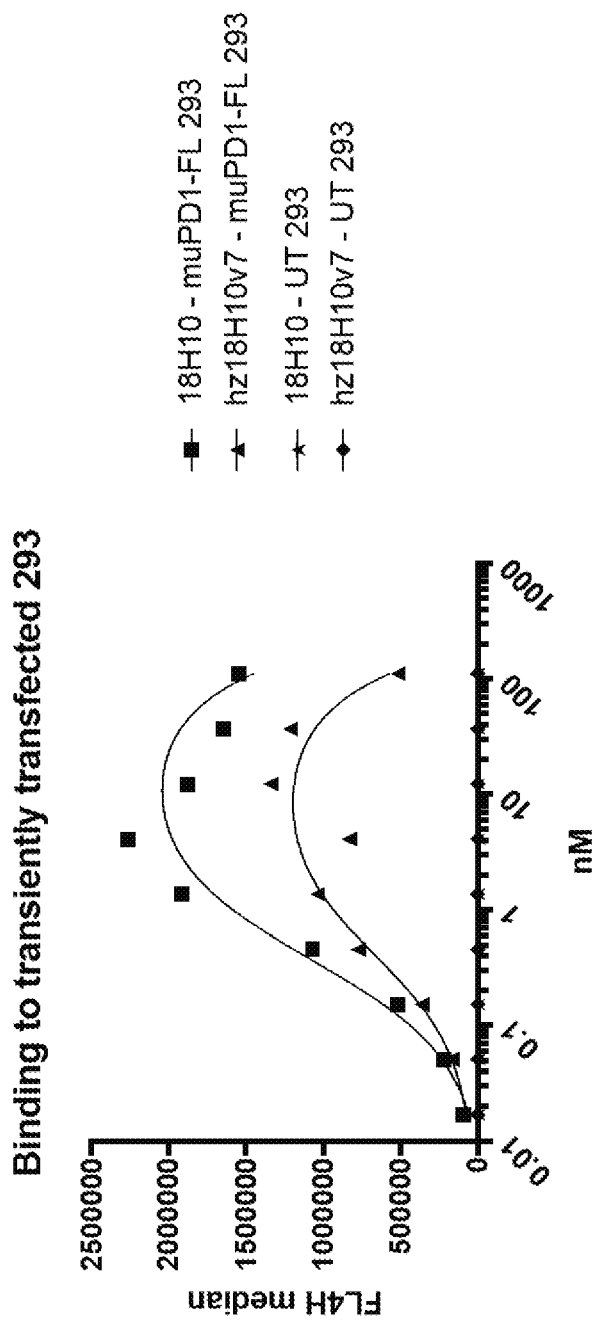
Figure 1D:
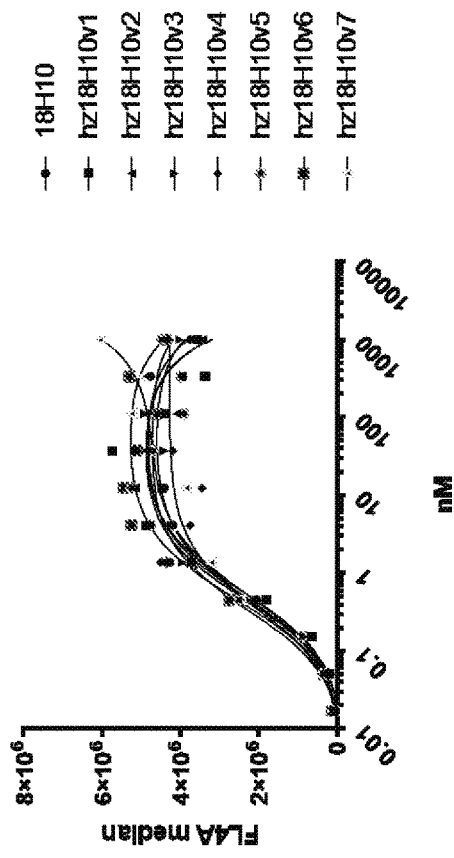
Figure 1E:
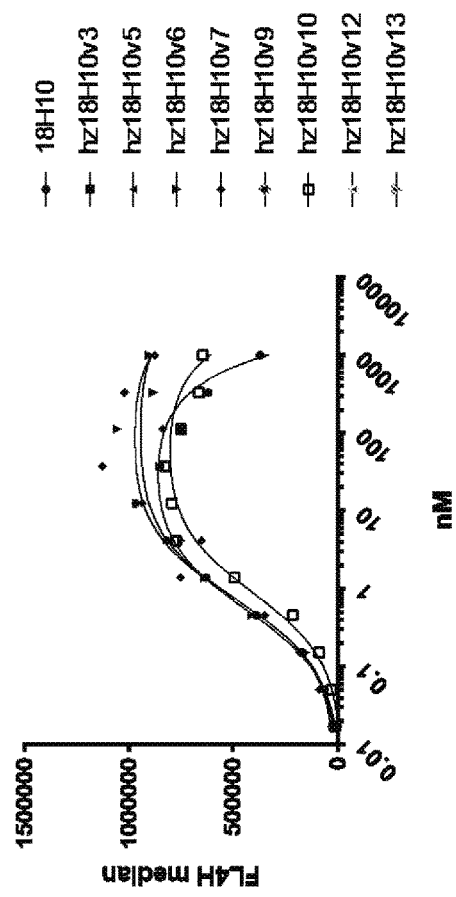
Figure 1F:
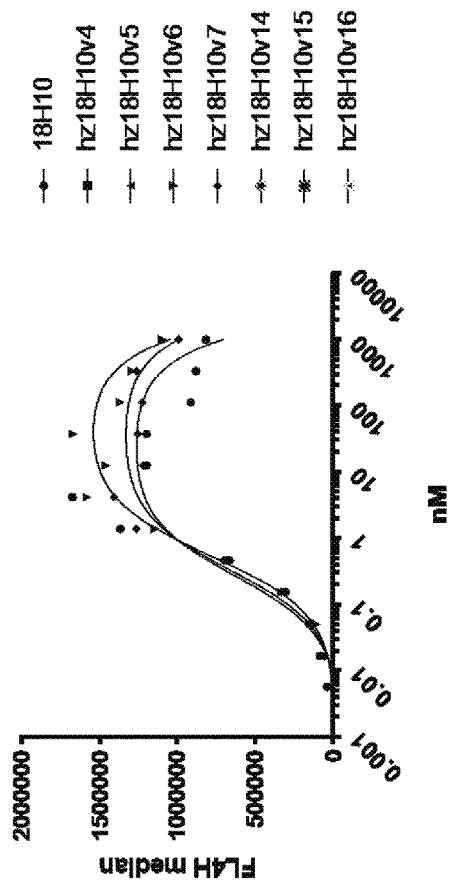
Figure 1G:
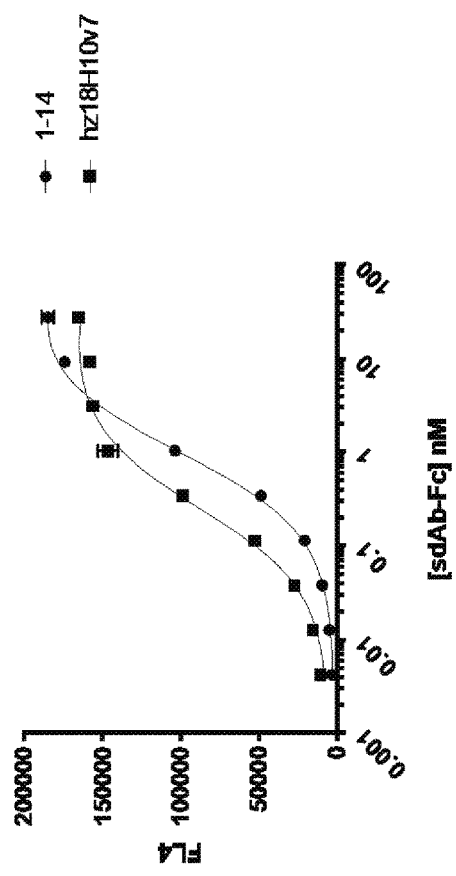

Provided herein are polypeptides that specifically bind to PD-1, hereinafter also called PD-1-binding polypeptides. In some embodiments, the provided binding polypeptides comprise at least one VHH domain that binds PD-1. In some embodiments, a PD-1-binding polypeptide provided herein comprises one, two, three, four, five, six, seven, or eight VHH domains that each individually bind PD-1. In some embodiments, a PD-1-binding polypeptide provided herein comprises one, two, three, or four VHH domains that bind PD-1. In some embodiments, the PD-1-binding polypeptides are monospecific. In some embodiments, the PD-1-binding polypeptides are multispecific. For example, provided PD-1-binding polypeptides include polypeptides that may comprise at least one VHH domain that binds PD-1 and one or more additional binding domains, such as one or more additional VHH domains, that bind one or more target proteins other than PD-1.

In some embodiments, a PD-1-binding polypeptide comprises at least one VHH domain that binds PD-1 and an Fc domain. In some embodiments, a PD-1-binding polypeptide provided herein comprises one, two, three, or four VHH domains that bind PD-1 and an Fc domain. In some embodiments, an Fc domain mediates dimerization of the PD-1-binding polypeptide at physiological conditions such that a dimer is formed that doubles the number of PD-1 binding sites. For example, a PD-1-binding polypeptide comprising three VHH domains that bind PD-1 and an Fc region is trivalent as a monomer, but at physiological conditions, the Fc region may mediate dimerization, such that the PD-1-binding polypeptide exists as a hexavalent dimer under such conditions.

Programmed cell death protein-1 (PD-1) is a type I membrane protein and is a member of the extended CD28/CTLA-4 family of T cell regulators PD-1 (The EMBO Journal (1992), vol. 11, issue 11, p. 3887-3895). It is reported that PD-1 expression in periphery is observed in myeloid cells including T cells or B lymphocytes activated by stimulation from antigen receptors, or activated macrophages (International Immunology (1996), vol. 18, issue 5, p. 765-772). Expression of PD-1 on the cell surface has also been shown to be upregulated through IFN-γ stimulation. Two cell surface glycoprotein ligands for PD-1 have been identified, PD-1 and PDL-2, and have been shown to downregulate T cell activation and cytokine secretion upon binding to PD-1 (Freeman et al. (2000) J. Exp. Med. 192:1027-34; Latchman et al. (2001) Nat. Immunol. 2:261-8; Carter et al. (2002) Eur. J. Immunol. 32:634-43; Ohigashi et al. (2005) Clin. Cancer Res. 11:2947-53). Both PD-1 (B7-H1) and PD-L2 (B7-DC) are B7 homologs that bind to PD-1. PD-L1 and PD-L2 are normally expressed on the surface of T cells, B cells, and myeloid cells. PD-L1 and PD-L2 are negative regulators of immune activation and are capable of downmodulating the immune response via interactions with PD-1 receptor. In some aspects, PD-1 is expressed on NK cells and T cells, including CD4+ and CD8+ T cells, whereby engagement of PD-1 can inhibit activation cell activation, proliferation, and/or expansion.

An exemplary sequence of human PD-1 is set forth as follows:

MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQTLVVGVVGGLLGSLVLLVWVLAVICSRAARGTI

-continued

GARRTGQPLKEDPSAVPVFSVDYGELDFQWREKTPEPPVPCVPEQTEYAT

IVFPSGMGTSSPARRGSADGPRSAQPLRPEDGHCSWPL (SEQ ID NO:
286, signal sequence underlined)

In some cases, the provided PD-1 binding polypeptides directly block or inhibit the interaction between PD-L1/L2 and PD-1. In some embodiments, provided molecules that inhibit or reduce the interaction between PD-L1 and/or PD-L2 and PD-1 modulate immune responses. While transmission of an inhibitory signal may lead to downmodulation in immune cell responses (and a resulting downmodulation in the overall immune response), blocking an inhibitory signal in immune cells leads to upmodulation of immune cell responses (and a resulting upmodulation of an immune response). In some cases, modulation by enhancement of an immune response can be used to treat certain disease or conditions in which the immune response is suppressed, such as cancers. In some embodiments, the provided PD-1 binding polypeptides can be used as a therapeutic to inhibit or reduce tumor cell growth or survival.

A variety of PD-1 polypeptide binding formats are provided. In some embodiments, a PD-1 polypeptide provided herein is bivalent, such as by fusion with an Fc protein. In some examples, PD-1 binding polypeptides include PD-1 VHH-Fc polypeptides. In some embodiments, the Fc is an Fc that exhibits immune effector activity, such as one or more effector functions such as antibody-dependent cellular cytotoxicity (ADCC), antibody-dependent cellular phagocytosis (ADCP) and/or complement-dependent cytotoxicity (CDC). In other embodiments, the PD-1 polypeptide may be a multispecific polypeptide containing at least one additional molecule. In some embodiments, the additional molecule is capable of engaging with another molecule in a tumor-associated microenvironment, such as with a tumor associated antigen or an immune cell, e.g. a T cell. In particular embodiments, the provided PD-1 polypeptide binding formats block the interaction between PD-1 and PD-L1 and/or PD-L1 and/or reduce, inhibit or suppress the inhibitory signal mediated by PD-1 in a cell, such as a T cell.

In some embodiments, the provided PD-1-binding polypeptides can be used to stimulate an immune response in a subject, which, in some aspects, treats a disease or disorder, such as a cancer, in the subject. In some aspects, a PD-1-binding polypeptide provided herein, such as a PD-1-Fc, can bind to PD-1-expressing cells and block their interaction with PD-L1 and/or PD-L2 on adjacent cells in the immune synapse, e.g. tumor cells, which, in some aspects, can induce an active immune response in the environment. In some cases, the active immune response can inhibit the growth (e.g., block cells cycle progression) of the cancerous cells.

In other aspects, also provided herein are VHH-binding polypeptides that exhibit multispecific binding. In some cases, the binding polypeptides include polypeptides that exhibit dual affinity for PD-1 and a tumor associated antigen (TAA). Alternatively or additionally, PD-1 binding polypeptides include polypeptides that exhibit affinity for PD-1 and a T cell antigen, such as CD3. In some aspects, such multispecific molecules are capable of engaging or activating T cells at the site of a tumor upon binding to a tumor or T cell and simultaneously blocking interactions of PD-1 and PD-L1/PD-L2 to reduce an inhibitory signal in the T cells. In particular, among such molecules provided herein are molecules that exhibit constrained CD3 binding. Also provided herein are engineered cells, such as engineered T cells, that express a chimeric antigen receptor and that are capable of secreting a PD-1 binding polypeptide.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993); and updated versions thereof.

The section headings used herein are for organizational purposes only and are not to be construed as limiting the subject matter described.

I. DEFINITIONS

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

It is understood that embodiments of the invention described herein include "consisting" and/or "consisting essentially of" embodiments. As used herein, the singular form "a", "an", and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides comprised in the nucleic acid molecule or polynucleotide.

The term "isolated polynucleotide" as used herein shall mean a polynucleotide of genomic, cDNA, or synthetic origin or some combination thereof, which by virtue of its origin (1) is not associated with all or a portion of a polynucleotide found in nature, (2) is operably linked to a polynucleotide that it is not linked to in nature, or (3) does not occur in nature as part of a larger sequence.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially pure or substantially free from proteins or polypeptides or other contaminants that are found in its natural environment that would interfere with its use (therapeutic, diagnostic, prophylactic, research or otherwise).

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present. Generally, a substantially pure composition will comprise more than about 80 percent of all macromolecular species present in the composition, for example, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. A single-domain antibody (sdAb) or VHH-containing polypeptide "specifically binds" or "preferentially binds" to a target if it binds with greater affinity, avidity, more readily, and/or with greater duration than it binds to other substances. For example, a sdAb or VHH-containing polypeptide that specifically or preferentially binds to a PD-1 epitope is a sdAb or VHH-containing polypeptide that binds this epitope with greater affinity, avidity, more readily, and/or with greater duration than it binds to other PD-1 epitopes or non-PD-1 epitopes. It is also understood by reading this definition that; for example, a sdAb or VHH-containing polypeptide that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

As used herein, the term "epitope" refers to a site on a target molecule (for example, an antigen, such as a protein, nucleic acid, carbohydrate or lipid) to which an antigen-binding molecule (for example, a sdAb or VHH-containing polypeptide) binds. Epitopes often include a chemically active surface grouping of molecules such as amino acids, polypeptides or sugar side chains and have specific three-dimensional structural characteristics as well as specific charge characteristics. Epitopes can be formed both from contiguous and/or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some embodiments, an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between a residue of the antigen-binding molecule and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antigen-binding molecule. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

A "nonlinear epitope" or "conformational epitope" comprises noncontiguous polypeptides, amino acids and/or sugars within the antigenic protein to which an antigen-binding molecule specific to the epitope binds. In some embodiments, at least one of the residues will be noncontiguous with the other noted residues of the epitope; however, one or more of the residues can also be contiguous with the other residues.

A "linear epitope" comprises contiguous polypeptides, amino acids and/or sugars within the antigenic protein to which an antigen-binding molecule specific to the epitope binds. It is noted that, in some embodiments, not every one of the residues within the linear epitope need be directly bound (or involved in a bond) by the antigen-binding molecule. In some embodiments, linear epitopes can be from immunizations with a peptide that effectively consisted of the sequence of the linear epitope, or from structural sections of a protein that are relatively isolated from the remainder of the protein (such that the antigen-binding molecule can interact, at least primarily, just with that sequence section.

The terms "antibody" and "antigen-binding molecule" are used interchangeably in the broadest sense and encompass various polypeptides that comprise antibody-like antigen-binding domains, including but not limited to conventional antibodies (typically comprising at least one heavy chain and at least one light chain), single-domain antibodies (sdAbs, comprising just one chain, which is typically similar to a heavy chain), VHH-containing polypeptides (polypeptides comprising at least one heavy chain only antibody variable domain, or VHH), and fragments of any of the foregoing so long as they exhibit the desired antigen-binding activity. In some embodiments, an antibody comprises a dimerization domain. Such dimerization domains include, but are not limited to, heavy chain constant domains (comprising CH1, hinge, CH2, and CH3, where CH1 typically pairs with a light chain constant domain, CL, while the hinge mediates dimerization) and Fc domains (comprising hinge, CH2, and CH3, where the hinge mediates dimerization).

The term antibody also includes, but is not limited to, chimeric antibodies, humanized antibodies, and antibodies of various species such as camelid (including llama), shark, mouse, human, cynomolgus monkey, etc.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity, e.g. a single domain antibody, such as a VHH. Furthermore, antibodies that bind a particular antigen may be isolated using a $V_H$ or $V_L$ domain from an antibody that binds the antigen to screen a library of complementary VL or $V_H$ domains, respectively. See, e.g., Portolano et al., J. Immunol. 150:880-887 (1993); Clarkson et al., Nature 352:624-628 (1991).

An "antibody fragment" or "antigen-binding fragment" refers to a molecule other than a conventional or intact antibody that comprises a portion of an conventional or intact antibody containing at least a variable region that binds an antigen. Examples of antibody fragments include but are not limited to Fv, single chain Fvs (sdFvs), Fab, Fab', Fab'-SH, F(ab')2; diabodies; linear antibodies; an single-domain antibodies comprising only the $V_H$ region (VHH).

As used herein, "monovalent" with reference to a binding molecule refers to binding molecules that have a single antigen recognition site that is specific for a target antigen. Examples of monovalent binding molecules include, for example, a monovalent antibody fragment, a proteinaceous binding molecule with antibody-like binding properties or an MHC molecule. Examples of monovalent antibody fragments include, but are not limited to, a Fab fragment, an Fv fragment, and a single-chain Fv fragment (scFv).

The terms "single domain antibody", "sdAb," "VHH" are used interchangeably herein to refer to an antibody having a single monomeric domain antigen binding/recognition domain. Such antibodies include a camelid antibody or shark antibody. In some embodiments, a VHH comprises three CDRs and four framework regions, designated FR1, CDR1, FR2, CDR2, FR3, CDR3, and FR4. In some embodiments, a VHH may be truncated at the N-terminus or C-terminus such that it comprise only a partial FR1 and/or FR4, or lacks one or both of those framework regions, so long as the VHH substantially maintains antigen binding and specificity.

The term "VHH-containing polypeptide" refers to a polypeptide that comprises at least one VHH domain. In some embodiments, a VHH polypeptide comprises two, three, or four or more VHH domains, wherein each VHH domain may be the same or different. In some embodiments, a VHH-containing polypeptide comprises an Fc domain. In some such embodiments, the VHH polypeptide may form a dimer. Nonlimiting structures of VHH-containing polypeptides include $VHH_1$-Fc, $VHH_1$-$VHH_2$-Fc, and $VHH_1$-$VHH_2$-$VHH_3$-Fc, wherein $VHH_1$, $VHH_2$, and $VHH_3$ may be the same or different. In some embodiments of such structures, one VHH may be connected to another VHH by a linker, or one VHH may be connected to the Fc by a linker. In some such embodiments, the linker comprises 1-20 amino acids, preferably 1-20 amino acids predominantly composed of glycine and, optionally, serine. In some embodiments, when a VHH-containing polypeptide comprises an Fc, it forms a dimer. Thus, the structure $VHH_1$-$VHH_2$-Fc, if it forms a dimer, is considered to be tetravalent (i.e., the dimer has four VHH domains). Similarly, the structure $VHH_1$-$VHH_2$-$VHH_3$-Fc, if it forms a dimer, is considered to be hexavalent (i.e., the dimer has six VHH domains).

As used herein, a PD-1-binding polypeptide is a polypeptide or protein that specifically binds PD-1. Typically, a PD-1-binding polypeptide herein is a VHH-containing polypeptide containing at least one VHH domain that binds PD-1. A PD-1-binding polypeptide includes conjugates, including fusion proteins. A PD-1-binding polypeptide includes fusion proteins, including those containing an Fc domain. In some embodiments, a PD-1-binding polypeptide contains two, three, or four or more VHH domains that each specifically bind to PD-1, wherein each VHH domain may be the same or different. In some embodiments, a PD-1-binidng polypeptide is multivalent. In some embodiments, a PD-1-binding polypeptide is multispecific. In some cases, a PD-1-binding polypeptide may contain one or more additional domains that bind to one or more further or additional antigens other than PD-1.

The term "monoclonal antibody" refers to an antibody (including an sdAb or VHH-containing polypeptide) of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The term "CDR" denotes a complementarity determining region as defined by at least one manner of identification to one of skill in the art. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme); Al-Lazikani et al., (1997) JMB 273,927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23):9268-9272, ("AbM" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software.

In some embodiments, CDRs can be defined in accordance with any of the Chothia numbering schemes, the Kabat numbering scheme, a combination of Kabat and Chothia, the AbM definition, and/or the contact definition. A VHH comprises three CDRs, designated CDR1, CDR2, and CDR3. Table 1, below, lists exemplary position boundaries of CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-H1 located before CDR-H1, FR-H2 located between CDR-H1 and CDR-H2, FR-H3 located between CDR-H2 and CDR-H3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

Boundaries of CDRs according to various numbering schemes.

| CDR | Kabat | Chothia | AbM | Contact |
|---|---|---|---|---|
| CDR-H1 (Kabat Numbering[1]) | H31--H35B | H26--H32 . . . 34 | H26--H35B | H30--H35B |
| CDR-H1 (Chothia Numbering[2]) | H31--H35 | H26--H32 | H26--H35 | H30--H35 |
| CDR-H2 | H50--H65 | H52--H56 | H50--H58 | H47--H58 |
| CDR-H3 | H95--H102 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given VHH amino acid sequence, it is understood that such a CDR has a sequence of the corresponding CDR (e.g., CDR-H3) within the VHH, as defined by any of the aforementioned schemes. In some embodiments, specific CDR sequences are specified. Exemplary CDR sequences of provided antibodies are described using various numbering schemes (see e.g. Table 1), although it is understood that a provided antibody can include CDRs as described according to any of the other aforementioned numbering schemes or other numbering schemes known to a skilled artisan.

As used herein, "conjugate," "conjugation" or grammatical variations thereof refers the joining or linking together of two or more compounds resulting in the formation of another compound, by any joining or linking methods known in the art. It can also refer to a compound which is generated by the joining or linking together two or more compounds. For example, a VHH domain linked directly or indirectly to one or more chemical moieties or polypeptide is an exemplary conjugate. Such conjugates include fusion proteins, those produced by chemical conjugates and those produced by any other methods.

An immunoglobulin Fc fusion ("Fc-fusion"), such as VHH-Fc, is a molecule comprising one or more VHH domains operably linked to an Fc region of an immunoglobulin. An immunoglobulin Fc region may be linked indirectly or directly to one or more VHH domains. Various linkers are known in the art and can optionally be used to link an Fc to a fusion partner to generate an Fc-fusion. In some such embodiments, the linker comprises 1-20 amino acids, preferably 1-20 amino acids predominantly composed of glycine and, optionally, serine. Fc-fusions of identical species can be dimerized to form Fc-fusion homodimers, or using non-identical species to form Fc-fusion heterodimers. In some embodiments, the Fc is a mammalian Fc such as human Fc.

The term "heavy chain constant region" as used herein refers to a region comprising at least three heavy chain constant domains, $C_H1$, hinge, $C_H2$, and $C_H3$. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an c constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

A "Fc region" as used herein refers to a portion of a heavy chain constant region comprising CH2 and CH3. In some embodiments, an Fc region comprises a hinge, CH2, and CH3. In various embodiments, when an Fc region comprises a hinge, the hinge mediates dimerization between two Fc-containing polypeptides. An Fc region may be of any antibody heavy chain constant region isotype discussed herein. In some embodiments, an Fc region is an IgG1, IgG2, IgG3, or IgG4.

A "functional Fc region" possesses an "effector function" of a native sequence Fc region. Exemplary "effector functions" include Fc receptor binding; Clq binding and complement dependent cytotoxicity (CDC); Fc receptor binding; antibody-dependent cell-mediated cytotoxicity (ADCC); phagocytosis; down regulation of cell surface receptors (for example B-cell receptor); and B-cell activation, etc. Such effector functions generally require the Fc region to be combined with a binding domain (for example, an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, a "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some embodiments, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

In general, the numbering of the residues in an immunoglobulin heavy chain or portion thereof, such as an Fc region, is that of the EU index as in Kabat et al., *Sequences of Proteins of Immunological Interest*, 5th Ed. Public Health Service, National Institutes of Health, Bethesda, Md. (1991). The "EU index as in Kabat" refers to the residue numbering of the human IgG1 EU antibody.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (See, for example, Daeron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. For example, the term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, for example, Ghetie and Ward, *Immunol. Today* 18(12):592-598 (1997); Ghetie et al., *Nature Biotechnology*, 15(7):637-640 (1997); Hinton et al., *J. Biol. Chem.* 279(8):6213-6216 (2004); WO 2004/92219 (Hinton et al.).

An "acceptor human framework" as used herein is a framework comprising the amino acid sequence of a heavy chain variable domain ($V_H$) framework derived from a human immunoglobulin framework or a human consensus framework, as discussed herein. An acceptor human framework derived from a human immunoglobulin framework or a human consensus framework can comprise the same amino acid sequence thereof, or it can contain amino acid sequence changes. In some embodiments, the number of amino acid changes are fewer than 10, or fewer than 9, or fewer than 8, or fewer than 7, or fewer than 6, or fewer than 5, or fewer than 4, or fewer than 3, across all of the human frameworks in a single antigen binding domain, such as a VHH.

As used herein, a "chimeric antigen receptor" or "CAR" refers to an engineered receptor, which introduces an antigen specificity, via an antigen binding domain, onto cells to which it is engineered (for example T cells such as naive T cells, central memory T cells, effector memory T cells or combination thereof) thus combining the antigen binding properties of the antigen binding domain with the T cell activity (e.g. lytic capacity and self renewal) of T cells. A CAR typically includes an extracellular antigen-binding domain (ectodomain), a transmembrane domain and an intracellular signaling domain. The intracellular signaling domain generally contains at least one ITAM signaling domain, e.g. derived from CD3zeta, and optionally at least one costimulatory signaling domain, e.g. derived from CD28 or 4-1BB.

"Affinity" refers to the strength of the sum total of noncovalent interactions between a single binding site of a molecule (for example, an antibody or VHH-containing polypeptide) and its binding partner (for example, an antigen). The affinity or the apparent affinity of a molecule X for its partner Y can generally be represented by the dissociation constant ($K_D$) or the $K_{D\text{-}apparent}$, respectively. Affinity can be measured by common methods known in the art (such as, for example, ELISA $K_D$, KinExA, flow cytometry, and/or surface plasmon resonance devices), including those described herein. Such methods include, but are not limited to, methods involving BIAcore®, Octet®, or flow cytometry.

The term "$K_D$", as used herein, refers to the equilibrium dissociation constant of an antigen-binding molecule/antigen interaction. When the term "$K_D$" is used herein, it includes $K_D$ and $K_{D\text{-}apparent}$.

In some embodiments, the $K_D$ of the antigen-binding molecule is measured by flow cytometry using an antigen-expressing cell line and fitting the mean fluorescence measured at each antibody concentration to a non-linear one-site binding equation (Prism Software graphpad). In some such embodiments, the $K_D$ is $K_{D\text{-}apparent}$.

The term "biological activity" refers to any one or more biological properties of a molecule (whether present naturally as found in vivo, or provided or enabled by recombinant means). Biological properties include, but are not limited to, binding a ligand, inducing or increasing cell proliferation (such as T cell proliferation), and inducing or increasing expression of cytokines.

An "affinity matured" VHH-containing polypeptide refers to a VHH-containing polypeptide with one or more alterations in one or more CDRs compared to a parent VHH-containing polypeptide that does not possess such alterations, such alterations resulting in an improvement in the affinity of the VHH-containing polypeptide for antigen.

A "humanized VHH" as used herein refers to a VHH in which one or more framework regions have been substantially replaced with human framework regions. In some instances, certain framework region (FR) residues of the human immunoglobulin are replaced by corresponding non-human residues. Furthermore, the humanized VHH can comprise residues that are found neither in the original VHH nor in the human framework sequences, but are included to further refine and optimize VHH or VHH-containing polypeptide performance. In some embodiments, a humanized VHH-containing polypeptide comprises a human Fc region. As will be appreciated, a humanized sequence can be identified by its primary sequence and does not necessarily denote the process by which the antibody was created.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 2. Amino acid substitutions may be introduced into an antibody of interest and the products screened for a desired activity, for example, retained/improved antigen binding, decreased immunogenicity, or improved ADCC or CDC.

TABLE 2

| Original Residue | Exemplary Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E, CHO-DG44, CHO-K1, CHO-S, and CHO-DS cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) a provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" and "subject" are used interchangeably herein to refer to an animal; for example a mammal. The term patient includes human and veterinary subjects. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. The subject can be male or female and can be any suitable age, including infant, juvenile, adolescent, adult, and geriatric subjects. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder. In particular embodiments, the subject is a human, such as a human patient.

A "disease" or "disorder" as used herein refers to a condition where treatment is needed and/or desired.

The term "tumor cell", "cancer cell", "cancer", "tumor", and/or "neoplasm", unless otherwise designated, are used herein interchangeably and refer to a cell (or cells) exhibiting an uncontrolled growth and/or abnormal increased cell survival and/or inhibition of apoptosis which interferes with the normal functioning of bodily organs and systems. Included in this definition are benign and malignant cancers, polyps, hyperplasia, as well as dormant tumors or micrometastases.

The terms "cancer" and "tumor" encompass solid and hematological/lymphatic cancers and also encompass malignant, pre-malignant, and benign growth, such as dysplasia. Also, included in this definition are cells having abnormal proliferation that is not impeded (e.g. immune evasion and immune escape mechanisms) by the immune system (e.g. virus infected cells). Exemplary cancers include, but are not limited to: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NEIL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

The term "non-tumor cell" as used herein refers to a normal cells or tissue. Exemplary non-tumor cells include, but are not limited to: T-cells, B-cells, natural killer (NK) cells, natural killer T (NKT) cells, dendritic cells, monocytes, macrophages, epithelial cells, fibroblasts, hepatocytes, interstitial kidney cells, fibroblast-like synoviocytes, osteoblasts, and cells located in the breast, skeletal muscle, pancreas, stomach, ovary, small intestines, placenta, uterus, testis, kidney, lung, heart, brain, liver, prostate, colon, lymphoid organs, bone, and bone-derived mesenchymal stem cells. The term "a cell or tissue located in the periphery" as used herein refers to non-tumor cells not located near tumor cells and/or within the tumor microenvironment.

The term "cells or tissue within the tumor microenvironment" as used herein refers to the cells, molecules, extracellular matrix and/or blood vessels that surround and/or feed a tumor cell. Exemplary cells or tissue within the tumor microenvironment include, but are not limited to: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T-cells (Treg cells); macrophages; neutrophils; myeloid-derived suppressor cells (MDSCs) and other immune cells located proximal to a tumor. Methods for identifying tumor cells, and/or cells/tissues located within the tumor microenvironment are well known in the art, as described herein, below.

In some embodiments, an "increase" or "decrease" refers to a statistically significant increase or decrease, respectively. As will be clear to the skilled person, "modulating" can also involve effecting a change (which can either be an increase or a decrease) in affinity, avidity, specificity and/or selectivity of a target or antigen, for one or more of its ligands, binding partners, partners for association into a homomultimeric or heteromultimeric form, or substrates; effecting a change (which can either be an increase or a decrease) in the sensitivity of the target or antigen for one or more conditions in the medium or surroundings in which the target or antigen is present (such as pH, ion strength, the presence of co-factors, etc.); and/or cellular proliferation or cytokine production, compared to the same conditions but without the presence of a test agent. This can be determined in any suitable manner and/or using any suitable assay known per se or described herein, depending on the target involved.

As used herein, "an immune response" is meant to encompass cellular and/or humoral immune responses that are sufficient to inhibit or prevent onset or ameliorate the symptoms of disease (for example, cancer or cancer metastasis). "An immune response" can encompass aspects of both the innate and adaptive immune systems.

As used herein, the terms "treating," "treatment," or "therapy" of a disease, disorder or condition is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

As used herein in the context of cancer, the terms "treatment" or, "inhibit," "inhibiting" or "inhibition" of cancer refers to at least one of: a statistically significant decrease in the rate of tumor growth, a cessation of tumor growth, or a reduction in the size, mass, metabolic activity, or volume of the tumor, as measured by standard criteria such as, but not limited to, the Response Evaluation Criteria for Solid Tumors (RECIST), or a statistically significant increase in progression free survival (PFS) or overall survival (OS).

"Ameliorating" means a lessening or improvement of one or more symptoms as compared to not administering a therapeutic agent. "Ameliorating" also includes shortening or reduction in duration of a symptom.

"Preventing," "prophylaxis," or "prevention" of a disease or disorder refers to administration of a pharmaceutical composition, either alone or in combination with another compound, to prevent the occurrence or onset of a disease or disorder or some or all of the symptoms of a disease or disorder or to lessen the likelihood of the onset of a disease or disorder.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 10% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control over the same period of time.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. Unless otherwise specified, the terms "reduce", "inhibit", or "prevent" do not denote or require complete prevention over all time, but just over the time period being measured.

The term "anti-cancer agent" is used herein in its broadest sense to refer to agents that are used in the treatment of one or more cancers. Exemplary classes of such agents in include, but are not limited to, chemotherapeutic agents, anti-cancer biologics (such as cytokines, receptor extracellular domain-Fc fusions, and antibodies), radiation therapy, CAR-T therapy, therapeutic oligonucleotides (such as antisense oligonucleotides and siRNAs) and oncolytic viruses.

The term "biological sample" means a quantity of a substance from a living thing or formerly living thing. Such substances include, but are not limited to, blood, (for example, whole blood), plasma, serum, urine, amniotic fluid, synovial fluid, endothelial cells, leukocytes, monocytes, other cells, organs, tissues, bone marrow, lymph nodes and spleen.

The term "control" or "reference" refers to a composition known to not contain an analyte ("negative control") or to contain an analyte ("positive control"). A positive control can comprise a known concentration of analyte.

The terms "effective amount" or "therapeutically effective amount" refer to a quantity and/or concentration of a composition containing an active ingredient (e.g. sdAb or VHH-containing polypeptide) that when administered into a patient either alone (i.e., as a monotherapy) or in combination with additional therapeutic agents, yields a statistically significant decrease in disease progression as, for example, by ameliorating or eliminating symptoms and/or the cause of the disease. An effective amount may be an amount that relieves, lessens, or alleviates at least one symptom or biological response or effect associated with a disease or disorder, prevents progression of the disease or disorder, or improves physical functioning of the patient. A therapeutically effective amount of a composition containing an active agent may vary according to factors such as the disease state, age, sex, and weight of the individual, and the ability of the active agent to elicit a desired response in the individual. A therapeutically effective amount is also one in which any toxic or detrimental effects of the active agent are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

As used herein, a composition refers to any mixture of two or more products, substances, or compounds, including cells. It may be a solution, a suspension, liquid, powder, a paste, aqueous, non-aqueous or any combination thereof.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Hence, it is a composition suitable for pharmaceutical use in a mammalian subject, often a human. A pharmaceutical composition typically comprises an effective amount of an active agent (e.g., sdAb or VHH-containing polypeptide) and a carrier, excipient, or diluent. The carrier, excipient, or diluent is typically a pharmaceutically acceptable carrier, excipient or diluent, respectively. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and are compatible with other ingredients of the formulation. The pharmaceutically acceptable carrier is appropriate for the formulation employed.

Administration "in combination with" one or more further therapeutic agents includes simultaneous (concurrent) and sequential administration in any order.

The term "concurrently" is used herein to refer to administration of two or more therapeutic agents, where at least part of the administration overlaps in time, or where the administration of one therapeutic agent falls within a short period of time relative to administration of the other therapeutic agent, or wherein the therapeutic effect of both agents overlap for at least a period of time.

The term "sequentially" is used herein to refer to administration of two or more therapeutic agents that does not overlap in time, or wherein the therapeutic effects of the agents do not overlap.

As used herein, "in conjunction with" refers to administration of one treatment modality in addition to another treatment modality. As such, "in conjunction with" refers to administration of one treatment modality before, during, or after administration of the other treatment modality to the individual.

The term "package insert" is used to refer to instructions customarily included in commercial packages of therapeutic products, that contain information about the indications, usage, dosage, administration, combination therapy, contain dications and/or warnings concerning the use of such therapeutic products.

An "article of manufacture" is any manufacture (for example, a package or container) or kit comprising at least one reagent, for example, a medicament for treatment of a disease or disorder (for example, cancer), or a probe for specifically detecting a biomarker described herein. In some embodiments, the manufacture or kit is promoted, distributed, or sold as a unit for performing the methods described herein.

The terms "label" and "detectable label" mean a moiety attached, for example, to an antibody or antigen to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^{3}$H $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

II. VHH DOMAINS BINDING PD-1

Provided herein are PD-1-binding polypeptides that are VHH-containing polypeptides containing at least one VHH domain that specifically binds to PD-1. In some embodiments, the VHH domain binds human PD-1. In some embodiments, the VHH domain binds cynomolgus PD-1. In some embodiments, the VHH domain binds murine PD-1. In some embodiments, the VHH-containing polypeptides incorporate multiple copies of a VHH domain provided herein. In such embodiments, the VHH-containing polypeptide may incorporate multiple copies of the same VHH domain. In some embodiments, the VHH-containing polypeptides may incorporate multiple copies of a VHH domain that are different but that recognize the same epitope on PD-1. The VHH-containing polypeptides can be formatted in a variety of formats, including any as described in Section III below.

A VHH domain is an antibody fragment that is a single monomeric variable antibody domain that is able to bind selectively to a specific antigen. With a molecular weight of only 12-15 kDa, VHH domains (also called single-domain antibodies) are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain).

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be derived from any species including, but not limited to mouse, human, camel, llama, alpaca, vicuna, guanaco, shark, goat, rabbit, and/or bovine. In some embodiments, a single domain antibody as used herein is a naturally occurring single domain antibody known as heavy chain antibody devoid of light chains. For clarity reasons, this variable domain derived from a heavy chain antibody naturally devoid of light chain is known herein as a VHH to distinguish it from the conventional VH of four chain immunoglobulins. Such a VHH molecule can be derived from antibodies raised in Camelidae species, for example in camel, llama, dromedary, alpaca, vicuna and guanaco. Other species besides Camelidae may produce heavy chain antibodies naturally devoid of light chain; such VHHs are within the scope of the disclosure.

Methods for the screening of VHH domains, including VHH-binding polypeptides, that possess the desired specificity for PD-1 include, but are not limited to, enzyme linked immunosorbent assay (ELISA), enzymatic assays, flow cytometry, and other immunologically mediated techniques known within the art.

Among the provided VHH domains provided herein are PD-1 VHH (llama or alpaca-derived) and humanized sequences, such as any described below.

In some embodiments, a VHH domain that binds PD-1 may be humanized. Humanized antibodies (such as VHH-containing polypeptides) are useful as therapeutic molecules because humanized antibodies reduce or eliminate the human immune response to non-human antibodies, which can result in an immune response to an antibody therapeutic, and decreased effectiveness of the therapeutic. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (for example, the antibody from which the CDR residues are derived), for example, to restore or improve antibody specificity or affinity.

Humanized antibodies and methods of making them are reviewed, for example, in Almagro and Fransson, (2008) *Front. Biosci.* 13: 1619-1633, and are further described, for example, in Riechmann et al., (1988) *Nature* 332:323-329; Queen et al., (1989) *Proc. Natl Acad. Sci. USA* 86: 10029-10033; U.S. Pat. Nos. 5,821,337, 7,527,791, 6,982,321, and 7,087,409; Kashmiri et al., (2005) *Methods* 36:25-34; Padlan, (1991)*Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. J. Cancer,* 83:252-260 (describing the "guided selection" approach to FR shuffling).

Human framework regions that can be used for humanization include but are not limited to: framework regions selected using the "best-fit" method (see, for example, Sims et al. (1993) *J. Immunol.* 151:2296); framework regions derived from the consensus sequence of human antibodies of a particular subgroup of heavy chain variable regions (see, for example, Carter et al. (1992) *Proc. Natl. Acad. Sci. USA,* 89:4285; and Presta et al. (1993) *J. Immunol,* 151:2623); human mature (somatically mutated) framework regions or human germline framework regions (see, for example, Almagro and Fransson, (2008) *Front. Biosci.* 13:1619-1633); and framework regions derived from screening FR libraries (see, for example, Baca et al., (1997) *J. Biol. Chem.* 272: 10678-10684 and Rosok et al., (1996) *J. Biol. Chem.* 271:22611-22618). Typically, the FR regions of a VHH are replaced with human FR regions to make a humanized VHH. In some embodiments, certain FR residues of the human FR are replaced in order to improve one or more properties of the humanized VHH. VHH domains with such replaced residues are still referred to herein as "humanized."

Provided herein is a VHH domain that binds PD-1 comprising a CDR1, CDR2 and CDR3 contained in a VHH amino acid sequences selected from any of SEQ ID NO: 251-267, or 284, or an amino acid sequence that has at least 90%, 91%, 92%, 93%, 94%, 95%, 96%, 97%, 98%, or 99% sequence identity to the VHH region amino acid selected from any one of SEQ ID NOs: 251-267 or 284.

In some embodiments, a PD-1 VHH domain provided herein contains a CDR1, CDR2, CDR3 contained in a VHH domain set forth in SEQ ID NO:284, or an amino acid sequence that has at least 90%, 91%, 92%, 93%, 94%, 95%, 96%, 97%, 98%, or 99% sequence identity to the VHH region amino acid selected set forth in SEQ ID NO: 284. In some embodiments, the PD-1 VHH domain has the amino acid sequence set forth in SEQ ID NO: 284 or an amino acid sequence that has at least 90%, 91%, 92%, 93%, 94%, 95%, 96%, 97%, 98%, or 99% sequence identity to the amino acid selected set forth in SEQ ID NO: 284. In some embodiments, the PD-1 VHH domain is a humanized variant of the amino acid sequence set forth in SEQ ID NO: 284.

In some embodiments, a PD-1 VHH domain provided herein contains a CDR1, CDR2, CDR3 contained in a VHH domain set forth in SEQ ID NO: 312, or an amino acid sequence that has at least 90%, 91%, 92%, 93%, 94%, 95%, 96%, 97%, 98%, or 99% sequence identity to the VHH region amino acid selected set forth in SEQ ID NO: 312. In some embodiments, the PD-1 VHH domain has the amino acid sequence set forth in SEQ ID NO: 312 or an amino acid sequence that has at least 90%, 91%, 92%, 93%, 94%, 95%, 96%, 97%, 98%, or 99% sequence identity to the amino acid selected set forth in SEQ ID NO: 312. In some embodiments, the PD-1 VHH domain is a humanized variant of the amino acid sequence set forth in SEQ ID NO: 312.

In some embodiments, a PD-1 VHH domain provided herein contains a CDR1 set forth in any one of SEQ ID NOS: 268, 272, 273 or 313, a CDR2 set forth in SEQ ID NO: 278 or 314 and a CDR3 set forth in SEQ ID NO: 283 or 315.

In some embodiments, the PD-1 VHH domain provided herein contains a CDR1, CDR2, and CDR3 set forth in SEQ ID NOs: 272, 278, and 283, respectively. In some embodiments, the PD-1 VHH domain provided herein contains a CDR1, CDR2 and CDR3 set forth in SEQ ID NOs: 268, 278, and 283, respectively. In some embodiments, the PD-1 VHH domain provided herein contains a CDR1, CDR2 and CDR3 set forth in SEQ ID NOs: 272, 278, and 283, respectively. In some embodiments, the PD-1 VHH domain provided herein contains a CDR1, CDR2 and CDR3 set forth in SEQ ID NOs: 273, 278, and 283, respectively. In some embodiments, the PD-1 VHH domain provided herein contains a CDR1, CDR2, and CDR3 set forth in SEQ ID NOs: 313, 314, and 315, respectively.

In some aspects, a VHH domain that binds PD-1 comprises a CDR1, CDR2 and CDR3 contained in a VHH amino acid sequences selected from any of SEQ ID NO:251-267, or an amino acid sequence that has at least 90%, 91%, 92%, 93%, 94%, 95%, 96%, 97%, 98%, or 99% sequence identity to the VHH region amino acid selected from any one of SEQ ID NOs: 251-267.

In some cases, the provided PD-1 VHH domain is a humanized variant that has the amino acid sequence set forth in any of SEQ ID NOS: 251-267 or an amino acid sequence that has at least 90%, 91%, 92%, 93%, 94%, 95%, 96%, 97%, 98%, or 99% sequence identity to the VHH region amino acid selected from any one of SEQ ID NOs: 251-267. In some embodimetns, the PD-1 humanized VHH domain has the sequence of amino acids set forth in any one of SEQ ID NOS: 251-267.

Provided herein is a VHH domain that binds PD-1 comprising a CDR1, CDR2 and CDR3 contained in a VHH amino acid sequences selected from any of SEQ ID NO: 287, 288, 289, or 290, or an amino acid sequence that has at least 90%, 91%, 92%, 93%, 94%, 95%, 96%, 97%, 98%, or 99% sequence identity to the VHH region amino acid selected from any one of SEQ ID NOs: 296, 297, 298, or 299.

In some embodiments, the PD-1 VHH domain is a humanized variant of the amino acid sequence set forth in SEQ ID NO: 296, 297, 298, or 299.

In some embodiments, a PD-1 VHH domain provided herein contains a CDR1 set forth in any one of SEQ ID NOS: 300, 303, 306, or 309, a CDR2 set forth in SEQ ID NO: 301, 304, 307, or 310, a CDR3 set forth in SEQ ID NO: 302, 305, 308, or 311. In some embodiments, a PD-1 VHH domain provided herein contains a CDR1 set forth in SEQ ID NO: 300, a CDR2 set forth in SEQ ID NO: 301, and a CDR3 set forth in SEQ ID NO: 302; a PD-1 VHH domain provided herein contains a CDR1 set forth in SEQ ID NO: 303, a CDR2 set forth in SEQ ID NO: 304, and a CDR3 set forth in SEQ ID NO: 305; a PD-1 VHH domain provided herein contains a CDR1 of SEQ ID NO: 306, a CDR2 set forth in SEQ ID NO: 307, and a CDR3 set forth in SEQ ID NO: 308; or a PD-1 VHH domain provided herein contains a CDR1 set forth in SEQ ID NO: 309, a CDR2 set forth in SEQ ID NO: 310, and a CDR3 set forth in SEQ ID NO: 311.

III. FUSION PROTEINS AND CONJUGATES CONTAINING PD-1-BINDING POLYPEPTIDES

Provided herein are fusion proteins and conjugates containing PD-1-binding polypeptides containing at least one VHH domain that specifically binds PD-1 linked, directly or indirectly, to one or more additional domains or moieties. In some embodiments, the fusion protein or conjugate of the present disclosure is composed of a single polypeptide. In other embodiments, the fusion protein or conjugate of the present disclosure is composed of more than one polypeptide. In some embodiments, the PD-1-binding polypeptide of the present disclosure incorporates at least one VHH domain that specifically binds PD-1. In some aspects, the PD-1-binding polypeptide is multivalent. In some embodiments, the PD-1-binding polypeptides include two or more copies of a VHH domain that specifically binds PD-1, for example, three or more, four or more, five or more, or six or more copies of a VHH domain that specifically binds PD-1. In certain aspects, the PD-1-binding polypeptide is multi-specific. For example, in some cases, the one or more additional domain may be one or more additional binding domain that binds to one or more further antigen or protein.

In some embodiments, the PD-1-binding polypeptides of the present disclosure include two or more polypeptide sequences that are operably linked via amino acid linkers. In some embodiments, these linkers are composed predominately of the amino acids Glycine and Serine, denoted as GS-linkers herein. The GS-linkers of the fusion proteins of the present disclosure can be of various lengths, for example, 5, 6, 7, 8, 9, 10, 11, 12, 13, 14, 15, 16, 17, 18, 19, 20 amino acids in length. In some embodiments, the GS-linker comprises an amino acid sequence selected from the group consisting of GGSGGS, i.e., $(GGS)_2$ (SEQ ID NO: 1); GGSGGSGGS, i.e., $(GGS)_3$ (SEQ ID NO: 2); GGSGGSGGSGGS, i.e., $(GGS)_4$ (SEQ ID NO: 3); and GGSGGSGGSGGSGGS, i.e., $(GGS)_5$ (SEQ ID NO: 4). In some embodiments, the linker is a flexible linker comprising Glycine residues, such as, by way of non-limiting example, GG, GGG, GGGG (SEQ ID NO: 5), GGGGG (SEQ ID NO: 6), and GGGGGG (SEQ ID NO: 7). In some embodiments, the PD-1-binding polypeptide includes a combination of a GS-linker and a Glycine linker.

A. Fc Fusions

Provided herein is a PD-1-binding polypeptide that is a fusion protein containing at least one VHH domain that binds PD-1 provided herein and an Fc domain. In some embodiments, a PD-1-binding polypeptide provided herein comprises one, two, three, or four VHH domains that bind PD-1 and an Fc domain.

In some embodiments, incorporation of an immunoglobulin Fc region into the fusion protein can, in some aspects, be composed of two polypeptides that together form a dimer. In some embodiments, an Fc domain mediates dimerization of the PD-1-binding polypeptide at physiological conditions, such as when expressed from a cell, such that a dimer is formed that doubles the number of PD-1 binding sites. For example, a PD-1-binding polypeptide comprising three VHH domains that bind PD-1 and an Fc region is trivalent as a monomer, but the Fc region may mediate dimerization, such that the PD-1-binding polypeptide exists as a hexavalent dimer under such conditions. In some embodiments, a PD-1 VHH domain is fused to an IgG Fc region and in these embodiments, the fusion protein is bivalent having two PD-1 VHH domains per molecule. In some embodiments, two PD-1 binding domains (2×) are fused to an IgG Fc region and in these embodiments, the fusion protein is tetravalent having four PD-1 VHH domains per molecule. In some embodiments, three PD-1 VHH domain (3×) are fused to an IgG Fc region and in these embodiments, the fusion protein is hexavalent having six PD-1 VHH domains per molecule.

In some embodiments, the multivalent PD-1-binding polypeptide is bivalent. In some embodiments, the bivalent PD-1-binding polypeptide of the disclosure includes two copies of a PD-1-binding polypeptide having the following structure: (PD-1 VHH)-Linker-Fc. In some embodiments, the multivalent PD-1-binding polypeptide is tetravalent. In some embodiments, the tetravalent PD-1-binding polypeptide of the disclosure includes two copies of a PD-1-polypeptide having the following structure: (PD-1 VHH)-Linker-(PD-1 VHH)-Linker-Fc. In some embodiments, the multivalent PD-1-binding polypeptide is hexavalent. In some embodiments, the hexavalent PD-1-binding polypeptide of the disclosure includes two copies of a PD-1-binding polypeptide having the following structure: (PD-1 VHH)-Linker-(PD-1 VHH)-Linker-(PD-1 VHH)-Linker-Fc.

In some cases, the CH3 domain of the Fc region can be used as homodimerization domain, such that the resulting fusion protein is formed from two identical polypeptides. In other cases, the CH3 dimer interface region of the Fc region can be mutated so as to enable heterodimerization. For example, a heterodimerization domain can be incorporated into the fusion protein such that the construct is an asymmetric fusion protein.

In any of the provided embodiments, a PD-1 VHH domain can be any as described above. In come embodiments, the PD-1 VHH domain is a humanized VHH domain that binds PD-1.

In various embodiments, an Fc domain included in a PD-1-binding polypeptide is a human Fc domain, or is derived from a human Fc domain. In some embodiments, the fusion protein contains an immunoglobulin Fc region. In some embodiments, the immunoglobulin Fc region is an IgG isotype selected from the group consisting of IgG1 isotype, IgG2 isotype, IgG3 isotype, and IgG4 subclass.

In some embodiments, the immunoglobulin Fc region or immunologically active fragment thereof is an IgG isotype.

For example, the immunoglobulin Fc region of the fusion protein is of human IgG1 isotype, having an amino acid sequence:

```
                                            (SEQ ID NO: 8)
PAPELLGGPS VFLFPPKPKD TLMISRTPEV TCVVVDVSHE

DPEVKFNWYV DGVEVHNAKT KPREEQYNST YRVVSVLTVL

HQDWLNGKEY KCKVSNKALP APIEKTISKA KGQPREPQVY

TLPPSRDELT KNQVSLTCLV KGFYPSDIAV EWESNGQPEN

NYKTTPPVLD SDGSFFLYSK LTVDKSRWQQ GNVFSCSVMH

EALHNHYTQK SLSLSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 8.

In some embodiments where the fusion protein of the disclosure includes an Fc polypeptide, the Fc polypeptide is mutated or modified. In some cases, the mutations include one or more amino acid substitutions to reduce an effector function of the Fc polypeptide. Various examples of mutations to Fc polypeptides to alter, such as reduce, effector function are known, including any as described below. In some embodiments, reference to amino acid substitutions in an Fc region is by EU numbering by Kabat (also called Kabat numbering) unless described with reference to a specific SEQ ID NO. EU numbering is known and is according to the most recently updated IMGT Scientific Chart (IMGT®, the international ImMunoGeneTics information System®, http://www.imgt.org/IMGTScientific-Chart/Numbering/Hu IGHGnber.html (created: 17 May 2001, last updated: 10 Jan. 2013) and the EU index as reported in Kabat, E. A. et al. Sequences of Proteins of Immunological interest. 5th ed. US Department of Health and Human Services, NIH publication No. 91-3242 (1991).

In some embodiments, an Fc region that exhibits reduced effector functions may be a desirable candidate for applications in which PD-1 or CD3 binding is desired yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the multispecific polypeptide constructs and/or cleaved components thereof lack FcγR binding (hence likely lacking ADCC activity), but retains FcRn binding ability. The primary cells for mediating ADCC, NK cells, express FcγRIII only, whereas monocytes express FcγRI, FcγRII and FcγRIII. Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166: 1351-1361 (1987)). Alternatively, non-radioactive assay methods may be employed (see, for example, ACTI™ non-radioactive cytotoxicity assay for flow cytometry (CellTechnology, Inc. Mountain View, Calif.; and Cyto-Tox96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the multispecific polypeptide construct or cleaved components thereof is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

In some embodiments, the human IgG Fc region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11.

Examples of mutations that enhance ADCC include modification at Ser239 and Ile332, for example Ser239Asp and Ile332Glu (S239D, I332E). Examples of mutations that enhance CDC include modifications at Lys326 and Glu333. In some embodiments, the Fc region is modified at one or both of these positions, for example Lys326Ala and/or Glu333Ala (K326A and E333A) using the Kabat numbering system.

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327) or Pro329 (P329). For example, Leu 234Ala (L234A), Leu235Ala (L235A), Leu235Glu (L235E), Asp265Asn (D265N), Asp265Ala (D265A), Asp270Asn (D270N), Ser298Asn (S298N), Asn297Ala (N297A), Pro329Ala (P329A) or Pro239Gly (P329G), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the human IgG1 Fc region is modified at amino acid Asn297 (Kabat Numbering) to prevent glycosylation of the fusion protein, e.g., Asn297Ala (N297A) or Asn297Asp (N297D). In some embodiments, the Fc region of the fusion protein is modified at amino acid Leu235 (Kabat Numbering) to alter Fc receptor interactions, e.g., Leu235Glu (L235E) or Leu235Ala (L235A). In some embodiments, the Fc region of the fusion protein is modified at amino acid Leu234 (Kabat Numbering) to alter Fc receptor interactions, e.g., Leu234Ala (L234A). In some embodiments, the Fc region of the fusion protein is modified at amino acid Leu234 (Kabat Numbering) to alter Fc receptor interactions, e.g., Leu235Glu (L235E). In some embodiments, the Fc region of the fusion protein is altered at both amino acids 234 and 235, e.g., Leu234Ala and Leu235Ala (L234A/L235A) or Leu234Val and Leu235Ala (L234V/L235A). In some embodiments, the Fc region of the fusion protein is altered at amino acids at 234, 235, and 297, e.g., Leu234Ala, Leu235Ala, Asn297Ala (L234A/L235A/N297A). In some embodiments, the Fc region of the fusion protein is altered at amino acids at 234, 235, and 329, e.g., Leu234Ala, Leu235Ala, Pro239Ala (L234A/L235A/P329A). In some embodiments, the Fc region of the fusion protein is modified at amino acid Asp265 (Kabat Numbering) to alter Fc receptor interactions, e.g Asp265Ala (D265A). In some embodiments, the Fc region of the fusion protein is modified at amino acid Pro329 (Kabat Numbering) to alter Fc receptor interactions, e.g Pro329Ala (P329A) or Pro329Gly (P329G). In some embodiments, the Fc region of the fusion protein is altered at both amino acids 265 and 329, e.g., Asp265Ala and Pro329Ala (D265A/P329A) or Asp265Ala and Pro329Gly (D265A/P329G). In some embodiments, the Fc region of the fusion protein is altered at amino acids at 234, 235, and 265, e.g., Leu234Ala, Leu235Ala, Asp265Ala (L234A/L235A/D265A). In some embodiments, the Fc region of the fusion protein is altered at amino acids at 234, 235, and 329, e.g., Leu234Ala, Leu235Ala, Pro329Gly (L234A/L235A/P329G). In some embodiments, the Fc region of the fusion protein is altered at amino acids at 234, 235, 265 and 329, e.g., Leu234Ala, Leu235Ala, Asp265Ala, Pro329Gly (L234A/L235A/D265A/P329G). In some embodiments, the Fc region of the fusion protein is altered at Gly235 to reduce Fc receptor binding. For example, wherein Gly235 is deleted from the fusion protein. In some embodiments, the human IgG1 Fc region is modified at amino acid Gly236 to enhance the interaction with CD32A, e.g., Gly236Ala (G236A). In some embodiments, the human IgG1 Fc region lacks Lys447 (EU index of Kabat et al 1991 Sequences of Proteins of Immunological Interest).

In some embodiments, the Fc region of the fusion protein is lacking an amino acid at one or more of the following positions to reduce Fc receptor binding: Glu233 (E233), Leu234 (L234), or Leu235 (L235). In some embodiments, the Fc region of the fusion protein is lacking an amino acid at one or more of the following positions Glu233 (E233), Leu234 (L234), or Leu235 (L235) and is modified at one or more of the Asp265 (D265), Asn297 (N297), or Pro329 (P329) to reduce Fc receptor binding. For example, an Fc region included in a PD-1-bindng polypeptide is derived from a human Fc domain, and comprises a three amino acid deletion in the lower hinge corresponding to IgG1 E233, L234, and L235. In some aspects, such Fc polypeptides do not engage FcγRs and thus are referred to as "effector silent" or "effector null." For example, Fc deletion of these three amino acids reduces the complement protein C1q binding. In some embodiments, a polypeptide with an Fc region with Fc deletion of these three amino acids retains binding to FcRn and therefore has extended half-life and transcytosis associated with FcRn mediated recycling. Such a modified Fc region is referred to as "Fc xELL" or "Fc deletion" and has the following amino acid sequence:

```
                                          (SEQ ID NO: 9)
PAPGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSRDELTKNQ VSLTCLVKGF YPSDIAVEWE SNGQPENNYK
```

```
TTPPVLDSDG SFFLYSKLTV DKSRWQQGNV FSCSVMHEAL

HNHYTQKSLS LSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 9.

In some embodiments, the human IgG Fc region is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et al 2006, J. Biol Chem Vol. 281(33) 23514-23524), Met428Leu and Asn434Ser (M428L, N434S) (Zalevsky et al 2010 Nature Biotech, Vol. 28(2) 157-159), or Met252Ile, Thr256Asp, Met428Leu (M252I, T256D, M428L, respectively), (EU index of Kabat et al 1991 Sequences of Proteins of Immunological Interest).

In some embodiments, the Fc domain included in a PD-1-bindng polypeptide is derived from a human Fc domain and comprises mutations M252Y and M428V, herein referred to as "Fc-YV". In some embodiments, the mutated or modified Fc polypeptide includes the following mutations: M252Y and M428L using the Kabat numbering system. In some embodiments, such mutations enhance binding to FcRn at the acidic pH of the endosome (near 6.5), while losing detectable binding at neutral pH (about 7.2), allowing for enhanced FcRn mediated recycling and extended half-life.

In some embodiments, the Fc domain included in a PD-1-binding polypeptide is derived from a human Fc domain and comprises mutations to induce heterodimerization. In some embodiments, such mutations include those referred to as "knob" and "hole" mutations. For example, having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). In some embodiments, the "knob" Fc domain comprises the mutation T366W. In some embodiments, the "hole" Fc domain comprises mutations T366S, L368A, and Y407V. Heterodimerization via CH3 modifications can be further stabilized by the introduction of a disulfide bond, for example by changing Ser354 to Cys (S354C) and Y349 to Cys (Y349C) on opposite CH3 domains (Reviewed in Carter, 2001 Journal of Immunological Methods, 248: 7-15). In some embodiments, Fc domains used for heterodimerization comprise additional mutations, such as the mutation S354C on a first member of a heterodimeric Fc pair that forms an asymmetric disulfide with a corresponding mutation Y349C on the second member of a heterodimeric Fc pair. In some embodiments, one member of a heterodimeric Fc pair comprises the modification H435R or H435K to prevent protein A binding while maintaining FcRn binding. In some embodiments, one member of a heterodimeric Fc pair comprises the modification H435R or H435K, while the second member of the heterodimeric Fc pair is not modified at H435. In various embodiments, the hole Fc domain comprises the modification H435R or H435K (referred to as "hole-R" in some instances when the modification is H435R), while the knob Fc domain does not. In some instances, the hole-R mutation improves purification of the heterodimer over homodimeric hole Fc domains that may be present.

In some embodiments, the human IgG Fc region is modified to prevent dimerization. In these embodiments, the fusion proteins of the present disclosure are monomeric. For example modification at residue Thr366 to a charged residue, e.g. Thr366Lys, Thr366Arg, Thr366Asp, or Thr366Glu (T366K, T366R, T366D, or T366E, respectively), prevents CH3-CH3 dimerization.

In some embodiments, the immunoglobulin Fc region or immunologically active fragment of the fusion protein is of human IgG2 isotype, having an amino acid sequence:

```
                                        (SEQ ID NO: 10)
PAPPVAGPSV FLFPPKPKDT LMISRTPEVT CVVVDVSHED

PEVQFNWYVD GVEVHNAKTK PREEQFNSTF RVVSVLTVVH

QDWLNGKEYK CKVSNKGLPA PIEKTISKTK GQPREPQVYT

LPPSREEMTK NQVSLTCLVK GFYPSDISVE WESNGQPENN

YKTTPPMLDS DGSFFLYSKL TVDKSRWQQG NVFSCSVMHE

ALHNHYTQKS LSLSPGK
```

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 10.

In some embodiments, the human IgG2 Fc region is modified at amino acid Asn297 (e.g. to prevent to glycosylation of the antibody, e.g., Asn297Ala (N297A) or Asn297Asp (N297D). In some embodiments, the human IgG2 Fc region is lacks Lys447 (EU index of Kabat et al 1991 Sequences of Proteins of Immunological Interest).

In some embodiments, the immunoglobulin Fc region or immunologically active fragment of the fusion protein is of human IgG3 isotype, having an amino acid sequence:

```
                                        (SEQ ID NO: 11)
PAPELLGGPS VFLFPPKPKD TLMISRTPEV TCVVVDVSHE

DPEVQFKWYV DGVEVHNAKT KPREEQYNST FRVVSVLTVL

HQDWLNGKEY KCKVSNKALP APIEKTISKT KGQPREPQVY

TLPPSREEMT KNQVSLTCLV KGFYPSDIAV EWESSGQPEN

NYNTTPPMLD SDGSFFLYSK LTVDKSRWQQ GNIFSCSVMH

EALHNRFTQK SLSLSPGK
```

In some embodiments, the antibody or immunologically active fragment thereof comprises a human IgG3 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 11.

In some embodiments, the human IgG3 Fc region is modified at amino acid Asn297 (Kabat Numbering) to prevent to glycosylation of the antibody, e.g., Asn297Ala (N297A) or Asn297Asp (N297D). In some embodiments, the human IgG3 Fc region is modified at amino acid 435 to extend the half-life, e.g., Arg435His (R435H). In some embodiments, the human IgG3 Fc region is lacks Lys447 (EU index of Kabat et al 1991 Sequences of Proteins of Immunological Interest).

In some embodiments, the immunoglobulin Fc region or immunologically active fragment of the fusion protein is of human IgG4 isotype, having an amino acid sequence:

```
                                            (SEQ ID NO: 12)
PAPEFLGGPS  VFLFPPKPKD  TLMISRTPEV  TCVVVDVSQE

DPEVQFNWYV  DGVEVHNAKT  KPREEQFNST  YRVVSVLTVL

HQDWLNGKEY  KCKVSNKGLP  SSIEKTISKA  KGQPREPQVY

TLPPSQEEMT  KNQVSLTCLV  KGFYPSDIAV  EWESNGQPEN

NYKTTPPVLD  SDGSFFLYSR  LTVDKSRWQE  GNVFSCSVMH

EALHNHYTQK  SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 12.

In some embodiments, the immunoglobulin Fc region or immunologically active fragment of the fusion protein is of human IgG4 isotype, having an amino acid sequence:

```
                                            (SEQ ID NO: 13)
PAPELLGGPS  VFLFPPKPKD  TLMISRTPEV  TCVVVDVSQE

DPEVQFNWYV  DGVEVHNAKT  KPREEQFNST  YRVVSVLTVL

HQDWLNGKEY  KCKVSNKGLP  SSIEKTISKA  KGQPREPQVY

TLPPSQEEMT  KNQVSLTCLV  KGFYPSDIAV  EWESNGQPEN

NYKTTPPVLD  SDGSFFLYSR  LTVDKSRWQE  GNVFSCSVMH

EALHNHYTQK  SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 13.

In some embodiments, the human IgG4 Fc region is modified at amino acid 235 to alter Fc receptor interactions, e.g., Leu235Glu (L235E). In some embodiments, the human IgG4 Fc region is modified at amino acid Asn297 (Kabat Numbering) to prevent to glycosylation of the antibody, e.g., Asn297Ala (N297A) or Asn297Asp (N297D). In some embodiments, the human IgG4 Fc region is lacks Lys447 (EU index of Kabat et al 1991 Sequences of Proteins of Immunological Interest).

In some embodiments, the fusion protein contains a polypeptide derived from an immunoglobulin hinge region. The hinge region can be selected from any of the human IgG subclasses. For example, the fusion protein may contain a modified IgG1 hinge having the sequence of EPKSSDKTH-TCPPC (SEQ ID NO: 14), where in the Cys220 that forms a disulfide with the C-terminal cysteine of the light chain is mutated to serine, e.g., Cys220Ser (C220S). In other embodiments, the fusion protein contains a truncated hinge having a sequence DKTHTCPPC (SEQ ID NO: 15).

In some embodiments, the fusion protein has a modified hinge from IgG4, which is modified to prevent or reduce strand exchange, e.g., Ser228Pro (S228P), having the sequence ESKYGPPCPPC (SEQ ID NO: 16). In some embodiments, the fusion protein contains linker polypeptides. In other embodiments, the fusion protein contains linker and hinge polypeptides.

In some embodiments, the Fc region lacks or has reduced Fucose attached to the N-linked glycan-chain at N297. There are numerous ways to prevent fucosylation, including but not limited to production in a FUT8 deficient cell line; addition inhibitors to the mammalian cell culture media, for example Castanospermine; and metabolic engineering of the production cell line.

In some embodiments, the Fc region is engineered to eliminate recognition by pre-existing antibodies found in humans. In some embodiments, VHH-containing polypeptides of the present disclosure are modified by mutation of position Leu11, for example Leu11Glu (L11E) or Leu11Lys (L11K). In other embodiments, single domain antibodies of the present disclosure are modified by changes in carboxy-terminal region, for example the terminal sequence has the sequence GQGTLVTVKPGG (SEQ ID NO: 17) or GQGTLVTVEPGG (SEQ ID NO: 18) or modification thereof. In some embodiments, the VHH-containing polypeptides of the present disclosure are modified by mutation of position 11 and by changes in carboxy-terminal region.

In some embodiments, the one or more polypeptides of the fusion proteins of the present disclosure are operably linked via amino acid linkers. In some embodiments, these linkers are composed predominately of the amino acids Glycine and Serine, denoted as GS-linkers herein. The GS-linkers of the fusion proteins of the present disclosure can be of various lengths, for example, 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., (GGS)$_2$ (SEQ ID NO: 1); GGSGGSGGS, i.e., (GGS)$_3$ (SEQ ID NO: 2); GGSGGSGGSGGS, i.e., (GGS)$_4$ (SEQ ID NO: 3); and GGSGGSGGSGGSGGS, i.e., (GGS)$_5$ (SEQ ID NO: 4). In some embodiments, the linker is a flexible linker comprising Glycine residues, such as, by way of non-limiting example, GG, GGG, GGGG (SEQ ID NO: 5), GGGGG (SEQ ID NO: 6), and GGGGGG (SEQ ID NO: 7). In some embodiments, the fusion proteins can include a combination of a GS-linker and a Glycine linker.

B. Conjugates

Provided herein are conjugates containing at least one VHH domain that specifically binds PD-1 provided herein and one or more further moiety. The further moiety can be a therapeutic agent, such as a cytotoxic agent, or can be a detection agent. In some embodiments, the moiety can be a targeting moiety, a small molecule drug (non-polypeptide drug of less than 500 Daltons molar mass), a toxin, a cytostatic agent, a cytotoxic agent, an immunosuppressive agent, a radioactive agent suitable for diagnostic purposes, a radioactive metal ion for therapeutic purposes, a prodrug-activating enzyme, an agent that increases biological half-life, or a diagnostic or detectable agent.

In some embodiments, the conjugate is an antibody drug conjugate (ADC, also called immunoconjugates) containing one or more PD-1 VHH domain provided herein conjugated to a therapeutic agent, which is either cytotoxic, cytostatic or otherwise provides some therapeutic benefit. In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In some embodiments, provided antibody drug conjugates of the present disclosure allow targeted-delivery of the drug moiety to tumors. In some cases, this can result in targeted killing of the tumor cell.

In some embodiments, there is provided a PD-1-binding conjugate comprising at least one PD-1 VHH domain provided herein conjugated with a therapeutic agent. In some embodiments, the therapeutic agent includes, for example, daunomycin, doxorubicin, methotrexate, and vindesine (Rowland et al., Cancer Immunol. Immunother. 21:183-187, 1986). In some embodiments, the therapeutic agent has an intracellular activity. In some embodiments, the PD-1-binding conjugate is internalized and the therapeutic agent is a cytotoxin that blocks the protein synthesis of the cell, therein leading to cell death. In some embodiments, the therapeutic agent is a cytotoxin comprising a polypeptide having ribosome-inactivating activity including, for example, gelonin, bouganin, saporin, ricin, ricin A chain, bryodin, diphtheria toxin, restrictocin, Pseudomonas exotoxin A and variants thereof. In some embodiments, where the therapeutic agent is a cytotoxin comprising a polypeptide having a ribosome-inactivating activity, the PD-1-binding conjugate must be internalized upon binding to the target cell in order for the protein to be cytotoxic to the cells.

In some embodiments, there is provided a PD-1-binding conjugate comprising at least one PD-1 VHH domain provided herein conjugated with a toxin. In some embodiments, the toxin includes, for example, bacterial toxins such as diphtheria toxin, plant toxins such as ricin, small molecule toxins such as geldanamycin (Mandler et al., J. Nat. Cancer Inst. 92(19):1573-1581 (2000); Mandler et al., Bioorganic & Med. Chem. Letters 10:1025-1028 (2000); Mandler et al., Bioconjugate Chem. 13:786-791 (2002)), maytansinoids (EP 1391213; Liu et al., Proc. Natl. Acad. Sci. USA 93:8618-8623 (1996)), and calicheamicin (Lode et al., Cancer Res. 58:2928 (1998); Hinman et al., Cancer Res. 53:3336-3342 (1993)). The toxins may exert their cytotoxic and cytostatic effects by mechanisms including tubulin binding, DNA binding, or topoisomerase inhibition.

In some embodiments, there is provided a PD-1-binding conjugate comprising at least one PD-1 VHH domain provided herein conjugated with a label, which can generate a detectable signal, indirectly or directly. These IgSF conjugates can be used for research or diagnostic applications, such as for the in vivo detection of cancer. The label is preferably capable of producing, either directly or indirectly, a detectable signal. For example, the label may be radio-opaque or a radioisotope, such as 3H, 14C, 32P, 35S, 123I, 125I, 131I; a fluorescent (fluorophore) or chemiluminescent (chromophore) compound, such as fluorescein isothiocyanate, rhodamine or luciferin; an enzyme, such as alkaline phosphatase, β-galactosidase or horseradish peroxidase; an imaging agent; or a metal ion. In some embodiments, the label is a radioactive atom for scintigraphic studies, for example 99Tc or 123I, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The PD-1-binding conjugates may be prepared using any methods known in the art. See, e.g., WO 2009/067800, WO 2011/133886, and U.S. Patent Application Publication No. 2014322129, incorporated by reference herein in their entirety.

In some embodiments, the attachment can be covalent or non-covalent, e.g., via a biotin-streptavidin non-covalent interaction. In some embodiments, 1, 2, 3, 4, 5 or more moieties, which can be the same or different, are conjugated, linked or fused to a PD-1 VHH domain to form a PD-1-binding conjugate. In some embodiments, such moieties can be attached to the VHH domain using various molecular biological or chemical conjugation and linkage methods known in the art and described below. In some embodiments, linkers such as peptide linkers, cleavable linkers, non-cleavable linkers or linkers that aid in the conjugation reaction, can be used to link or conjugate the effector moieties to the variant polypeptide or immunomodulatory protein.

In some embodiments, a PD-1 VHH domain is conjugated to one or more moieties, e.g. about 1 to about 20 drug moieties per VHH, through a linker (L). In some embodiments, the PD-1-binding conjugate comprises the following components: (VHH domain), $(L)_q$ and $(moiety)_m$, wherein the VHH domain is any of the described VHH domains capable of specifically binding PD-1 as described; L is a linker for linking the protein or polypeptide to the moiety; m is at least 1; q is 0 or more; and the resulting PD-1-binding conjugate binds to PD-1. In particular embodiments, m is 1 to 4 and q is 0 to 8.

The linker may be composed of one or more linker components. For covalent attachment of the antibody and the drug moiety the linker typically has two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p 234-242).

Exemplary linker components include 6-maleimido-caproyl ("MC"), maleimidopropanoyl ("MP"), valine-citrulline ("val-cit"), a alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-I carboxylate ("SMCC"), and N-Succinimidyl(4-iodo-acetyl)aminobenzoate ("STAB").

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by particular enzymes, for example, a tumor-associated protease, cathepsin B, C and D, at a plasmin protease.

Conjugates of a VHH domain and cytotoxic agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl substrate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

The antibody drug conjugate can be prepared by a variety of methods, such as organic chemistry reactions, conditions, and reagents known to those skilled in the art. In one embodiments, methods include: (1) reaction of a nucleophilic group of a VHH domain with a bivalent linker reagent, to form VHH-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of a VHH domain.

Nucleophilic groups on antibodies, including VHH domains, include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Conjugates, such as antibody drug conjugates, may also be produced by modification of an antibody, such as a VHH domain, to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may lead with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid. Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBi esters, haloformates, and acid halides; (ii) alkyl and benzyl halides such as haloacetamides; (iii) aldehydes, ketones, carboxyl, and maleimide groups.

Alternatively, a fusion protein containing a VHH domain and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

C. Multispecific Formats

Provided herein are PD-1-binding polypeptides that are multispecific containing at least one VHH domain that binds PD-1 and one or more additional binding domains. Typically, the one or more additional domains bind to a second antigen or protein other than PD-1. In some aspects, the further antigen or protein may be an antigen expressed on a tumor, a molecule or receptor expressed on an immune cell, such as a T cell, e.g. a CD3, or an additional inhibitory receptor (e.g. CTLA-4, LAG3, TIM3, VISTA, TIGIT, SIRPα, NKG2A, B7H3, B7H4) or an activating receptor (e.g. OX40, GITR, 41BB, CD40, CD27, CD28 or ICOS) or to confer an additional specificity to a target cell (e.g. CD8 or CD4). In some embodiments, the one or more additional domain is an antibody or antigen-binding fragment specific for the second antigen or protein. In some embodiments, the additional domain is a VHH domain.

In some embodiments, a multispecific PD-1-binding polypeptide comprises at least one VHH domain that binds PD-1 and at least one additional binding domain that binds a second antigen or protein. In some embodiments, this second antigen is a tumor associated antigen (TAA) or tumor microenvironment associated antigen (TMEAA). In some embodiments, this second antigen is an immunomodulatory antigen, wherein said antigen is involved with enhancing or dampening a signaling pathway in an immune cell.

In some cases, a multispecific PD-1-binding polypeptide can further contain an Fc domain, such as any described above. In some embodiments, a multispecific PD-1-binding polypeptide provided herein at least one VHH domains that bind PD-1, at least one additional binding domain that binds a second antigen or protein, and an Fc domain. In some embodiments, an Fc domain mediates dimerization of the multispecific PD-1-binding polypeptide at physiological conditions such that a dimer is formed that doubles the number of binding sites for PD-1 and for the additional antigen or protein.

Non-limiting exemplary multispecific PD-1-binding polypeptides are described below.

1. Bispecific T Cells Engager

In some embodiments, the PD-1-binding polypeptide is a bispecific construct that is or comprises at least one PD-1 VHH domain provided herein and at least one additional binding molecule capable of binding to a surface molecule expressed on a T cell. In some embodiments, the surface molecule is an activating component of a T cell, such as a component of the T cell receptor complex. In particular aspects, the surface molecule is an activating T cell antigen that is expressed on a T cell and is capable of inducing T cell activation upon interaction with an antigen binding molecule. For example, in some aspects, interaction of an antigen binding molecule with an activating T cell antigen may induce T cell activation by triggering the signaling cascade of the T cell receptor complex. Suitable assays to measure T cell activation are known, and include any assay to measure or assess proliferation, differentiation, cytokine secretion, cytotoxic activity and/or expression of one or more activation marker. In some embodiments, the simultaneous or near simultaneous binding of such a PD-1-binding polypeptide to both of its targets, PD-1 expressed on target cell and a T cell molecule expressed on a T cell, e.g. activating T cell antigen, can result in a temporary interaction between the target cell and T cell, thereby resulting in activation, e.g. cytotoxic activity, of the T cell and subsequent lysis of the target cell.

In some embodiments, the T surface molecule, such as activating T cell antigen, is CD3 or is CD2. Specifically, a provided bispecific PD-1-binding polypeptide is capable of specifically binding an activating T cell antigen expressed on a human T cell, such as human CD3 or human CD3. In particular aspects, the additional binding domain that is specific to the activating T cell antigen (e.g. CD3 or CD2) is an antibody or antigen-binding fragment. In some embodiments, a PD-1-binding polypeptide can be a bispecific antibody T cell-engager containing at least one PD-1 VHH domain that specifically binds to PD-1 and an additional binding molecule that is an antibody or antigen-binding fragment specific for an activating component of a T cell (e.g. a T cell surface molecule, e.g. CD3 or CD2).

Among bispecific antibody T cell-engagers are bispecific T cell engager (BiTE) molecules, which contain tandem scFv molecules fused by a flexible linker (see e.g. Nagorsen and Bauerle, Exp Cell Res 317, 1255-1260 (2011); tandem scFv molecules fused to each other via, e.g. a flexible linker, and that further contain an Fc domain composed of a first and a second subunit capable of stable association (WO2013026837); diabodies and derivatives thereof, including tandem diabodies (Holliger et al, Prot Eng 9, 299-305 (1996); Kipriyanov et al, J Mol Biol 293, 41-66 (1999)); dual affinity retargeting (DART) molecules that can include the diabody format with a C-terminal disulfide bridge; or triomabs that include whole hybrid mouse/rat IgG molecules (Seimetz et al, Cancer Treat Rev 36, 458-467 (2010). Similar formats of any of the above molecules can be generated using any of the PD-1 VHH domains provided herein.

In some embodiments, the additional binding domain specific to an activating T cell antigen is an antigen-binding fragment selected from a Fab fragment, a F(ab')$_2$ fragment, an Fv fragment, a scFv, disulfide stabilized Fv fragment (dsFv), a scAb, a dAb, a single domain heavy chain antibody (VHH), or a single domain light chain antibody. In some embodiments, the additional binding domain is monovalent for binding the activating T cell antigen, such as CD2 or CD3.

In some embodiments, the additional binding domain is capable of binding to CD3 or a CD3 complex. A CD3 complex is a complex of at least five membrane-bound polypeptides in mature T-lymphocytes that are non-covalently associated with one another and with the T-cell receptor. The CD3 complex includes the gamma, delta, epsilon, zeta, and eta chains (also referred to as subunits). In some embodiments, the additional binding molecule is an antibody or antigen-binding fragment capable of specifically binding to CD3 or a CD3 complex, also called a CD3-binding domain. In some embodiments, the CD3-binding domain capable of binding CD3 or a CD3 complex includes one or more copies of an anti-CD3 Fab fragment, an anti-CD3 F(ab')$_2$ fragment, an anti-CD3 Fv fragment, an anti-CD3 scFv, an anti-CD3 dsFv, an anti-CD3 scAb, an anti-CD3 dAb, an anti-CD3 single domain heavy chain antibody (VHH), and an anti-CD3 single domain light chain antibody. In some embodiments, the anti-CD3 binding domain is monovalent for binding CD3.

In some cases, the CD3-binding domain recognizes the CD3ε-chain. In some embodiments, the anti-CD3ε binding domain includes one or more copies of an anti-CD3ε Fab fragment, an anti-CD3ε F(ab')$_2$ fragment, an anti-CD3ε Fv fragment, an anti-CD3ε scFv, an anti-CD3ε dsFv, an anti-CD3ε scAb, an anti-CD3ε dAb, an anti-CD3ε single domain heavy chain antibody (VHH), and an anti-CD3ε single domain light chain antibody. In some embodiments, the anti-CD3ε binding domain is monovalent for binding CD3ε.

Exemplary monoclonal antibodies against CD3 or a CD3 complex include, but are not limited to, OKT3, SP34, UCHT1 or 64.1, or an antigen-binding fragment thereof (See e.g., June, et al., J. Immunol. 136:3945-3952 (1986); Yang, et al., J. Immunol. 137:1097-1100 (1986); and Hayward, et al., Immunol. 64:87-92 (1988)). In some aspects, clustering of CD3 on T cells, e.g., by immobilized or cell-localized or tethered anti-CD3-antibodies, leads to T cell activation similar to the engagement of the T cell receptor but independent from its clone typical specificity. In one embodiment, the CD3-binding domain monovalently and specifically binds a CD3 antigen, and is derived from OKT3 (ORTHOCLONE-OKT3™ (muromonab-CD3); humanized OKT3 (U.S. Pat. No. 7,635,475 and published international application No. WO2005040220); SP34 (Pessano et al. The EMBO Journal. 4: 337-344, 1985); humanized variant of SP34 (WO2015001085); Teplizumab™ (MGA031, Eli Lilly); an anti-CD3 binding molecule described in US2011/0275787; UCHT1 (Pollard et al. 1987 J Histochem Cytochem. 35(11):1329-38; WO2000041474); NI0401 (WO2007/033230); visilizumab (U.S. Pat. No. 5,834,597); BC-3 (Anasetti et al., Transplantation 54: 844 (1992); H2C (described in PCT publication no. WO2008/119567); V9 (described in Rodrigues et al., Int J Cancer Suppl 7, 45-50 (1992) and U.S. Pat. No. 6,054,297)). Other anti-CD3 antibodies also can be used in the constructs provided herein, including any described in International published PCT application Nos. WO199404679, WO2008119567, WO2015095392, WO2016204966, WO2019133761; published patent application Nos. US20170369563, US20180194842, US20180355038; U.S. Pat. Nos. 7,728,114, 7,381,803, 7,994,289.

In some embodiments, the CD3-binding domain contains a variable heavy (VH) chain set forth in SEQ ID NO:19 and/or a variable light chain set forth in SEQ ID NO:20, or VH and/or VL sequences having at least 60%, 70%, 80%, 90%, 95%, 97%, 98%, 99% identity with these sequences and specifically binds CD3. In some embodiments, the CD3-binding domain contains a CDRH1, CDRH2 and CDRH3 of the variable heavy (VH) chain set forth in SEQ ID NO:19 and a CDRL1, CDRL2 and CDRL3 variable light chain set forth in SEQ ID NO:20. In some cases, the CD3-binding region comprises a humanized version of the VH sequence set forth in SEQ ID NO:209 and a humanized version of the VL sequence set forth in SEQ ID NO:210. In some embodiments a CD3-binding region can contain a humanized OKT3 derived VH domain sequence set forth in any one of SEQ ID NOs 21, 22, 23 and/or a VL domain sequence set forth in any one of SEQ ID NOs 24, 25, 26, or VH and/or VL sequences having at least 60%, 70%, 80%, 90%, 95%, 97%, 98%, 99% identity with these sequences and specifically binds CD3. In some embodiments, the CD3-binding domain is a Fab, scFv, Fv or dsFv, in which is contained any combination of the above VH and VL sequence, particularly any combination of a VH sequence set forth in any of SEQ ID NOS: 21, 22, 23 and a VL sequence set forth in any of SEQ ID NOS: 24, 25, 26.

In some embodiments, the anti-CD3ε binding domain includes a VH CDR1 sequence that includes at least the amino acid sequence TYAMN (SEQ ID NO: 29); a VH CD2 sequence that includes at least the amino acid sequence RIRSKYNNYATYYADSVKD (SEQ ID NO: 30); a VH CDR3 sequence that includes at least the amino acid sequence HGNFGNSYVSWFAY (SEQ ID NO: 31), a VL CDR1 sequence that includes at least the amino acid sequence RSSTGAVTTSNYAN (SEQ ID NO: 32); a VL CDR2 sequence that includes at least the amino acid sequence GTNKRAP (SEQ ID NO: 33); and a VL CDR3 sequence that includes at least the amino acid sequence ALWYSNLWV (SEQ ID NO: 34). In some embodiments, the CD3-binding domain is a Fab, scFv, Fv or dsFv, in which is contained a VH CDR1 sequence that includes at least the amino acid sequence TYAMN (SEQ ID NO: 29); a VH CD2 sequence that includes at least the amino acid sequence RIRSKYNNYATYYADSVKD (SEQ ID NO: 30); a VH CDR3 sequence that includes at least the amino acid sequence HGNFGNSYVSWFAY (SEQ ID NO: 31), a VL CDR1 sequence that includes at least the amino acid sequence RSSTGAVTTSNYAN (SEQ ID NO: 32); a VL CDR2 sequence that includes at least the amino acid sequence GTNKRAP (SEQ ID NO: 33); and a VL CDR3 sequence that includes at least the amino acid sequence ALWYSNLWV (SEQ ID NO: 34).

In some embodiments, the CD3-binding domain contains a variable heavy (VH) chain set forth in SEQ ID NO:27 and/or a variable light chain set forth in SEQ ID NO:28, or VH and/or VL sequences having at least 60%, 70%, 80%, 90%, 95%, 97%, 98%, 99% identity with these sequences and specifically binds to CD3. In some embodiments, the CD3-binding domain contains a CDRH1, CDRH2 and CDRH3 of the variable heavy (VH) chain set forth in SEQ ID NO:27 and a CDRL1, CDRL2 and CDRL3 variable light chain set forth in SEQ ID NO:28. In some embodiments, the CD3-binding domain contains a CDRH1, CDRH2 and CDRH3 set forth in SEQ ID NOs:29, 30 and 31, respectively and a CDRL1, CDRL2 and CDRL3 variable light chain set forth in SEQ ID NO:32, 33, and 34, respectively. In some cases, the CD3-binding region comprises a humanized version of the VH sequence set forth in SEQ ID NO:27 and a humanized version of the VL sequence set forth in SEQ ID NO:28. In some embodiments a CD3-binding region can contain a humanized VH domain sequence set forth in any one of SEQ ID NOs 35-65 and/or a VL domain sequence set forth in any one of SEQ ID NOs: 66-84, or VH and/or VL sequences having at least 60%, 70%, 80%, 90%, 95%, 97%, 98%, 99% identity with these sequences and specifically binds to CD3. In some embodiments, the anti-CD3ε binding domain thereof includes a variable heavy chain (Hv) comprising the amino acid sequence of SEQ ID NO: 47 and a variable light chain (Lv) comprising the amino acid sequence of SEQ ID NO: 75.

In some embodiments, the CD3-binding domain is a Fab, scFv, Fv or dsFv, in which is contained any combination of the above VH and VL sequence, particularly any combination of a VH sequence set forth in any of SEQ ID NOS: 35-65 and a VL sequence set forth in any of SEQ ID NOS: 66-84. In some embodiments, the anti-CD3 binding domain is a Fab, scFv, Fv or dsFv, in which is contained a variable heavy chain (VH) comprising the amino acid sequence of SEQ ID NO: 47 and a variable light chain (VL) comprising the amino acid sequence of SEQ ID NO: 75.

In some embodiments, the CD3-binding domain contains a variable heavy (VH) chain set forth in any one of SEQ ID NO:313, 314, 317, or 318. In some embodiments, the CD3-binding domain contains a variable light (VL) chain set forth in any one of SEQ ID NO:315, 316, 319, or 320.

The provided bispecific constructs can be formatted in any of a number of formats containing the at least one PD-1 VHH domain and the at least one additional domain specific to an activating T cell antigen, such as a CD3-binding domain.

In one embodiment, the bispecific construct is a bispecific single-domain antibody-linked Fab (S-Fab) containing at least one PD-1 VHH domain as described linked, directly or indirectly to a Fab antigen binding fragment specific to a T cell activating antigen, e.g. CD3, such as an anti-CD3 Fab. The Fab against a T cell activating antigen, e.g. anti-CD3 Fab, can contain any of the VH and VL sequences as described. In some embodiments, the PD-1 VHH domain is linked to the C-terminus of the VH or VL chain of an anti-CD3 Fab. In some embodiments, the S-Fab can be further modified, such as by conjugation with polyethylene glycol (PEG), N-(2-hydroxypropyl) methacrylamide (HPMA) copolymers, proteins (such as albumin), polyglutamic acid or PASylation (Pan et al. (2018) International Journal of Nanomedicine, 2018:3189-3201).

In another embodiment, the bispecific construct is a scFv-single domain antibody in which the construct contains at least one PD-1 VHH as described linked, directly or indirectly, to an scFv containing a VH and a VL of an antigen binding domain specific to a T cell activating antigen, e.g. CD3. The scFv against a T cell activating antigen, e.g. anti-CD3 scFv, can contain any of the VH and VL sequences as described. In some embodiments, the VHH domain and the scFv are connected by a linker, such as a peptide linker. In some embodiments, the peptide linker can be a peptide linker as described herein. In some embodiments, the VHH domain and the scFv are each connected, optionally through a hinge region or a linker (e.g. peptide linker), to an Fc region, such as an N-terminus of an Fc region. The Fc region can be any described herein, such as a human Fc region or a variant thereof, e.g. a human IgG1 Fc region or a variant thereof. In particular examples, the Fc region is formed by variant Fc domains, e.g. variant human IgG1 domains, that are mutated or modified to promote heterodimerization in which different polypeptides can be dimerized to yield a heterodimer.

In a further embodiment, the CD3-binding domain is a single domain antibody, such as is a VHH domain that specifically binds to CD3. Single domain antibodies, including VHH domains that bind to CD3 are known, see e.g. published U.S. patent application No. US20160280795. In some embodiments, the CD3-binding domain is an anti-CD3 VHH set forth in SEQ ID NO:85, or a sequence that exhibits at least 60%, 70%, 80%, 90%, 95%, 97%, 98%, 99% identity with SEQ ID NO:85 and specifically binds to CD3. In such aspects, a bispecific construct provided herein can include at least one PD-1 VHH domain and at least one CD3 VHH domain. For formatting the constructs, in some cases, each VHH domain is connected, optionally through a hinge region or linker (e.g. peptide linker), to an Fc region, such as an N-terminus of an Fc region. The Fc region can be any described herein, such as a human Fc region or a variant thereof, e.g. a human IgG1 Fc region or a variant thereof. In particular examples, the Fc region is formed by variant Fc domains, e.g. variant human IgG1 domains, that are mutated or modified to promote heterodimerization in which different polypeptides can be dimerized to yield a heterodimer.

In the above embodiments, exemplary modifications of an Fc region to promote heterodimerization are known, including any as described below, e.g. Table 3. In some embodiments, one Fc polypeptide of a heterodimeric Fc comprises the sequence of amino acids set forth in any of SEQ ID NOS:103, 107, 115 or 117, and the other Fc polypeptide of the heterodimeric Fc contains the sequence of amino acids set forth in any of SEQ ID NOS:104, 108, 111, 113, 119 or 121. In some embodiments, one Fc polypeptide of a heterodimeric Fc comprises the sequence of amino acids set forth in any of SEQ ID NOS: 105, 109, 116 or 118 and the other Fc polypeptide of the heterodimeric Fc comprises the sequence of amino acids set forth in any of SEQ ID NOS: 106, 110, 112, 114, 120 or 122.

2. Constrained CD3 Multispecific Construct

In some embodiments, the PD-1-binding polypeptide is a multispecific polypeptide construct that is a constrained T-cell engaging fusion protein. In particular aspects, the constrained multispecific constructs provided herein bind an activating T cell antigen, such as a CD3, and PD-1. Typically, the provided constrained multispecific polypeptide constructs also contain at least one antigen binding domain that binds a tumor associated antigen (TAA). The constrained multispecific polypeptide constructs provided herein include at least a first component that includes an immunoglobulin Fc region, a second component that includes one or more copies of at least a binding domain that binds CD3 (referred to herein as an anti-CD3 binding domain or a CD3 binding domain, which are terms that are used interchangeably herein), and a linker, such as a polypeptide linker, that joins the first component and the second component. In the provided multispecific polypeptide constructs, one or both of the first and second components contain at least one provided VHH domain that binds to PD-1, and one or both of the first and second components contain at least one TAA antigen binding domain, which, when engaged upon binding to antigen, render the constrained CD3 binding region substantially able to bind CD3

In some embodiments, the constrained multispecific polypeptide constructs provided herein exist in two states in terms of capacity to bind CD3 and subsequently activate T-cells: (1) the "inactive" state occurs when there is no binding of any or all of the antigen binding domain(s) to PD-1, such that the CD3 binding is constrained and T-cell interaction is obviated or reduced, and (2) the "active" state occurs upon antigen binding by any or all of the antigen binding domain(s), such that the CD3 binding region is able to bind CD3 and the T-cell interaction is allowed.

In some embodiments, the Fc region is linked to the CD3 binding domain via a linker or linkers. In some embodiments, the Fc region is linked to the CD3 binding region via a non-cleavable linker or linkers. In some embodiments, the Fc region is linked to the CD3 binding region via a cleavable linker or an otherwise labile linker or linkers. In some embodiments, cleavable linker is a linker that can be specifically cleaved in the presence of a protease. In some aspects, enhanced CD3 binding occurs following cleavage of the cleavable linker. In some such aspects, the "active" state can be further amplified via several mechanisms, including via cleavage of the linker joining the CD3 binding region and the Fc region. In some embodiments, the cleavable linker is a linker that contains a substrate recognition site for a protease. In some embodiments, wherein the Fc region and the CD3 binding region are linked by a cleavable linker, enhanced CD3 binding may occur following cleavage within the linker(s).

Further, in aspects wherein the Fc region and the CD3 binding region are operably linked by a cleavable linker, cleavage of the linker(s) between the Fc region and the CD3 binding region may separate the constrained multispecific polypeptide constructs into a first and second component. Depending on the composition of the constrained multispecific polypeptide construct, the first and second component may have distinct functionalities. In some embodiments, the Fc region is a region that exhibits one or more effector functions, such as ADCC, CDC or ADCP functions. In such examples, the constrained multispecific polypeptide constructs of the disclosure can be used to produce a self-amplifying system. For example, in some aspects, the incorporation of a protease cleavable linker between the Fc and the components of the CD3 binding domain enables for amplification of the T-cell activating capacity by allowing full exposure of the CD3 binding domain. Depending on the specific linker included, the amplification can be mediated by tumor associated proteases or by granzymes released following antigen dependent-T-cell activation. If a tumor protease cleavable linker is included the amplification is mediated by the tumor or tumor-microenvironment. Whereas, if a granzyme B cleavable linker is included the amplification may be self-mediated by T-cells following antigen-dependent activation. Furthermore, in cases wherein an effector enabled Fc is included in the construct, amplification may be mediated by granzymes released from NK cell that occurs through an ADCC mechanism.

The provided constrained multispecific polypeptide constructs include a configuration in which the first component containing the Fc region is N-terminal to the second component containing the CD3 binding region. In such an embodiment, the first and second components are joined via a linker that is C-terminal to the end of the Fc region. In some embodiments, the at least one PD-1 VHH domain is positioned on the amino-terminal (N-term) region of the multispecific polypeptide construct. In some embodiments, the at least one PD-1 VHH domain is positioned on the carboxy-terminal (C-term) region of the multispecific polypeptide construct. In some embodiments, the constrained multispecific polypeptide construct contains only one PD-1 VHH domains that is positioned on either the N- or C-terminal regions of the multispecific polypeptide construct. n some embodiments, the at least one TAA antigen binding domain is positioned on the amino-terminal (N-term) region of the multispecific polypeptide construct. In some embodiments, the at least one TAA antigen binding domain is positioned on the carboxy-terminal (C-term) region of the multispecific polypeptide construct. In some embodiments, the constrained multispecific polypeptide construct contains at least two TAA antigen binding domains that are positioned on both the N- and C-terminal regions of the multispecific polypeptide construct.

In some embodiments, the constrained multispecific polypeptide construct is a dimer, in which dimerization is formed by covalent or non-covalent interactions between two polypeptide chains. In some embodiments, the two polypeptide chains are covalently bonded to each other by, for example, interchain disulfide bonds. In some embodiments, the Fc region mediates dimerization via interchain disulfide bonds. In particular embodiments, a constrained multispecific polypeptide construct contains a heterodimeric Fc region in which, in some cases, the polypeptide chains of the multispecific polypeptide construct are different (heterodimer). In particular examples of a heterodimeric multispecific polypeptide construct, the CD3-binding region is a two chain polypeptide containing a VH and a VL chain, such as is an Fv antibody fragment containing the VH and VL. In some embodiments, the Fv antibody fragment includes a disulfide stabilized anti-CD3 binding Fv fragment (dsFv).

In some embodiments, a constrained multispecific polypeptide construct is formed from or includes two polypeptides, including a first polypeptide comprising a first Fc polypeptide of a heterodimeric Fc region, a linker (e.g. cleavable or non-cleavable linker), a VH domain of an anti-CD3 antibody or antigen binding fragment (e.g. Fv); and a second polypeptide comprising a second Fc polypeptide of the heterodimeric Fc region, the linker (e.g. the cleavable or non-cleavable linker), a VL domain of the anti-CD3 antibody or antigen binding fragment (e.g. Fv). In some embodiments, the first polypeptide contains one or two VHH domains that bind to PD-1. In some embodiments, the second polypeptide contains one or two VHH domains that bind to PD-1. In some embodiments, a constrained multispecific polypeptide construct contains only one PD-1 VHH domains. In some embodiments, the first polypeptide contains one or two TAA antigen binding domains. In some embodiments, the second polypeptide contains one or two TAA antigen binding domains. In some embodiments, a constrained multispecific polypeptide construct contains at least two TAA antigen binding domains. In some cases, at least one TAA antigen binding domain is located N-terminally to the Fc polypeptide and at least one TAA antigen binding domain is located C-terminally to the chain of the CD3-binding region. In particular embodiments, the at least one VHH domain that binds to PD-1 is on a separate polypeptide of the heterodimeric molecule than the polypeptide containing the last least one, e.g. two, TAA antigen binding domains.

In some embodiments, a constrained multispecific polypeptide construct contains at least two TAA antigen binding domains and at least one VHH domain that binds PD-1. In some embodiments, a constrained multispecific polypeptide construct contains (1) a first polypeptide comprising in order of N-terminus to C-terminus: a first TAA antigen binding domain, the first Fc polypeptide of a heterodimeric Fc region, a linker (e.g. a cleavable or non-cleavable linker), a chain (e.g. VH or VL) of an anti-CD3 antibody or antigen binding fragment (e.g. Fv or dsFv), and a second TAA antigen binding domain; and (2) a second polypeptide comprising in order of N-terminus to C-terminus: the second Fc polypeptide of the heterodimeric Fc region, the same linker (e.g. same cleavable or non-cleavable linker), the other chain (other of the VH or VL) of the anti-CD3 antibody or antigen binding fragment, and a VHH domain that binds PD-1. In some embodiments, a constrained multispecific polypeptide construct contains (1) a first polypeptide comprising in order of N-terminus to C-terminus: a first TAA antigen binding domain, the first Fc polypeptide of a heterodimeric Fc region, a linker (e.g. a cleavable or non-cleavable linker), a chain (e.g. VH or VL) of an anti-CD3 antibody or antigen binding fragment (e.g. Fv or dsFv), and a second TAA antigen binding domain; and (2) a second polypeptide comprising in order of N-terminus to C-terminus: a VHH domain that binds PD-1, the second Fc polypeptide of the heterodimeric Fc region, the same linker (e.g. same cleavable or non-cleavable linker), and the other chain (other of the VH or VL) of the anti-CD3 antibody or antigen binding fragment.

In some embodiments, the first polypeptide or second polypeptide or both the first and second polypeptide further include a co-stimulatory receptor binding region (CRBR) that binds a co-stimulatory receptor. In some embodiments, the CRBR of the first and/or second polypeptide can be located N-terminally to the Fc polypeptide and/or C-terminally to the chain of the CD3-binding region.

In some embodiments, a constrained multispecific polypeptide construct contains at least two antigen binding domains that binds a TAA, a co-stimulatory receptor binding region (CRBR) that binds a co-stimulatory receptor and a VHH domain that binds PD-1. In some embodiments, a constrained multispecific polypeptide construct contains (1) a first polypeptide comprising in order of N-terminus to C-terminus: a first TAA antigen binding domain, the first Fc polypeptide of a heterodimeric Fc region, a linker (e.g. a cleavable linker), a chain (e.g. VH or VL) of an anti-CD3 antibody or antigen binding fragment (e.g. Fv or dsFv), and a second TAA antigen bind domain; and (2) a second polypeptide comprising in order of N-terminus to C-terminus: one of VHH domain that binds PD-1 or CRBR, the second Fc polypeptide of the heterodimeric Fc region, the same linker (e.g. same cleavable linker), the other chain (other of the VH or VL) of the anti-CD3 antibody or antigen binding fragment, and the other of the VHH domain that binds PD-1 or CRBR.

Each of the components of the multispecific polypeptide constructs of the disclosure is described in more detail below.

a. Antigen Binding Domain

The multispecific polypeptide constructs of the present disclosure include at least one antigen binding domain, such as at least a first antigen binding domain and a second antigen binding domain. In some aspects, the antigen binding domain, or independently each of the antigen binding domains, is selected from an antibody or antigen binding fragment, a natural (or native) cognate binding partner, an Anticalin (engineered lipocalin), a Darpin, a Fynomer, a Centyrin (engineered fibroneticin III domain), a cystine-knot domain, an Affilin, an Affibody, or an engineered CH3 domain. In some embodiments, the natural cognate binding partner comprises an extracellular domain or binding fragment thereof of the native cognate binding partner of the TAA, or a variant thereof that exhibits binding activity to the TAA.

In some embodiments, the antigen binding domain, or independently each of the antigen binding domains, such as the first antigen-binding domain and the second antigen binding domains, includes one or more copies of an antibody or an antigen-binding fragment thereof. In some embodiments, the antigen binding domain or independently each of the antigen binding domains, such as the first antigen-binding domain and the second antigen binding domains, includes one or more copies of an antibody or an antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

In some embodiments, the antigen binding domain, or independently each of the antigen binding domains, such as the first antigen-binding domain and the second antigen binding domains, is a single chain antibody. In some examples, the single chain is an scFv, a scAb, a single domain heavy chain antibody, or a single domain light chain antibody.

In some embodiments, the antigen binding domain or independently each of the antigen binding domains, such as the first antigen-binding domain and the second antigen binding domains, includes one or more single domain antibody (sdAb) fragments, for example VHH, VNAR, engineered VH or VK domains. VHHs can be generated from natural camelid heavy chain only antibodies, genetically modified rodents that produce heavy chain only antibodies, or naïve/synthetic camelid or humanized camelid single domain antibody libraries. VNARs can be generated from cartilaginous fish heavy chain only antibodies. Various methods have been implemented to generate monomeric sdAbs from conventionally heterodimeric VH and VK domains, including interface engineering and selection of specific germline families.

In some embodiments, the antigen binding domain or independently each of the antigen binding domains, such as the first antigen-binding domain and/or the second antigen binding domains, of the multispecific polypeptide constructs contains at least one sdAb or an scFv that binds a TAA. In some embodiments, the at least one scFv or sdAb that binds a TAA is positioned amino-terminally relative to the Fc region and/or carboxy-terminally relative to the CD3 binding region of the multispecific polypeptide construct. In some embodiments, the multispecific polypeptide construct contains only one scFv or sdAb that binds to a TAA, which can be positioned either amino-terminally relative to the Fc region and/or carboxy-terminally relative to the CD3 binding region. In some embodiments, the multispecific polypeptide construct contains two scFvs or sdAbs that bind to a TAA, positioned amino-terminally relative to the Fc region and/or carboxy-terminally relative to the CD3 binding region. In some embodiments, the multispecific polypeptide construct contains three scFv or sdAb, in which two are positioned amino-terminally relative to the Fc region or carboxy-terminally relative to the CD3 binding region, and the third is positioned at the other end of the multispecific polypeptide construct.

In some embodiments, the multispecific polypeptide construct is formed from or includes two polypeptides, including a first polypeptide comprising a first Fc polypeptide of a heterodimeric Fc region, a linker, a VH domain of an anti-CD3 antibody or antigen binding fragment (e.g. Fv), and an scFv or sdAb that binds to a tumor-associated antigen; and a second polypeptide comprising a second Fc polypeptide of the heterodimeric Fc region, the linker, a VL domain of the anti-CD3 antibody or antigen binding fragment (e.g. Fv) and, optionally, the same or different scFv or sdAb that binds to a tumor-associated antigen. The scFv or sdAb that binds to a TAA can be positioned amino terminally relative to an Fc polypeptide of the heterodimeric Fc and/or carboxy-terminally relative to a VH or VL chain of the CD3 binding region. At least one of the first and/or second polypeptide of the multispecific polypeptide construct also includes VHH domain that binds PD-1, such as any set forth in the present disclosure. In some aspects, at least one of the first and/or second polypeptide of the multispecific polypeptide construct may also include a CRBR that binds a costimulatory receptor or a chain thereof as described.

In some embodiments, the antigen binding domain or independently each of the antigen binding domains, such as the first antigen-binding domain and/or the second antigen binding domains, of the multispecific polypeptide constructs contains binding domains as single domain antibodies (sdAbs).

In some embodiments, the antigen binding domain or independently each of the antigen binding domains, such as the first antigen-binding domain and the second antigen binding domains, contains more than one chain. In some embodiments, the antigen binding domain or independently each of the antigen binding domains, such as the first antigen-binding domain and/or the second antigen binding domains, of the multispecific polypeptide constructs contains VH and VL sequences assembled as FABs.

In some embodiments, the antigen binding domain or independently each of the antigen binding domains, such as the first antigen-binding domain and/or the second antigen binding domains, of the multispecific polypeptide constructs contains a VH-CH1 (Fd) and a VL-CL of a Fab antibody that binds a TAA. In some embodiments, the Fab antibody containing a VH-CH1 (Fd) and a VL-CL is positioned amino-terminally relative to the Fc region and/or carboxy-terminally relative to the CD3 binding region of the multispecific polypeptide construct. In some embodiments, the multispecific polypeptide construct contains only one Fab antibody, containing a VH-CH1 (Fd) and VL-CL, that binds to a TAA, which can be positioned either amino-terminally relative to the Fc region and/or carboxy-terminally relative to the CD3 binding region. In some embodiments, the multispecific polypeptide construct contains two Fab antibody fragments, each containing a VH-CH1 (Fd) and VL-CL, that binds to a TAA, in which one is positioned amino-terminally relative to the Fc region and the other is positioned carboxy-terminally relative to the CD3 binding region.

In some embodiments, the multispecific polypeptide construct is formed from or includes three or more polypeptides, including a first polypeptide comprising a first Fc polypeptide of a heterodimeric Fc region, a linker and a VH-CH1 (Fd) or VL-CL of a Fab antibody fragment that binds to a tumor-associated antigen; a second polypeptide comprising a second Fc polypeptide of the heterodimeric Fc region, the linker and, optionally, the same VH-CH1 (Fd) or VL-CL of the Fab antibody fragment that binds to a tumor-associated antigen, and a third polypeptide comprising the other of the VH-CH1 (Fd) or VL-CL of the Fab antibody fragment that binds to the TAA.

In some embodiments, the antigen binding domain, or independently each of the antigen binding domains, is or includes an extracellular domain or binding fragment thereof of the natural (or native) cognate binding partner of the TAA, or a variant thereof that exhibits binding activity to the TAA.

In some embodiments, the antigen binding domain or independently each of the antigen binding domains, such as the first antigen-binding domain and the second antigen binding domains, bind the same antigen. In some embodiments, there are more than one antigen binding domain that binds a TAA and each of the antigen binding domains, such as the first antigen-binding domain and the second antigen binding domains, bind a different antigen. In some embodiments, each of the antigen binding domains, such as the first antigen-binding domain and the second antigen binding domains, bind the same tumor associated antigen (TAA). In some embodiments, each of the antigen binding domains, such as the first antigen-binding domain and the second antigen binding domains bind a different TAA. In some embodiments, the each of the antigen binding domains, such as the first antigen-binding domain and the second antigen binding domains bind a different epitope on the same TAA. In some embodiments, each of the antigen binding domains, such as the first antigen-binding domain and the second antigen binding domains, bind the same epitope on the same TAA.

In some embodiments, the antigen binding domain, or independently each of the antigen binding domains that binds TAA results in monovalent, bivalent, trivalent, or tetravalent binding to the TAA.

In some embodiments, the TAA is selected from the group consisting of 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsxl), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidyl-serine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, at least one antigen binding domain, or independently each antigen binding domain, binds the tumor associated antigen (TAA) folate receptor alpha (FRα). For example, the antigen binding domain contains the binding domain as an sdAb that binds FRα. Exemplary FRα-binding sdAbs are set forth in SEQ ID NOS: 86, 87, or 88. The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any the foregoing SEQ ID No and bind FRα.

In some embodiments, at least one antigen binding domain, or independently each antigen binding domain, binds the tumor associated antigen (TAA) cMET. For example, the antigen binding domain contains the binding domain as a sdAb that binds cMET. An exemplary cMET-binding sdAb is set forth in SEQ ID NO: 89 (U.S. Pat. No. 9,346,884). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to a the foregoing SEQ ID No and bind cMET.

In some embodiments, at least one antigen binding domain, or independently each antigen binding domain, binds the tumor associated antigen (TAA) B7H3. For example, the antigen binding domain contains the binding domain as an scFv that binds B7H3. In some embodiments, the antigen binding domain is or contains a Fab antibody fragment comprising a VH-CH1 (Fd) and LC. An exemplary B7H3 Fd is described in PCT Publication No, WO2017/030926.

In some embodiments, at least one antigen binding domain, or independently each antigen binding domain, binds the tumor associated antigen (TAA) CD20. For example, the antigen binding domain contains the binding domain as an scFv that binds CD20. Exemplary CD20-binding scFvs are set forth in SEQ ID NO: 90 or containing a VL and VH set forth in SEQ ID NO: 91 and 92 (U.S. Pub. No. US 2005/0123546). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind CD20.

In some embodiments, at least one antigen binding domain, or independently each antigen binding domain, binds the tumor associated antigen (TAA) DLL3. For example, the antigen binding domain contains the binding domain as an scFv that binds DLL3. Exemplary DLL3-binding scFv is set forth in SEQ ID NO: 93 and 94 (U.S. Pub. No. US 2017/0037130). In some embodiments, the antigen binding domain is or contains a Fab antibody fragment comprising a Fd and LC that binds DLL3. An exemplary DLL3 Fd is set forth in SEQ ID NO: 95 and an exemplary DLL3 LC is set forth in SEQ ID NO: 96 (U.S. Pat. No. 8,044,178). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind DLL3.

In some embodiments, at least one antigen binding domain, or independently each antigen binding domain, binds the tumor associated antigen (TAA) 5T4. An exemplary 5T4 Fd is set forth in SEQ ID NO: 97 and an exemplary 5T4 LC is set forth in SEQ ID NO: 98. In some embodiments, the antibody binding domain comprises a VH and VL as set forth in SEQ ID NOS: 99 and 100 (U.S. Pat. No. 8,044,178). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind 5T4.

In some embodiments, at least one antigen binding domain, or independently each antigen binding domain, binds the tumor associated antigen (TAA) gpNMB. In some embodiments, the antigen binding domain is or contains a Fab fragment comprising a Fd and LC chain. An exemplary gpNMB Fd is set forth in SEQ ID NO: 101 and an exemplary gpNMB LC is set forth in SEQ ID NO: 102. The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind gpNMB.

In some embodiments, the antigen binding domain is linked, directly or indirectly via a linker, to the Fc region and/or to the CD3 binding region. In some embodiments, linkage is via a linker. In some embodiments, the linker is a linking peptide (LP), which can include any flexible or rigid linker as described. In some embodiments, the linker is selected from the group consisting of GGSGGS, i.e., (GGS)$_2$ (SEQ ID NO: 1); GGSGGSGGS, i.e., (GGS)$_3$ (SEQ ID NO: 2); GGSGGSGGSGGS, i.e., (GGS)$_4$ (SEQ ID NO: 3); and GGSGGSGGSGGSGGS, i.e., (GGS)$_5$ (SEQ ID NO: 4). In some embodiments, the linker is a flexible linker comprising Glycine residues, such as, by way of non-limiting example, GG, GGG, GGGG (SEQ ID NO: 5), GGGGG (SEQ ID NO: 6), and GGGGGG (SEQ ID NO: 7). In some embodiments, the linker includes a combination of a GS-linker and a Glycine linker.

b. Fc Region

A constrained multispecific polypeptide construct includes an immunoglobulin Fc region. Generally, the constrained multispecific polypeptide construct is a dimer formed by polypeptides, each containing an Fc. The Fc polypeptide can be any as set forth above. In particular embodiments, the Fc region is formed by Fc domains that are mutated or modified to promote heterodimerization in which different polypeptides can be dimerized to yield a heterodimer. Thus, in some embodiments, the dimer is a heterodimer in which two polypeptide chains of the multi-specific polypeptide construct are different.

Various methods are known for promoting heterodimerization of complementary Fc polypeptides, see e.g. Ridgway et al, Protein Eng. 9:617-621 (1996); Merchant et al, Nat. Biotechnol. 16(7): 677-81 (1998); Moore et al. (2011) MAbs, 3:546-57; Von Kreudenstein et al. MAbs, (2013) 5:646-54; Gunasekaran et al. (2010) J. Biol. Chem., 285:19637-46; Leaver-Fay et al. (2016) Structure, 24:641-51; Ha et al. (2016) Frontiers in Immunology, 7:1; Davis et al. (2010) Protein Eng Des Sel, 23:195-202; published international PCT Appl. No. WO 1998/050431, WO 2009/089004, WO2011143545 WO 2014/067011, WO 2012/058768, WO2018027025; published U.S. patent Appl. No. US20140363426, US20150307628, US20180016354, US20150239991; and U.S. patent Nos. U.S. Pat. Nos. 5,731,168, 7,183,076, 9,701,759, 9,605,084, and 9,650,446. Methods to promote heterodimerization of Fc chains include mutagenesis of the Fc region, such as by including a set of "knob-into-hole" mutations or including mutations to effect electrostatic steering of the Fc to favor attractive interactions among different polypeptide chains. For example, in some embodiments, the Fc polypeptides of a heterodimer includes a mutation to alter charge polarity across the Fc dimer interface such that coexpression of electrostatically matched Fc chains support favorable attractive interactions thereby promoting desired Fc heterodimer formation, whereas unfavorable repulsive charge interactions suppress unwanted Fc homodimer formation (Guneskaran et al. (2010) JBC, 285: 19637-19646). When co-expressed in a cell, association between the chains is possible but the chains do not substantially self-associate due to charge repulsion. Other strategies for generating a heterodimeric Fc include mixing human IgG and IgA CH3 domain segments to create a complementary CH3 heterodimer, which is referred to as a SEED Fc.

In some embodiments, to promote heterodimerization both polypeptides of the Fc heterodimer contain paired or complementary amino acid modifications. Exemplary paired amino acid modification of polypeptides of an Fc fusion are set forth in Table 3.

TABLE 3

Paired amino acids of Heterodimeric Fc

| First Fc polypeptide | Second Fc Polypeptide |
| --- | --- |
| T366W | T366S/L368W/Y407V |
| T366W/S354C | T366S/L368A/Y407V/Y349C |
| S364H/F405A | Y349T/Y349F |
| T350V/L351Y/F405A/Y407V | T350V/T366L/K392L/T394W |
| K360D/D399M/Y407A | E345R/Q347R/T366V/K409V |
| K409D/K392D | D399K/E356K |
| K360E/K409W | Q347R/D399V/F405T |
| L360E/K409W/Y349C | Q347R/399V/F405T/S354C |
| K370E/K409W | E357N/D399V/F405T |

In some embodiments, modifications include introduction of a protuberance (knob) into a first Fc polypeptide and a cavity (hole) into a second Fc polypeptide such that the protuberance is positionable in the cavity to promote complexing of the first and second Fc-containing polypeptides. Amino acids targeted for replacement and/or modification to create protuberances or cavities in a polypeptide are typically interface amino acids that interact or contact with one or more amino acids in the interface of a second polypeptide.

In some embodiments, a first Fc polypeptide that is modified to contain protuberance (hole) amino acids include replacement of a native or original amino acid with an amino acid that has at least one side chain which projects from the interface of the first Fc polypeptide and is therefore positionable in a compensatory cavity (hole) in an adjacent interface of a second polypeptide. Most often, the replacement amino acid is one which has a larger side chain volume than the original amino acid residue. One of skill in the art knows how to determine and/or assess the properties of amino acid residues to identify those that are ideal replacement amino acids to create a protuberance. In some embodiments, the replacement residues for the formation of a protuberance are naturally occurring amino acid residues and include, for example, arginine (R), phenylalanine (F), tyrosine (Y), or tryptophan (W). In some examples, the original residue identified for replacement is an amino acid residue that has a small side chain such as, for example, alanine, asparagine, aspartic acid, glycine, serine, threonine, or valine.

In some embodiments, a second Fc polypeptide that is modified to contain a cavity (hole) is one that includes replacement of a native or original amino acid with an amino acid that has at least one side chain that is recessed from the interface of the second polypeptide and thus is able to accommodate a corresponding protuberance from the interface of a first polypeptide. Most often, the replacement amino acid is one which has a smaller side chain volume than the original amino acid residue. One of skill in the art knows how to determine and/or assess the properties of amino acid residues to identify those that are ideal replacement residues for the formation of a cavity. Generally, the replacement residues for the formation of a cavity are naturally occurring amino acids and include, for example, alanine (A), serine (S), threonine (T) and valine (V). In some examples, the original amino acid identified for replacement is an amino acid that has a large side chain such as, for example, tyrosine, arginine, phenylalanine, or tryptophan.

The CH3 interface of human IgG1, for example, involves sixteen residues on each domain located on four anti-parallel β-strands which buries 1090 Å2 from each surface (see e.g., Deisenhofer et al. (1981) Biochemistry, 20:2361-2370; Miller et al., (1990) J Mol. Biol., 216, 965-973; Ridgway et al., (1996) Prot. Engin., 9: 617-621; U.S. Pat. No. 5,731, 168). Modifications of a CH3 domain to create protuberances or cavities are described, for example, in U.S. Pat. No. 5,731,168; International Patent Applications WO98/50431 and WO 2005/063816; and Ridgway et al., (1996) Prot. Engin., 9: 617-621. In some examples, modifications of a CH3 domain to create protuberances or cavities are typically targeted to residues located on the two central anti-parallel β-strands. The aim is to minimize the risk that the protuberances which are created can be accommodated by protruding into the surrounding solvent rather than being accommodated by a compensatory cavity in the partner CH3 domain.

For example, in some embodiments the heterodimeric Fc includes a polypeptide having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). Heterodimerization via CH3 modifications can be further stabilized by the introduction of a disulfide bond, for example by changing Ser354 to Cys (S354C) and Tyr349 to Cys (Y349C) on opposite CH3 domains (Reviewed in Carter, 2001 Journal of Immunological Methods, 248: 7-15).

The resulting constrained multispecific polypeptide constructs can be purified by any suitable method such as, for example, by affinity chromatography over Protein A or Protein G columns. Where two nucleic acid molecules encoding different polypeptides are transformed into cells, formation of homo- and heterodimers will occur. Conditions for expression can be adjusted so that heterodimer formation is favored over homodimer formation.

Techniques for recovery of heterodimers from homodimers based on a differential affinity of the heterodimers for an affinity reagent are known. In some aspects, such techniques include designing a heterodimer so that one of the Fc polypeptide chains does not bind to the affinity reagent protein A. In some cases, one of the polypeptide chain can contain one or more amino acid substitution to abrogate or reduce affinity for the protein A reagent in one of the polypeptides of the Fc heterodimer, see e.g. WO2017134440, WO2010151792, Jendeberg et al. (Jendeberg et al., (1997) J. Immunol. Methods, 201(1): 25-34. In some of these embodiments, the Fc region may be modified at the protein-A binding site on one member of the heterodimer so as to prevent protein-A binding and thereby enable more efficient purification of the heterodimeric fusion protein. An exemplary modification within this binding site is Ile253, for example Ile253Arg (I253R). In some embodiments, the modification may be H435R or H435R/Y436F. In some embodiments, an Fc polypeptide of an Fc heterodimer can contain a modification so that it is capable of binding protein A but not protein G (pA+/pG−). Exemplary pA+/pG-amino acid modifications include an Fc containing serine at position 428, serine at position 434 and optionally histidine at position 436, with reference to human IgG1 or comprising these residues at the corresponding positions in human IgG 2, 3, or 4. In some aspects, such amino acid modifications in one IgG Fc polypeptide at positions 428, 434 and optionally 436 reduces or prevents the binding of protein G, enhancing the purification of the protein.

In some embodiments, any of such modifications to confer differential affinity to an affinity reagent can be combined with any one or more other amino acid modifications described above. For example, the I253R modification may be combined with either the T366S/L368A/Y407V modifications or with the T366W modifications. The T366S/L368A/Y407V modified Fc is capable of forming homodimers as there is no steric occlusion of the dimerization interface as there is in the case of the T336W modified Fc. Therefore, in some embodiments, the I253R modification is combined with the T366S/L368A/Y407V modified Fc to disallow purification any homodimeric Fc that may have formed. Similar modifications can be employed by combining T366S/L368A/Y407V and H453R.

In some embodiments, the Fc regions of the heterodimeric molecule additionally can contain one or more other Fc mutation, such as any described above. In some embodiments, the heterodimer molecule contains an Fc region with a mutation that reduces effector function.

In some embodiments, one Fc polypeptide of a heterodimeric Fc comprises the sequence of amino acids set forth in any of SEQ ID NOS:103, 107, 115, or 117, and the other Fc polypeptide of the heterodimeric Fc contains the sequence of amino acids set forth in any of SEQ ID NOS: 104, 108, 111, 113, 119 or 121. In some embodiments, one Fc polypeptide of a heterodimeric Fc comprises the sequence of amino acids set forth in any of SEQ ID NOS: 105, 109, 116 or 118 and the other Fc polypeptide of the heterodimeric Fc comprises the sequence of amino acids set forth in any of SEQ ID NOS: 106, 110, 112, 114, 120 or 122.

In some embodiments, the Fc region of the provided multispecific polypeptide constructs exhibit one or more effector functions. In some cases, the Fc region is capable of providing Fc-mediated effector functions, such as for example, ADCC (e.g., release of granzyme B by NK cells), ADCP, and/or CDC. In general, the Fc region is responsible for effector functions, such as complement-dependent cytotoxicity (CDC) and antibody-dependent cell cytotoxicity (ADCC), in addition to the antigen-binding capacity, which is the main function of immunoglobulins. Additionally, the FcRn sequence present in the Fc region plays the role of regulating the IgG level in serum by increasing the in vivo half-life by conjugation to an in vivo FcRn receptor. In some embodiments in which the multispecific polypeptide constructs contain a cleavable linker, cleavage of the linker can produce two components that each have biological activity: the CD3-binding region that is able to bind and engage CD3 on a T cell, which, in some aspects, also can contain a CRBR for inducing a costimulatory signal on the T cell and/or a VHH domain that binds PD-1 for blocking an inhibitory signal on the T cell; and the Fc region linked to the TAA antigen binding domain that can exhibit target-specific effector function.

In some embodiments, the Fc region includes an Fc polypeptide that is mutated or modified to alter one or more effector functions. Thus, in some cases, effector functions such as on or more of ADCC, ADCP and/or CDC can be altered, such as reduced or enhanced, in an Fc for use with the provided constrained multispecific polypeptide constructs. Exemplary mutations to reduce effector function include any as described above.

c. CD3 Binding Domain

A constrained multispecific polypeptide construct includes a CD3 binding domain. The anti-CD3 binding domains of the disclosure activate T cells via engagement of CD3 or a member of the CD3 complex on the T cells. In preferred embodiments, the anti-CD3 binding domains of the disclosure specifically bind the epsilon chain of CD3, also known as CD3ε. The anti-CD3ε binding domains of the disclosure activate T cells via engagement of CD3ε on the T cells. The anti-CD3 binding domains of the disclosure agonize, stimulate, activate, and/or otherwise augment CD3-mediated T cell activation. Biological activities of CD3 include, for example, T cell activation and other signaling through interaction between CD3 and the antigen-binding subunits of the T-Cell Receptor (TCR). For example, the anti-CD3 binding domains of the disclosure completely or partially activate T cells via engagement of CD3ε on T cells by partially or completely modulating, e.g., agonizing, stimulating, activating or otherwise augmenting CD3-mediated T cell activation.

The CD3 binding domain can be any as described above. In particular embodiments, the CD3 binding domain is an Fv antibody fragment that binds CD3ε (referred to herein as an anti-CD38 Fv fragment). In some embodiments, the anti-CD3ε Fv antibody fragment is a disulfide stabilized anti-CD3 binding Fv fragment (dsFv). In some embodiments, the anti-CD3 binding domain is monovalent for binding CD3.

In some embodiments, the CD3 binding region is an Fv antibody fragment containing a variable heavy chain (Hv, also called VH) and variable light chain (Lv, also called VL), such as any as described. In aspects of such embodiments, the immunoglobulin Fc region is a heterodimeric Fc region containing two different Fc polypeptides capable of heterodimeric association between both polypeptides of the Fc heterodimer, such as any as described. In such embodiments, the variable heavy chain (VH) and variable light chain (VL) of the CD3 binding region are linked on opposite chains of the heterodimeric Fc.

In some embodiments, the CD3 binding region is an Fv or dsFv of SP34 (Pessano et ai. The EMBO Journal. 4: 337-344, 1985) or of a humanized variant of SP34 (WO2015001085).

In some embodiments, the anti-CD3ε binding domain thereof is an Fv or dsFv fragment that includes a combination of heavy chain variable amino acid sequence and a light chain variable amino acid sequence. In some embodiments, the CD3-binding domain is an Fv or dsFv fragment in which is contained a VH CDR1 sequence that includes at least the amino acid sequence TYAMN (SEQ ID NO: 29); a VH CD2 sequence that includes at least the amino acid sequence RIRSKYNNYATYYADSVKD (SEQ ID NO: 30); a VH CDR3 sequence that includes at least the amino acid sequence HGNFGNSYVSWFAY (SEQ ID NO: 31), a VL CDR1 sequence that includes at least the amino acid sequence RSSTGAVTTSNYAN (SEQ ID NO: 32); a VL CDR2 sequence that includes at least the amino acid sequence GTNKRAP (SEQ ID NO: 33); and a VL CDR3 sequence that includes at least the amino acid sequence ALWYSNLWV (SEQ ID NO: 34). In some embodiments, the anti-CD3ε binding domain thereof is an Fv or dsFv fragment that includes a heavy chain variable amino acid sequence selected from the group of SEQ ID NO: 35-65 and a light chain variable amino acid sequence selected from the group consisting of SEQ ID NO: 66-84, 285. In some embodiments, the anti-CD3ε binding domain thereof is an Fv or dsFv fragment that includes a heavy chain variable amino acid sequence that is at least 90%, 91%, 92%, 93%, 94%, 95%, 96%, 97%, 98%, 99% or more identical to an amino acid sequence selected from the group consisting of SEQ ID NO: 35-65 and an amino acid sequence that is at least 90%, 91%, 92%, 93%, 94%, 95%, 96%, 97%, 98%, 99% or more identical to an amino acid sequence selected from the group consisting of SEQ ID NO: 66-84, 285 an amino acid sequence. In some embodiments, the anti-CD3 binding domain is an Fv or dsFv, in which is contained a variable heavy chain (VH) comprising the amino acid sequence of SEQ ID NO: 47 and a variable light chain (VL) comprising the amino acid sequence of SEQ ID NO: 285.

d. Linker

A constrained multispecific polypeptide constructs contain a linker that joins or couples the first component containing the immunoglobulin Fc region and the second component containing the CD3 binding region. In some embodiments, the linker is positioned at the end of the C-terminal region of the Fc region, such that the Fc region is N-terminal to the CD3 binding region. It is understood that because the provided constrained multispecific polypeptide constructs are multimers, such as dimers containing a first and second polypeptide that together form the first and second component, the provided constructs include a linker joining the Fc portion and the CD3 binding region of the first and a linker joining the Fc portion and the CD3 binding region of the second polypeptide. In some embodiments, the first polypeptide includes a first Fc polypeptide of a heterodimeric Fc region, a linker, and a first domain (e.g. VH) of a CD3 binding region, and the second polypeptide includes a second Fc polypeptide of the heterodimeric Fc region, a linker and second domain (e.g. VL) of the CD3 binding region. Typically, the linkers present in the first and second polypeptides of the constrained multispecific polypeptide construct are the same. Thus, in some embodiments, each domain of the CD3 binding domain is linked via a linker, such as the same linker, to opposite polypeptides of the Fc, such as heterodimeric Fc.

Various polypeptide linkers for use in fusion proteins are known (see e.g. Chen et al. (2013) Adv. Drug. Deliv. 65:1357-1369; and International PCT publication No. WO 2014/099997, WO2000/24884; U.S. Pat. Nos. 5,258,498; 5,525,491; 5,525,491, 6,132,992).

In some embodiments, the linker is chosen so that, when the CD3 binding region is joined to the Fc region of the multispecific polypeptide conjugate, the CD3 binding region is constrained and not able to, or not substantially able to, bind or engage CD3 on the surface of a cell, e.g. T cell, upon contact of the multispecific polypeptide construct with the cell. Various assays can be employed to assess binding or engagement of CD3 by the multispecific polypeptide construct, including assays to assess T cell binding, NFAT activation using a reporter system, cytolytic T cell activity, cytokine production and/or expression of T cell activation markers. Exemplary assays are shown in the provided Examples. Typically, the linker also is one that ensures correct folding of the polypeptide construct, does not exhibit a charge that would be inconsistent with the activity or function of the linked polypeptides or form bonds or other interactions with amino acid residues in one or more of the domains that would impede or alter activity of the linked polypeptides. In some embodiments, the linker is a polypeptide linker. The polypeptide linker can be a flexible linker or a rigid linker or a combination of both. In some aspects, the linker is a short, medium or long linker. In some embodiments, the linker is up to 40 amino acids in length. In some embodiments, the linker is up to 25 amino acids in length. In some embodiments, the linker is at least or is at least about 2 amino acids in length. In some aspects, a suitable length is, e.g., a length of at least one and typically fewer than about 40 amino acid residues, such as 2-25 amino acid residues, 5-20 amino acid residues, 5-15 amino acid residues, 8-12 amino acid. In some embodiments, the linker is from or from about 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 24 amino acids, 8 to 20 amino acids, 8 to 18 amino acids, 8 to 14 amino acids, 8 to 12 amino acids, 8 to 10 amino acids, 10 to 24 amino acids, 10 to 20 amino acids, 10 to 18 amino acids, 10 to 14 amino acids, 10 to 12 amino acids, 12 to 24 amino acids, 12 to 20 amino acids, 12 to 18 amino acids, 12 to 14 amino acids, 14 to 24 amino acids, 14 to 20 amino acids, 14 to 18 amino acids, 18 to 24 amino acids, 18 to 20 amino acids or 20 to 24 amino acids. In some embodiments, the linker is 2, 3, 4, 5, 6, 7, 8, 9, 10, 11, 12, 13, 14, 15, 16, 17, 18, 19 or 20 amino acids in length.

In certain aspects, the longer the linker length, the greater the CD3 binding when the multispecific polypeptide conjugate is bounds to its antigen, e.g. TAA. Thus, in some aspects, the linker is greater than 12 amino acids in length, such as greater than 13, 14, 15, 16, 17 or 18 amino acids in length. In some embodiments, the linker is 12 to 40 amino acids in length, 12 to 30 amino acids, 12 to 24 amino acids, 12 to 18 acids, 12 to 15 amino acids, 15 to 40 amino acids, 15 to 30 amino acids, 15 to 24 amino acids, 15 to 18 amino acids, 18 to 40 amino acids, 18 to 30 amino acids, 18 to 24 amino acids, 24 to 40 amino acids, 24 to 30 amino acids or 30 to 40 amino acids.

The linkers can be naturally-occurring, synthetic or a combination of both. Particularly suitable linker polypeptides predominantly include amino acid residues selected from Glycine (Gly), Serine (Ser), Alanine (Ala), and Threonine (Thr). For example, the linker may contain at least 75% (calculated on the basis of the total number of residues present in the peptide linker), such as at least 80%, at least 85%, or at least 90% of amino acid residues selected from Gly, Ser, Ala, and Thr. The linker may also consist of Gly, Ser, Ala and/or Thr residues only. In some embodiments, the linker contains 1-25 glycine residues, 5-20 glycine residues, 5-15 glycine residues, or 8-12 glycine residues. In some aspects, suitable peptide linkers typically contain at least 50% glycine residues, such as at least 75% glycine residues. In some embodiments, a peptide linker comprises glycine residues only. In some embodiments, a peptide linker comprises glycine and serine residues only.

In some embodiments, these linkers are composed predominately of the amino acids Glycine and Serine, denoted as GS-linkers herein. In some embodiments, the linker contains (GGS)n, wherein n is 1 to 10, such as 1 to 5, for example 1 to 3, such as GGS(GGS)n (SEQ ID NO:123), wherein n is 0 to 10. In particular embodiments, the linker contains the sequence (GGGGS)n (SEQ ID NO: 123), wherein n is 1 to 10 or n is 1 to 5, such as 1 to 3. In further embodiments, the linker contains (GGGGGS)n (SEQ ID NO:124), wherein n is 1 to 4, such as 1 to 3. The linker can include combinations of any of the above, such as repeats of 2, 3, 4, or 5 GS, GGS, GGGGS, and/or GGGGGS linkers may be combined. In some embodiments, such a linker is 2, 3, 4, 5, 6, 7, 8, 9, 10, 11, 12, 13, 14, 15, 16, 17, 18 or 19 amino acids in length.

In some embodiments, the linker is (in one-letter amino acid code): GGS, GGGGS (SEQ ID NO: 125), or GGGGGS (SEQ ID NO: 126). In some embodiments, the GS-linker comprises an amino acid sequence of GGSGGS, i.e., (GGS)$_2$ (SEQ ID NO: 1); GGSGGSGGS, i.e., (GGS)$_3$ (SEQ ID NO: 2); GGSGGSGGSGGS, i.e., (GGS)$_4$ (SEQ ID NO: 3); GGSGGSGGSGGSGGS, i.e., (GGS)$_5$ (SEQ ID NO: 4); GGGGGSGGGGGSGGGGGS, i.e., (G5S)$_3$ (SEQ ID NO: 127), GGSGGGGSGGGGSGGGGS (SEQ ID NO: 129) and GGGGSGGGGSGGGGS (SEQ ID NO:128). In some embodiments, the linker is GGGG (SEQ ID NO:5). In some of any of the above examples, serine can be replaced with alanine (e.g., (Gly4Ala) or (Gly3Ala)).

In some embodiments, the linker includes a peptide linker having the amino acid sequence Gly$_x$Xaa-Gly$_y$-Xaa-Gly$_z$ (SEQ ID NO:130), wherein each Xaa is independently selected from Alanine (Ala), Valine (Val), Leucine (Leu), Isoleucine (Ile), Methionine (Met), Phenylalanine (Phe), Tryptophan (Trp), Proline (Pro), Glycine (Gly), Serine (Ser), Threonine (Thr), Cysteine (Cys), Tyrosine (Tyr), Asparagine (Asn), Glutamine (Gln), Lysine (Lys), Arginine (Arg), Histidine (His), Aspartate (Asp), and Glutamate (Glu), and wherein x, y, and z are each integers in the range from 1-5. In some embodiments, each Xaa is independently selected from the group consisting of Ser, Ala, and Thr. In a specific variation, each of x, y, and z is equal to 3 (thereby yielding a peptide linker having the amino acid sequence Gly-Gly-Gly-Xaa-Gly-Gly-Gly-Xaa-Gly-Gly-Gly (SEQ ID NO:131), wherein each Xaa is selected as above.

In some embodiments, the linker is serine-rich linkers based on the repetition of a (SSSSG)y (SEQ ID NO:132) motif where y is at least 1, though y can be 2, 3, 4, 5, 6, 7, 8 and 9.

In some cases, it may be desirable to provide some rigidity into the peptide linker. This may be accomplished by including proline residues in the amino acid sequence of the peptide linker. Thus, in some embodiments, a linker comprises at least one proline residue in the amino acid sequence of the peptide linker. For example, a peptide linker can have an amino acid sequence wherein at least 25% (e.g., at least 50% or at least 75%) of the amino acid residues are proline residues. In one particular embodiment, the peptide linker comprises proline residues only.

In some aspects, a peptide linker comprises at least one cysteine residue, such as one cysteine residue. For example, in some embodiments, a linker comprises at least one cysteine residue and amino acid residues selected from the group consisting of Gly, Ser, Ala, and Thr. In some such embodiments, a linker comprises glycine residues and cysteine residues, such as glycine residues and cysteine residues only. Typically, only one cysteine residue will be included per peptide linker. One example of a specific linker comprising a cysteine residue includes a peptide linker having the amino acid sequence Gly$_m$-Cys-Gly$_n$, wherein n and m are each integers from 1-12, e.g., from 3-9, from 4-8, or from 4-7. In a specific variation, such a peptide linker has the amino acid sequence GGGGG-C-GGGGG (SEQ ID NO: 133).

In some embodiments, the linker of the fusion protein is a structured or constrained linker. In particular embodiments, the structured linker contains the sequence (AP)n or (EAAAK)n (SEQ ID NO:134), wherein n is 2 to 20, preferably 4 to 10, including but not limited to, AS-(AP)n-GT (SEQ ID NO:135) or AS-(EAAAK)n-GT (SEQ ID NO:136), wherein n is 2 to 20, such as 2, 3, 4, 5, 6, 7, 8, 9, 10, 11, 12, 13, 14 or 15. In other embodiments, the linker comprises the sequences (GGGGA)n (SEQ ID NO:137), (PGGGS)n (SEQ ID NO:138), (AGGGS)n (SEQ ID NO:139) or GGS-(EGKSSGSGSESKST)n-GGS (SEQ ID NO:140, wherein n is 2 to 20. In some embodiments, the linker is SSSASASSA (SEQ ID NO:141), GSPGSPG (SEQ ID NO:142), or ATTTGSSPGPT (SEQ ID NO:143). In some embodiments, such linkers, by virtue of their structure, may be more resistant to proteolytic degradation, thereby offering an advantage when injected in vivo.

In some embodiments, the linker is not a cleavable linker, also called non-cleavable linker. In some embodiments, the linker is not a cleavable by a protease. In some embodiments, a linker that is not a cleavable linker or that is not cleavable by a protease is one that is generally stable for in vivo delivery or recombinant production. In some aspects, a linker that is not cleavable by a protease includes those that do not contain at least one peptide bond which preferably lies within a cleavable peptide sequence or recognition site of a protease. In particular embodiments, a non-cleavable linker is not a target substrate for a protease, such that it is not preferentially or specifically cleaved by a protease compared to a linker that contains a substrate recognition site for the same protease.

In some embodiments, the linker does not contains a substrate recognition site or cleavage site for a particular protease, which is the sequence recognized by the active site of a protease that is cleaved by a protease. Typically, for example, for a serine protease, a cleavage sequence is made up of the P1-P4 and P1'-P4' amino acids in a substrate, where cleavage occurs after the P1 position. Typically, a cleavage sequence for a serine protease is six residues in length to match the extended substrate specificity of many proteases, but can be longer or shorter depending upon the protease. Typically, the linker does not include a P1-P1' scissile bond sequence that is recognized by a protease. In some aspects, a non-cleavable linker or a linker that does not contain a substrate recognition site that is specifically recognized for cleavage by a protease is one whose cleavage by a protease is substantially less than cleavage of a target substrate of the protease.

In some embodiments, the linker is a cleavable linker. In some aspects, a cleavable linker is a linker, such as any described above, that further includes a sequence that is a substrate for a protease due to the presence of at least one bond that can be broken under physiological conditions. In some cases, a cleavable linker is susceptible to or sensitive to cleavage under specific conditions that exist in vivo, such as following exposure to an extracellular protease, including those present in cellular environments in vivo. In some cases, the protease may be present in a particular physiological microenvironment, such as the tumor microenvironment, thereby restricting the sites at which cleavage may occur.

A protease typically exhibits specificity or preference for cleavage of a particular target substrate compared to another non-target substrate. Such a degree of specificity can be determined based on the rate constant of cleavage of a sequence, e.g. linker, which is a measure of preference of a protease for its substrate and the efficiency of the enzyme. Any method to determine the rate of increase of cleavage over time in the presence of various concentrations of substrate can be used to calculate the specificity constant. For example, a substrate is linked to a fluorogenic moiety, which is released upon cleavage by a protease. By determining the rate of cleavage at different protease concentrations the specificity constant for cleavage ($k_{cat}/K_m$) can be determined for a particular protease towards a particular linker. In some embodiments, a cleavable linker is a linker that is capable of being specifically cleaved by a protease at a rate of about at least $1\times10^4$ $M^{-1}S^{-1}$, or at least $5\times10^4$ $M^{-1}S$, at least $10\times10^4$ $M^{-1}S$. at least $10\times10^5$ $M^{-1}S$ or more.

In some embodiments, a constrained multispecific polypeptide constructs of the disclosure include a cleavable linker that joins the first and second components. In some embodiments, the cleavable linker includes an amino acid sequence that can serve as a substrate for a protease, usually an extracellular protease. For example, the cleavable linker may include a cleavage sequence containing at least one peptide bond which preferably lies within a cleavable peptide sequence of a protease. Suitable proteases include, for example, matrix metalloproteases (MMP), cysteine proteases, serine proteases and plasmin activators, which are formed or activated in intensified manner in diseases such as rheumatoid arthritis or cancer, leading to excessive tissue degradation, inflammations and metastasis. In particular embodiments, the protease is a protease that is produced by a tumor, an activated immune effector cell (e.g. a T cell or a NK cell), or a cell in a tumor microenvironment. In some embodiments, the protease is a granzyme B, a matriptase or an MMP, such as MMP-2.

The cleavable linker may be selected based on a protease that is produced by a tumor that is in proximity to cells that express the target and/or produced by a tumor that is co-localized in tissue with the desired target of the multispecific polypeptide constructs. There are reports in the literature of increased levels of proteases having known substrates in a number of cancers, e.g., solid tumors. See, e.g., La Rocca et al, (2004) British J. of Cancer 90(7): 1414-1421.

In some embodiments, the cleavable linker that joins the first and second component of a constrained multispecific polypeptide construct is cleaved by a protease produced by an immune effector cell that is activated by one of the components. For example, multispecific polypeptide constructs that encompass an effector enabled or enhanced IgG Fc region are capable of eliciting ADCC when engaged with the target antigen. Central to ADCC is the release of granzyme B and perforin from the effector cells, namely NK cells and cytotoxic T-cells. Upon release granzyme B enters the target cell in a perforin dependent manner wherein it mediates apoptosis. Importantly, granzyme B is active within the extracellular synapse between the effector cell and the target cell. In some embodiments, the cleavable linker that joins the first and second component multispecific polypeptide construct is cleaved by granzyme B. Granzyme B is released during effector cell activation mediated by one of the components of the multispecific polypeptide construct. In some embodiments, granzyme B and other proteases can be produced by immune effector cells, including activated T cells or NK cells. In some embodiments, activation of T cells by CD3 engagement upon binding of a TAA by a multispecific polypeptide construct may release such proteases, which then can cleave a specific cleavable linker thereby potentiating or increasing activity of the CD3 binding molecule to engage CD3. In some embodiments, the cleavage can amplify or increase the activity achieved by the multispecific construct when bound to TAA in an uncleaved state.

Exemplary substrates include but are not limited to substrates cleavable by one or more of the following enzymes or proteases: ADAMS, ADAMTS, e.g. ADAMS; ADAMS; ADAM10; ADAM12; ADAM15; ADAM17/TACE; ADAMDEC1; ADAMTS1; ADAMTS4; ADAMTS5; aspartate proteases, e.g., BACE or Renin; aspartic cathepsins, e.g., Cathepsin D or Cathepsin E; Caspases, e.g., Caspase 1, Caspase 2, Caspase 3, Caspase 4, Caspase 5, Caspase 6, Caspase 7, Caspase 8, Caspase 9, Caspase 10, or Caspase 14; cysteine cathepsins, e.g., Cathepsin B, Cathepsin C, Cathepsin K, Cathepsin L, Cathepsin S, Cathepsin V/L2, Cathepsin X/Z/P; Cysteine proteinases, e.g., Cruzipain; Legumain; Otubain-2; KLKs, e.g., KLK4, KLK5, KLK6, KLK7, KLK8, KLK10, KLK11, KLK13, or KLK14; Metallo proteinases, e.g., Meprin; Neprilysin; PSMA; BMP-1; MMPs, MMP2, MMP3, MMP7, MMP8, MMP9, MMP10, MMP11, MMP12, MMP13, MMP14, MMP15, MMP16, MMP17, MMP19, MMP20, MMP23, MMP24, MMP26, or MMP27, serine proteases, e.g., activated protein C, Cathepsin A, Cathepsin G, Chymase, coagulation factor proteases (e.g., FVIIa, FIXa, FXa, FXIa, FXIIa), Elastase, granzyme B, Guanidinobenzoatase, HtrA1, Human Neutrophil Elastase, Lactoferrin, Marapsin, NS3/4A, PACE4, Plasmin, PSA, tPA, Thrombin, Tryptase, uPA; Type II Transmembrane Serine Proteases (TTSPs), e.g., DESC1, DPP-4, FAP, Hepsin, Matriptase-2, Matriptase, TMPRSS2, TMPRSS3, or TMPRSS4; and any combination thereof.

In some embodiments, the cleavable linker is cleaved by multiple proteases, e.g., 2 or more proteases, 3 or more proteases, 4 or more proteases, and so on.

In some embodiments, the cleavable linker is selected for use with a specific protease, for example a protease that is known to be produced by a tumor that is in proximity to cells that express the target and/or produced by a tumor that is co-localized with the target of the multispecific polypeptide construct.

In some embodiments, the cleavable linker contains a substrate recognition site or cleavage site for a particular protease, which is the sequence recognized by the active site of a protease that is cleaved by a protease. Typically, for example, for a serine protease, a cleavage sequence is made up of the P1-P4 and P1'-P4' amino acids in a substrate, where cleavage occurs after the P1 position. Typically, a cleavage sequence for a serine protease is six residues in length to match the extended substrate specificity of many proteases, but can be longer or shorter depending upon the protease. Typically, the cleavable linker includes a P1-P1' scissile bond sequence that is recognized by a protease. In some aspects, the cleavable linker is engineered to introduce a peptide bond able to be cleaved by a specific protease, for example by introducing a substrate recognition site sequence or cleavage sequence of the protease.

In some embodiments, the cleavable linker includes a combination of two or more substrate sequences. In some embodiments, each substrate sequence is cleaved by the same protease. In some embodiments, at least two of the substrate sequences are cleaved by different proteases. In some embodiments, the cleavable linker comprises an amino acid that is a substrate for granzyme B. In some embodiments, a granzyme B cleavable linker contains an amino acid sequence having the general formula P4 P3 P2 P1↓P1' (SEQ ID NO: 144), wherein P4 is amino acid I, L, Y, M, F, V, or A; P3 is amino acid A, G, S, V, E, D, Q, N, or Y; P2 is amino acid H, P, A, V, G, S, or T; P1 is amino acid D or E; and P1' is amino acid I, L, Y, M, F, V, T, S, G or A. In some embodiments, a granzyme B cleavable linker contains an amino acid sequence having the general formula P4 P3 P2 P1↓P1' (SEQ ID NO: 145), wherein P4 is amino acid I or L; P3 is amino acid E; P2 is amino acid P or A; P1 is amino acid D; and P1' is amino acid I, V, T, S, or G.

In some embodiments, the substrate for granzyme B comprises the amino acid sequence LEAD (SEQ ID NO: 146), LEPG (SEQ ID NO: 147), or LEAE (SEQ ID NO:148). In some embodiments, the cleavable linker contains the amino acid sequence the cleavable linker comprises the amino acid sequence IEPDI (SEQ ID NO:149), LEPDG (SEQ ID NO:150), LEADT (SEQ ID NO:151), IEPDG (SEQ ID NO:152), IEPDV (SEQ ID NO:153), IEPDS (SEQ ID NO:154), IEPDT (SEQ ID NO:155), IEPDP (SEQ ID NO:144), LEPDG (SEQ ID NO:152) or LEADG (SEQ ID NO:153).

In some embodiments, the cleavable linker comprises an amino acid that is a substrate for matriptase. In some embodiments, the cleavable linker comprises the sequence P4QAR↓(A/V) (SEQ ID NO: 156), wherein P4 is any amino acid. In some embodiments, the cleavable linker comprises the sequence RQAR(A/V) (SEQ ID NO: 157). In some embodiments, the substrate for matriptase comprises the amino acid sequence RQAR (SEQ ID NO: 158). In some embodiments, the cleavable linker comprises the amino acid sequence RQARV (SEQ ID NO: 159).

In some embodiments, the cleavable linker comprises an amino acid that is a substrate for one or more matrix metalloproteases (MMPs). In some embodiments, the MMP is MMP-2. In some embodiments, the cleavable linker contains. the general formula P3 P2 P1↓P1' (SEQ ID NO: 160), wherein P3 is P, V or A; P2 is Q or D; P1 is A or N; and P1' is L, I or M. In some embodiments, the cleavable linker contains the general formula P3 P2 P1↓P1' (SEQ ID NO: 161), wherein P3 is P; P2 is Q or D; P1 is A or N; and P1' is L or I. In some embodiments, the substrate for MMP comprises the amino acid sequence PAGL (SEQ ID NO: 162).

In some embodiments, the cleavable linker comprises a combination of an amino acid sequence that is a substrate for granzyme B and an amino acid sequence that is a substrate for matriptase. In some embodiments, the cleavable linker comprises a combination of the amino acid sequence LEAD (SEQ ID NO: 146) and the amino acid sequence RQAR (SEQ ID NO: 158).

In some embodiments, the cleavable linker comprises a combination of an amino acid sequence that is a substrate for granzyme B and an amino acid sequence that is a substrate for MMP. In some embodiments, the cleavable linker comprises a combination of the amino acid sequence LEAD (SEQ ID NO: 146) and the amino acid sequence PAGL (SEQ ID NO: 162).

In some embodiments, the cleavable linker comprises a combination of an amino acid sequence that is a substrate for matriptase and an amino acid sequence that is a substrate for MMP. In some embodiments, the cleavable linker comprises a combination of the amino acid sequence RQAR (SEQ ID NO: 158) and the amino acid sequence PAGL (SEQ ID NO: 162).

In some embodiments, the cleavable linker comprises a combination of an amino acid sequence that is a substrate for granzyme B, an amino acid sequence that is a substrate for matriptase, and an amino acid sequence that is a substrate for MMP. In some embodiments, the cleavable linker comprises a combination of an amino acid sequence that is a substrate for granzyme B and an amino acid sequence that is a substrate for MMP. In some embodiments, the cleavable linker comprises a combination of the amino acid sequence LEAD (SEQ ID NO: 146), the amino acid sequence RQAR (SEQ ID NO: 158), and the amino acid sequence PAGL (SEQ ID NO: 162).

The cleavable linker can include any known linkers. Examples of cleavable linkers are described in Be'liveau et al. (2009) FEBS Journal, 276; U.S. published application Nos. US20160194399; US20150079088; US20170204139; US20160289324; US20160122425; US20150087810; US20170081397; U.S. Pat. No. 9,644,016.

In some embodiments, the cleavable linker comprises an amino acid sequence selected from the group consisting of TGLEADGSPAGLGRQARVG (SEQ ID NO: 163); TGLEADGSRQARVGPAGLG (SEQ ID NO: 164); TGSPAGLEADGSRQARVGS (SEQ ID NO: 162); TGPAGLGLEADGSRQARVG (SEQ ID NO: 166); TGRQARVGLEADGSPAGLG (SEQ ID NO: 167); TGSRQARVGPAGLEADGS (SEQ ID NO: 168); and TGPAGLGSRQARVGLEADGS (SEQ ID NO:169); GPAGLGLEPDGSRQARVG (SEQ ID NO: 170); GGSGGGGIEPDIGGSGGS (SEQ ID NO: 171); GGSGGGGLEADTGGSGGS (SEQ ID NO: 172); GSIEPDIGS (SEQ ID NO: 173); GSLEADTGS (SEQ ID NO: 174); GGSGGGGIEPDGGGSGGS (SEQ ID NO: 175); GGSGGGGIEPDVGGSGGS (SEQ ID NO: 176); GGSGGGGIEPDSGGSGGS (SEQ ID NO: 177); GGSGGGGIEPDTGGSGGS (SEQ ID NO: 178); GGGSLEPDGSGS (SEQ ID NO: 179); and GPAGLGLEADGSRQARVG (SEQ ID NO: 180), GGEGGGGSGGSGGGS (SEQ ID NO: 181); GSSAGSEAGGSGQAGVGS (SEQ ID NO: 182); GGSGGGGLEAEGSGGGGS (SEQ ID NO: 183); GGSGGGIEPDPGGSGGS(SEQ ID NO: 184); TGGSGGGGIEPDIGGSGGS (SEQ ID NO: 185).

e. Anti-PD-1 VHH Domain

A constrained multispecific polypeptide construct of the disclosure includes at least one PD-1 VHH domain from among any provided herein. In some embodiments, the PD-1 VHH domain comprises the sequence of amino acids set forth in any of SEQ ID NOS: 245-287, 294-299, and 312-315.

In particular embodiments, a constrained multispecific polypeptide construct contains at least two PD-1 VHH domain, such as any as described. In some cases, at least one PD-1 VHH domain is positioned amino terminally relative to an Fc polypeptide of the heterodimeric Fc and at least one PD-1 VHH domain is positioned carboxy-terminally relative to VH or VL chain of the CD3 binding region. In some aspects, each of the two PD-1 VHH domain are the same.

In particular embodiments, a constrained multispecific polypeptide construct contains only PD-1 domain. In some cases, the PD-1 VHH domain is positioned amino terminally relative to an Fc polypeptide of the heterodimeric Fc. In some embodiments, the PD-1 VHH domain is positioned carboxy-terminally relative to VH or VL chain of the CD3 binding region.

In some embodiments, the anti-PD-1 VHH domain is linked, directly or indirectly via a linker, to the Fc region and/or to the CD3 binding region. In some embodiments, linkage is via a linker. In some embodiments, the linker is a linking peptide (LP), which can include any flexible or rigid linker as described. In some embodiments, the linker is selected from the group consisting of GGSGGS, i.e., $(GGS)_2$ (SEQ ID NO: 244); GGSGGSGGS, i.e., $(GGS)_3$ (SEQ ID NO: 245); GGSGGSGGSGGS, i.e., $(GGS)_4$ (SEQ ID NO: 246); and GGSGGSGGSGGSGGS, i.e., $(GGS)_5$ (SEQ ID NO: 247). In some embodiments, the linker is a flexible linker comprising Glycine residues, such as, by way of non-limiting example, GG, GGG, GGGG (SEQ ID NO: 248), GGGGG (SEQ ID NO: 249), and GGGGGG (SEQ ID NO: 7). In some embodiments, the linker includes a combination of a GS-linker and a Glycine linker.

f. Costimulatory Binding Domain

A multispecific polypeptide constructs of the present disclosure include one or more co-stimulatory receptor binding region (CRBR) that binds a costimulatory receptor. In some embodiments, the one or more CRBR of the provided multispecific polypeptide constructs bind a co-stimulatory receptor expressed on T cells. In some embodiments, the co-stimulatory receptor is upregulated, induced, or expressed on the surface of an activated T cell. In some aspects, the CRBR binds a co-stimulatory receptor and stimulates the co-stimulatory receptor. In some embodiments, agonistic binding of the co-stimulatory receptor to the CRBR of the multispecific polypeptide induces downstream signaling in the T cell to potentiate or enhance T cell activation or functionalities following engagement of CD3. In some embodiments, the CRBR, or independently each of the CRBRs, is an antibody or antigen binding fragment, a natural cognate binding partner of the co-stimulatory receptor, an Anticalin (engineered lipocalin), a Darpin, a Fynomer, a Centyrin (engineered fibroneticin III domain), a cystine-knot domain, an Affilin, an Affibody, or an engineered CH3 domain.

In some embodiments, the CRBR, or independently each of the CRBRs, such as the first CRBR and the second CRBRs, includes one or more copies of an antibody or an antigen-binding fragment thereof. In some embodiments, the CRBR or independently each of the CRBRs, such as the first antigen-binding domain and the second CRBRs, includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody.

In some embodiments, the CRBR, or independently each of the CRBRs, such as the first CRBR and the second CRBRs, is a single chain antibody. In some examples, the single chain is an scFv, a scAb, a single domain heavy chain antibody, or a single domain light chain antibody.

In some embodiments, the CRBR, or independently each of the CRBRs, such as the first CRBR and the second CRBR, includes one or more single domain antibody (sdAb) fragments, for example $V_H H$, $V_{NAR}$, engineered $V_H$ or $V_K$ domains. $V_H Hs$ can be generated from natural camelid heavy chain only antibodies, genetically modified rodents that produce heavy chain only antibodies, or naïve/synthetic camelid or humanized camelid single domain antibody libraries. VNARS can be generated from cartilaginous fish heavy chain only antibodies. Various methods have been implemented to generate monomeric sdAbs from conventionally heterodimeric $V_H$ and $V_K$ domains, including interface engineering and selection of specific germline families.

In some embodiments, the CRBR, or independently each of the CRBRs such as the first CRBR and/or the second CRBR, of the multispecific polypeptide constructs contains at least one sdAb or an scFv that binds a costimulatory receptor. In some embodiments, the at least one scFv or sdAb that binds a costimulatory receptor is positioned amino-terminally relative to the Fc region and/or carboxy-terminally relative to the CD3 binding region of the multispecific polypeptide construct. In some embodiments, the multispecific polypeptide construct contains only one scFv or sdAb that binds to a costimulatory receptor, which can be positioned either amino-terminally relative to the Fc region and/or carboxy-terminally relative to the CD3 binding region. In some embodiments, the multispecific polypeptide construct contains two scFv or sdAb that bind to a costimulatory receptor, positioned amino-terminally relative to the Fc region and/or carboxy-terminally relative to the CD3 binding region.

In some embodiments, the multispecific polypeptide construct is formed from or includes two polypeptides, including a first polypeptide comprising a first Fc polypeptide of a heterodimeric Fc region, a linker, a VH domain of an anti-CD3 antibody or antigen binding fragment (e.g. Fv), and an scFv or sdAb that binds to a costimulatory receptor; and a second polypeptide comprising a second Fc polypeptide of the heterodimeric Fc region, the linker, a VL domain of the anti-CD3 antibody or antigen binding fragment (e.g. Fv) and, optionally, another, the same or different, scFv or sdAb that binds to a costimulatory receptor. The scFv or sdAb that binds the costimulatory receptor can be positioned amino terminally relative to an Fc polypeptide of the heterodimeric Fc and/or carboxy-terminally relative to a VH or VL chain of the CD3 binding region. At least one of the first and/or second polypeptide of the multispecific polypeptide construct also includes an antigen binding domain that binds a TAA or a chain thereof as described in Section II.4. In some embodiments, the antigen binding domain that binds a TAA is a scFv or sdAb and is included as part of the first and/or second polypeptide of the multispecific polypeptide construct. In some embodiments, the antigen binding domain that binds a TAA is a Fab, and the multispecific polypeptide construct is additionally formed from a third polypeptide where at least the first and second polypeptide include a chain of the Fab that binds TAA (e.g. VH-CH1 or VL-CL of a Fab) and the third polypeptide contains the other chain of the Fab that binds TAA (e.g. the other of VH-CH1 or VL-CL of a Fab).

In some embodiments, the CRBR or independently each of the CRBRs, such as the first CRBR and/or the second CRBRs, contains more than one chain. In some embodiments, the CRBR or independently each of the CRBRs, such as the first CRBR and/or the second CRBRs, of the multispecific polypeptide constructs contains VH and VL sequences assembled as FABs.

In some embodiments, the CRBR antigen binding domain or independently each of the CRBR antigen binding domains, such as the first antigen-binding domain and/or the second antigen binding domains, of the multispecific polypeptide constructs contains a VH-CH1 (Fd) and a VL-CL of a Fab antibody that binds a costimulatory receptor. In some embodiments, the Fab antibody containing a VH-CH1 (Fd) and a VL-CL is positioned amino-terminally relative to the Fc region and/or carboxy-terminally relative to the CD3 binding region of the multispecific polypeptide construct. In some embodiments, the multispecific polypeptide construct contains only one Fab antibody, containing a VH-CH1 (Fd) or VL-CL, that binds to a costimulatory receptor, which can be positioned either amino-terminally relative to the Fc region and/or carboxy-terminally relative to the CD3 binding region. In some embodiments, the multispecific polypeptide construct contains two Fab antibody fragments, each containing a VH-CH1 (Fd) and VL-CL, that binds to a costimulatory receptor, in which one is positioned amino-terminally relative to the Fc region and the other is positioned carboxy-terminally relative to the CD3 binding region.

In some embodiments, the multispecific polypeptide construct is formed from or includes three or more polypeptides, including a first polypeptide comprising a first Fc polypeptide of a heterodimeric Fc region, a linker and a VH-CH1 (Fd) or VL-CL of a Fab antibody fragment that binds to a costimulatory receptor; a second polypeptide comprising a second Fc polypeptide of the heterodimeric Fc region, the linker and, optionally, the same VH-CH1 (Fd) or VL-CL of the Fab antibody fragment that binds to a costimulatory receptor, and a third polypeptide comprising the other of the VH-CH1 (Fd) or VL-CL of the Fab antibody fragment that binds to the costimulatory receptor. The first, second and/or third polypeptide of the multispecific polypeptide construct also can include a PD-1 VHH domain, such as any as described.

In some embodiments, the CRBR, or independently each of the CRBRs, is or includes a natural (native) cognate binding partner of the co-stimulatory receptor (e.g. a natural ligand), or a variant thereof that exhibits binding activity to the co-stimulatory receptor.

In some embodiments, the one or more CRBR of the provided multispecific polypeptide constructs bind a co-stimulatory receptor expressed on T cells. In some embodiments, there are more than one CRBR that binds to a costimulatory receptor and each of the CRBRs, such as the first CRBR and the second CRBR, bind the same co-stimulatory receptor. In some embodiments, each of the CRBRs, such as the first CRBR and the CRBRs, bind a different co-stimulatory receptor. In some embodiments, each of the CRBRs, such as the first CRBR and the second CRBR bind a different epitope on the same co-stimulatory receptor. In some embodiments, each of the CRBRs, such as the first antigen-CRBR and the CRBR, bind the same epitope on the same co-stimulatory receptor.

In some embodiments, the CRBR, or independently each of the CRBRs that binds a co-stimulatory receptor results in monovalent, bivalent, trivalent, or tetravalent binding to the co-stimulatory receptor.

In some embodiments, the co-stimulatory receptor is expressed on T cells, such as primary T cells obtained from a subject. In some embodiments, the co-stimulatory receptor is expressed on human T cells, such as primary human T cells obtained from a human subject.

In some embodiments, the co-stimulatory receptor is a member of the tumor necrosis factor (TNF) receptor family. In some embodiments, the costimulatory receptor is a member of the immunoglobulin superfamily (IgSF). In some embodiments, the costimulatory receptor is a member of the B7 family of receptors.

In some embodiments, the co-stimulatory receptor is selected from the group consisting of 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), and NKG2D. In some embodiments, the co-stimulatory receptor is selected from 41BB, OX40, GITR, ICOS, or CD28. In some embodiments, the co-stimulatory receptor is selected from 41BB, OX40, or GITR.

In some embodiments, the costimulatory receptor is 41BB. In some embodiments, the costimulatory receptor is OX40. In some embodiments, the costimulatory receptor is GITR. In some embodiments, the costimulatory receptor is ICOS. In some embodiments, the costimulatory receptor is CD28.

In some embodiments, the CRBR of the multispecific polypeptide is or comprises an agonistic binding molecule to the co-stimulatory receptor. The CRBR can bind to the co-stimulatory receptor and initiate, induce, or stimulate a reaction or activity that is similar to or die same as that initiated, induced, or stimulated by the receptor's natural ligand. In some aspects, the binding of the CRBR to the co-stimulatory receptor induces or stimulates a downstream signal that is more than 5%, more than 10%, more than 20%, more than 30%, more than 40%, more than 50%, more than 60%, more than 70%, more than 80%, more than 90%, or more than 100% of the signal that is initiated, induced, or stimulated by the receptor's natural ligand.

In some embodiments, the one or more CRBR is an antibody or fragment thereof that binds to the co-stimulatory receptor 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA). In some embodiments, the one or more CRBR is an antibody or fragment thereof that binds to the co-stimulatory receptor 41BB, OX40, GITR, ICOS, or CD28. In some embodiments, the one or more CRBR is an antibody or fragment thereof that binds to the co-stimulatory receptor 41BB, OX40, or GITR. Exemplary polypeptides for binding 41BB, OX40 and GITR are described in PCT publication. No. WO2017123650, WO2017123673, and WO2017015623, respectively. In some embodiments, the one or more CRBR is a single domain antibody (sdAb) that binds the co-stimulatory receptor, such as those described in PCT publication. No. WO2017123650, WO2017123673, and WO2017015623.

In some examples, the co-stimulatory receptor binding region (CRBR) binds or comprises a natural cognate binding partner of 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), NKG2D. In some embodiments, the natural cognate binding partner is selected from 41BB ligand (41BBL), OX40L (CD252), CD70, GITR Ligand/TNFSF18, CD80 (B7-1), CD86 (B7-2), ICOS Ligand (ICOSL), CD154 (CD40L), B-cell activating factor (BAFF), A proliferation-inducing ligand (APRIL), NKG2D ligands, or a functional fragment thereof.

Exemplary sequences of CRBRs are set forth in Table 4.

In some embodiments, at least one CRBR, or independently each CRBR, binds the co-stimulatory receptor 41BB. In some examples, the CRBR is or contains an antibody or antigen binding fragment specific to or that binds 41BB, such as a sdAb or fragments containing a VH and VL (e.g. scFv). In some embodiments, at least on CRBR, or independently each CRBR, is a natural ligand of 41BB or is a functional binding fragment thereof. In some embodiments, at least one CRBR, or independently each CRBR, is an anticalin. Exemplary of such 41BB-binding CRBRs are set forth in any of SEQ ID NOS: 186-210. In some embodiments, the 41BB binding CRBR contains a VH set forth in any of SEQ ID NOS: 187, 189 and 191, and a VL set forth in any of SEQ ID NO: 188, 190, or 192. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind 41BB.

In some embodiments, at least one CRBR, or independently each CRBR, binds the co-stimulatory receptor OX40. In some examples, the CRBR is or contains an antibody or antigen binding fragment specific to or that binds OX40, such as a sdAb or fragments containing a VH and VL (e.g. scFv). In some embodiments, at least on CRBR, or independently each CRBR, is a natural ligand of OX40 or is a functional binding fragment thereof. Exemplary of such OX40-binding CRBRs are set forth in any of SEQ ID NOS: 211-220. In some embodiments, the OX40-binding CRBR contains an VH set forth in any of SEQ ID NOS: 216 and 218, and a VL set forth in any of SEQ ID NO: 217 and 219. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind OX40.

In some embodiments, at least one CRBR, or independently each CRBR, binds the co-stimulatory receptor GITR. In some examples, the CRBR is or contains an antibody or antigen binding fragment specific to or that binds GITR, such as a sdAb or fragments containing a VH and VL (e.g. scFv). In some embodiments, at least one CRBR, or independently each CRBR, is a natural ligand of GITR or is a functional binding fragment thereof. Exemplary of such GITR-binding CRBRs are set forth in any of SEQ ID NOS: 221-230. In some embodiments, the GITR binding CRBR contains a VH set forth in any of SEQ ID NOS: 222, 224, 226, and 228 and a VL set forth in any of SEQ ID NO: 223, 225, 227, and 229. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind GITR.

In some embodiments, at least one CRBR, or independently each CRBR, binds the co-stimulatory receptor CD27. In some examples, the CRBR is or contains an antibody or antigen binding fragment specific to or that binds CD27, such as a sdAb or fragments containing a VH and VL (e.g. scFv). In some embodiments, at least one CRBR, or independently each CRBR, is a natural ligand of CD27 or is a functional binding fragment thereof. Exemplary of such CD27-binding CRBRs are set forth in any of SEQ ID NOS: 231. In some embodiments, the CD27 binding CRBR contains a VH set forth SEQ ID NO: 232 and a VL set forth in SEQ ID NO: 233. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind CD27.

In some embodiments, at least one CRBR, or independently each CRBR, binds the co-stimulatory receptor ICOS. In some examples, the CRBR is or contains an antibody or antigen binding fragment specific to or that binds ICOS, such as a sdAb or fragments containing a VH and VL (e.g. scFv). In some embodiments, at least one CRBR, or independently each CRBR, is a natural ligand of ICOS or is a functional binding fragment thereof. An exemplary ICOS-binding CRBR sequence is set forth in SEQ ID NO: 234.

In some embodiments, at least one CRBR, or independently each CRBR, binds the co-stimulatory receptor CD28. In some examples, the CRBR is or contains an antibody or antigen binding fragment specific to or that binds CD28, such as a sdAb or fragments containing a VH and VL (e.g. scFv). In some embodiments, at least one CRBR, or independently each CRBR, is a natural ligand of CD28 or is a functional binding fragment thereof. An exemplary CD28-binding CRBR sequence is set forth in SEQ ID NO: 235.

TABLE 4

Exemplary CRBR Sequences

| CRBR | Format | Reference | SEQ ID NO |
| --- | --- | --- | --- |
| 41BB binding CRBR Sequences | | | |
| 41BBL | Natural Ligand | UniProt accession no. P41273 | 186 |
| PF-05082566 | VH | US 2012/0237498 (SEQ ID NO: 43) | 187 |
| | VL | US 2012/0237498 (SEQ ID NO: 45) | 188 |
| BMS663513 | VH | WO 2005/035584 (SEQ ID NO: 9) | 189 |
| | VL | WO 2005/035584 (SEQ ID NO: 6) | 190 |
| MSB7 | VH | US 2017/0226215 (SEQ ID NO: 138) | 191 |
| | VL | US 2017/0226215 (SEQ ID NO: 28) | 192 |
| 41BB Anticalin | Anticalin | WO 2016/177762 (SEQ ID NO: 12) | 193 |
| 41BB Anticalin | Anticalin | WO 2016/177762 (SEQ ID NO: 13) | 194 |
| 41BB Anticalin | Anticalin | WO 2016/177762 (SEQ ID NO: 14) | 195 |
| 41BB Anticalin | Anticalin | WO 2016/177762 (SEQ ID NO: 15) | 196 |
| 41BB Anticalin | Anticalin | WO 2016/177762 (SEQ ID NO: 16) | 197 |
| 41BB Anticalin | Anticalin | WO 2016/177762 (SEQ ID NO: 17) | 198 |

TABLE 4-continued

Exemplary CRBR Sequences

| CRBR | Format | Reference | SEQ ID NO |
|---|---|---|---|
| 41BB Anticalin | Anticalin | WO 2016/177762 (SEQ ID NO: 18) | 199 |
| 41BB Anticalin | Anticalin | WO 2016/177762 SEQ ID NO: 19) | 200 |
| 41BB Anticalin | Anticalin | WO 2016/177762 (SEQ ID NO: 20) | 200 |
| 71-254 of human 41BBL | 41BB ligand | WO 2017/167672 (SEQ ID NO: 3) | 201 |
| 85-254 of human 41BBL | 41BB ligand | WO 2017/167672 (SEQ ID NO: 4) | 202 |
| 80-254 of human 41BBL | 41BB ligand | WO 2017/167672 (SEQ ID NO: 5) | 203 |
| 52-254 of human 41BBL | 41BB ligand | WO 2017/167672 (SEQ ID NO: 6) | 204 |
| 71-248 of human 41BBL | 41BB ligand | WO 2017/167672 (SEQ ID NO: 7) | 206 |
| 85-248 of human 41BBL | 41BB ligand | WO 2017/167672 (SEQ ID NO: 8) | 207 |
| 80-248 of human 41BBL | 41BB ligand | WO 2017/167672 (SEQ ID NO: 9) | 208 |
| 52-248 of human 41BBL | 41BB ligand | WO 2017/167672 (SEQ ID NO: 10) | 209 |
| 41BB sdAb | sdAb | US 2017/0198050 | 210 |
| OX40-binding CRBR Sequences | | | |
| OX40 ligand | Natural Ligand | UniProt accession no. P23510 | 211 |
| OX40 ligand | Natural Ligand | U.S. Pat No. 7,959,925 (SEQ ID NO: 2) | 212 |
| human OX40L: 51-183 | Natural Ligand | WO 2017/167672 (SEQ ID NO: 11) | 213 |
| Human Ox40L: 51-183 N90D | Natural Ligand | WO 2017/167672 (SEQ ID NO: 12) | 214 |
| Human OX40L: 52-183 | Natural Ligand | WO 2017/167672 (SEQ ID NO: 13) | 215 |
| 1A07 | VH | US 2015/0307617 (SEQ ID NO: 56) | 216 |
|  | VL | US 2015/0307617 (SEQ ID NO: 59) | 217 |
| 1949 | VH | WO 2016/179517 (SEQ ID NO: 16) | 218 |
|  | VL | WO 2016/179517 | 219 |
| 1D10v1 | sdAb | U.S. Pat. No. 9,006,399 | 220 |
| GITR-binding CRBR Sequences | | | |
| GITR ligand | Natural Ligand | UniProt no. Q9UNG2 | 221 |
| 36E5 | VH | US 2014/0348841 (SEQ ID NO: 104) | 222 |
|  | VL | US 2014/0348841 (SEQ ID NO: 105) | 223 |
| TRX-518 | VH | US 2013/0183321 (SEQ ID NO: 54) | 224 |
|  | VL | US 2013/0183321 (SEQ ID NO: 44) | 225 |
| 5H7v2 | VH | US 2015/0064204 (SEQ ID NO: 282) | 226 |
|  | VL | US 2015/0064204 (SEQ ID NO: 134) | 227 |
| 41G5v2 | VH | US 2015/0064204 (SEQ ID NO: 312) | 228 |
|  | VL | US 2015/0064204 (SEQ ID NO: 124) | 229 |
| C06v3 | sdAb | US 2017/0022284 (SEQ ID NO: 59) | 230 |
| CD27-binding CRBR Sequences | | | |
| CD70-ECD | Natural Ligand | UniProt no. P32970 | 231 |
| 1F5 | VH | US 2011/0274685 | 232 |
|  | VL | US 2011/0274685 | 233 |
| ICOS-binding CRBR Sequences | | | |
| ICOS sdAb | sdAb |  | 234 |
| CD28 binding CRBR Sequences | | | |
| CD28 sdAb | sdAb |  | 235 |

In some embodiments, the one or more CRBR is linked, directly or indirectly via a linker, to the Fc region and/or to the CD3 binding region. In some embodiments, linkage is via a linker. In some embodiments, the linker is a linking peptide (LP), which can include any flexible or rigid linker as described herein, although generally the peptide linking the CRBR or regions is not a cleavable linker.

In some embodiments, the multispecific polypeptide construct comprises a linking peptide (LP) between the CRBR and the Fc region. In some embodiments, the multispecific polypeptide construct comprises a linking peptide (LP) between the CD3 binding region and the CRBR.

3. NK Recruitment

In some embodiments, the PD-1-binding polypeptide is a bispecific construct that is or comprises at least one PD-1 VHH domain provided herein and at least one additional binding molecule capable of binding to a surface molecule expressed on a Natural Killer (NK) cells and/or recruiting NK cells. In particular aspects, the multispecific construct is bispecific for PD-1 and the NK cell surface molecule. In some embodiments, the surface molecule is CD16 (FcγRIII). Specifically, a provided bispecific PD-1-binding polypeptide is capable of specifically binding an NK activating receptor expressed on a human NK cells cell, such as human CD16a.

CD16, a low affinity receptor for the Fc portion of some IgGs known to be involved in antibody-dependent cellular cytotoxicity (ADCC), is the best-characterized membrane receptor responsible for triggering of target cell lysis by NK cells (Mandelboim et al., 1999, PNAS 96:5640-5644). Generally, a large majority (approximately 90%) of human NK cells express CD56 at low density (CD56dim) and FcγRIII (CD16) at a high level (Cooper et al., 2001, Trends Immunol. 22:633-640). Human FcγRIII exists as two isoforms, CD16a (FcγRIIIA) and CD16b (FcγRIIIB), that share 96% sequence identity in their extracellular immunoglobulin-binding regions (van de Winkel and Capel, 1993, Immunol. Today 14(5):215-221). In particular embodiments, the additional binding molecule is capable of specifically binding CD16a.

CD16a is expressed on macrophages, mast cells, and NK cells as a transmembrane receptor. On NK cells, the alpha chain of CD16a associates with the immunoreceptor tyrosine-based activation motif (ITAM) containing FcεRI γ-chain and/or the T-cell receptor (TCR)/CD3ζ-chain to mediate signaling (Wirthmueller et al., 1992, J. Exp. Med. 175:1381-1390). The interaction of CD16a with different combinations of homo- and hetero-dimers of the γ and ζ chains has been observed in NK cells, indicating the ability to mediate signaling via different signaling pathways via variations of the CD16a complex in NK cells (Anderson et al., 1990, PNAS 87(6):2274-2278; Ackerly et al., 1992, Int. J. Cancer Suppl. 7:11-14). FcγR-expressing effector cells have been shown to be involved in destroying tumor cells via ADCC. For example, engagement of CD16a, such as with an agonist binding molecule capable of specifically binding CD16a can result in activating of NK cells expressing CD16a, thereby eliciting a biological response, in particular a signaling response. In some cases, the binding molecule is capable of triggering cell killing, in a manner analogous to antibody-dependent cellular cytotoxicity (ADCC), by virtue of its binding to such cells.

In particular example, PD-1-binding polypeptides include bispecific molecules that can specifically bind to PD-1 and to CD16a may target NK cells to cells bearing such antigen, so that the cell bearing the antigen may be eradicated via NK cell mediated cell killing. For example, a binding molecule that specifically binds PD-1 expressed on a tumor cell may target NK-cells to the tumor cell. In some cases, activation of the NK cell caused by the binding molecule binding to CD16a can lead to killing of the tumor cells.

In some embodiments, the additional binding domain specific to an activating NK cell receptor, such as CD16a, is an antigen-binding fragment selected from a Fab fragment, a F(ab')2 fragment, an Fv fragment, a scFv, disulfide stabilized Fv fragment (dsFv), a scAb, a dAb, a single domain heavy chain antibody (VHH), or a single domain light chain antibody. In some embodiments, the additional binding domain is monovalent for binding the activating T NK cell receptor, such as CD16a.

In some cases, the additional binding domain recognizes CD16a. In some embodiments, the anti-CD16a binding domain includes one or more copies of an anti-CD16a Fab fragment, an anti-CD16a F(ab')$_2$ fragment, an anti-CD16a Fv fragment, an anti-CD16a scFv, an anti-CD16a dsFv, an anti-CD16a scAb, an anti-CD16a dAb, an anti-CD16a single domain heavy chain antibody (VHH), and an anti-CD16a single domain light chain antibody. In some embodiments, the anti-CD16a binding domain is monovalent for binding CD16a. In some embodiments, the BH73-binding polypeptide is a bispecific construct that binds BH73 and agonizes the activity of CD16a.

Antibodies and antigen-binding fragments thereof specific for CD16a are known and include, for example, NM3E2 (McCall et al. (1999) Mol. Immunol., 36:433-045. Other anti-CD16a antibodies also can be used in the constructs provided herein, including any described in published U.S. patent application Ser. No. 10/160,280,795; U.S. Pat. No. 9,701,750; Behar et al. (2008) Protein Eng Des Sel. 21:1-10; Arndt et al., (1999) Blood 94:2562-2568. In particular examples, the anti-CD16a is an anti-CD16a scFv. In some embodiments, the anti-CD16a is an anti-CD16a antibody included in a TandAb molecule (see e.g. Reush et al. (2014) Mabs, 6:727-738). In some aspects, the anti-CD16a is an anti-CD16a or antigen binding fragment, such as an scFv, described in U.S. Pat. No. 9,035,026.

The provided bispecific constructs can be formatted in any of a number of formats containing the at least one PD-1 VHH domain and the at least one additional domain specific to an activating NK cell receptor, such as a CD16a-binding domain.

In one embodiment, the bispecific construct is a bispecific single-domain antibody-linked Fab (S-Fab) containing at least one PD-1 VHH domain as described linked, directly or indirectly to a Fab antigen binding fragment specific to an NK cell activating receptor, e.g. CD16a, such as an anti-CD16a Fab. In some embodiments, the PD-1 VHH domain is linked to the C-terminus of the VH or VL chain of an anti-C16a Fab. In some embodiments, the S-Fab can be further modified, such as by conjugation with polyethylene glycol (PEG), N-(2-hydroxypropyl) methacrylamide (HPMA) copolymers, proteins (such as albumin), polyglutamic acid or PASylation (Pan et al. (2018) International Journal of Nanomedicine, 2018:3189-3201).

In another embodiment, the bispecific construct is a scFv-single domain antibody in which the construct contains at least one PD-1 VHH as described linked, directly or indirectly, to an scFv containing a VH and a VL of an antigen binding domain specific to an NK cell activating receptor, e.g. CD16a. The scFv against an NK cell activating receptor, e.g. anti-CD16a scFv, can contain any of the VH and VL sequences as described. In some embodiments, the VHH domain and the scFv are connected by a linker, such as a peptide linker. In some embodiments, the peptide linker can be a peptide linker as described herein. In some embodiments, the VHH domain and the scFv are each connected, optionally through a hinge region or a linker (e.g. peptide linker), to an Fc region, such as an N-terminus of an Fc region. The Fc region can be any described herein, such as a human Fc region or a variant thereof, e.g. a human IgG1 Fc region or a variant thereof. In particular examples, the Fc region is formed by variant Fc domains, e.g. variant human IgG1 domains, that are mutated or modified to promote heterodimerization in which different polypeptides can be dimerized to yield a heterodimer.

In a further embodiment, the antigen binding domain specific to an NK cell activating receptor, e.g. CD16a, is a single domain antibody, such as is a VHH domain that specifically binds to CD16a. Single domain antibodies, including VHH domains that bind to CD16a are known, see e.g. published U.S. patent application No. US20160280795. In such aspects, a bispecific construct provided herein can include at least one PD-1 VHH domain and at least one CD16a VHH domain. For formatting the constructs, in some cases, each VHH domain is connected, optionally through a hinge region or linker (e.g. peptide linker), to an Fc region, such as an N-terminus of an Fc region. The Fc region can be any described herein, such as a human Fc region or a variant thereof, e.g. a human IgG1 Fc region or a variant thereof. In particular examples, the Fc region is formed by variant Fc domains, e.g. variant human IgG1 domains, that are mutated or modified to promote heterodimerization in which different polypeptides can be dimerized to yield a heterodimer.

In the above embodiments, exemplary modifications of an Fc region to promote heterodimerization are known, including any as described below, e.g. Table 1. In some embodiments, one Fc polypeptide of a heterodimeric Fc comprises the sequence of amino acids set forth in any of SEQ ID NOS: 103, 107, 115, or 117, and the other Fc polypeptide of the heterodimeric Fc contains the sequence of amino acids set forth in any of SEQ ID NOS: 104, 108, 111, 113, 119 or 121. In some embodiments, one Fc polypeptide of a heterodimeric Fc comprises the sequence of amino acids set forth in any of SEQ ID NOS: 105, 109, 116 or 118 and the other Fc polypeptide of the heterodimeric Fc comprises the sequence of amino acids set forth in any of SEQ ID NOS: 106, 110, 112, 114, 120 or 122.

4. Cytokine Fusion and/or Cytokine Receptor Targeting

In some embodiments, the PD-1-binding polypeptide is a multispecific polypeptide construct that is a cytokine-antibody fusion protein (also called a PD-1 VHH-cytokine fusion). In some aspects, at least one PD-1 VHH domain provided herein is linked, directly or indirectly, to at least one cytokine, such as to an interferon. In particular embodiments, the cytokine is an interferon capable of exhibiting anti-proliferative activity, apoptotic activity and/or anti-viral activity. In some embodiments, the interferon of a PD-1 VHH-cytokine fusion provided herein is capable of binding to a receptor composed of IFNAR1 and/or 2. Any of a variety of assays can be used to assess the effect of such fusion proteins on binding IFNAR1 and/or 2, reducing or decreasing the growth rather and/or proliferation rate of a cancer cell, reducing tumor size, eliminating tumors or inducing the death of a cancer cell (e.g. via apoptosis). Such assays in include in vitro assays with various cancer cell lines known to express PD-1 or in vivo assays employing animal tumor models.

In some embodiments, the interferon is a type I interferon, such as a human type I interferon or a variant thereof. In some aspects, the human type I interferon is a variant that is a truncated human type I interferon or a human mutant type I interferon. In some embodiments, the type I interferon or variant thereof is a wild-type human IFN-alpha (IFN-alpha; alpha2 and natural higher affinity variants such as alpha 14), interferon beta (IFN-beta) as well as mutants and/or truncated forms thereof. In some embodiments, the interferon is a type II interferon, such as a human type II interferon or a variant thereof. In some aspects, the human type II interferon is a variant that is a truncated human type II interferon or a human mutant type II interferon. In some embodiments, the type II interferon or variant thereof is a wild-type human interferon gamma (IFN-gamma) as well as mutants and/or truncated forms thereof. In some embodiments, the provided cytokine-antibody fusion proteins can be used to inhibit the growth and/or proliferation of target cells (e.g. cancer cells) that express or overexpress PD-1.

In some embodiments, the PD-1 VHH-cytokine fusion protein is similar in format to any as described in International PCT published application No. WO2014194100; U.S. Pat. No. 9,803,021; Valedkarimi et al. (2017) Biomed Pharmacother., 95:731-742; or Young et al. (2014) Semin Oncol., 41:623-636.

In particular embodiments, the interferon, e.g. a type I interferon, such as a human type I interferon (e.g. IFN-alpha, IFN-beta, or IFN-gamma) is one that possesses the endogenous binding affinity and/or activity of the native or wild-type interferon, preferably at a level of at least 60%, or of at least or at least about 80%, such as at least 90%, 95%, 98%, 99%, 100%, or a level greater than the native wild-type interferon (in its isolated form).

Interferons and interferon mutants are a well-known and well characterized group of cytokines (see e.g., WO 2002/095067; WO 2002/079249; WO 2002/101048; WO 2002/095067; WO 2002/083733; WO 2002/086156; WO 2002/083733; WO 2003/000896; WO 2002/101048; WO 2002/079249; WO 2003/000896; WO 2004/022593; WO2004/022747; WO 2003/023032; WO 2004/022593 and also in Kim et al. (2003) Cancer Lett. 189(2): 183-188; Hussain et al. (2000) J. Interferon Cytokine Res. 20(9): 763-768; Hussain et al. (1998) J. Interferon Cytokine Res. 18(7): 469-477; Nyman et al. (1988) Biochem. J. 329 (Pt 2): 295-302; Golovleva et al. (1997) J. Interferon Cytokine Res. 17(10): 637-645; Hussain et al. (1997) J. Interferon Cytokine Res. 17(9): 559-566; Golovleva et al. (1997) Hum. Hered. 47(4): 185-188; Kita et al. (1991) J. Interferon Cytokine Res. 17(3): 135-140; Golovleva et al. (1996) Am. J. Hum. Genet. 59(3): 570-578; Hussain et al. (1996) J. Interferon Cytokine Res. 16(7): 523-529; Linge et al. (1995) Biochim Biophys Acta. Any of such can be used in the provided cytokine-antibody fusion proteins.

In some embodiments, the interferon is a human type I interferon. Alleles of the human interferon family of genes/proteins are known, see e.g. Pestka (10983) Arch Biochem Biophys., 221:1-37; Diaz et al. (1994) Genomics, 22:540-52; Pestka (1986) Meth. Enzymol, 199: 3-4; and Krause et al. (2000) J. Biol. Chem., 275:22995-3004.

In some embodiments, the interferon is a full-length IFN-alpha (e.g. human IFN-alpha), a full-length IFN-beta (e.g. human IFN-beta) or a full-length IFN-gamma (e.g. human IFN-gamma). In some embodiments, the interferon is a biologically active truncated IFN-alpha (e.g. human IFN-alpha), a biologically active truncated IFN-beta (e.g. human IFN-beta) or a biologically active truncated IFN-gamma (e.g. human IFN-gamma). In some embodiments, a biologically active truncated interferon contains a contiguous sequence of amino acids of a wild-type or native interferon that is truncated at the N- and/or C-terminus and comprises a length that is at least or at least about 50%, 55%, 60%, 65%, 70%, 75%, 80%, 85%, 90% or more the length of the native or wild-type interferon. Any of a variety of standard assays for assessing biological activity of an interferon can be used. For example, IFN-alpha activity can be assayed by measuring antiviral activity against a particular test virus. Kits for assaying for IFN-alpha activity are commercially available (see, e.g., ILITE™ alphabeta kit by Neutekbio, Ireland). In some aspects, the IFN-alpha is an IFN-α2a (e.g. Acc. No. CAA23805), IFN-a-c (Acc. No. P01566), IFN-α-d (Acc. No. AAB59403); IFNa-5 (Acc. No. CAA26702); IFNa-6 (Acc. No. AA26704); IFNa-4 (Acc. No. NP 066546); IFNa-4b (Acc. No. CAA26701); IFNa-I (Acc. No. AAA52725); IFNa-J (Acc. No. CAA23792); IFNa-H (Acc. No. CAA23794); IFNa-F (Acc. No. AAA52718); IFNa-7 (Acc. No. CAA26903), or is a biologically active fragment thereof. In some aspects, the IFN-beta is IFN-beta set forth in Acc. No. AAC41702 or is a biologically active fragment thereof. In some aspects, the IFN-gamma is IFN-gamma set forth in Acc. No. P01579 or is a biologically active fragment thereof.

In some embodiments, a provided PD-1 VHH-cytokine fusion contains a variant or mutant interferon alpha 2 (IFNa2) is contemplated. Certain mutants include a mutation of the His at position 57, and/or the Eat position 58, and/or the Q at position 61. In certain embodiments the mutants include the mutation H57Y, and/or E58N, and/or Q61S. In certain embodiments the mutants include a mutated IFNa2 having the mutations H57Y, E58N, and Q61S (YNS) (see, e.g., Kalie et al. (2007) J. Biol. Chem., 282: 11602-11611). In other embodiments mutants include a mutation of the His at position 57, and/or the E at position 58, and/or the Q at position 61 to A (alanine). In certain embodiments the mutants include a mutated IFNa2 having the mutations H57A, E58A, and Q61A (HEQ) (see, e.g., Jaitin et al. (2006) Mo/. Cellular Biol, 26(5): 1888-1897). In certain embodiments the mutant interferon comprises a mutation of His at position 57 to A, Y, or M, and/or a mutation of E at position 58 to A, or N, or D, or L, and/or a mutation of Q at position 61 to A, or S, or L, or D. In certain embodiments mutant include mutants of interferon alpha 8 (IFN-a8), such as variants with amino acid replacement corresponding to R145 to V, I, or L, and/or A146 to N, or S, and/or M149 to Y, e.g. R145V/A146N/M149Y), R145I,/A146S/M149Y or R145L/A146S/M149Y (see, e.g., Yamamoto et. al., (2009) J. Interferon & cytokine Res, 29: 161-170.

In some embodiments, a provided PD-1 VHH-cytokine fusion contains a mutant or variant IFN-beta containing a serine substituted for the naturally occurring cysteine at amino acid 17 (see, e.g., Hawkins et al. (1985) Cancer Res., 45, 5914-5920).

In some embodiments, a provided PD-1 VHH-cytokine fusion contains a truncated interferon. In one embodiment, a truncated interferon includes a human IFN-alpha with deletions of up to the first 15 amino-terminal amino acid residues and/or up to the last 10-13 carboxyl-terminal amino acid residues, which has been shown to retain activity of the native or wild-type human IFN-alpha (see e.g. Ackerman (1984) Proc. Natl. Acad. Sci, USA, 81: 1045-1047). In some embodiments, a truncated human IFN-alpha has 1, 2, 3, 4, 5, 6, 7, 8, 9, 10, 11, 12 or 13 carboxyl terminal amino acid residues deleted and/or 1, 2, 3, 4, 5, 6, 7, 8, 9, 10, 11, 12, 13, 14, or 15 amino terminal amino acid residues deleted.

In some embodiments, a provided PD-1 VHH-cytokine fusion contains a truncated interferon, such as described in published U.S. patent appl. No. US2009/0025106. In some embodiments, a provided PD-1 VHH-cytokine fusion contains a truncated IFN-gamma containing N- and/or C-terminal deletions, such as described in Lundell et al. (1991) Protein Neg., 4:335-341; Pan et al. (1987) Eur. J. Biochem., 166:145-149.

In some embodiments, the interferon, e.g. human interferon, is a mutant interferon that is resistant to proteolysis compared to the unmodified, typically wild-type protein, see e.g. U.S. Pat. Nos. 7,998,469; 8,052,964; 4,832,959 U.S. Pat. No. 6,120,762; WO1992/008737; and EP219781.

In aspects of the provided PD-1 VHH-cytokine fusion proteins, the antibody and the cytokine, e.g. interferon, are attached directly or are attached indirectly via a linker, such as a peptide linker. The attachment can be to the N- or C-terminus of the VHH domain, so long as the attachment does not interfere with binding of the antibody to PD-1. Any linker, e.g. peptide linker, described herein can be used. In some embodiments, the linker is a GS-linker that comprises an amino acid sequence selected from the group consisting of GGSGGS, i.e., (GGS)$_2$ (SEQ ID NO: 1); GGSGGSGGS, i.e., (GGS)$_3$ (SEQ ID NO: 2); GGSGGSGGSGGS, i.e., (GGS)$_4$ (SEQ ID NO: 3); and GGSGGSGGSGGSGGS, i.e., (GGS)$_5$ (SEQ ID NO: 4). In some embodiments, the linker is a flexible linker comprising Glycine residues, such as, by way of non-limiting example, GG, GGG, GGGG (SEQ ID NO: 5), GGGGG (SEQ ID NO: 6), and GGGGGG (SEQ ID NO: 7). In some embodiments, the fusion proteins can include a combination of a GS-linker and a Glycine linker.

D. Engineered Cells

Provided herein are engineered cells that express any of the provided PD-1 binding molecules described herein. In particular example, the provided PD-1 bind molecules are secreted from the cell. In some embodiments, the PD-1 binding molecule, e.g. containing an anti-PD-1 VHH domain as provided herein, comprises a signal peptide, e.g., an antibody signal peptide or other efficient signal sequence to get domains outside of cell. When the PD-1 binding molecule comprises a signal peptide and is expressed by an engineered cell, the signal peptide causes the immunomodulatory protein to be secreted by the engineered cell. Generally, the signal peptide, or a portion of the signal peptide, is cleaved from the binding molecule with secretion. The PD-1 binding molecule can be encoded by a nucleic acid (which can be part of an expression vector). In some embodiments, the PD-1 binding molecule is expressed and secreted by a cell (such as an immune cell, for example a primary immune cell).

In some embodiments, provided engineered cells further contain a chimeric antigen receptors (CARs). CARs are synthetic receptors typically containing an extracellular targeting/binding moiety that is associated with one or more signaling domains in a single fusion molecule, and that is expressed on the surface of a cell, such as a T cell. Thus, CARs combine antigen-specificity and T cell activating properties in a single fusion molecule. First generation CARs typically included the cytoplasmic region of the CD3zeta or Fc 1 receptor γ chain as their signaling domain. First generation CARs have been tested in phase I clinical studies in patients with ovarian cancer, renal cancer, lymphoma, and neuroblastoma, where they have induced modest responses (reviewed in Sadelain et al., Curr Opin Immunol, 21 (2): 215-223, 2009). Second generation CARs, which contain the signaling domains of a costimulatory molecule, such as CD28, and CD3zeta, provide dual signaling to direct combined activating and co-stimulatory signals. Third generation CARs are more complex with three or more signaling domains (reviewed in Sadelain et al., Cancer Discovery (3), 388-398, 2013 and Dotti et al, Immuno. Rev, 257 (1), 1-36, 2014).

In some embodiments, a CAR contains an extracellular domain comprising one or more antigen binding domain specific to a tumor antigen. In some aspects, the tumor antigen and/or antigen binding domain specific to a TAA can be any as described herein. CAR constructs include an extracellular domain containing the one or more extracellular antigen binding domain, a transmembrane domain and an intracellular signaling region. In some cases, the extracellular antigen binding domain is an scFv or a single domain antibody (VHH). In general, the extracellular antigen binding domain which form the antigen binding unit of the CAR "binds" or is "capable of binding", i.e. targets, a target antigen with sufficient affinity such the CAR is useful in therapy in targeting a cell or tissue expressing the target antigen.

The transmembrane domain of a CAR is a domain that typically crosses or is capable of crossing or spanning the plasma membrane and is connected, directly or indirectly (e.g. via a spacer, such as an immunoglobulin hinge sequence) to the extracellular antigen binding domain and the endoplasmic portion containing the intracellular signaling domain. In one embodiment, the transmembrane domain of the CAR is a transmembrane region of a transmembrane protein (for example Type I transmembrane proteins), an artificial hydrophobic sequence or a combination thereof. In one embodiment, the transmembrane domain comprises the CD3zeta domain or CD28 transmembrane domain. Other transmembrane domains will be apparent to those of skill in the art and may be used in connection with embodiments of a CAR provided herein.

The intracellular signaling region of a CAR provided herein contains one or more intracellular signaling domain that transmits a signal to a T cell upon engagement of the antigen binding domain of the CAR, such as upon binding antigen. In some embodiments, the intracellular region contains an intracellular signaling domain that is or contains an ITAM signaling domain. Exemplary intracellular signaling domains include, for example, a signaling domain derived from ζ chain of the T-cell receptor complex or any of its homologs (e.g., η chain, FcεRIγ and β chains, MB 1 (Igα) chain, B29 (Ig) chain, etc.), human CD3zeta chain, CD3 polypeptides (Δ, δ and ε), syk family tyrosine kinases (Syk, ZAP 70, etc.), src family tyrosine kinases (Lck, Fyn, Lyn, etc.) and other molecules involved in T-cell transduction, such as CD2, CD5, OX40 and CD28. In particular embodiments, the intracellular signaling region contains an intracellular signaling domain derived from the human CD3 zeta chain.

In some embodiments, the endodomain comprises at CD3-zeta signaling domain. In some embodiments, the CD3-zeta signaling domain comprises the sequence of amino acids set forth in SEQ ID NO: 236 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO: 236 and retains the activity of T cell signaling.

In some embodiments, the intracellular signaling region of a CAR can further contain an intracellular signaling domain derived from a costimulatory molecule. In such examples, such a signaling domain may enhance CAR-T cell activity, such as via enhancement of proliferation, survival and/or development of memory cells, after antigen specific engagement, for example, compared to a CAR that only contains an ITAM containing signaling domain, e.g. CD3 zeta. In some embodiments, the co-stimulatory domain is a functional signaling domain obtained from a protein selected from: CD28, CD137 (4-1BB), CD134 (OX40), DapIO, CD27, CD2, CD5, ICAM-1, LFA-1 (CD1 la/CD18), Lck, TNFR-I, TNFR-II, Fas, CD30, CD40 or combinations thereof. In particular embodiments, the costimulatory signaling domain is derived or obtained from a human protein. In some aspects, the costimulatory signaling domain is derived or obtained from human CD28 or human CD137 (4-1BB).

In some embodiments, the costimulatory signaling domain is a derived from CD28 or 4-1BB and comprises the sequence of amino acids set forth in any of SEQ ID NOS: 237-240 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO: 237-240 and retains the activity of T cell costimulatory signaling.

In particular embodiments, the CAR further comprises a hinge or spacer region which connects the extracellular antigen binding domain and the transmembrane domain. This hinge or spacer region can be used to achieve different lengths and flexibility of the resulting CAR. Examples of the hinge or spacer region that can be used include, but are not limited to, Fc fragments of antibodies or fragments or derivatives thereof, hinge regions of antibodies, or fragments or derivatives thereof, $C_H2$ regions of antibodies, $C_H3$ regions of antibodies, artificial spacer sequences, for example peptide sequences, or combinations thereof. Other hinge or spacer region will be apparent to those of skill in the art and may be used. In one embodiment, the hinge is an IgG4 hinge or a CD8A hinge.

In some embodiments, the spacer and transmembrane domain are the hinge and transmembrane domain derived from CD8, such as having an exemplary sequence set forth in SEQ ID NO: 241-243 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 241-243.

Also provided herein is an isolated nucleic acid construct comprising a polynucleotide encoding a PD-1 binding molecule as provided herein. Also provided herein is an isolated nucleic acid construct comprising a polynucleotide encoding a CAR and encoding the PD-1 binding molecule as provided herein. In some a first nucleic acid encoding the CAR is separated from a second nucleic acid encoding the PD-1 binding molecule by a biscistronic element, such as an IRES or a ribosome skip sequence (e.g. T2A or P2A). In some aspects, the construct is an expression vector for expression of the PD-1 binding molecule and/or CAR in a cell. The expression vector may be a viral vector. Viral vector technology is well known in the art and is described, for example, in Sambrook et al. (Molecular Cloning: A Laboratory Manual, Cold Spring Harbor Laboratory, New York, 2013). A number of viral based systems have been developed for gene transfer into mammalian cells. For example, retroviruses such as, adenovirus vectors are used. In one embodiment, a lentivirus vector is used.

In a further aspect, also provided is an isolated cell or cell population comprising one or more nucleic acid construct as described above. Also provided is an isolated cell or cell population that has been genetically modified to express a PD-1 binding molecule and/or CAR provided herein. Thus, provided herein are genetically engineered cells which comprise, such as stably express, a CAR provided herein. In one embodiment, the cell is selected from the group consisting of a T cell, a Natural Killer (NK) cell, a cytotoxic T lymphocyte (CTL), a regulatory T cell, hematopoietic stem cells and/or pluripotent embryonic/induced stem cells. In some cases, the cell is a T cell, such as a CD4 and/or CD8 T cell. In some embodiments, the cells are autologous to the subject. For example, in some embodiments, T cells may be isolated from a patient (also called primary T cells) for engineering, e.g. transfection or transduction, with a CAR nucleic acid construct.

In an exemplary example, primary T-cells can be purified ex vivo (CD4 cells or CD8 cells or both) and stimulated with a TCR/CD28 agonists, such as anti-CD3/anti-CD28 coated beads. After a 2 or 3 day activation process, a recombinant expression vector encoding the CAR can be stably introduced into the primary T cells through standard lentiviral or retroviral transduction protocols or plasmid electroporation strategies. Cells can be monitored for secretion of an PD-1 binding molecule and/or CAR expression by, for example, flow cytometry using anti-epitope tag or antibodies that cross-react with native parental molecule. T-cells that express the CAR can be enriched through sorting with anti-epitope tag antibodies or enriched for high or low expression depending on the application.

The PD-1 binding molecule and/or CAR engineered T-cells can be assayed for appropriate function by a variety of means. In some cases, in vitro cytotoxicity, proliferation, or cytokine assays (e.g., IFN-gamma expression) can be used to assess the function of engineered T-cells. Exemplary standard endpoints are percent lysis of a tumor line, proliferation of the engineered T-cell, or IFN-gamma protein expression in culture supernatant. In some cases, the ability to stimulate activation of T cells upon stimulation of the CAR, e.g. via antigen, can be assessed, such as by monitoring expression of activation markers such as CD69, CD44, or CD62L, proliferation and/or cytokine production.

Also provided herein are methods for the prevention and/or treatment of a disease or condition in a subject, such as a cancer, that includes administering to a subject engineered cells provided herein. Generally, the subject is in need of treatment for the disease or condition. pharmaceutically active amount of a cell and/or of a pharmaceutical composition of the invention.

IV. POLYPEPTIDE EXPRESSION AND PRODUCTION

Nucleic acid molecules comprising polynucleotides that encode any of the provided sdAb and PD-1-binding polypeptides are provided. In some embodiments, the provided nucleic acid sequences and particularly DNA sequences encode fusion proteins as provided herein. In any of the foregoing embodiments, the nucleic acid molecule may also encode a leader sequence that directs secretion of the PD-1-binding polypeptide, which leader sequence is typically cleaved such that it is not present in the secreted polypeptide. The leader sequence may be a native heavy chain (or VHH) leader sequence, or may be another heterologous leader sequence.

Nucleic acid molecules can be constructed using recombinant DNA techniques conventional in the art. In some embodiments, a nucleic acid molecule is an expression vector that is suitable for expression in a selected host cell.

Vectors comprising nucleic acids that encode the PD-1-binding polypeptides described herein are provided. Such vectors include, but are not limited to, DNA vectors, phage vectors, viral vectors, retroviral vectors, etc. In some embodiments, a vector is selected that is optimized for expression of polypeptides in a desired cell type, such as CHO or CHO-derived cells, or in NSO cells. Exemplary such vectors are described, for example, in Running Deer et al., *Biotechnol. Prog.* 20:880-889 (2004).

In particular, a DNA vector that encodes a desired PD-1-binding polypeptides, such as a fusion protein, can be used to facilitate the methods of preparing the PD-1-binding polypeptides described herein and to obtain significant quantities. The DNA sequence can be inserted into an appropriate expression vector, i.e., a vector which contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used.

The disclosure also provides methods of producing a PD-1-binding polypeptides by culturing a cell under conditions that lead to expression of the polypeptide, wherein the cell comprises an isolated nucleic acid molecule encoding a PD-1-binding polypeptide described herein, and/or vectors that include these isolated nucleic acid sequences.

In some embodiments, a PD-1-binding polypeptide may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, the PD-1-binding polypeptides may be expressed in yeast. See, e.g., U.S. Publication No. US 2006/0270045 A1. In some embodiments, a particular eukaryotic host cell is selected based on its ability to make desired post-translational modifications to the polypeptide. For example, in some embodiments, CHO cells produce polypeptides that have a higher level of sialylation than the same polypeptide produced in 293 cells.

Introduction of one or more nucleic acids (such as vectors) into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, $3^{rd}$ ed. Cold Spring Harbor Laboratory Press (2001). Nucleic acids may be transiently or stably transfected in the desired host cells, according to any suitable method.

Host cells comprising any of the nucleic acids or vectors described herein are also provided. In some embodiments, a host cell that expresses a PD-1-binding polypeptide described herein is provided. The PD-1-binding polypeptides expressed in host cells can be purified by any suitable method. Such methods include, but are not limited to, the use of affinity matrices or hydrophobic interaction chromatography. Suitable affinity ligands include the ROR1 ECD and agents that bind Fc regions. For example, a Protein A, Protein G, Protein A/G, or an antibody affinity column may be used to bind the Fc region and to purify a PD-1-binding polypeptide that comprises an Fc region. Hydrophobic interactive chromatography, for example, a butyl or phenyl column, may also suitable for purifying some polypeptides such as antibodies. Ion exchange chromatography (for example anion exchange chromatography and/or cation exchange chromatography) may also suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

In some embodiments, the PD-1-binding polypeptide is produced in a cell-free system. Nonlimiting exemplary cell-free systems are described, for example, in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

In some embodiments, PD-1-binding polypeptides prepared by the methods described above are provided. In some embodiments, the PD-1-binding polypeptide is prepared in a host cell. In some embodiments, the PD-1-binding polypeptide is prepared in a cell-free system. In some embodiments, the PD-1-binding polypeptide is purified. In some embodiments, a cell culture media comprising a PD-1-binding polypeptide is provided.

In some embodiments, compositions comprising antibodies prepared by the methods described above are provided. In some embodiments, the composition comprises a PD-1-binding polypeptide prepared in a host cell. In some embodiments, the composition comprises a PD-1-binding polypeptide prepared in a cell-free system. In some embodiments, the composition comprises a purified PD-1-binding polypeptide.

V. PHARMACEUTICAL COMPOSITIONS AND FORMULATIONS

Provided herein are pharmaceutical compositions containing any of the PD-1-binding polypeptides provided herein or engineered cells expressing the same. In some embodiments, PD-1-binding polypeptides, such as fusion proteins of the disclosure (also referred to herein as "active compounds"), and derivatives, fragments, analogs and homologs thereof, can be incorporated into pharmaceutical compositions suitable for administration. In some embodiments, engineered cells expressing a chimeric receptor, such as a chimeric antigen receptor, containing a PD-1-binding polypeptide provided herein can be incorporated into pharmaceutical compositions suitable for administration.

Such compositions typically contain a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, intratumoral, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a kit, container, pack, or dispenser together with instructions for administration. These pharmaceutical compositions can be included in diagnostic kits with instructions for use.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In some embodiments, the pharmaceutical composition may be administered in an amount in the range of about 50 µg/kg body weight to about 50 mg/kg body weight per dose. In some embodiments, the pharmaceutical composition may be administered in an amount in the range of about 100 µg/kg body weight to about 50 mg/kg body weight per dose. In some embodiments, the pharmaceutical composition may be administered in an amount in the range of about 100 µg/kg body weight to about 20 mg/kg body weight per dose. In some embodiments, the pharmaceutical composition may be administered in an amount in the range of about 0.5 mg/kg body weight to about 20 mg/kg body weight per dose.

In some embodiments, the pharmaceutical composition may be administered in an amount in the range of about 10 mg to about 1,000 mg per dose. In some embodiments, the pharmaceutical composition may be administered in an amount in the range of about 20 mg to about 500 mg per dose. In some embodiments, the pharmaceutical composition may be administered in an amount in the range of about 20 mg to about 300 mg per dose. In some embodiments, the pharmaceutical composition may be administered in an amount in the range of about 20 mg to about 200 mg per dose.

The pharmaceutical composition may be administered as needed to subjects. In some embodiments, an effective dose of the pharmaceutical composition is administered to a subject one or more times. In various embodiments, an effective dose of the pharmaceutical composition is administered to the subject once a month, less than once a month, such as, for example, every two months, every three months, or every six months. In other embodiments, an effective dose of the pharmaceutical composition is administered more than once a month, such as, for example, every two weeks, every week, twice per week, three times per week, daily, or multiple times per day. An effective dose of the pharmaceutical composition is administered to the subject at least once. In some embodiments, the effective dose of the pharmaceutical composition may be administered multiple times, including for periods of at least a month, at least six months, or at least a year. In some embodiments, the pharmaceutical composition is administered to a subject as-needed to alleviate one or more symptoms of a condition.

VI. METHODS OF TREATMENT AND USES

The PD-1-binding polypeptides or engineered cells expressing the same described herein are useful in a variety of therapeutic, diagnostic and prophylactic indications. For example, the PD-1-binding polypeptides or engineered cells are useful in treating a variety of diseases and disorders in a subject. Such methods and uses include therapeutic methods and uses, for example, involving administration of the molecules or engineered cells, or compositions containing the same, to a subject having a disease, condition, or disorder, such as a tumor or cancer. In some embodiments, the molecule ore engineered cell is administered in an effective amount to effect treatment of the disease or disorder. Uses include uses of molecules containing the PD-1-binding polypeptides or engineered cells in such methods and treatments, and in the preparation of a medicament in order to carry out such therapeutic methods. In some embodiments, the methods are carried out by administering the PD-1-binding polypeptides or engineered cells, or compositions comprising the same, to the subject having or suspected of having the disease or condition. In some embodiments, the methods thereby treat the disease or condition or disorder in the subject.

In one embodiment, a PD-1-binding polypeptide or engineered cell of the disclosure may be used as therapeutic agents. Such agents will generally be employed to diagnose, prognose, monitor, treat, alleviate, and/or prevent a disease or pathology in a subject. A therapeutic regimen is carried out by identifying a subject, e.g., a human patient or other mammal suffering from (or at risk of developing) a disorder using standard methods. In some cases, a subject is selected that is known, suspected or that has been identified as having a tumor expressing PD-1. A PD-1-binding polypeptide or engineered cell is administered to the subject. A PD-1-binding polypeptide or engineered cell is administered to the subject and will generally have an effect due to its binding with the target(s).

In some embodiments, a provided PD-1 polypeptide multi-specific polypeptide construct or engineered cell is capable of modulating, e.g. increasing, an immune response when administered to a subject, such as by engagement of CD3 and/or a CD3 signal in a cell and/or by blocking the interaction of PD-1 and PD-L1/PD-L2. In some embodiments, provided herein is a method of modulating an immune response in a subject by administering a therapeutically effective amount of a provided multispecific construct or engineered cell, or pharmaceutical compositions thereof. In some embodiments, the method of modulating an immune response increases or enhances an immune response in a subject. For example, the increase or enhanced response may be an increase in cell-mediated immunity. In some examples, the method increases T-cell activity, such as cytolytic T-cell (CTL) activity. In some embodiments, the modulated (e.g., increased) immune response is against a tumor or cancer.

In some embodiments, administration of a PD-1-binding polypeptide, such as an PD-1-Fc fusion protein or a multispecific construct containing an Fc region, may activate innate immune cells via engagement of FcγRs through the Fc-region of the multispecific polypeptide construct. Administration of such multispecific polypeptide constructs may agonize, stimulate, activate, and/or augment innate immune cell effector functions, including ADCC, cytokine release, degranulation and/or ADCP. In the case of a constrained multispecific polypeptide construct, administration of such multispecific polypeptide constructs may activate T-cells once the linker(s) joining the first and second component is cleaved by a protease and/or upon binding of tumor antigen on a target cell (e.g. tumor cell), thereby allowing the anti-CD3 binding portion to bind CD3ε on the T cells. In some cases, administration of the multispecific polypeptide constructs may agonize, stimulate, activate, and/or augment CD3-mediated T cell activation, cytotoxicity, cytokine release and/or proliferation.

In some embodiments, the provided methods are for treating a disease or condition in a subject by administering a therapeutically effective amount of any of the provided PD-1-binding polypeptides or engineered cells or pharmaceutical compositions thereof. In some embodiments, the disease or condition is a tumor or a cancer. Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this disclosure can be used to prevent the onset or reoccurrence of the disease or disorder in a subject, e.g., a human or other mammal, such as a non-human primate, companion animal (e.g., cat, dog, horse), farm animal, work animal, or zoo animal. The terms subject and patient are used interchangeably herein.

In some embodiments, the PD-1-binding polypeptides or engineered cells, or pharmaceutical compositions thereof, can be used to inhibit growth of mammalian cancer cells (such as human cancer cells). A method of treating cancer can include administering an effective amount of any of the pharmaceutical compositions described herein to a subject with cancer. The effective amount of the pharmaceutical composition can be administered to inhibit, halt, or reverse progression of cancers. Human cancer cells can be treated in vivo, or ex vivo. In ex vivo treatment of a human patient, tissue or fluids containing cancer cells are treated outside the body and then the tissue or fluids are reintroduced back into the patient. In some embodiments, the cancer is treated in a human patient in vivo by administration of the therapeutic composition into the patient.

Non-liming examples of disease include: all types of cancers (breast, lung, colorectal, prostate, melanomas, head and neck, pancreatic, etc.), rheumatoid arthritis, Crohn's disuse, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic, and breast, including triple negative breast cancer. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; endometrial cancer; gastric cancer; glioblastoma; head and neck cancer, such as esophageal cancer; lung cancer, such as by way of non-limiting example, non-small cell lung cancer; multiple myeloma ovarian cancer; pancreatic cancer; prostate cancer; sarcoma, such as osteosarcoma; renal cancer, such as by way of nonlimiting example, renal cell carcinoma; and/or skin cancer, such as by way of nonlimiting example, squamous cell cancer, basal cell carcinoma, or melanoma. In some embodiments, the cancer is a squamous cell cancer. In some embodiments, the cancer is a skin squamous cell carcinoma. In some embodiments, the cancer is an esophageal squamous cell carcinoma. In some embodiments, the cancer is a head and neck squamous cell carcinoma. In some embodiments, the cancer is a lung squamous cell carcinoma.

In some embodiments, the PD-1-binding polypeptides or engineered cells, or pharmaceutical compositions thereof, or are useful in treating, alleviating a symptom of, ameliorating and/or delaying the progression of a cancer or other neoplastic condition. In some embodiments, the cancer is bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer. In certain embodiments, the cancer is a metastatic cancer, refractory cancer, or recurrent cancer.

In some embodiments, a therapeutically effective amount of a PD-1-binding polypeptide, such as a fusion protein or multispecific polypeptide construct, of the disclosure relates generally to the amount needed to achieve a therapeutic objective. Typically, precise amount of the compositions of the present disclosure to be administered can be determined by a physician with consideration of individual differences in age, weight, tumor size, extent of infection or metastasis, and condition of the patient (subject).

In some embodiments, a therapeutically effective dose may be, by way of nonlimiting example, from about 0.01 µg/kg body weight to about 10 mg/kg body weight. In some embodiments, the therapeutically effective dose may be, by way of nonlimiting example, from about 0.01 mg/kg body weight to about 5-10 mg/kg body weight. Common dosing frequencies may range, for example, from twice daily to once a week.

In some embodiments, a therapeutic amount of an engineered cell composition of the present disclosure is administered. It can generally be stated that a pharmaceutical composition comprising engineered cells, e.g., T cells, as described herein may be administered at a dosage of $10^4$ to $10^9$ cells/kg body weight, such as $10^5$ to $10^6$ cells/kg body weight, including all integer values within those ranges. Engineered cell compositions, such as T cell compositions, may also be administered multiple times at these dosages. The cells can be administered by using infusion techniques that are commonly known in immunotherapy (see, e.g., Rosenberg et al, New Eng. J. of Med. 319: 1676, 1988). The optimal dosage and treatment regime for a particular patient can readily be determined by one skilled in the art of medicine by monitoring the patient for signs of disease and adjusting the treatment accordingly.

Efficaciousness of treatment is determined in association with any known method for diagnosing or treating the particular disorder. Methods for the screening of PD-1-binding polypeptides, or engineered cells containing the same, that possess the desired specificity include, but are not limited to, enzyme linked immunosorbent assay (ELISA) and other immunologically mediated techniques known within the art. A variety of means are known for determining if administration of the provided PD-1-binding polypeptides or engineered cells sufficiently modulates immunological activity by eliminating, sequestering, or inactivating immune cells mediating or capable of mediating an undesired immune response; inducing, generating, or turning on immune cells that mediate or are capable of mediating a protective immune response; changing the physical or functional properties of immune cells; or a combination of these effects. Examples of measurements of the modulation of immunological activity include, but are not limited to, examination of the presence or absence of immune cell populations (using flow cytometry, immunohistochemistry, histology, electron microscopy, polymerase chain reaction (PCR)); measurement of the functional capacity of immune cells including ability or resistance to proliferate or divide in response to a signal (such as using T-cell proliferation assays and pepscan analysis based on 3H-thymidine incorporation following stimulation with anti-CD3 antibody, anti-T-cell receptor antibody, anti-CD28 antibody, calcium ionophores, PMA (phorbol 12-myristate 13-acetate) antigen presenting cells loaded with a peptide or protein antigen; B cell proliferation assays); measurement of the ability to kill or lyse other cells (such as cytotoxic T cell assays); measurements of the cytokines, chemokines, cell surface molecules, antibodies and other products of the cells (e.g., by flow cytometry, enzyme-linked immunosorbent assays, Western blot analysis, protein microarray analysis, immunoprecipitation analysis); measurement of biochemical markers of activation of immune cells or signaling pathways within immune cells (e.g., Western blot and immunoprecipitation analysis of tyrosine, serine or threonine phosphorylation, polypeptide cleavage, and formation or dissociation of protein complexes; protein array analysis; DNA transcriptional, profiling using DNA arrays or subtractive hybridization); measurements of cell death by apoptosis, necrosis, or other mechanisms (e.g., annexin V staining, TUNEL assays, gel electrophoresis to measure DNA laddering, histology; fluorogenic caspase assays, Western blot analysis of caspase substrates); measurement of the genes, proteins, and other molecules produced by immune cells (e.g., Northern blot analysis, polymerase chain reaction, DNA microarrays, protein microarrays, 2-dimensional gel electrophoresis, Western blot analysis, enzyme linked immunosorbent assays, flow cytometry); and measurement of clinical symptoms or outcomes such as improvement of autoimmune, neurodegenerative, and other diseases involving self-proteins or self-polypeptides (clinical scores, requirements for use of additional therapies, functional status, imaging studies) for example, by measuring relapse rate or disease severity.

The provided PD-1-binding polypeptides are also useful in a variety of diagnostic and prophylactic formulations. In one embodiment, a PD-1-binding polypeptide is administered to patients that are at risk of developing one or more of the aforementioned disorders. A patient's or organ's predisposition to one or more of the disorders can be determined using genotypic, serological or biochemical markers.

In another embodiment of the disclosure, a PD-1-binding polypeptide or engineered cell is administered to human individuals diagnosed with a clinical indication associated with one or more of the aforementioned disorders. Upon diagnosis, such a therapeutic agent is administered to mitigate or reverse the effects of the clinical indication.

Combination Therapy

PD-1-binding polypeptides or engineered cells of the present disclosure can be administered alone or in combination with other modes of treatment, such as other anti-cancer agents. They can be provided before, substantially contemporaneous with, or after other modes of treatment (i.e., concurrently or sequentially). In some embodiments, the method of treatment described herein can further include administering: radiation therapy, chemotherapy, vaccination, targeted tumor therapy, CAR-T therapy, oncolytic virus therapy, cancer immunotherapy, cytokine therapy, surgical resection, chromatin modification, ablation, cryotherapy, an antisense agent against a tumor target, a siRNA agent against a tumor target, a microRNA agent against a tumor target or an anti-cancer/tumor agent, or a biologic, such as an antibody, cytokine, or receptor extracellular domain-Fc fusion.

In some embodiments, a PD-1-binding polypeptide provided herein is given concurrently with one or more chemotherapeutic agent, CAR-T (chimeric antigen receptor T-cell) therapy, oncolytic virus therapy, cytokine therapy, and/or agents that target other checkpoint molecules, such as VISTA, gpNMB, B7H4, HHLA2, CD73, CTLA4, TIGIT, etc.

In some embodiments, the PD-1-binding polypeptide or engineered cells of the present disclosure is used in combination with other anti-tumor agents, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib)(TARCEVA®), platelet derived growth factor inhibitors (e.g., GLEEVEC® (Imatinib Mesylate)), a COX-2 inhibitor (e.g., celecoxib), interferons, CTLA4 inhibitors (e.g., anti-CTLA antibody ipilimumab (YERVOY®))), PD-1 inhibitors (e.g., anti-PD1 antibodies, BMS-936558), PDL1 inhibitors (e.g., anti-PDL1 antibodies, MPDL3280A), PDL2 inhibitors (e.g., anti-PDL2 antibodies), cytokines, antagonists (e.g., neutralizing antibodies) that bind to one or more of the following targets ErbB2, ErbB3, ErbB4, PDGFR-beta, BlyS, APRIL, BCMA, PD-1, PDL1, PDL2, CTLA4, or VEGF receptor(s), TRAIL/Apo2, and other bioactive and organic chemical agents, etc.

In some embodiments, a PD-1-binding polypeptide or engineered cell provided herein is given concurrently with a PD-1/PD-L1 therapy. Examples of PD-1/PD-L1 therapy include nivolumab (BMS); pidilizumab (CureTech, CT-011), pembrolizumab (Merck); durvalumab (Medimmune/AstraZeneca); atezolizumab (Genentech/Roche); avelumab (Pfizer); AMP-224 (Amplimmune); BMS-936559; AMP-514 (Amplimmune); MDX-1105 (Merck); TSR-042 (Tesaro/AnaptysBio, ANB-011); STI-A1010 (Sorrento Therapeutics); STI-A1110 (Sorrento Therapeutics); and other agents that are directed against programmed death-1 (PD-1) or programmed death ligand 1 (PD-L1).

In some embodiments, the PD-1-binding polypeptide or engineered cell of the present disclosure may be used in combination with a chemotherapeutic agent. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKx polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® (aldesleukin) rIL-2; LURTOTECAN topoisomerase 1 inhibitor; ABARELIX® GnRH agoninst; and pharmaceutically acceptable salts, acids or derivatives of any of the above.

In some embodiments, the PD-1-binding polypeptide and the additional agent are formulated into a single therapeutic composition, and the PD-1-binding polypeptide and additional agent are administered simultaneously. Alternatively, the PD-1-binding polypeptide or engineered cell and the additional agent are separate from each other, e.g., each is formulated into a separate therapeutic composition, and the PD-1-binding polypeptide or engineered cell and the additional agent are administered simultaneously, or the PD-1-binding polypeptide or engineered cell and the additional agent are administered at different times during a treatment regimen. For example, the PD-1-binding polypeptide or engineered cell is administered prior to the administration of the additional agent, the PD-1-binding polypeptide or engineered cell is administered subsequent to the administration of the additional agent, or the PD-1-binding polypeptide or engineered cell and the additional agent are administered in an alternating fashion. The PD-1-binding polypeptide and additional agent may be administered in single doses or in multiple doses.

In some embodiments, the PD-1-binding polypeptide or engineered cell and the additional agent(s) are administered simultaneously. For example, the PD-1-binding polypeptide and the additional agent(s) can be formulated in a single composition or administered as two or more separate compositions. In some embodiments, the PD-1-binding polypeptide or engineered cell and the additional agent(s) are administered sequentially, or the PD-1-binding polypeptide or engineered cell and the additional agent are administered at different times during a treatment regimen.

VII. EXEMPLARY EMBODIMENTS

Among the provided embodiments are:

1. A PD-1-binding polypeptide construct, comprising at least one heavy chain only variable domain (PD-1 VHH domain) that specifically binds PD-1 and one or more additional binding domain that binds to a target other than PD-1.

2. The PD-1-binding construct of embodiment 1, wherein the at least one VHH domain comprises a complementarity determining region 1 (CDR1) comprising an amino acid sequence selected from the group consisting of SEQ ID NO: 268, 272,273 and 313; a complementarity determining region 2 (CDR2) comprising an amino acid sequence set forth in SEQ ID NO: 278 or 314; and a complementarity determining region 3 (CDR3) comprising an amino acid sequence set forth in SEQ ID NO: 283 or 315.

3. A PD-1-binding construct, comprising at least one heavy chain only variable domain (PD-1 VHH domain) comprising a complementarity determining region 1 (CDR1) comprising an amino acid sequence selected from the group consisting of SEQ ID NO: 268, 272, 273 and 313; a complementarity determining region 2 (CDR2) comprising an amino acid sequence set forth in SEQ ID NO: 278 or 314; and a complementarity determining region 3 (CDR3) comprising an amino acid sequence set forth in SEQ ID NO: 283.

4. The PD-1-binding polypeptide construct of any of embodiments 1-3, wherein the PD-1 is a human PD-1.

5. The PD-1-binding polypeptide construct of any of embodiments 1-4, wherein the at least one PD-1 VHH domain is humanized.

6. The PD-1-binding polypeptide construct of any of embodiments 1, 2, 4 and 5, wherein the one or more additional binding domains binds to an activating receptor on an immune cell.

7. The PD-1-binding polypeptide construct of embodiment 6, wherein the immune cell is a T cell.

8. The PD-1-binding polypeptide construct of embodiment 6 or embodiment 7, wherein the activating receptor is CD3 (CD3ε).

9. The PD-1-binding polypeptide construct of embodiment 8 that is bispecific for PD-1 and CD3.

10. The PD-1-binding polypeptide construct of embodiment 9, wherein the immune cell is a Natural Killer (NK) cell.

11. The PD-1-binding polypeptide construct of embodiment 6 or embodiment 10, wherein the activating receptor is CD16 (CD16a).

12. The PD-1-binding polypeptide construct of embodiment 11 that is bispecific for PD-1 and CD16a.

13. The PD-1-binding polypeptide construct of any of embodiments 1, 2, 4 and 5, wherein the one or more additional domains binds to a tumor associated antigen (TAA).

14. The PD-1-binding polypeptide construct of any of embodiments 1, 2, 4 and 5, wherein the one or more additional binding domain binds to a cytokine receptor.

15. The PD-1-binding polypeptide construct of any of embodiments 1, 2 and 4-14, wherein the one or more additional binding domain comprises an antibody or antigen-binding fragment thereof.

16. The PD-1-binding polypeptide construct of any of embodiments 1, 2 and 4-15, wherein the one or more additional binding domain is monovalent.

17. The PD-1-binding polypeptide construct of embodiment 16, wherein the antibody or antigen-binding fragment thereof is an Fv, a disulfide-stabilized Fv (dsFv), scFv, a Fab, a single domain antibody (sdAb), a VNAR, or a VHH.

18. The PD-1-binding polypeptide construct of embodiment 14, wherein the one or more additional binding domain is a cytokine or is a truncated fragment or variant thereof capable of binding to the cytokine receptor.

19. The PD-1-binding polypeptide construct of embodiment 18, wherein the cytokine is an interferon that is a type I interferon or a type II interferon, is a truncated fragment or variant of a type I interferon or is a truncated fragment or variant of a type II interferon.

20. The PD-1-binding polypeptide construct of embodiment 19, wherein:
the type I interferon is an IFN-alpha or an IFN-beta or is a truncated fragment or variant thereof; or
the type II interferon is an IFN-gamma or is a truncated fragment or variant thereof.

21. The PD-1-binding polypeptide construct of any of embodiments 1-20, wherein the polypeptide comprises an immunoglobulin Fc region.

22. The PD-1-binding polypeptide construct of any of embodiments 1, 2 and 4-21, wherein the polypeptide comprises an immunoglobulin Fc region that links the at least one single domain antibody and the one or more additional binding domain.

23. The PD-1-binding polypeptide construct of any of embodiments 1-22 that is a dimer.

24. The PD-1-binding polypeptide construct of any of embodiments 21-23, wherein the Fc region is a homodimeric Fc region.

25. The PD-1-binding polypeptide construct of any of embodiments 21-24, wherein the Fc region comprises the sequence of amino acids set forth in any of SEQ ID NOS: 8, 10, 11, 12 or 13, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 8, 10, 11, 12 or 13.

26. The PD-1-binding polypeptide construct of any of embodiments 21-24, wherein the Fc region is a human IgG1.

27. The PD-1-binding polypeptide construct of embodiment 26, wherein the Fc region comprises the sequence of amino acids set forth in SEQ ID NO:8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8.

28. The PD-1-binding polypeptide construct of any of embodiments 21-23, wherein the Fc region is a heterodimeric Fc region.

29. The PD-1-binding polypeptide construct of any of embodiments 21-28, wherein the Fc region exhibits effector function.

30. The PD-1-binding polypeptide construct of any of embodiments 21-29, wherein the Fc region comprises a polypeptide comprising one or more amino acid modification that reduces effector function and/or reduces binding to an effector molecule selected from an Fc gamma receptor or C1q.

31. The PD-1-binding polypeptide construct of embodiment 30, wherein the one or more amino acid modification is deletion of one or more of Glu233, Leu234 or Leu235.

32. The PD-1-binding polypeptide construct of embodiment 30 or embodiment 31, wherein the Fc region comprises the sequence of amino acids set forth in SEQ ID NO:9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9.

33. The PD-1-binding polypeptide construct of any of embodiments 1-32, wherein the at least one PD-1 VHH domain comprises the sequence set forth in any of SEQ ID NOS: 251-267 or 284, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 251-267 or 284 and binds PD-1.

34. The PD-1-binding polypeptide construct of any of embodiments 1-33, wherein the at least one PD-1 VHH domain comprises the sequence set forth in (i) SEQ ID NO:284, (ii) a humanized variant of SEQ ID NO:284, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:284 and binds PD-1.

35. The PD-1-binding polypeptide construct of any of embodiments 1-34, wherein the at least one PD-1 VHH domain comprises the sequence set forth in SEQ ID NO:284.

36. The PD-1-binding polypeptide of any of embodiments 1-34, wherein the at least one PD-1 VHH domain comprises a CDR1 comprising an amino acid sequence selected from the group consisting of SEQ ID NO: 268, 272 and 273; a CDR2 comprising an amino acid sequence set forth in SEQ ID NO: 278; and a CDR3 comprising an amino acid sequence set forth in SEQ ID NO: 283.

37. The PD-1-binding polypeptide construct of any of embodiments 1-34 and 36, wherein the at least one PD-1 VHH domain comprises a CDR1, CDR2 and CDR3 set forth in SEQ ID NOS: 268, 278, and 283, respectively; SEQ ID NOS: 272, 278, and 283, respectively; or SEQ ID NOS: 273, 278, and 283, respectively.

38. The PD-1-binding polypeptide construct of any of embodiments 1-34, 36 and 37, wherein the at least one PD-1 VHH domain comprises the sequence of amino acids set forth in any one of SEQ ID NOs: 251-267 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 251-267 and binds PD-1.

39. The PD-1-binding polypeptide construct of embodiments 1-34 and 36-38, wherein the at least one PD-1 VHH domain comprises the sequence of amino acids set forth in any one of SEQ ID NOS: 251-267.

40. The PD-1-binding polypeptide construct of any of embodiments 1-34 and 36-39, wherein the at least one PD-1 VHH domain comprises the sequence of amino acids set forth in SEQ ID NO: 257 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 257 and binds PD-1.

41. The PD-1-binding polypeptide construct of any of embodiments 1-34 and 36-40, wherein the at least one PD-1 VHH domain comprises the sequence of amino acids set forth in SEQ ID NO: 257.

42. The PD-1-binding polypeptide construct of any of embodiments 1-34 and 36-39, wherein the at least one PD-1 VHH domain comprises the sequence of amino acids set forth in SEQ ID NO: 251 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 251 and binds PD-1.

43. The PD-1-binding polypeptide construct of any of embodiments 1-34 and 36-39, wherein the at least one PD-1 VHH domain comprises the sequence of amino acids set forth in SEQ ID NO: 252 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 252 and binds PD-1.

44. The PD-1 binding polypeptide construct of any of embodiments 1-34 and 36-39, wherein the at least one PD-1 VHH domain comprises the sequence of amino acids set forth in SEQ ID NO: 253 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 253 and binds PD-1.

45. The PD-1-binding polypeptide construct of any of embodiments 1-34 and 36-39, wherein the at least one PD-1 VHH domain comprises the sequence of amino acids set forth in SEQ ID NO: 254 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 254 and binds PD-1.

46. The PD-1-binding polypeptide construct of any of embodiments 1-34 and 36-39, wherein the at least one PD-1 VHH domain comprises the sequence of amino acids set forth in SEQ ID NO: 255 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 255 and binds PD-1.

47. The PD-1-binding polypeptide construct of any of embodiments 1-34 and 36-39, wherein the at least one PD-1 VHH domain comprises the sequence of amino acids set forth in SEQ ID NO: 256 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 256 and binds PD-1.

48. The PD-1-binding polypeptide construct of any of embodiments 1-34 and 36-39, wherein the at least one PD-1 VHH domain comprises the sequence of amino acids set forth in SEQ ID NO: 258 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 258 and binds PD-1.

49. The PD-1-binding polypeptide construct of any of embodiments 1-34 and 36-39, wherein the at least one PD-1 VHH domain comprises the sequence of amino acids set forth in SEQ ID NO: 259 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 259 and binds PD-1.

50. The PD-1-binding polypeptide construct of any of embodiments 1-34 and 36-39, wherein the at least one PD-1 VHH domain comprises the sequence of amino acids set forth in SEQ ID NO: 260 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 260 and binds PD-1.

51. The PD-1-binding polypeptide construct of any of embodiments 1-34 and 36-39, wherein the at least one PD-1 VHH domain comprises the sequence of amino acids set forth in SEQ ID NO: 261 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 261 and binds PD-1.

52. The PD-1-binding polypeptide construct of any of embodiments 1-34 and 36-39, wherein the at least one PD-1 VHH domain comprises the sequence of amino acids set forth in SEQ ID NO: 262 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 262 and binds PD-1.

53. The PD-1-binding polypeptide construct of any of embodiments 1-34 and 36-39, wherein the at least one PD-1 VHH domain comprises the sequence of amino acids set forth in SEQ ID NO: 263 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 263 and binds PD-1.

54. The PD-1-binding polypeptide construct of any of embodiments 1-34 and 36-39, wherein the at least one PD-1 VHH domain comprises the sequence of amino acids set forth in SEQ ID NO: 264 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 264 and binds PD-1.

55. The PD-1-binding polypeptide construct of any of embodiments 1-34 and 36-39, wherein the at least one PD-1 VHH domain comprises the sequence of amino acids set forth in SEQ ID NO: 265 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 265 and binds PD-1.

56. The PD-1-binding polypeptide construct of any of embodiments 1-34 and 36-39, wherein the at least one PD-1 VHH domain comprises the sequence of amino acids set forth in SEQ ID NO: 266 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 266 and binds PD-1.

57. The PD-1-binding polypeptide construct of any of embodiments 1-34 and 36-39, wherein the at least one PD-1 VHH domain comprises the sequence of amino acids set forth in SEQ ID NO: 267 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 267 and binds PD-1.

58. The PD-1-binding polypeptide construct of any of embodiments 1-34 and 36-39, wherein the at least one PD-1 VHH domain comprises least 95% sequence identity to SEQ ID NO: 251, 252, 253, 254, 255, 256, 257, 258, 259, 260, 261, 262, 263, 264, 265, 266, 267 or 284 and binds PD-1.

59. The PD-1-binding polypeptide construct of any of embodiments 1-34 and 36-39, wherein the at least one PD-1 VHH domain is set forth in SEQ ID NO: 251, 252, 253, 254, 255, 256, 257, 258, 259, 260, 261, 262, 263, 264, 265, 266, 267 or 284.

60. A multispecific polypeptide construct, comprising: (a) a first component comprising a heterodimeric Fc region comprising a first Fc polypeptide and a second Fc polypeptide and (b) a second component comprising an anti-CD3 antibody or antigen-binding fragment comprising a variable heavy chain region (VH) and a variable light chain region (VL), wherein:

the VH and VL that comprise the anti-CD3 antibody or antigen binding fragment are linked to opposite polypeptides of the heterodimeric Fc;

the first and second components are coupled by a linker, wherein the heterodimeric Fc region is positioned N-terminal to the anti-CD3 antibody;

one or both of the first and second components comprises at least one antigen binding domain that binds a tumor associated antigen (TAA); and one or both of the first and second components comprises at least one heavy chain only variable domain (PD-1 VHH domain).

61. The multispecific polypeptide construct of embodiment 60, wherein the multispecific polypeptide construct comprises at least (i) a first polypeptide comprising the first Fc polypeptide of the heterodimeric Fc region, the linker and the VH or VL domain of the anti-CD3 antibody or antigen binding fragment; and (ii) a second polypeptide comprising the second Fc polypeptide of the heterodimeric Fc region, the linker, optionally the same linker as present in the first polypeptide, and the other of the VH or VL domain of the anti-CD3 antibody or antigen binding fragment, wherein one or both of the first and second polypeptide independently comprise the at least one antigen binding domain that binds a TAA and the at least one PD-1 VHH domain.

62. The multispecific polypeptide construct of embodiment 60 or embodiment 61, wherein one or both of the first and second Fc polypeptides of the heterodimeric Fc region comprises at least one modification to induce heterodimerization compared to a polypeptide of a homodimeric Fc region, optionally compared to the Fc polypeptide set forth in SEQ ID NO: 245 or an immunologically active fragment thereof.

63. The multispecific polypeptide construct of embodiment 62, wherein each of the first and second Fc polypeptides of the heterodimeric Fc independently comprise at least one amino acid modification.

64. The multispecific polypeptide construct of embodiment 63, wherein each of the first and second Fc polypeptides of the heterodimeric Fc comprise a knob-into-hole modification or comprise a charge mutation to increase electrostatic complementarity of the polypeptides.

65. The multispecific polypeptide construct of embodiment 64, wherein the amino acid modification is a knob-into-hole modification.

66. The multispecific polypeptide construct of any of embodiments 60-65, wherein the first Fc polypeptide of the heterodimeric Fc comprises the modification selected from among Thr366Ser, Leu368Ala, Tyr407Val, and combinations thereof and the second Fc polypeptide of the heterodimeric Fc comprises the modification Thr366Trp.

67. The multispecific polypeptide of embodiment 66, wherein the first and second Fc polypeptides further comprises a modification of a non-cysteine residue to a cysteine residue, wherein the modification of the first polypeptide is at one of the position Ser354 and Tyr349 and the modification of the second Fc polypeptide is at the other of the position Ser354 and Tyr349.

68. The multispecific polypeptide construct of any of embodiments 60-64, wherein the amino acid modification is a charge mutation to increase electrostatic complementarity of the polypeptides.

69. The multispecific polypeptide construct of any of embodiments 60-64 and 68, wherein the first and/or second Fc polypeptides or each of the first and second Fc polypeptide comprise a modification in complementary positions, wherein the modification is replacement with an amino acid having an opposite charge to the complementary amino acid of the other polypeptide.

70. The multispecific polypeptide construct of any of embodiments 60-69, wherein one of the first or second Fc polypeptide of the heterodimeric Fc further comprises a modification at residue Ile253.

71. The multispecific polypeptide construct of embodiment 70, wherein the modification is Ile253Arg.

72. The multispecific polypeptide construct of any of embodiments 60-71, wherein one of the first or second Fc polypeptide of the heterodimeric Fc further comprises a modification at residue His435.

73. The multispecific polypeptide construct of embodiment 72, wherein the modification is His435Arg.

74. The multispecific polypeptide construct of any of embodiments 60-73, wherein the Fc region comprises a polypeptide that lacks Lys447.

75. The multispecific polypeptide construct of any of embodiments 60-74, wherein the Fc region comprises a polypeptide comprising at least one modification to enhance FcRn binding.

76. The multispecific polypeptide construct of embodiment 75, wherein the modification is at a position selected from the group consisting of Met252, Ser254, Thr256, Met428, Asn434, and combinations thereof.

77. The multispecific polypeptide construct of embodiment 76, wherein the modification is at a position selected from the group consisting of Met252Y, Ser254T, Thr256E, Met428L, Met428V, Asn434S, and combinations thereof.

78. The multispecific polypeptide construct of embodiment 76, wherein the modification is at position Met252 and at position Met428.

79. The multispecific polypeptide construct of embodiment 78, wherein the modification is Met252Y and Met428L.

80. The multispecific polypeptide construct of embodiment 76, wherein the modification is Met252Y and Met428V.

81. The multispecific polypeptide construct of any of embodiments 60-80, wherein the first polypeptide of the heterodimeric Fc comprises the sequence of amino acids set forth in any of SEQ ID NOS:103, 107, 115 or 117, and the second polypeptide of the heterodimeric Fc comprises the sequence of amino acids set forth in any of SEQ ID NOS:104, 108, 111, 113, 119 or 121.

82. The multispecific polypeptide construct of any of embodiments 1-81, wherein the Fc region comprises a polypeptide comprising at least one amino acid modification that reduces effector function and/or reduces binding to an effector molecule selected from an Fc gamma receptor or C1q.

83. The multispecific polypeptide construct of embodiment 82, wherein the one or more amino acid modification is deletion of one or more of Glu233, Leu234 or Leu235.

84. The multispecific polypeptide construct of any of embodiments 60-83, wherein the first polypeptide of the heterodimeric Fc comprises the sequence of amino acids set forth in any of SEQ ID NOS: 105, 109, 116 or 118 and the second polypeptide of the heterodimeric Fc comprises the sequence of amino acids set forth in any of SEQ ID NOS: 106, 110, 112, 114, 120 or 122.

85. The multispecific polypeptide construct of any of embodiment 60-84, wherein the anti-CD3 antibody or antigen binding fragment is monovalent.

86. The multispecific polypeptide construct of any of embodiments 60-85, wherein the anti-CD3 antibody or antigen binding fragment is not a single chain antibody, optionally is not a single chain variable fragment (scFv).

87. The multispecific polypeptide construct of any of embodiments 60-86, wherein the anti-CD3 antibody or antigen binding fragment is an Fv antibody fragment.

88. The multispecific polypeptide construct of embodiment 87, wherein the Fv antibody fragment comprises a disulfide stabilized anti-CD3 binding Fv fragment (dsFv).

89. The multispecific polypeptide construct of 60-88, wherein the anti-CD3 antibody or antigen-binding fragment comprises a VH CDR1 comprising the amino acid sequence TYAMN (SEQ ID NO: 29); a VH CD2 comprising the amino acid sequence RIRSKYNNYATYYADSVKD (SEQ ID NO: 30); a VH CDR3 comprising the amino acid sequence HGNFGNSYVSWFAY (SEQ ID NO: 31), a VL CDR1 comprising the amino acid sequence RSSTGAVTTSNYAN (SEQ ID NO: 32); a VL CDR2 comprising the amino acid sequence GTNKRAP (SEQ ID NO: 33); and a VL CDR3 comprising the amino acid sequence ALWYSNLWV (SEQ ID NO: 34).

90. The multispecific polypeptide construct of any of embodiments 60-89, wherein the anti-CD3 antibody or antigen-binding fragment comprises:
a VH having the amino acid sequence of any of SEQ ID NOS: 35-65 or a sequence that exhibits at least 90%, 91%, 92%, 93%, 94%, 95%, 96%, 97%, 98% or 99% sequence identity to any of SEQ ID NOS: 35-65; and
a VL having the amino acid sequence of any of SEQ ID NOS: 66-85 and 293 or a sequence that exhibits at least 90%, 91%, 92%, 93%, 94%, 95%, 96%, 97%, 98% or 99% sequence identity to any of SEQ ID NOS: 66-85 and 293.

91. The multispecific polypeptide construct of any of embodiments 60-90, wherein the anti-CD3 antibody or antigen-binding fragment comprises the amino acid sequence of SEQ ID NO: 47 and the amino acid sequence of SEQ ID NO: 75.

92. The multispecific polypeptide construct of any of embodiments 60-90, wherein the anti-CD3 antibody or antigen-binding fragment comprises the amino acid sequence of SEQ ID NO: 47 and the amino acid sequence of SEQ ID NO: 285.

93. The multispecific polypeptide construct of any of embodiment 60-92, wherein the at least one PD-1 VHH domain is positioned amino-terminally relative to the Fc region and/or carboxy-terminally relative to the CD3 binding region of the multispecific polypeptide construct.

94. The multispecific polypeptide construct of any of embodiments 60-93, wherein the first polypeptide comprises in order of N-terminus to C-terminus a first antigen binding domain that binds a TAA, a first polypeptide comprising the first Fc polypeptide of the heterodimeric Fc region, the linker, the VH or VL domain of the anti-CD3 antibody or antigen binding fragment and a second antigen binding domain that binds a TAA; and
the second polypeptide comprises the at least one PD-1 VHH domain and comprises in order of N-terminus to C-terminus the second Fc polypeptide of the heterodimeric Fc region, the linker, optionally the same linker as present in the first polypeptide, and the other of the VH or VL domain of the anti-CD3 antibody or antigen binding fragment, wherein the at least one PD-1 VHH domain is positioned amino-terminally relative to the Fc region and/or carboxy-terminally relative to the CD3 binding region.

95. The multispecific polypeptide construct of any of embodiments 60-94, wherein the multispecific polypeptide construct comprises only one PD-1 VHH domain that specifically binds PD-1.

96. The multispecific polypeptide construct of any of embodiments 60-95, wherein the PD-1 VHH domain is positioned amino-terminally relative to the Fc region of the multispecific construct.

97. The multispecific polypeptide construct of any of embodiments 60-96, wherein
the first polypeptide comprises in order of N-terminus to C-terminus a first antigen binding domain that binds a TAA, a first polypeptide comprising the first Fc polypeptide of the heterodimeric Fc region, the linker, the VH or VL domain of the anti-CD3 antibody or antigen binding fragment and a second antigen binding domain that binds a TAA; and
the second polypeptide comprises in order of N-terminus to C-terminus the second Fc polypeptide of the heterodimeric Fc region, the linker, optionally the same linker as present in the first polypeptide, the other of the VH or VL domain of the anti-CD3 antibody or antigen binding fragment and the PD-1 VHH domain.

98. The multispecific polypeptide construct of any of embodiments 60-95, wherein the PD-1 VHH domain is positioned amino-terminally relative to the Fc region of the multispecific construct.

99. The multispecific polypeptide construct of any of embodiments 60-95 and 98, wherein
the first polypeptide comprises in order of N-terminus to C-terminus a first antigen binding domain that binds a TAA, a first polypeptide comprising the first Fc polypeptide of the heterodimeric Fc region, the linker, the VH or VL domain of the anti-CD3 antibody or antigen binding fragment and a second antigen binding domain that binds a TAA; and
the second polypeptide comprises in order of N-terminus to C-terminus the PD-1 VHH domain, the second Fc polypeptide of the heterodimeric Fc region, the linker, optionally the same linker as present in the first polypeptide, and the other of the VH or VL domain of the anti-CD3 antibody or antigen binding fragment.

100. The multispecific polypeptide construct of any of embodiments 60-99, wherein the at least one PD-1 VHH domain comprises the sequence set forth in any of SEQ ID NOS: 251-267 or 284, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 251-267 or 284 and binds PD-1.

101. The multispecific polypeptide construct of any of embodiments 60-100, wherein the at least one PD-1 VHH domain comprises the sequence set forth in (i) SEQ ID NO:284, (ii) a humanized variant of SEQ ID NO:284, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:284 and binds PD-1.

102. The multispecific polypeptide construct of any of embodiments 60-101, wherein the at least one PD-1 VHH domain comprises the sequence set forth in SEQ ID NO:284.

103. The multispecific polypeptide construct of any of embodiments 60-101, wherein the at least one PD-1 VHH domain comprises a CDR1 comprising an amino acid sequence selected from the group consisting of SEQ ID NO: 268, 272 and 273; a CDR2 comprising an amino acid sequence set forth in SEQ ID NO: 278; and a CDR3 comprising an amino acid sequence set forth in SEQ ID NO: 283.

104. The multispecific polypeptide construct of any of embodiments 60-100 and 103, wherein the at least one PD-1 VHH domain comprises a CDR1, CDR2 and CDR3 set forth in SEQ ID NOS: 268, 278, and 283, respectively; SEQ ID NOS: 272, 278, and 283, respectively; or SEQ ID NOS: 273, 278, and 283, respectively.

105. The multispecific polypeptide construct of any of embodiments 60-100, 103 and 104, wherein the at least one PD-1 VHH domain comprises the sequence of amino acids set forth in any one of SEQ ID NOs: 251-267 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 251-267 and binds PD-1.

106. The multispecific polypeptide construct of embodiments 60-100 and 103-105, wherein the at least one PD-1 VHH domain comprises the sequence of amino acids set forth in any one of SEQ ID NOS: 251-267.

107. The multispecific polypeptide construct of any of embodiments 60-100 and 103-106, wherein the at least one PD-1 VHH domain comprises the sequence of amino acids set forth in SEQ ID NO: 257 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 257 and binds PD-1.

108. The multispecific polypeptide construct of any of embodiments 60-100 and 103-107, wherein the at least one PD-1 VHH domain comprises the sequence of amino acids set forth in SEQ ID NO: 257.

109. The multispecific polypeptide construct of any of embodiments 60-100 and 103-106, wherein the at least one PD-1 VHH domain comprises the sequence of amino acids set forth in SEQ ID NO: 251 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 251 and binds PD-1.

110. The multispecific polypeptide construct of any of embodiments 60-100 and 103-106, wherein the at least one PD-1 VHH domain comprises the sequence of amino acids set forth in SEQ ID NO: 252 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 252 and binds PD-1.

111. The multispecific polypeptide construct of any of embodiments 60-100 and 103-106, wherein the at least one PD-1 VHH domain comprises the sequence of amino acids set forth in SEQ ID NO: 253 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 253 and binds PD-1.

112. The multispecific polypeptide construct of any of embodiments 60-100 and 103-106, wherein the at least one PD-1 VHH domain comprises the sequence of amino acids set forth in SEQ ID NO: 254 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 254 and binds PD-1.

113. The multispecific polypeptide construct of any of embodiments 60-100 and 103-106, wherein the at least one PD-1 VHH domain comprises the sequence of amino acids set forth in SEQ ID NO: 255 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 255 and binds PD-1.

114. The multispecific polypeptide construct of any of embodiments 60-100 and 103-106, wherein the at least one PD-1 VHH domain comprises the sequence of amino acids set forth in SEQ ID NO: 256 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 256 and binds PD-1.

115. The multispecific polypeptide construct of any of embodiments 60-100 and 103-106, wherein the at least one PD-1 VHH domain comprises the sequence of amino acids set forth in SEQ ID NO: 258 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 258 and binds PD-1.

116. The multispecific polypeptide construct of any of embodiments 60-100 and 103-106, wherein the at least one PD-1 VHH domain comprises the sequence of amino acids set forth in SEQ ID NO: 259 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 259 and binds PD-1.

117. The multispecific polypeptide construct of any of embodiments 60-100 and 103-106, wherein the at least one PD-1 VHH domain comprises the sequence of amino acids set forth in SEQ ID NO: 260 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 260 and binds PD-1.

118. The multispecific polypeptide construct of any of embodiments 60-100 and 103-106, wherein the at least one PD-1 VHH domain comprises the sequence of amino acids set forth in SEQ ID NO: 261 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 261 and binds PD-1.

119. The multispecific polypeptide construct of any of embodiments 60-100 and 103-106, wherein the at least one PD-1 VHH domain comprises the sequence of amino acids set forth in SEQ ID NO: 262 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 262 and binds PD-1.

120. The multispecific polypeptide construct of any of embodiments 60-100 and 103-106, wherein the at least one PD-1 VHH domain comprises the sequence of amino acids set forth in SEQ ID NO: 263 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 263 and binds PD-1.

121. The multispecific polypeptide construct of any of embodiments 60-100 and 103-106, wherein the at least one PD-1 VHH domain comprises the sequence of amino acids set forth in SEQ ID NO: 264 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 264 and binds PD-1.

122. The multispecific polypeptide construct of any of embodiments 60-100 and 103-106, wherein the at least one PD-1 VHH domain comprises the sequence of amino acids set forth in SEQ ID NO: 265 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 265 and binds PD-1.

123. The multispecific polypeptide construct of any of embodiments 60-100 and 103-106, wherein the at least one PD-1 VHH domain comprises the sequence of amino acids set forth in SEQ ID NO: 266 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 266 and binds PD-1.

124. The multispecific polypeptide construct of any of embodiments 60-100 and 103-106, wherein the at least one PD-1 VHH domain comprises the sequence of amino acids set forth in SEQ ID NO: 267 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 267 and binds PD-1.

125. The multispecific polypeptide construct of any of embodiments 60-100 and 103-106, wherein the at least one PD-1 VHH domain comprises a sequence of amino acids that exhibits at least 95% sequence identity to SEQ ID NO: 251, 252, 253, 254, 255, 256, 257, 258, 259, 260, 261, 262, 263, 264, 265, 266, 267 or 284 and binds PD-1.

126. The multispecific polypeptide construct of any of embodiments 60-100 and 103-106, wherein the at least one PD-1 VHH domain is set forth in SEQ ID NO: 251, 252, 253, 254, 255, 256, 257, 258, 259, 260, 261, 262, 263, 264, 265, 266, 267 or 284.

127. The multispecific polypeptide construct of any of embodiments 60-126, wherein one or both of the first and second components comprises at least one co-stimulatory receptor binding region (CRBR) that binds a co-stimulatory receptor.

128. The multispecific polypeptide construct of embodiment 127, wherein the at least one co-stimulatory receptor binding region (CRBR) is positioned amino-terminally relative to the Fc region and/or carboxy-terminally relative to the CD3 binding region of the multispecific polypeptide construct.

129. The multispecific polypeptide construct of embodiment 127 or embodiment 128, wherein the multispecific polypeptide construct comprises only one co-stimulatory receptor binding region (CRBR).

130. The multispecific polypeptide construct of any of embodiments 127-129, wherein the multispecific polypeptide construct comprises two co-stimulatory receptor binding region (CRBR), optionally which are the same or different.

131. The multispecific polypeptide construct of any of embodiments 127-129, wherein the at least one co-stimulatory receptor binding region (CRBR) is or comprises the extracellular domain or binding fragment thereof of the native cognate binding partner of the co-stimulatory receptor, or a variant thereof that exhibits binding activity to the co-stimulatory receptor.

132. The multispecific polypeptide construct of any of embodiments 127-130, wherein the at least one co-stimulatory receptor binding region (CRBR) is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

133. The multispecific polypeptide construct of embodiment 132, wherein the antibody or antigen-binding fragment thereof is a Fv, a scFv, a Fab, a single domain antibody (sdAb), a VNAR, or a VHH.

134. The multispecific polypeptide construct of embodiment 1132 or embodiment 133, wherein the antibody or antigen-binding fragment is an sdAb.

135. The multispecific polypeptide construct of embodiment 134, wherein the sdAb is a human or humanized sdAb.

136. The multispecific polypeptide construct of any of embodiments 127-135, wherein the at least one co-stimulatory receptor binding region (CRBR) binds a co-stimulatory receptor selected from among 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), and NKG2D.

137. The multispecific polypeptide construct of any of embodiments 127-136, wherein the at least one co-stimulatory receptor binding region (CRBR) binds a co-stimulatory receptor selected from among 41BB (CD137), OX40 (CD134), and glucocorticoid-induced TNFR-related protein (GITR).

138. The multispecific polypeptide construct of any of embodiments 127-137, wherein the at least one co-stimulatory receptor binding region (CRBR) comprises the sequence of amino acids set forth in SEQ ID NO:210 or a sequence that has at least 85%, 86%, 87%, 88%, 89%, 90%, 91%, 92%, 93%, 94%, 95%, 96%, 97%, 98%, or 99% sequence identity to the sequence set forth in SEQ ID NO:210 and binds 4-1BB.

139. The multispecific polypeptide construct of any of embodiments 60-138, wherein the multispecific polypeptide construct comprises a first and a second antigen binding domains that binds to a TAA.

140. The multispecific polypeptide construct of embodiment 139, wherein the antigen binding domains bind to the same tumor-associated antigen (TAA).

141. The multispecific polypeptide construct of embodiment 139 or embodiment 149, wherein the first antigen binding domain and the second antigen binding domain binds a different or nonoverlapping epitope of the same TAA and/or compete for binding to the same TAA.

142. The multispecific polypeptide construct of embodiment 139, wherein the first antigen binding domain and the second antigen binding domain bind a different TAA.

143. The multispecific polypeptide construct of any of embodiments 139-142, wherein one antigen binding domain is positioned amino-terminally relative to the Fc region and one antigen binding domain is positioned carboxy-terminally relative to the CD3 binding region.

144. The multispecific polypeptide construct of any of embodiments 60-143, wherein the antigen binding domain that binds a TAA, or independently each of the antigen binding domains that binds a TAA, comprises an extracellular domain or binding fragment thereof of the native cognate binding partner of the TAA, or a variant thereof that exhibits binding activity to the TAA.

145. The multispecific polypeptide construct of any of embodiments 60-143, wherein the antigen binding domain that binds a TAA, or independently each of the antigen binding domains that binds a TAA, is an antibody or antigen-binding fragment thereof.

146. The multispecific polypeptide construct of embodiment 145, wherein the antibody or antigen-binding fragment thereof is a Fv, a scFv, a Fab, a single domain antibody (sdAb), a VNAR, or a VHH.

147. The multispecific polypeptide construct of embodiment 145 or embodiment 146, wherein the antibody or antigen-binding fragment is an sdAb.

148. The multispecific polypeptide construct of embodiment 147, wherein the sdAb is a human or humanized sdAb.

149. The multispecific polypeptide construct of any of embodiments 60-148, wherein the antigen binding domain, or independently each of the antigen binding domains, binds to a tumor antigen selected from among 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsxl), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

150. The multispecific polypeptide construct of any of embodiments 139-149, wherein:
the first polypeptide comprises in order of N-terminus to C-terminus a first antigen binding domain that binds a TAA, a first polypeptide comprising the first Fc polypeptide of the heterodimeric Fc region, the linker, the $V_H$ or $V_L$ domain of the anti-CD3 antibody or antigen binding fragment and a second antigen binding domain that binds a TAA; and
the second polypeptide comprises in order of N-terminus to C-terminus one of the PD-1 VHH domain or the CRBR, the second Fc polypeptide of the heterodimeric Fc region, the linker, optionally the same linker as present in the first polypeptide, the other of the $V_H$ or $V_L$ domain of the anti-CD3 antibody or antigen binding fragment, and the other of the PD-1 VHH domain or the CRBR.

151. The multispecific polypeptide construct of any of embodiments 60-150, wherein the linker is a peptide or polypeptide linker, optionally wherein the linker is 3, 4, 5, 6, 7, 8, 9, 10, 11, 12, 13, 14, 15, 16, 17, 18, 19 or 20 amino acids in length.

152. The multispecific polypeptide construct of any of embodiments 60-151, wherein the linker is a non-cleavable linker.

153. The multispecific polypeptide construct of embodiment 152, wherein the non-cleavable linker comprises GS, GGS, GGGGS (SEQ ID NO:125), GGGGGS (SEQ ID NO:126) and combinations thereof.

154. The multispecific polypeptide construct of any of embodiments 60-153, wherein the linker is or comprises the sequence GGGGGSGGGGGSGGGGGS (SEQ ID NO:127).

155. The multispecific polypeptide construct of any of embodiments 60-151, wherein the linker is a cleavable linker.

156. The multispecific polypeptide construct of embodiment 155, wherein the cleavable linker is a polypeptide that functions as a substrate for a protease.

157. The multispecific polypeptide construct of embodiment 156, wherein the protease is produced by an immune effector cell, by a tumor, or by cells present in the tumor microenvironment.

158. The multispecific polypeptide construct of embodiment 156 or embodiment 157, wherein the protease is produced by an immune effector cell and the immune effector cell is an activated T cell, a natural killer (NK) cell, or an NK T cell.

159. The multispecific polypeptide construct of any of embodiments 156-158, wherein the protease is selected from among matriptase, a matrix metalloprotease (MMP), granzyme B, and combinations thereof.

160. The multispecific polypeptide construct of embodiment 159, wherein the protease is granzyme B.

161. The multispecific polypeptide construct of any of embodiments 156-160, wherein the cleavable linker comprises the amino acid sequence GGSGGGGIEPDIGGSGGS (SEQ ID NO:171).

162. An isolated single domain antibody that binds PD-1, comprising a complementarity determining region 1 (CDR1) comprising an amino acid sequence selected from the group consisting of SEQ ID NO: 268, 272 and 273; a complementarity determining region 2 (CDR2) comprising an amino acid sequence set forth in SEQ ID NO: 278; and a complementarity determining region 3 (CDR3) comprising an amino acid sequence set forth in SEQ ID NO: 283.

163. The isolated single domain antibody of embodiment 162, comprising the amino acid sequence set forth in any of SEQ ID NOS: 251-267 or 284, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 251-267 or 284 and binds PD-1.

164. The isolated single domain antibody of embodiment 162 or embodiment 163, wherein the single domain antibody comprises the sequence set forth in (i) SEQ ID NO:284, (ii) a humanized variant of SEQ ID NO:284, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:284 and binds PD-1.

165. The isolated single domain antibody of any of embodiments 162-164, wherein the sdAb comprises the sequence set forth in SEQ ID NO:284.

166. The isolated single domain antibody of any of embodiments 162-164, wherein the sdAb comprises a CDR1 comprising an amino acid sequence selected from the group consisting of SEQ ID NO: 268, 272 and 273; a CDR2 comprising an amino acid sequence set forth in SEQ ID NO: 278; and a CDR3 comprising an amino acid sequence set forth in SEQ ID NO: 283.

167. The isolated single domain antibody of any of embodiments 162-164 and 166, wherein the sdAb comprises a CDR1, CDR2 and CDR3 set forth in SEQ ID NOS: 268, 278, and 283, respectively; SEQ ID NOS: 272, 278, and 283, respectively; or SEQ ID NOS: 273, 278, and 283, respectively.

168. The isolated single domain antibody of any of embodiments 162-164, 166 and 167, wherein the at least one PD-1 sdAb comprises the sequence of amino acids set forth in any one of SEQ ID NOs: 251-267 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 251-267 and binds PD-1.

169. The isolated single domain antibody of any of embodiments 162-164, and 166-168, wherein the sdAb comprises the sequence of amino acids set forth in any one of SEQ ID NOS: 251-267.

170. The isolated single domain antibody of any of embodiments 162-164 and 166-169, wherein the at least one PD-1 sdAb comprises the sequence of amino acids set forth in SEQ ID NO: 257 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 257 and binds PD-1.

171. The isolated single domain antibody of any of embodiments 162-164 and 166-169, wherein the at least one PD-1 sdAb comprises the sequence of amino acids set forth in SEQ ID NO: 257.

172. The isolated single domain antibody of any of embodiments 162-164 and 166-169, wherein the at least one PD-1 sdAb comprises the sequence of amino acids set forth in SEQ ID NO: 251 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 251 and binds PD-1.

173. The isolated single domain antibody of any of embodiments 162-164 and 166-169, wherein the at least one PD-1 sdAb comprises the sequence of amino acids set forth in SEQ ID NO: 252 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 252 and binds PD-1.

174. The isolated single domain antibody of any of embodiments 162-164 and 166-169, wherein the at least one PD-1 sdAb comprises the sequence of amino acids set forth in SEQ ID NO: 253 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 253 and binds PD-1.

175. The isolated single domain antibody of any of embodiments 162-164 and 166-169, wherein the at least one PD-1 sdAb comprises the sequence of amino acids set forth in SEQ ID NO: 254 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 254 and binds PD-1.

176. The isolated single domain antibody of any of embodiments 162-164 and 166-169, wherein the at least one PD-1 sdAb comprises the sequence of amino acids set forth in SEQ ID NO: 255 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 255 and binds PD-1.

177. The isolated single domain antibody of any of embodiments 162-164 and 166-169, wherein the at least one PD-1 sdAb comprises the sequence of amino acids set forth in SEQ ID NO: 256 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 256 and binds PD-1.

178. The isolated single domain antibody of any of embodiments 162-164 and 166-169, wherein the at least one PD-1 sdAb comprises the sequence of amino acids set forth in SEQ ID NO: 258 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 258 and binds PD-1.

179. The isolated single domain antibody of any of embodiments 162-164 and 166-169, wherein the at least one PD-1 sdAb comprises the sequence of amino acids set forth in SEQ ID NO: 259 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 259 and binds PD-1.

180. The isolated single domain antibody of any of embodiments 162-164 and 166-169, wherein the at least one PD-1 sdAb comprises the sequence of amino acids set forth in SEQ ID NO: 260 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 260 and binds PD-1.

181. The isolated single domain antibody of any of embodiments 162-164 and 166-169, wherein the at least one PD-1 sdAb comprises the sequence of amino acids set forth in SEQ ID NO: 261 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 261 and binds PD-1.

182. The isolated single domain antibody of any of embodiments 162-164 and 166-169, wherein the at least one PD-1 sdAb comprises the sequence of amino acids set forth in SEQ ID NO: 262 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 262 and binds PD-1.

183. The isolated single domain antibody of any of embodiments 162-164 and 166-169, wherein the at least one PD-1 sdAb comprises the sequence of amino acids set forth in SEQ ID NO: 263 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 263 and binds PD-1.

184. The isolated single domain antibody of any of embodiments 162-164 and 166-169, wherein the at least one PD-1 sdAb comprises the sequence of amino acids set forth in SEQ ID NO: 264 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 264 and binds PD-1.

185. The isolated single domain antibody of any of embodiments 162-164 and 166-169, wherein the at least one PD-1 sdAb comprises the sequence of amino acids set forth in SEQ ID NO: 265 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 265 and binds PD-1.

186. The isolated single domain antibody of embodiment any of embodiments 162-164 and 166-169, wherein the at least one PD-1 sdAb comprises the sequence of amino acids set forth in SEQ ID NO: 266 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 266 and binds PD-1.

187. The isolated single domain antibody of any of embodiments 162-164 and 166-169, wherein the at least one PD-1 sdAb comprises the sequence of amino acids set forth in SEQ ID NO: 267 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 267 and binds PD-1.

188. The isolated single domain antibody of any of embodiments 162-164 and 166-169, wherein the sdAb comprises the sequence of amino acids set forth in SEQ ID NO: 251, 252, 253, 254, 255, 256, 257, 258, 259, 260, 261, 262, 263, 264, 265, 266, 267 or 284.

189. A polynucleotide(s) encoding the PD-1-binding polypeptide of any of embodiments 1-59.

190. A polynucleotide(s) encoding the multispecific polypeptide construct of any of embodiments 60-161.

191. A polynucleotide, comprising a first nucleic acid sequence encoding a first polypeptide of a multispecific construct of any of embodiments 60-161 and a second nucleic acid sequence encoding a second polypeptide of the multispecific construct, wherein the first and second nucleic acid sequence are separated by an internal ribosome entry site (IRES), or a nucleic acid encoding a self-cleaving peptide or a peptide that causes ribosome skipping.

192. The polynucleotide of embodiment 191, wherein the first nucleic acid sequence and second nucleic acid sequence are operably linked to the same promoter.

193. The polynucleotide of embodiment 192, wherein the nucleic acid encoding a self-cleaving peptide or a peptide that causes ribosome skipping is selected from a T2A, a P2A, a E2A or a F2A.

194. A polynucleotide encoding the single domain antibody of any of embodiments 162-188.

195. A vector, comprising the polynucleotide of any of embodiments 189-194.

196. The vector of embodiment 195 that is an expression vector. 197. The vector of embodiment 195 or embodiment 196 that is a viral vector or a eukaryotic vector, optionally wherein the eukaryotic vector is a mammalian vector.

198. A cell, comprising polynucleotide or polynucleotides of any of embodiments 189-194, or a vector or vectors of any of embodiments 195-197.

199. The cell of embodiment 198, wherein the cell is recombinant or isolated.

200. The cell of embodiment 199, wherein the cell is a mammalian cell.

201. A method of producing a polypeptide, the method comprising introducing into a cell a polynucleotide or polynucleotides of any of embodiments 189-194 or a vector or vectors of any of embodiments 195-197 and culturing the cell under conditions to produce the multispecific polypeptide construct.

202. The method of embodiment 201, further comprising isolating or purifying the polypeptide from the cell.

203. A polypeptide produced by the method of embodiment 201 or embodiment 202.

204. An engineered immune cell, comprising a binding molecule comprising the binding molecule of any of embodiments 1-59 or the single domain antibody of any of embodiments 162-188, optionally wherein the binding molecule is secretable from the cell.

205. The engineered cell of embodiment 204, further comprising a chimeric antigen receptor (CAR).

206. The engineered immune cell of embodiment 204 or embodiment 205, wherein the cell is a lymphocyte.

207. The engineered immune cell of any of embodiments 205-206, wherein the cell is a T cell or a natural killer (NK) cell.

208. The engineered immune cell of any of embodiments 205-207, wherein the CAR comprises an extracellular domain comprising an antigen binding domain that binds a TAA, a transmembrane domain; and an intracellular signaling domain.

209. The engineered immune cell of embodiment 208, wherein the intracellular signaling domain comprises an immunoreceptor tyrosine-based activation motif (ITAM) signaling domain, optionally wherein the intracellular signaling domain is or comprises a CD3zeta signaling domain, optionally a human CD3zeta signaling domain.

210. The engineered immune cell of embodiment 209, wherein the intracellular signaling domain further comprises a signaling domain of a costimulatory molecule.

211. A pharmaceutical composition comprising the PD-1-binding polypeptide of any of embodiments 1-59, the multispecific polypeptide construct of any of embodiments 60-161, the single domain antibody of any of embodiments 162-188 or the engineered immune cell of any of embodiments 204-210.

212. The pharmaceutical composition of embodiment 211, comprising a pharmaceutically acceptable carrier.

213. The pharmaceutical composition of embodiment 211 or embodiment 212 that is sterile.

214. A method of stimulating or inducing an immune response in a subject, the method comprising administering, to a subject in need thereof, the PD-1-binding polypeptide of any of embodiments 1-59, the multispecific polypeptide construct of any of embodiments 60-161, the single domain antibody of any of embodiments 162-188 or the engineered immune cell of any of embodiments 204-210 or a pharmaceutical composition of embodiment 211-213.

215. The method of embodiment 214, wherein the immune response is increased against a tumor or cancer, optionally a tumor or a cancer that expresses PD-1.

216. The method of embodiment 214 or embodiment 215, wherein the method treats a disease or condition in the subject.

217. A method of treating a disease or condition in a subject, the method comprising administering, to a subject in need thereof, a therapeutically effective amount of the PD-1-binding polypeptide of any of embodiments 1-59, the multispecific polypeptide construct of any of embodiments 60-161, the single domain antibody of any of embodiments 162-188 or the engineered immune cell of any of embodiments 204-210 or a pharmaceutical composition of embodiment 211-213.

218. The method of embodiment 216 or embodiment 217, wherein the disease or condition is a tumor or a cancer.

219. The method of any of embodiments 214-218, wherein said subject is a human.

220. The PD-1-binding construct of embodiment 1, wherein the at least one VHH domain comprises a complementarity determining region 1 (CDR1) comprising an amino acid sequence set forth in SEQ ID NO:300; complementarity determining region 2 (CDR2) comprising an amino acid sequence set forth in SEQ ID NO: 301; and a complementarity determining region 3 (CDR3) comprising an amino acid sequence set forth in SEQ ID NO: 302.

221. The PD-1-binding construct of embodiment 1, wherein the at least one VHH domain comprises a complementarity determining region 1 (CDR1) comprising an amino acid sequence set forth in SEQ ID NO:303; complementarity determining region 2 (CDR2) comprising an amino acid sequence set forth in SEQ ID NO: 304; and a complementarity determining region 3 (CDR3) comprising an amino acid sequence set forth in SEQ ID NO: 305.

222. The PD-1-binding construct of embodiment 1, wherein the at least one VHH domain comprises a complementarity determining region 1 (CDR1) comprising an amino acid sequence set forth in SEQ ID NO:306; complementarity determining region 2 (CDR2) comprising an amino acid sequence set forth in SEQ ID NO: 307; and a complementarity determining region 3 (CDR3) comprising an amino acid sequence set forth in SEQ ID NO: 308.

223. The PD-1-binding construct of embodiment 1, wherein the at least one VHH domain comprises a complementarity determining region 1 (CDR1) comprising an amino acid sequence set forth in SEQ ID NO:309; complementarity determining region 2 (CDR2) comprising an amino acid sequence set forth in SEQ ID NO: 310; and a complementarity determining region 3 (CDR3) comprising an amino acid sequence set forth in SEQ ID NO: 311.

224. A PD-1-binding construct, comprising at least one heavy chain only variable domain (PD-1 VHH domain) comprising a complementarity determining region 1 (CDR1) comprising an amino acid sequence selected set forth in SEQ ID NO: 300; a complementarity determining region 2 (CDR2) comprising an amino acid sequence set forth in SEQ ID NO: 301; and a complementarity determining region 3 (CDR3) comprising an amino acid sequence selected set forth in SEQ ID NO: 302.

225. A PD-1-binding construct, comprising at least one heavy chain only variable domain (PD-1 VHH domain) comprising a complementarity determining region 1 (CDR1) comprising an amino acid sequence selected set forth in SEQ ID NO: 303; a complementarity determining region 2 (CDR2) comprising an amino acid sequence set forth in SEQ ID NO: 304; and a complementarity determining region 3 (CDR3) comprising an amino acid sequence selected set forth in SEQ ID NO: 305.

226. A PD-1-binding construct, comprising at least one heavy chain only variable domain (PD-1 VHH domain) comprising a complementarity determining region 1 (CDR1) comprising an amino acid sequence selected set forth in SEQ ID NO: 306; a complementarity determining region 2 (CDR2) comprising an amino acid sequence set forth in SEQ ID NO: 307; and a complementarity determining region 3 (CDR3) comprising an amino acid sequence selected set forth in SEQ ID NO: 308.

227. A PD-1-binding construct, comprising at least one heavy chain only variable domain (PD-1 VHH domain) comprising a complementarity determining region 1 (CDR1) comprising an amino acid sequence selected set forth in SEQ ID NO: 309; a complementarity determining region 2 (CDR2) comprising an amino acid sequence set forth in SEQ ID NO: 310; and a complementarity determining region 3 (CDR3) comprising an amino acid sequence selected set forth in SEQ ID NO: 311.

228. The PD-1-binding polypeptide construct of any of embodiments 220-227, wherein the PD-1 is a human PD-1.

229. The PD-1-binding polypeptide construct of any of embodiments 220-228, wherein the at least one PD-1 VHH domain is humanized.

230. The PD-1-binding polypeptide construct of any of embodiments 220-224 and 228-229, wherein the one or more additional binding domains binds to an activating receptor on an immune cell.

231. The PD-1-binding polypeptide construct of embodiment 230, wherein the immune cell is a T cell.

232. The PD-1-binding polypeptide construct of embodiment 230 or embodiment 231, wherein the activating receptor is CD3 (CD3c).

233. The PD-1-binding polypeptide construct of embodiment 232 that is bispecific for PD-1 and CD3.

234. The PD-1-binding polypeptide construct of embodiment 233, wherein the immune cell is a Natural Killer (NK) cell.

235. The PD-1-binding polypeptide construct of embodiment 230 or embodiment 234, wherein the activating receptor is CD16 (CD16a).

236. The PD-1-binding polypeptide construct of embodiment 235 that is bispecific for PD-1 and CD16a.

237. The PD-1-binding polypeptide construct of any of embodiments 220-224 and 228-229, wherein the one or more additional domains binds to a tumor associated antigen (TAA).

238. The PD-1-binding polypeptide construct of any of embodiments 220-224 and 228-229, wherein the one or more additional binding domain binds to a cytokine receptor.

239. The PD-1-binding polypeptide construct of any of embodiments 220-224 and 228-238, wherein the one or more additional binding domain comprises an antibody or antigen-binding fragment thereof.

240. The PD-1-binding polypeptide construct of any of embodiments 220-224 and 228-239, wherein the one or more additional binding domain is monovalent.

241. The PD-1-binding polypeptide construct of embodiment 240, wherein the antibody or antigen-binding fragment thereof is an Fv, a disulfide-stabilized Fv (dsFv), scFv, a Fab, a single domain antibody (sdAb), a VNAR, or a VHH.

242. The PD-1-binding polypeptide construct of embodiment 238, wherein the one or more additional binding domain is a cytokine or is a truncated fragment or variant thereof capable of binding to the cytokine receptor.

243. The PD-1-binding polypeptide construct of embodiment 242, wherein the cytokine is an interferon that is a type I interferon or a type II interferon, is a truncated fragment or variant of a type I interferon or is a truncated fragment or variant of a type II interferon.

244. The PD-1-binding polypeptide construct of embodiment 243, wherein:
the type I interferon is an IFN-alpha or an IFN-beta or is a truncated fragment or variant thereof; or
the type II interferon is an IFN-gamma or is a truncated fragment or variant thereof. 245. The PD-1-binding polypeptide construct of any of embodiments 220-244, wherein the polypeptide comprises an immunoglobulin Fc region.

246. The PD-1-binding polypeptide construct of any of embodiments 220-224 and 228-245, wherein the polypeptide comprises an immunoglobulin Fc region that links the at least one single domain antibody and the one or more additional binding domain.

247. The PD-1-binding polypeptide construct of any of embodiments 220-246 that is a dimer.

248. The PD-1-binding polypeptide construct of any of embodiments 245-247, wherein the Fc region is a homodimeric Fc region.

249. The PD-1-binding polypeptide construct of any of embodiments 245-248, wherein the Fc region comprises the sequence of amino acids set forth in any of SEQ ID NOS: 8, 10, 11, 12 or 13, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 8, 10, 11, 12 or 13.

250. The PD-1-binding polypeptide construct of any of embodiments 245-248, wherein the Fc region is a human IgG1.

251. The PD-1-binding polypeptide construct of embodiment 250, wherein the Fc region comprises the sequence of amino acids set forth in SEQ ID NO:8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8.

252. The PD-1-binding polypeptide construct of any of embodiments 245-247, wherein the Fc region is a heterodimeric Fc region.

253. The PD-1-binding polypeptide construct of any of embodiments 245-252, wherein the Fc region exhibits effector function.

254. The PD-1-binding polypeptide construct of any of embodiments 245-253 wherein the Fc region comprises a polypeptide comprising one or more amino acid modification that reduces effector function and/or reduces binding to an effector molecule selected from an Fc gamma receptor or C1q.

255. The PD-1-binding polypeptide construct of embodiment 254, wherein the one or more amino acid modification is deletion of one or more of Glu233, Leu234 or Leu235.

256. The PD-1-binding polypeptide construct of embodiment 254 or embodiment 255, wherein the Fc region comprises the sequence of amino acids set forth in SEQ ID NO:9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9.

257. The PD-1-binding polypeptide construct of any of embodiments 220-256, wherein the at least one PD-1 VHH domain comprises the sequence set forth in any of SEQ ID NOS: 296-299, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 296-299 and binds PD-1.

258. The PD-1-binding polypeptide construct of any of embodiments 220-257, wherein the at least one PD-1 VHH domain comprises the sequence set forth in (i) SEQ ID NO:296, (ii) a humanized variant of SEQ ID NO:296, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:296 and binds PD-1.

259. The PD-1-binding polypeptide construct of any of embodiments 220-258, wherein the at least one PD-1 VHH domain comprises the sequence set forth in SEQ ID NO:296.

260. The PD-1-binding polypeptide of any of embodiments 220-258, wherein the at least one PD-1 VHH domain comprises a CDR1 comprising an amino acid sequence set forth in SEQ ID NO: 300; a CDR2 comprising an amino acid sequence set forth in SEQ ID NO: 301; and a CDR3 comprising an amino acid sequence set forth in SEQ ID NO: 302.

261. The PD-1-binding polypeptide construct of any of embodiments 220-258 and 260 36, wherein the at least one PD-1 VHH domain comprises a CDR1, CDR2 and CDR3 set forth in SEQ ID NOS: 300, 301, and 302, respectively.

262. The PD-1-binding polypeptide construct of any of embodiments 220-257, wherein the at least one PD-1 VHH domain comprises the sequence set forth in (i) SEQ ID NO:297, (ii) a humanized variant of SEQ ID NO:297, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:297 and binds PD-1.

263. The PD-1-binding polypeptide construct of any of embodiments 220-257 and 262, wherein the at least one PD-1 VHH domain comprises the sequence set forth in SEQ ID NO:297.

264. The PD-1-binding polypeptide of any of embodiments 220-257 and 262, wherein the at least one PD-1 VHH domain comprises a CDR1 comprising an amino acid sequence set forth in SEQ ID NO: 303; a CDR2 comprising an amino acid sequence set forth in SEQ ID NO: 304; and a CDR3 comprising an amino acid sequence set forth in SEQ ID NO: 305.

265. The PD-1-binding polypeptide construct of any of embodiments 220-257, 262, and 264 wherein the at least one PD-1 VHH domain comprises a CDR1, CDR2 and CDR3 set forth in SEQ ID NOS: 303, 304, and 305, respectively.

266. The PD-1-binding polypeptide construct of any of embodiments 220-257, wherein the at least one PD-1 VHH domain comprises the sequence set forth in (i) SEQ ID NO:298, (ii) a humanized variant of SEQ ID NO:298, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:298 and binds PD-1.

267. The PD-1-binding polypeptide construct of any of embodiments 220-257 and 266, wherein the at least one PD-1 VHH domain comprises the sequence set forth in SEQ ID NO:297.

268. The PD-1-binding polypeptide of any of embodiments 220-257 and 266, wherein the at least one PD-1 VHH domain comprises a CDR1 comprising an amino acid sequence set forth in SEQ ID NO: 306; a CDR2 comprising an amino acid sequence set forth in SEQ ID NO: 307; and a CDR3 comprising an amino acid sequence set forth in SEQ ID NO: 308.

269. The PD-1-binding polypeptide construct of any of embodiments 220-257, 266 and 268, wherein the at least one PD-1 VHH domain comprises a CDR1, CDR2 and CDR3 set forth in SEQ ID NOS: 306, 307, and 308, respectively.

270. The PD-1-binding polypeptide construct of any of embodiments 220-257, wherein the at least one PD-1 VHH domain comprises the sequence set forth in (i) SEQ ID NO:299, (ii) a humanized variant of SEQ ID NO:299, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:299 and binds PD-1.

271. The PD-1-binding polypeptide construct of any of embodiments 220-257 and 270, wherein the at least one PD-1 VHH domain comprises the sequence set forth in SEQ ID NO:299.

272. The PD-1-binding polypeptide of any of embodiments 220-257 and 270, wherein the at least one PD-1 VHH domain comprises a CDR1 comprising an amino acid sequence set forth in SEQ ID NO: 309; a CDR2 comprising an amino acid sequence set forth in SEQ ID NO: 310; and a CDR3 comprising an amino acid sequence set forth in SEQ ID NO: 311.

273. The PD-1-binding polypeptide construct of any of embodiments 220-257, 270, and 272, wherein the at least one PD-1 VHH domain comprises a CDR1, CDR2 and CDR3 set forth in SEQ ID NOS: 309, 310, and 311, respectively.

274. The PD-1-binding polypeptide construct of any of embodiments 220-258, 260-262, 264-266, 268-270, and 272-273, wherein the at least one PD-1 VHH domain comprises least 95% sequence identity to SEQ ID NO: 296-299 and binds PD-1.

275. The PD-1-binding polypeptide construct of any of embodiments 220-258, 260-262, 264-266, 268-270, and 272-274, wherein the at least one PD-1 VHH domain is set forth in SEQ ID NO: 296-299.

276. The multispecific polypeptide construct of any of embodiments 60-99, wherein the at least one PD-1 VHH domain comprises the sequence set forth in any of SEQ ID NOS: 296-299, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 296-299 and binds PD-1.

277. The multispecific polypeptide construct of any of embodiments 60-99 or 276, wherein the at least one PD-1 VHH domain comprises the sequence set forth in (i) SEQ ID NO:296, (ii) a humanized variant of SEQ ID NO:296, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:296 and binds PD-1.

278. The multispecific polypeptide construct of any of embodiments 60-99, 276, or 277, wherein the at least one PD-1 VHH domain comprises the sequence set forth in SEQ ID NO:296.

279. The multispecific polypeptide construct of any of embodiments 60-99, 276 or 277, wherein the at least one PD-1 VHH domain comprises a CDR1 comprising an amino acid sequence set forth in SEQ ID NO: 300; a CDR2 comprising an amino acid sequence set forth in SEQ ID NO: 301; and a CDR3 comprising an amino acid sequence set forth in SEQ ID NO: 302.

280. The multispecific polypeptide construct of any of embodiments 60-99, 276, 277 or 279, wherein the at least one PD-1 VHH domain comprises a CDR1, CDR2 and CDR3 set forth in SEQ ID NOS: 300, 301, and 302, respectively.

281. The multispecific polypeptide construct of any of embodiments 60-99 or 276, wherein the at least one PD-1 VHH domain comprises the sequence set forth in (i) SEQ ID NO:297, (ii) a humanized variant of SEQ ID NO:297, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:297 and binds PD-1.

282. The multispecific polypeptide construct of any of embodiments 60-99, 276, or 281, wherein the at least one PD-1 VHH domain comprises the sequence set forth in SEQ ID NO:297.

283. The multispecific polypeptide construct of any of embodiments 60-99, 276, or 281, wherein the at least one PD-1 VHH domain comprises a CDR1 comprising an amino acid sequence set forth in SEQ ID NO: 303; a CDR2 comprising an amino acid sequence set forth in SEQ ID NO: 304; and a CDR3 comprising an amino acid sequence set forth in SEQ ID NO: 305.

284. The multispecific polypeptide construct of any of embodiments 60-99, 276, 281 or 283, wherein the at least one PD-1 VHH domain comprises a CDR1, CDR2 and CDR3 set forth in SEQ ID NOS: 303, 304, and 305, respectively.

285. The multispecific polypeptide construct of any of embodiments 60-99 or 276, wherein the at least one PD-1 VHH domain comprises the sequence set forth in (i) SEQ ID NO:298, (ii) a humanized variant of SEQ ID NO:298, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:298 and binds PD-1.

286. The multispecific polypeptide construct of any of embodiments 60-99, 276, or 285, wherein the at least one PD-1 VHH domain comprises the sequence set forth in SEQ ID NO:297.

287. The multispecific polypeptide construct of any of embodiments 60-99, 276, or 285, wherein the at least one PD-1 VHH domain comprises a CDR1 comprising an amino acid sequence set forth in SEQ ID NO: 306; a CDR2 comprising an amino acid sequence set forth in SEQ ID NO: 307; and a CDR3 comprising an amino acid sequence set forth in SEQ ID NO: 308.

288. The multispecific polypeptide construct of any of embodiments 60-99, 276, 285 or 287, wherein the at least one PD-1 VHH domain comprises a CDR1, CDR2 and CDR3 set forth in SEQ ID NOS: 306, 307, and 308, respectively.

289. The multispecific polypeptide construct of any of embodiments 60-99 or 276, wherein the at least one PD-1 VHH domain comprises the sequence set forth in (i) SEQ ID NO:299, (ii) a humanized variant of SEQ ID NO:299, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:299 and binds PD-1.

290. The multispecific polypeptide construct of any of embodiments 60-99, 276, or 289, wherein the at least one PD-1 VHH domain comprises the sequence set forth in SEQ ID NO:299.

291. The multispecific polypeptide construct of any of embodiments 60-99, 276, or 289, wherein the at least one PD-1 VHH domain comprises a CDR1 comprising an amino acid sequence set forth in SEQ ID NO: 309; a CDR2 comprising an amino acid sequence set forth in SEQ ID NO: 310; and a CDR3 comprising an amino acid sequence set forth in SEQ ID NO: 311.

292. The multispecific polypeptide construct of any of embodiments 60-99, 276, 289, or 291 wherein the at least one PD-1 VHH domain comprises a CDR1, CDR2 and CDR3 set forth in SEQ ID NOS: 300, 301, and 302, respectively.

293. The multispecific polypeptide construct of any of embodiments 60-99 or 276-292, wherein the at least one PD-1 VHH domain comprises a sequence of amino acids that exhibits at least 95% sequence identity to SEQ ID NO: 296, 297, 298, or 299 and binds PD-1.

294. The multispecific polypeptide construct of any of embodiments 60-99 or 276-292, wherein the at least one PD-1 VHH domain is set forth in SEQ ID NO: 296, 297, 298, or 299.

295. The multispecific polypeptide construct of any of embodiments 276-294, wherein one or both of the first and second components comprises at least one co-stimulatory receptor binding region (CRBR) that binds a co-stimulatory receptor.

296. The multispecific polypeptide construct of embodiment 295, wherein the at least one co-stimulatory receptor binding region (CRBR) is positioned amino-terminally relative to the Fc region and/or carboxy-terminally relative to the CD3 binding region of the multispecific polypeptide construct.

297. The multispecific polypeptide construct of embodiment 295 or embodiment 296, wherein the multispecific polypeptide construct comprises only one co-stimulatory receptor binding region (CRBR).

298. The multispecific polypeptide construct of any of embodiments 295-297, wherein the multispecific polypeptide construct comprises two co-stimulatory receptor binding region (CRBR), optionally which are the same or different.

299. The multispecific polypeptide construct of any of embodiments 295-297, wherein the at least one co-stimulatory receptor binding region (CRBR) is or comprises the extracellular domain or binding fragment thereof of the native cognate binding partner of the co-stimulatory receptor, or a variant thereof that exhibits binding activity to the co-stimulatory receptor.

300. The multispecific polypeptide construct of any of embodiments 295-298, wherein the at least one co-stimulatory receptor binding region (CRBR) is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

301. The multispecific polypeptide construct of embodiment 300, wherein the antibody or antigen-binding fragment thereof is a Fv, a scFv, a Fab, a single domain antibody (sdAb), a VNAR, or a VHH.

302. The multispecific polypeptide construct of embodiment 300 or embodiment 301, wherein the antibody or antigen-binding fragment is an sdAb.

303. The multispecific polypeptide construct of embodiment 302, wherein the sdAb is a human or humanized sdAb.

304. The multispecific polypeptide construct of any of embodiments 295-303, wherein the at least one co-stimulatory receptor binding region (CRBR) binds a co-stimulatory receptor selected from among 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), and NKG2D.

305. The multispecific polypeptide construct of any of embodiments 295-304, wherein the at least one co-stimulatory receptor binding region (CRBR) binds a co-stimulatory receptor selected from among 41BB (CD137), OX40 (CD134), and glucocorticoid-induced TNFR-related protein (GITR).

306. The multispecific polypeptide construct of any of embodiments 295-305, wherein the at least one co-stimulatory receptor binding region (CRBR) comprises the sequence of amino acids set forth in SEQ ID NO:210 or a sequence that has at least 85%, 86%, 87%, 88%, 89%, 90%, 91%, 92%, 93%, 94%, 95%, 96%, 97%, 98%, or 99% sequence identity to the sequence set forth in SEQ ID NO:210 and binds 4-1BB.

307. The multispecific polypeptide construct of any of embodiments 276-306, wherein the multispecific polypeptide construct comprises a first and a second antigen binding domains that binds to a TAA.

308. The multispecific polypeptide construct of embodiment 307, wherein the antigen binding domains bind to the same tumor-associated antigen (TAA).

309. The multispecific polypeptide construct of embodiment 307 or embodiment 308, wherein the first antigen binding domain and the second antigen binding domain binds a different or nonoverlapping epitope of the same TAA and/or compete for binding to the same TAA.

310. The multispecific polypeptide construct of embodiment 307, wherein the first antigen binding domain and the second antigen binding domain bind a different TAA.

311. The multispecific polypeptide construct of any of embodiments 307-310, wherein one antigen binding domain is positioned amino-terminally relative to the Fc region and one antigen binding domain is positioned carboxy-terminally relative to the CD3 binding region.

312. The multispecific polypeptide construct of any of embodiments 276-311, wherein the antigen binding domain that binds a TAA, or independently each of the antigen binding domains that binds a TAA, comprises an extracellular domain or binding fragment thereof of the native cognate binding partner of the TAA, or a variant thereof that exhibits binding activity to the TAA.

313. The multispecific polypeptide construct of any of embodiments 276-311, wherein the antigen binding domain that binds a TAA, or independently each of the antigen binding domains that binds a TAA, is an antibody or antigen-binding fragment thereof.

314. The multispecific polypeptide construct of embodiment 313, wherein the antibody or antigen-binding fragment thereof is a Fv, a scFv, a Fab, a single domain antibody (sdAb), a VNAR, or a VHH.

315. The multispecific polypeptide construct of embodiment 313 or embodiment 314, wherein the antibody or antigen-binding fragment is an sdAb.

316. The multispecific polypeptide construct of embodiment 315, wherein the sdAb is a human or humanized sdAb.

317. The multispecific polypeptide construct of any of embodiments 276-316, wherein the antigen binding domain, or independently each of the antigen binding domains, binds to a tumor antigen selected from among 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsxl), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

318. The multispecific polypeptide construct of any of embodiments 310-317, wherein:

the first polypeptide comprises in order of N-terminus to C-terminus a first antigen binding domain that binds a TAA, a first polypeptide comprising the first Fc polypeptide of the heterodimeric Fc region, the linker, the VH or VL domain of the anti-CD3 antibody or antigen binding fragment and a second antigen binding domain that binds a TAA; and the second polypeptide comprises in order of N-terminus to C-terminus one of the PD-1 VHH domain or the CRBR, the second Fc polypeptide of the heterodimeric Fc region, the linker, optionally the same linker as present in the first polypeptide, the other of the VH or VL domain of the anti-CD3 antibody or antigen binding fragment, and the other of the PD-1 VHH domain or the CRBR.

319. The multispecific polypeptide construct of any of embodiments 276-318, wherein the linker is a peptide or polypeptide linker, optionally wherein the linker is 3, 4, 5, 6, 7, 8, 9, 10, 11, 12, 13, 14, 15, 16, 17, 18, 19 or 20 amino acids in length.

320. The multispecific polypeptide construct of any of embodiments 276-319, wherein the linker is a non-cleavable linker.

321. The multispecific polypeptide construct of embodiment 320, wherein the non-cleavable linker comprises GS, GGS, GGGGS (SEQ ID NO:125), GGGGGS (SEQ ID NO:126) and combinations thereof 322. The multispecific polypeptide construct of any of embodiments 276-321, wherein the linker is or comprises the sequence GGGGGSGGGGGSGGGGGS (SEQ ID NO:127).

323. The multispecific polypeptide construct of any of embodiments 276-319, wherein the linker is a cleavable linker.

324. The multispecific polypeptide construct of embodiment 323, wherein the cleavable linker is a polypeptide that functions as a substrate for a protease.

325. The multispecific polypeptide construct of embodiment 324, wherein the protease is produced by an immune effector cell, by a tumor, or by cells present in the tumor microenvironment.

326. The multispecific polypeptide construct of embodiment 324 or embodiment 325, wherein the protease is produced by an immune effector cell and the immune effector cell is an activated T cell, a natural killer (NK) cell, or an NK T cell.

327. The multispecific polypeptide construct of any of embodiments 324-326, wherein the protease is selected from among matriptase, a matrix metalloprotease (MMP), granzyme B, and combinations thereof.

328. The multispecific polypeptide construct of embodiment 327, wherein the protease is granzyme B.

329. The multispecific polypeptide construct of any of embodiments 324-328, wherein the cleavable linker comprises the amino acid sequence GGSGGGGIEPDIGGSGGS (SEQ ID NO:171).

330. An isolated single domain antibody that binds PD-1, comprising a complementarity determining region 1 (CDR1) comprising an amino acid sequence set forth in SEQ ID NO: 300; a complementarity determining region 2 (CDR2) comprising an amino acid sequence set forth in SEQ ID NO: 301; and a complementarity determining region 3 (CDR3) comprising an amino acid sequence set forth in SEQ ID NO: 302.

331. The isolated single domain antibody of embodiment 330, comprising the amino acid sequence set forth in SEQ ID NO:296, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 296 and binds PD-1.

332. The isolated single domain antibody of embodiment 330 or embodiment 331, wherein the single domain antibody comprises the sequence set forth in (i) SEQ ID NO:296, (ii) a humanized variant of SEQ ID NO:296, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:296 and binds PD-1.

333. The isolated single domain antibody of any of embodiments 330-332, wherein the sdAb comprises the sequence set forth in SEQ ID NO:296.

334. The isolated single domain antibody of any of embodiments 330-332, wherein the sdAb comprises a CDR1 comprising an amino acid sequence set forth in SEQ ID NO: 300; a CDR2 comprising an amino acid sequence set forth in SEQ ID NO: 301; and a CDR3 comprising an amino acid sequence set forth in SEQ ID NO: 302.

335. The isolated single domain antibody of any of embodiments 330-332 and 334, wherein the sdAb comprises a CDR1, CDR2 and CDR3 set forth in SEQ ID NOS: 300, 301, and 302, respectively.

336. An isolated single domain antibody that binds PD-1, comprising a complementarity determining region 1 (CDR1) comprising an amino acid sequence set forth in SEQ ID NO: 303; a complementarity determining region 2 (CDR2) comprising an amino acid sequence set forth in SEQ ID NO: 304; and a complementarity determining region 3 (CDR3) comprising an amino acid sequence set forth in SEQ ID NO: 305.

337. The isolated single domain antibody of embodiment 336, comprising the amino acid sequence set forth in SEQ ID NO:297, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 297 and binds PD-1.

338. The isolated single domain antibody of embodiment 336 or embodiment 337, wherein the single domain antibody comprises the sequence set forth in (i) SEQ ID NO:297, (ii) a humanized variant of SEQ ID NO:297, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:297 and binds PD-1.

339. The isolated single domain antibody of any of embodiments 336-338, wherein the sdAb comprises the sequence set forth in SEQ ID NO:297.

340. The isolated single domain antibody of any of embodiments 336-338, wherein the sdAb comprises a CDR1 comprising an amino acid sequence set forth in SEQ ID NO: 303; a CDR2 comprising an amino acid sequence set forth in SEQ ID NO: 304; and a CDR3 comprising an amino acid sequence set forth in SEQ ID NO: 305.

341. The isolated single domain antibody of any of embodiments 336-338 and 340, wherein the sdAb comprises a CDR1, CDR2 and CDR3 set forth in SEQ ID NOS: 303, 304, and 305, respectively.

342. An isolated single domain antibody that binds PD-1, comprising a complementarity determining region 1 (CDR1) comprising an amino acid sequence set forth in SEQ ID NO: 306; a complementarity determining region 2 (CDR2) comprising an amino acid sequence set forth in SEQ ID NO: 307; and a complementarity determining region 3 (CDR3) comprising an amino acid sequence set forth in SEQ ID NO: 308.

343. The isolated single domain antibody of embodiment 342, comprising the amino acid sequence set forth in SEQ ID NO:298, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 298 and binds PD-1.

344. The isolated single domain antibody of embodiment 342 or embodiment 343, wherein the single domain antibody comprises the sequence set forth in (i) SEQ ID NO:298, (ii) a humanized variant of SEQ ID NO:298, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:298 and binds PD-1.

345. The isolated single domain antibody of any of embodiments 342-344, wherein the sdAb comprises the sequence set forth in SEQ ID NO:298.

346. The isolated single domain antibody of any of embodiments 342-344, wherein the sdAb comprises a CDR1 comprising an amino acid sequence set forth in SEQ ID NO: 306; a CDR2 comprising an amino acid sequence set forth in SEQ ID NO: 307; and a CDR3 comprising an amino acid sequence set forth in SEQ ID NO: 308.

347. The isolated single domain antibody of any of embodiments 342-344 and 346, wherein the sdAb comprises a CDR1, CDR2 and CDR3 set forth in SEQ ID NOS: 306, 307, and 308, respectively.

348. An isolated single domain antibody that binds PD-1, comprising a complementarity determining region 1 (CDR1) comprising an amino acid sequence set forth in SEQ ID NO: 309; a complementarity determining region 2 (CDR2) comprising an amino acid sequence set forth in SEQ ID NO: 310; and a complementarity determining region 3 (CDR3) comprising an amino acid sequence set forth in SEQ ID NO: 311.

349. The isolated single domain antibody of embodiment 348, comprising the amino acid sequence set forth in SEQ ID NO:299, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 299 and binds PD-1.

350. The isolated single domain antibody of embodiment 348 or embodiment 349, wherein the single domain antibody comprises the sequence set forth in (i) SEQ ID NO:299, (ii) a humanized variant of SEQ ID NO:299, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:299 and binds PD-1.

351. The isolated single domain antibody of any of embodiments 348-350, wherein the sdAb comprises the sequence set forth in SEQ ID NO:299.

352. The isolated single domain antibody of any of embodiments 348-350, wherein the sdAb comprises a CDR1 comprising an amino acid sequence set forth in SEQ ID NO: 309; a CDR2 comprising an amino acid sequence set forth in SEQ ID NO: 310; and a CDR3 comprising an amino acid sequence set forth in SEQ ID NO: 311.

353. The isolated single domain antibody of any of embodiments 348-350 and 352, wherein the sdAb comprises a CDR1, CDR2 and CDR3 set forth in SEQ ID NOS: 309, 310, and 311, respectively.

354. The isolated single domain antibody of any of embodiments 330-332, 334-338, 340-344, 346-350, and 352-353, wherein the sdAb comprises the sequence of amino acids set forth in any one of SEQ ID NOS: 296-299.

355. The isolated single domain antibody of any of embodiments 330-332, 334-338, 340-344, 346-350, and 352-354, wherein the sdAb comprises the sequence of amino acids set forth in SEQ ID NO: 296, 297, 298, or 299.

356. A polynucleotide(s) encoding the PD-1-binding polypeptide of any of embodiments 220-275.

357. A polynucleotide(s) encoding the multispecific polypeptide construct of any of embodiments 276-329.

358. A polynucleotide, comprising a first nucleic acid sequence encoding a first polypeptide of a multispecific construct of any of embodiments 276-329 and a second nucleic acid sequence encoding a second polypeptide of the multispecific construct, wherein the first and second nucleic acid sequence are separated by an internal ribosome entry site (IRES), or a nucleic acid encoding a self-cleaving peptide or a peptide that causes ribosome skipping.

359. The polynucleotide of embodiment 358, wherein the first nucleic acid sequence and second nucleic acid sequence are operably linked to the same promoter.

360. The polynucleotide of embodiment 359, wherein the nucleic acid encoding a self-cleaving peptide or a peptide that causes ribosome skipping is selected from a T2A, a P2A, a E2A or a F2A.

361. A polynucleotide encoding the single domain antibody of any of embodiments 330-355.

362. A vector, comprising the polynucleotide of any of embodiments 356-361.

363. The vector of embodiment 362 that is an expression vector.

364. The vector of embodiment 362 or embodiment 363 that is a viral vector or a eukaryotic vector, optionally wherein the eukaryotic vector is a mammalian vector.

365. A cell, comprising polynucleotide or polynucleotides of any of embodiments 356-361, or a vector or vectors of any of embodiments 362-364.

366. The cell of embodiment 365, wherein the cell is recombinant or isolated.

367. The cell of embodiment 366, wherein the cell is a mammalian cell.

368. A method of producing a polypeptide, the method comprising introducing into a cell a polynucleotide or polynucleotides of any of embodiments 356-361 or a vector or vectors of any of embodiments 362-364 and culturing the cell under conditions to produce the multispecific polypeptide construct.

369. The method of embodiment 368, further comprising isolating or purifying the polypeptide from the cell.

370. A polypeptide produced by the method of embodiment 368 or embodiment 369.

371. An engineered immune cell, comprising a binding molecule comprising the binding molecule of any of embodiments 220-275 or the single domain antibody of any of embodiments 330-355, optionally wherein the binding molecule is secretable from the cell.

372. The engineered cell of embodiment 371, further comprising a chimeric antigen receptor (CAR).

373. The engineered immune cell of embodiment 371 or embodiment 372, wherein the cell is a lymphocyte.

374. The engineered immune cell of any of embodiments 372-373, wherein the cell is a T cell or a natural killer (NK) cell.

375. The engineered immune cell of any of embodiments 372-374, wherein the CAR comprises an extracellular domain comprising an antigen binding domain that binds a TAA, a transmembrane domain; and an intracellular signaling domain.

376. The engineered immune cell of embodiment 375, wherein the intracellular signaling domain comprises an immunoreceptor tyrosine-based activation motif (ITAM) signaling domain, optionally wherein the intracellular signaling domain is or comprises a CD3zeta signaling domain, optionally a human CD3zeta signaling domain.

377. The engineered immune cell of embodiment 376, wherein the intracellular signaling domain further comprises a signaling domain of a costimulatory molecule.

378. A pharmaceutical composition comprising the PD-1-binding polypeptide of any of embodiments 220-275, the multispecific polypeptide construct of any of embodiments 276-329, the single domain antibody of any of embodiments 330-355 or the engineered immune cell of any of embodiments 371-377.

379. The pharmaceutical composition of embodiment 378, comprising a pharmaceutically acceptable carrier.

380. The pharmaceutical composition of embodiment 378 or embodiment 379 that is sterile.

381. A method of stimulating or inducing an immune response in a subject, the method comprising administering, to a subject in need thereof, the PD-1-binding polypeptide of any of embodiments 220-275, the multispecific polypeptide construct of any of embodiments 276-329, the single domain antibody of any of embodiments 330-355 or the engineered immune cell of any of embodiments 371-377 or a pharmaceutical composition of embodiment 378-380.

382. The method of embodiment 381, wherein the immune response is increased against a tumor or cancer, optionally a tumor or a cancer that expresses PD-1.

383. The method of embodiment 381 or embodiment 382, wherein the method treats a disease or condition in the subject.

384. A method of treating a disease or condition in a subject, the method comprising administering, to a subject in need thereof, a therapeutically effective amount of the PD-1-binding polypeptide of any of embodiments 220-275, the multispecific polypeptide construct of any of embodiments 276-329, the single domain antibody of any of embodiments 330-355 or the engineered immune cell of any of embodiments 371-377 or a pharmaceutical composition of embodiment 378-380.

385. The method of embodiment 384 or embodiment 385, wherein the disease or condition is a tumor or a cancer.

386. The method of any of embodiments 381-385, wherein said subject is a human.

VIII. EXAMPLES

The following examples are included for illustrative purposes only and are not intended to limit the scope of the invention.

Example 1: Generation of PD-1 sdAb

Single domain antibodies targeting human PD-1 were generated via immunization of llamas and alpaca. Llamas and alpaca were immunized with a recombinant version of the human PD-1 extracellular domain (ECD; amino acids 25-167 of human PD-1 set forth in SEQ ID NO:286, e.g. UniProt No. Q15116) set forth as follows:

LDSPDRPWNPPTFSPALLVVTEGDNATFTCSFSNTSESFVLNWYRMSPSN

QTDKLAAFPEDRSQPGQDCRFRVTQLPNGRDFHMSVVRARRNDSGTYLCG

AISLAPKAQIKESLRAELRVTERRAEVPTAHPSPSPRSAGQFQ

Following the development of specific anti-PD1 antibody titers, llama/alpaca peripheral blood mononuclear cells (PBMCs) were isolated from 500 mL of blood from the immunized animal and total mRNA was isolated using the Qiagen RNeasy Maxi Kit and subsequently converted to first strand cDNA using Thermo Superscript IV Reverse Transcriptase and oligo-dT priming. Single domain antibody (sdAb; also called VHH) sequences were specifically amplified via PCR using the cDNA as template and cloned into a yeast surface display vector as sdAb-Fc-AGA2 fusion proteins. The Fc was a human IgG1 Fc (set forth in SEQ ID NO:8).

Yeast libraries displaying these sdAbs were enriched using recombinant forms of the PD-1 ECD via magnetic bead isolation followed by fluorescence activated cell sorting (FACS). Sorted yeast were plated out and isolated colonies were picked into 96-well blocks and grown in media that switched the expression from surface displayed sdAb-Fc to secretion into the media. Exemplary identified sdAbs are set forth in Table E1.

TABLE E1

PD-1 sdAbs

| Clone name | CDR1 | SEQ ID NO | CDR2 | SEQ ID NO | CDR3 | SEQ ID NO | VHH SEQ ID NO |
|---|---|---|---|---|---|---|---|
| 18H10 | GSVTGANTMG | 272 | LIGNYVTH | 278 | YTDNLGTS | 283 | 284 |
| 1-14 | GRTVSIYAMG | 313 | GIGWNGGTTY | 314 | ESAAGTLGDY | 315 | 312 |

Example 2: Humanization of Camelid Derived PD-1 sdAb

Exemplary camelid derived PD-1 sdAb, 18H10, were humanized using the human VH3-23 germline as scaffold. Camelid residues that contribute to solubility, specificity, stability and/or affinity remained unmodified. In addition all humanized variants contained the modification of Leu11Glu (L11E) and the carboxy-terminal modifications of Ser112Lys (S112K) and Ser113Pro (S113P) as these are known prevent or reduce the recognition of pre-existing ADA directed toward sdAbs (as described in US20160207981).

Table E2 sets forth exemplary PD-1 sdAbs humanized variants.

TABLE E2

PD-1 sdAbs Humanized Variants

| Clone name | CDR1 | SEQ ID NO | CDR2 | SEQ ID NO | CDR3 | SEQ ID NO | VHH SEQ ID NO |
|---|---|---|---|---|---|---|---|
| 18H10 Humanized Variants | | | | | | | |
| hz18H10v1 | GSMTGANTMG | 268 | LIGNYVTH | 278 | YTDNLGTS | 283 | 251 |
| hz18H10v2 | GSMTGANTMG | 268 | LIGNYVTH | 278 | YTDNLGTS | 283 | 252 |
| hz18H10v3 | GSMTGANTMG | 268 | LIGNYVTH | 278 | YTDNLGTS | 283 | 253 |
| hz18H10v4 | GSMTGANTMG | 268 | LIGNYVTH | 278 | YTDNLGTS | 283 | 254 |
| hz18H10v5 | GSMTGANTMG | 268 | LIGNYVTH | 278 | YTDNLGTS | 283 | 255 |
| hz18H10v6 | GSVTGANTMG | 272 | LIGNYVTH | 278 | YTDNLGTS | 283 | 256 |
| hz18H10v7 | GSITGANTMG | 273 | LIGNYVTH | 278 | YTDNLGTS | 283 | 257 |
| hz18H10v8 | GSVTGANTMG | 272 | LIGNYVTH | 278 | YTDNLGTS | 283 | 258 |
| hz18H10v9 | GSVTGANTMG | 272 | LIGNYVTH | 278 | YTDNLGTS | 283 | 259 |
| hz18H10v10 | GSMTGANTMG | 268 | LIGNYVTH | 278 | YTDNLGTS | 283 | 260 |
| hz18H10v11 | GSVTGANTMG | 272 | LIGNYVTH | 278 | YTDNLGTS | 283 | 261 |
| hz18H10v12 | GSVTGANTMG | 272 | LIGNYVTH | 278 | YTDNLGTS | 283 | 262 |
| hz18H10v13 | GSMTGANTMG | 268 | LIGNYVTH | 278 | YTDNLGTS | 283 | 263 |
| hz18H10v14 | GSVTGANTMG | 272 | LIGNYVTH | 278 | YTDNLGTS | 283 | 264 |

TABLE E2-continued

PD-1 sdAbs Humanized Variants

| Clone name | CDR1 | SEQ ID NO | CDR2 | SEQ ID NO | CDR3 | SEQ ID NO | VHH SEQ ID NO |
|---|---|---|---|---|---|---|---|
| hz18H10v15 | GSITGANTMG | 273 | LIGNYVTH | 278 | YTDNLGTS | 283 | 265 |
| hz18H10v16 | GSITGANTMG | 273 | LIGNYVTH | 278 | YTDNLGTS | 283 | 266 |
| hz18H10v17 | GSITGANTMG | 273 | LIGNYVTH | 278 | YTDNLGTS | 283 | 267 |

Example 3: Binding of sdAb to PD-1 Expressing Cells by Flow Cytometry

Specificity and relative affinity were assessed for purified sdAb-Fcs on PD-1-expressing cells. For transient transfection of 293 cells, freeStyle 293 cells were resuspended at 1×10⁶ cells per mL in fresh FreeStyle 293 expression medium. Cells were seeded into 50 mL per transfection and incubated on a shaker at 37° C. while transfection reagents were prepared. 50 µg of each transfection plasmid were diluted into 5004, of OptiMEM. In a separate tube for each transfection, 150 µg of polyethylenimine (PEI; 754, of a 2 mg/mL solution) were added to 5004, of OptiMEM and then mixed 1:1 with the DNA:OptiMEM solution. DNA and PEI were complexed for 15 minutes at room temperature. DNA:PEI complexes were then added drop-wise to a prepared flask of FreeStyle 293 cells and mixed by swirling. Transfected cells were incubated overnight in a 37° C. shaker to allow time for protein expression. Transfection plasmids used encoded citrine-tagged full-length PD1 proteins of human, cynomolgus and murine origin.

Binding of exemplary PD-1-sdAb-Fc fusion proteins described in Examples 1 and 2 were assessed by flow cytometry using the transiently transfected PD-1-expressing cells. Untransfected FreeStyle 293 cells or transiently transfected FreeStyle 293 cells were diluted to 0.5×10×10⁶ cells/mL in FACS Buffer (1×TBS, 0.01% FBS, 0.002% Sodium Azide) and plated at 100 µL/well in a 96-well round bottom assay plate. The assay plates were centrifuged at about 750 rpm for 5 minutes, then the supernatants were removed and primary antibody dilutions were added as follows. A titration diluted antibody was added to the assay plates containing 293 cells. Cells were incubated in the antibody dilutions for 30 minutes at 4° C. After the 30-minute incubation, the assay plates were centrifuged at about 750 rpm for 5 minutes, washed with 1504, FACS Buffer, and centrifuged again at about 750 rpm for 5 minutes. The wash was removed and 50 µL/well of Alexa Fluor 647 conjugated donkey-Anti-Human IgG diluted 1:1000 in FACS buffer was added and incubated for 20 minutes at 4° C. Assay plates were then centrifuged at 750 rpm for 5 minutes, washed with 1504, FACS Buffer, and centrifuged again at 750 rpm for 5 minutes. The wash was removed and the cells were resuspended in 30 µL/well of FACS Buffer for analysis by flow cytometry (iQue Intellicyte).

Exemplary results are set forth in FIGS. 1A-1G for 18H10 (parental derived from llama; SEQ ID NO:284), humanized variants of 18H10 (SEQ ID NOs: 251-257, 259-260, and 262-266) or 1-14 (SEQ ID NO: 312) for binding human PD-1 expressing cells (huPD1-FL 293), cynomolgus PD-1 expressing cells (cynoPD1-FL 293), mouse PD-1 expressing cells (muPD1-FL 293) or non-expressing (UT 293) cells.

Example 4: Assessment of Binding of PD-1 sdAb to Activated Human T Cells by Flow Cytometry Binding of PD-1-sdAb-Fc fusion proteins to activated human T cells was assessed by flow cytometry.

For enrichment and activation of human T cells, Peripheral blood mononuclear cells (PBMCs) were isolated from human donor blood using density gradient centrifugation. Blood samples were diluted with PBS/2% FBS (1:2) and 30 mL of diluted blood was layered onto 15 mL of Lymphoprep density gradient medium. After centrifugation, the PBMC layer at the interphase of plasma and Lymphoprep was removed and remaining red blood cells were lysed using red blood cell lysis buffer for 5 minutes at room temperature. Non-T cell populations were labeled with biotinylated anti-lineage marker antibodies against CD14, CD16, CD19, CD20, CD36, CD56, CD123, TCR γ/δ (20 minutes, room temperature) and depleted using magnetic streptavidin particles. The unbound cell supernatant containing the T cell fraction was retained. Enriched human T cells were activated for 3 days by plating them at a density of about 2×10⁶ cells per mL media in tissue culture plates coated with 1 µg/mL mouse anti-human CD3 (OKT3). Activated T cells were washed once in PBS before further use in binding assays.

Figure 2:
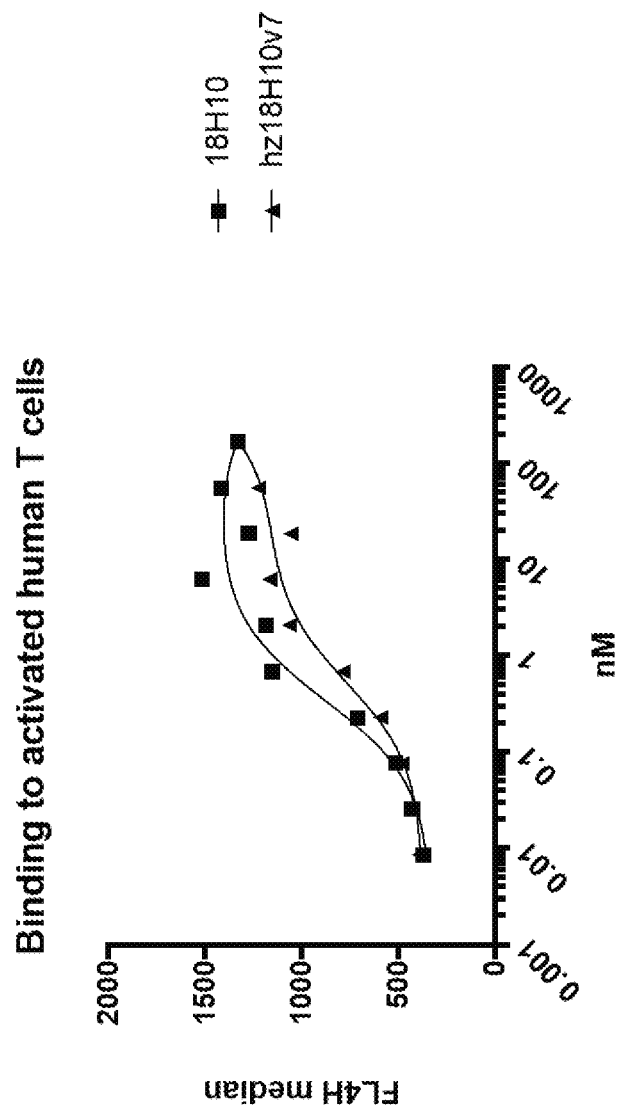
FIG. 2 is a graph depicting the binding of 18H10 and its humanized variant hz18H10v7 to activated human T cells. Test article binding to activated T cells was quantified by flow cytometry.

Binding was assessed and quantified by flow cytometry substantially as described in Example 3, except for binding to activated human T cells, a four-fold, 10-point serial dilution of 18H10 (SEQ ID NO: 284), humanized 18H10 (hzv7; SEQ ID NO: 257), or 1-14 (SEQ ID NO: 312) ranging from 167 nM to 0.00847 nM was used for incubation, As shown in FIG. 2, the tested exemplary PD-1-targeting construct and the humanized variant were found to bind the enriched and activated human T cells.

Example 5: Assessment of PD-1/PD-L1 Blockade Using a Reporter Assay

A PD-1-expressing Jurkat effector reporter cell line, in which TCR engagement leads to the transcription of a luciferase reporter gene, was used to assess the ability of exemplary sdAbs targeting PD-1 to block the interaction of PD-1 and PD-L1. In the assay, PD-L1-expressing aAPC/CHOK1 cells were co-cultured with the Jurkat reporter cells to provide a TCR-specific activation signal, while simultaneously suppressing this signal through the engagement of PD-1 on the effector cell. The ability of PD-1 sdAb to block the suppressed signal, and enhance TCR engagement, was monitored.

PD-L1 expressing aAPC/CHOK1 cells were plated in 100 µl Ham's F12 supplemented with 10% FBS one day before the assay. On the day of the assay, all media was discarded and replaced with 404, of assay media (RPMI 1640, supplemented with 1% FBS) containing titrations of the test proteins containing 18H10 (SEQ ID NO: 41) or humanized 18H10 (hzv7; SEQ ID NO: 14) (starting concentration: 50 nM, titrated 1:4). Jurkat PD-1 reporter cells were then added to the plates (40 µL) and the plate was incubated for 6 h (37° C., 5% CO2 in a humidified atmosphere). After the incubation, an equal volume of BioGlo Luciferase Assay Substrate was added to the wells and incubated for 10 minutes at room temperature and luminescence was assessed and analyzed.

Figure 3A:
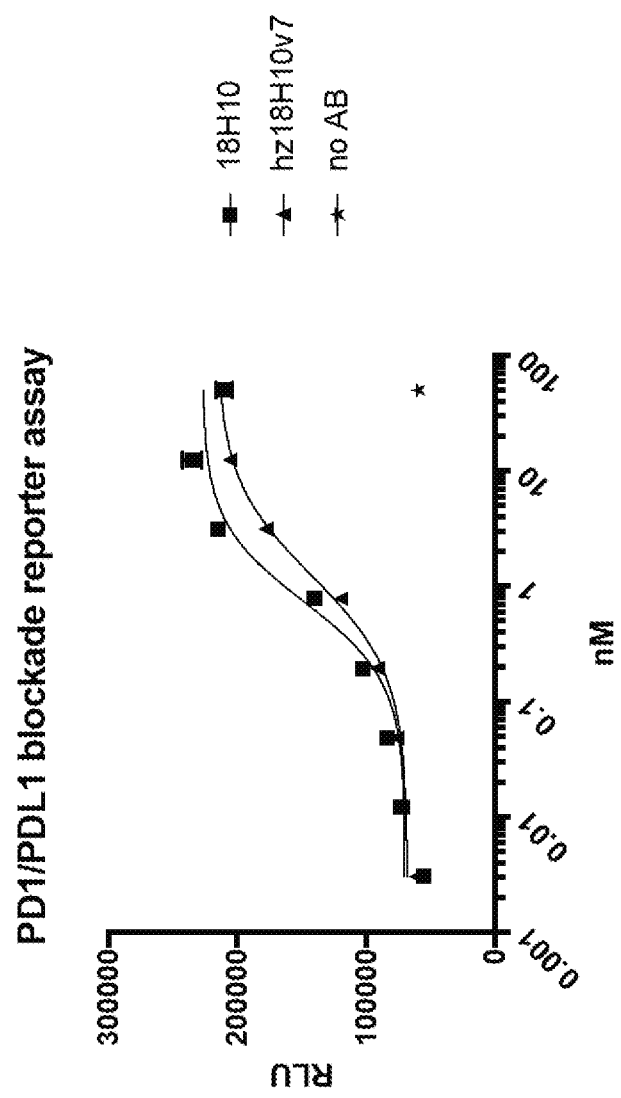
Figure 3B:
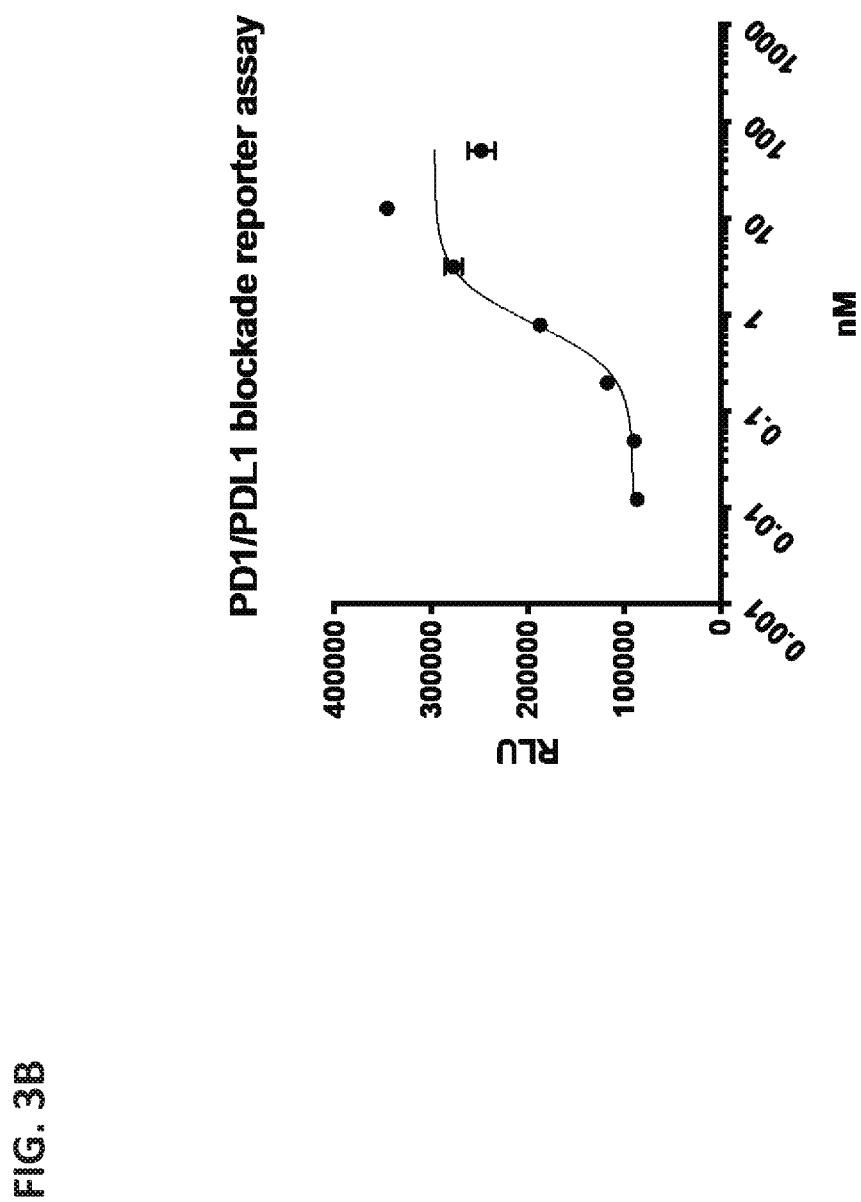
FIG. 3B depicts the PD1 blockade by 1-14.

As shown in FIGS. 3A and B, blockade of PD-1/PD-L1 by the exemplary tested proteins 18H10 (SEQ ID NO: 284), humanized 18H10 (hzv7; SEQ ID NO: 257) or 1-14 (SEQ ID NO: 312) was observed as indicated by the presence of TCR engagement and luciferase transcription.

Example 6: Method of Producing TAA-Targeted Constrained CD3 Binding Proteins with Anti-PD1 sdAbs Multispecific polypeptide constructs were generated containing a disulfide stabilized anti-CD3 Fv binding region that exhibits constrained CD3 binding, a heterodimeric Fc domain, one or more TAA antigen binding domains positioned amino-terminally relative to the Fc region and/or carboxy-terminally relative to the CD3 binding region, and an inhibitory receptor binding region (IRBR) containing a single domain antibody (sdAb) against PD-1, which was positioned amino-terminally relative to the Fc region and/or carboxy-terminally relative to the CD3 binding region. In some cases, the multispecific polypeptide constructs were generated to contain at least one co-stimulatory receptor binding region (CRBR), e.g. against 41BB, which was positioned amino-terminally relative to the Fc region and/or carboxy-terminally relative to the CD3 binding region.

In the exemplary constructs, polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, an Fc hole polypeptide (e.g. set forth in SEQ ID NO:112, or in some cases SEQ ID NO:114); a cleavable or a non-cleavable linker, such as one containing one or more substrate recognition sites for a protease; and a variable light (VL) domain of a dsFv anti-CD3 antibody (e.g. set forth in SEQ ID NO:285). The second polypeptide chain generally included in order, from the N-terminus to C-terminus, an Fc knob polypeptide (e.g. set forth in SEQ ID NO: 105, or in some cases SEQ ID NO:109); the same cleavable linker or the same non-cleavable linker as the first polypeptide chain; and a variable heavy domain of a dsFv anti-CD3 antibody (e.g. set forth in SEQ ID NO:47). The constructs were generated with the exemplary non-cleavable linker, GGGGGSGGGGGSGGGGGS (SEQ ID NO:127), or the exemplary cleavable linker, GGSGGGGIEPDIGGSGGS (SEQ ID NO:171) containing a substrate recognition site for granzyme B. One or both of the polypeptide chains additionally encoded PD-1 sdAb (e.g. SEQ ID NO:284 or SEQ ID NO: 257) amino terminal to the Fc domain and/or carboxy terminal to the CD3 binding region, and/or a 4-1BB sdAb (e.g. SEQ ID NO:210) co-stimulatory receptor binding domain amino terminal to the Fc domain and/or carboxy terminal to the CD3 binding region, in various configurations.

Separate plasmids encoding each chain of a heterodimeric constrained CD3 binding protein were transiently transfected at an equimolar ratio into mammalian cells (either HEK293 or CHO) using polyethylenimine. Recombinant protein secreted into the supernatant was collected after 3-7 days, and secreted recombinant protein was purified by protein A chromatography, followed by either preparative size exclusion chromatography (SEC) or flow-through hydrophobic interaction chromatography (HIC). Heterodimeric protein was selectively purified owing to a mutation designed into one chain of the heterodimeric Fc at position I253R or H435R (usually the hole-Fc) such that it did not bind protein A. The second chromatography step on SEC (AKTA with Superdex-200 resin) or FT-HIC (AKTA with butyl/phenyl sepharose) was used to remove undesired cross-paired species containing two heterodimeric Fcs that were more hydrophobic and twice the expected molecular weight.

The method favored production of heterodimeric multispecific polypeptide constructs, containing properly paired species of heterodimeric Fc and the disulfide stabilized anti-CD3 Fv as described (e.g. anti-CD3 VH with the mutation G44C as set forth in SEQ ID NO: 47 and VL with the mutation G100C as set forth in SEQ ID NO: 285). Purified heterodimeric constrained CD3 binding protein was stable and did not accumulate cross-paired species upon prolonged incubation at 4° C. or increased protein concentration.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

Sequences

| # | SEQUENCE | ANNOTATION |
|---|----------|------------|
| 1 | GGSGGS | (GGS)2 linker |
| 2 | GGSGGSGGS | (GGS)3 linker |
| 3 | GGSGGSGGSGGS | (GGS)4 linker |
| 4 | GGSGGSGGSGGSGGS | (GGS)5 linker |
| 5 | GGGG | glycine linker |
| 6 | GGGGG | glycine linker |
| 7 | GGGGGG | glycine linker |

| # | SEQUENCE | ANNOTATION |
|---|---|---|
| 8 | PAPELLGGPS VFLFPPKPKD TLMISRTPEV TCVVVDVSHE<br>DPEVKFNWYV DGVEVHNAKT KPREEQYNST YRVVSVLTVL<br>HQDWLNGKEY KCKVSNKALP APIEKTISKA KGQPREPQVY<br>TLPPSRDELT KNQVSLTCLV KGFYPSDIAV EWESNGQPEN<br>NYKTTPPVLD SDGSFFLYSK LTVDKSRWQQ GNVFSCSVMH<br>EALHNHYTQK SLSLSPGK | human IgG1 Fc |
| 9 | PAPGGPSVFL FPPKPKDTLM ISRTPEVTCV VVDVSHEDPE<br>VKFNWYVDGV EVHNAKTKPR EEQYNSTYRV VSVLTVLHQD<br>WLNGKEYKCK VSNKALPAPI EKTISKAKGQ PREPQVYTLP<br>PSRDELTKNQ VSLTCLVKGF YPSDIAVEWE SNGQPENNYK<br>TIPPVLDSDG SFFLYSKLTV DKSRWQQGNV FSCSVMHEAL<br>HNHYTQKSLS LSPGK | Fc xELL |
| 10 | PAPPVAGPSV FLFPPKPKDT LMISRTPEVT CVVVDVSHED<br>PEVQFNWYVD GVEVHNAKTK PREEQFNSTF RVVSVLTVVH<br>QDWLNGKEYK CKVSNKGLPA PIEKTISKTK GQPREPQVYT<br>LPPSREEMTK NQVSLTCLVK GFYPSDISVE WESNGQPENN<br>YKTTPPMLDS DGSFFLYSKL TVDKSRWQQG NVFSCSVMHE<br>ALHNHYTQKS LSLSPGK | human IgG2 Fc |
| 11 | PAPELLGGPS VFLFPPKPKD TLMISRTPEV TCVVVDVSHE<br>DPEVQFKWYV DGVEVHNAKT KPREEQYNST FRVVSVLTVL<br>HQDWLNGKEY KCKVSNKALP APIEKTISKT KGQPREPQVY<br>TLPPSREEMT KNQVSLTCLV KGFYPSDIAV EWESSGQPEN<br>NYNTTPPMLD SDGSFFLYSK LTVDKSRWQQ GNIFSCSVMH<br>EALHNRFTQK SLSLSPGK | human IgG3 Fc |
| 12 | PAPEFLGGPS VFLFPPKPKD TLMISRTPEV TCVVVDVSQE<br>DPEVQFNWYV DGVEVHNAKT KPREEQFNST YRVVSVLTVL<br>HQDWLNGKEY KCKVSNKGLP SSIEKTISKA KGQPREPQVY<br>TLPPSQEEMT KNQVSLTCLV KGFYPSDIAV EWESNGQPEN<br>NYKTTPPVLD SDGSFFLYSR LTVDKSRWQE GNVFSCSVMH<br>EALHNHYTQK SLSLSLGK | human IgG4 Fc |
| 13 | PAPELLGGPS VFLFPPKPKD TLMISRTPEV TCVVVDVSQE<br>DPEVQFNWYV DGVEVHNAKT KPREEQFNST YRVVSVLTVL<br>HQDWLNGKEY KCKVSNKGLP SSIEKTISKA KGQPREPQVY<br>TLPPSQEEMT KNQVSLTCLV KGFYPSDIAV EWESNGQPEN<br>NYKTTPPVLD SDGSFFLYSR LTVDKSRWQE GNVFSCSVMH<br>EALHNHYTQK SLSLSLGK | human IgG4 Fc |
| 14 | EPKSSDKTHTCPPC | modified IgG1 hinge |
| 15 | DKTHTCPPC | truncated IgG1 hinge |
| 16 | ESKYGPPCPPC | modified IgG4 hinge |
| 17 | GQGTLVTVKPGG | carboxy-terminal sequence |
| 18 | GQGTLVTVEPGG | carboxy-terminal sequence |
| 19 | QVQLVQSGGG VVQPGRSLRL SCKASGYTFT RYTMHWVRQA<br>PGKGLEWIGY<br>INPSRGYTNY NQKVKDRFTI SRDNSKNTAF LQMDSLRPED<br>TGVYFCARYY<br>DDHYCLDYWG QGTPVTVSS | OKT3 VH |
| 20 | DIQMTQSPSS LSASVGDRVT ITCSASSSVS YMNWYQQTPG<br>KAPKRWIYDT<br>SKLASGVPSR FSGSGSGTDY TFTISSLQPE DIATYYCQQW<br>SSNPFTFGQG<br>TKLQIT | OKT3 VL |
| 21 | QVQLVQSGGG VVQPGRSLRL SCKASGYTFT RYTMHWVRQA<br>PGKGLEWIGY<br>INPSRGYTNY NQKVKDRFTI SRDNSKNTAF LQMDSLRPED<br>TGVYFCARYY<br>DDHYSLDYWG QGTPVTVSS | OKT3 humanized VH |
| 22 | DVQLVQSGAE VKKPGASVKV SCKASGYTFT RYTMHWVRQA<br>PGQGLEWIGY<br>INPSRGYTNY ADSVKGRFTI TTDKSTSTAY MELSSLRSED | OKT3 humanized VH |

| # | SEQUENCE | ANNOTATION |
|---|---|---|
|  | TATYYCARYY DDHYCLDYWG QGTTVTVSS |  |
| 23 | QVQLVQSGAE LKKPGASVKV SCKASGYTFT RYTMHWVRQA PGQCLEWMGY INPSRGYTNY NQKFKDKATL TADKSTSTAY MELRSLRSDD TAVYYCARYY DDHYSLDYWG QGTLVTVSS | OKT3 humanized VH |
| 24 | QIVLTQSPAI MSASPGEKVT MTCSASSSVS YMNWYQQKSG TSPKRWIYDT SKLASGVPAH FRGSGSGTSY SLTISGMEAE DAATYYCQQW SSNPFTFGSG TKLEIN | OKT3 humanized VL |
| 25 | DIQMTQSPSS LSASVGDRVT ITCRASQSVS YMNWYQQKPG KAPKRWIYDT SKVASGVPAR FSGSGSGTDY SLTINSLEAE DAATYYCQQW SSNPLTFGGG TKVEIK | OKT3 humanized VL |
| 26 | DIQLTQSPSI LSASVGDRVT ITCRASSSVS YMNWYQQKPG KAPKRWIYDT SKVASGVPYR FSGSGSGTEY TLTISSMQPE DFATYYCQQW SSNPLTFGCG TKVEIKRT | OKT3 humanized VL |
| 27 | EVQLVESGGGLVQPKGSLKLSCAASGFTFNTYAMNWVRQAPGKGLEW VARIRSKYNNYATYYADSVKDRFTISRDDSQSILYLQMNNLKTEDTAMY YCVRHGNFGNSYVSWFAYWGQGTLVTVSA | anti-CD3 Hv |
| 28 | QAVVTQESALTTSPGETVTLTCRSSTGAVTTSNYANWVQEKPDHLFTGL IGGTNKRAPGVPARFSGSLIGDKAALTITGAQTEDEAIYFCALWYSNLW VFGGGTKLTVL | anti-CD3 Lv |
| 29 | TYAMN | anti-CD3 VH CDR1 |
| 30 | RIRSKYNNYATYYADSVKD | anti-CD3 VH CDR2 |
| 31 | HGNFGNSYVSWFAY | anti-CD3 VH CDR3 |
| 32 | RSSTGAVTTSNYAN | anti-CD3 VL CDR1 |
| 33 | GTNKRAP | anti-CD3 VL CDR2 |
| 34 | ALWYSNLWV | anti-CD3 VL CDR3 |
| 35 | EVQLVESGGGLVQPGGSLRLSCAASGFTFSTYAMNWVRQAPGKGLEWV GRIRSKYNNYATYYADSVKDRFTISRDDSKNSLYLQMNSLKTEDTAVYY CVRHGNFGNSYVSWFAYWGQGTLVTVSS | anti-CD3 VH1 |
| 36 | EVKLVESGGGLVQPGGSLRLSCAASGFTFNTYAMNWVRQAPGKGLEW VARIRSKYNNYATYYADSVKDRFTISRDDSKSSLYLQMNNLKTEDTAM YYCVRHGNFGNSYVSWFAYWGQGTLVTVSS | anti-CD3 VH2 |
| 37 | EVKLVESGGGLVKPGRSLRLSCAASGFTFNTYAMNWVRQAPGKGLEW VARIRSKYNNYATYYADSVKDRFTISRDDSKSILYLQMNNLKTEDTAMY YCVRHGNFGNSYVSWFAYWGQGTLVTVSS | anti-CD3 VH3 |
| 38 | EVKLVESGGGLVKPGRSLRLSCAASGFTFNTYAMNWVRQAPGKGLEW VARIRSKYNNYATYYADSVKDRFTISRDDSKSILYLQMNSLKTEDTAMY YCVRHGNFGNSYVSWFAYWGQGTLVTVSS | anti-CD3 VH4 |
| 39 | EVKLVESGGGLVKPGRSLRLSCAASGFTFNTYAMNWVRQAPGKGLEW VARIRSKYNNYATYYADSVKDRFTISRDDSKSILYLQMNSLKTEDTAMY YCVRHGNFGNSYVSWFAYWGQGTLVTVSS | anti-CD3 VH5 |
| 40 | EVQLLESGGGLVQPGGSLRLSCAASGFTFSTYAMNWVRQAPGKGLEWV SRIRSKYNNYATYYADSVKGRFTISRDDSKNTLYLQMNSLRAEDTAVYY CVRHGNFGNSYVSWFAYWGQGTLVTVSS | anti-CD3 VH6 |
| 41 | EVQLVESGGGLVQPGGSLRLSCAASGFTFSTYAMSWVRQAPGKGLEWV GRIRSKYNNYATYYADSVKGRFTISRDDSKNTLYLQMNSLRAEDTAVY YCVRHGNFGDSYVSWFAYWGQGTLVTVSS | anti-CD3 VH7 |

| # | SEQUENCE | ANNOTATION |
|---|---|---|
| 42 | EVQLVESGGGLVQPGGSLKLSCAASGFTFNKYAMNWVRQAPGKGLEW VARIRSKYNNYATYYADSVKDRFTISRDDSKNTAYLQMNNLKTEDTAV YYCVRHGNFGNSYISYWAYWGQGTLVTVS | anti-CD3 VH8 |
| 43 | EVQLVESGGGLVQPGGSLRLSCAASGFTFNTYAMNWVRQAPGKGLEW VARIRSKYNNYATYYADSVKGRFTISRDDSKNTLYLQMNSLRAEDTAV YYCVRHGNFGNSYVSWFAYWGQGTTVTVSS | anti-CD3 VH9 |
| 44 | EVQLVESGGGLVQPGGSLRLSCAASGFTFNTYAMNWVRQAPGKGLEW VARIRSKYNNYATYYADSVKGRFTISRDDSKNTLYLQMNSLRAEDTAV YYCVRHGNFGNSYVSYFAYWGQGTTVTVSS | anti-CD3 VH10 |
| 45 | EVQLVESGGGLVQPKGSLKLSCAASGFTFNTYAMNWVRQAPGKGLEW VARIRSKYNNYATYYADSVKDRFTISRDDSQSILYLQMNNLKTEDTAMY YCVRHGNFGNSYVSWFAYWGQGTLVTVSS | anti-CD3 VH11 |
| 46 | EVQLVESGGGLVQPGGSLRLSCAASGFTFNTYAMNWVRQAPGKGLEW VARIRSKYNNYATYYADSVKGRFTISRDDAKNTLYLQMSSLRAEDTAV YYCVRHGNFGNSYVSWFAYWGQGTLVTVKP | anti-CD3 VH12 |
| 47 | EVQLVESGGGLVQPGGSLRLSCAASGFTFNTYAMNWVRQAPGKCLEW VARIRSKYNNYATYYADSVKGRFTISRDDAKNTLYLQMSSLRAEDTAV YYCVRHGNFGNSYVSWFAYWGQGTLVTVKP | anti-CD3 VH13 |
| 48 | EVQLVESGGGLVQPGGSLRLSCAASGFTFNTYAMNWVRQAPGKGLEW VARIRSKYNNYATYYADSVKGRFTISRDDAKNTLYLQMSSLRAEDTAV YYCVRHGNFGNSYVSWFAYWGCGTLVTVKP | anti-CD3 VH14 |
| 49 | EVQLVESGGGLVQPGGSLRLSCAASGFTFSTYAMNWVRQAPGKGLEWV ARIRSKYNNYATYYADSVKGRFTISRDDAKNTLYLQMSSLRAEDTAVY YCVRHGNFGNSYVSWFAYWGQGTLVTVSS | anti-CD3 VH15 |
| 50 | EVQLVESGGGLVQPGGSLRLSCAASGFTFNTYAMNWVRQAPGKGLEW VSRIRSKYNNYATYYADSVKGRFTISRDDAKNTLYLQMSSLRAEDTAVY YCVRHGNFGNSYVSWFAYWGQGTLVTVSS | anti-CD3 VH16 |
| 51 | EVQLVESGGGLVQPGGSLRLSCAASGFTFSTYAMNWVRQAPGKGLEWV SRIRSKYNNYATYYADSVKGRFTISRDDAKNTLYLQMSSLRAEDTAVYY CVRHGNFGNSYVSWFAYWGQGTLVTVSS | anti-CD3 VH17 |
| 52 | EVQLVESGGGLVQPGGSLRLSCAASGFTFSTYAMNWVRQAPGKCLEWV ARIRSKYNNYATYYADSVKGRFTISRDDAKNTLYLQMSSLRAEDTAVY YCVRHGNFGNSYVSWFAYWGQGTLVTVSS | anti-CD3 VH18 |
| 53 | EVQLVESGGGLVQPGGSLRLSCAASGFTFNTYAMNWVRQAPGKCLEW VSRIRSKYNNYATYYADSVKGRFTISRDDAKNTLYLQMSSLRAEDTAVY YCVRHGNFGNSYVSWFAYWGQGTLVTVSS | anti-CD3 VH19 |
| 54 | EVQLVESGGGLVQPGGSLRLSCAASGFTFSTYAMNWVRQAPGKCLEWV SRIRSKYNNYATYYADSVKGRFTISRDDAKNTLYLQMSSLRAEDTAVYY CVRHGNFGNSYVSWFAYWGQGTLVTVSS | anti-CD3 VH20 |
| 55 | EVQLVESGGGLVQPGGSLRLSCAASGFTFSTYAMNWVRQAPGKCLEWV GRIRSKYNNYATYYADSVKDRFTISRDDSKNSLYLQMNSLKTEDTAVYY CVRHGNFGNSYVSWFAYWGQGTLVTVSS | anti-CD3 VH21 |
| 56 | EVKLVESGGGLVQPGGSLRLSCAASGFTFNTYAMNWVRQAPGKCLEW VARIRSKYNNYATYYADSVKDRFTISRDDSKSSLYLQMNNLKTEDTAM YYCVRHGNFGNSYVSWFAYWGQGTLVTVSS | anti-CD3 VH22 |
| 57 | EVKLVESGGGLVKPGRSLRLSCAASGFTFNTYAMNWVRQAPGKCLEW VARIRSKYNNYATYYADSVKDRFTISRDDSKSILYLQMNNLKTEDTAMY YCVRHGNFGNSYVSWFAYWGQGTLVTVSS | anti-CD3 VH23 |
| 58 | EVKLVESGGGLVKPGRSLRLSCAASGFTFNTYAMNWVRQAPGKCLEW VARIRSKYNNYATYYADSVKDRFTISRDDSKSILYLQMNSLKTEDTAMY YCVRHGNFGNSYVSWFAYWGQGTLVTVSS | anti-CD3 VH24 |
| 59 | EVKLVESGGGLVKPGRSLRLSCAASGFTFNTYAMNWVRQAPGKCLEW VARIRSKYNNYATYYADSVKDRFTISRDDSKSILYLQMNSLKTEDTAMY YCVRHGNFGNSYVSWFAYWGQGTLVTVSS | anti-CD3 VH25 |
| 60 | EVQLLESGGGLVQPGGSLRLSCAASGFTFSTYAMNWVRQAPGKCLEWV SRIRSKYNNYATYYADSVKGRFTISRDDSKNTLYLQMNSLRAEDTAVYY CVRHGNFGNSYVSWFAYWGQGTLVTVSS | anti-CD3 VH26 |

| # | SEQUENCE | ANNOTATION |
|---|---|---|
| 61 | EVQLVESGGGLVQPGGSLRLSCAASGFTFSTYAMSWVRQAPGKCLEWV GRIRSKYNNYATYYADSVKGRFTISRDDSKNTLYLQMNSLRAEDTAVY YCVRHGNFGDSYVSWFAYWGQGTLVTVSS | anti-CD3 VH27 |
| 62 | EVQLVESGGGLVQPGGSLKLSCAASGFTFNKYAMNWVRQAPGKCLEW VARIRSKYNNYATYYADSVKDRFTISRDDSKNTAYLQMNNLKTEDTAV YYCVRHGNFGNSYISYWAYWGQGTLVTVS | anti-CD3 VH28 |
| 63 | EVQLVESGGGLVQPGGSLRLSCAASGFTFNTYAMNWVRQAPGKCLEW VARIRSKYNNYATYYADSVKGRFTISRDDSKNTLYLQMNSLRAEDTAV YYCVRHGNFGNSYVSWFAYWGQGTTVTVSS | anti-CD3 VH29 |
| 64 | EVQLVESGGGLVQPGGSLRLSCAASGFTFNTYAMNWVRQAPGKCLEW VARIRSKYNNYATYYADSVKGRFTISRDDSKNTLYLQMNSLRAEDTAV YYCVRHGNFGNSYVSYFAYWGQGTTVTVSS | anti-CD3 VH30 |
| 65 | EVQLVESGGGLVQPKGSLKLSCAASGFTFNTYAMNWVRQAPGKCLEW VARIRSKYNNYATYYADSVKDRFTISRDDSQSILYLQMNNLKIEDTAMY YCVRHGNFGNSYVSWFAYWGQGTLVTVSS | anti-CD3 VH31 |
| 66 | QAVVTQESALTTSPGETVTLTCRSSTGAVTTSNYANWVQEKPDHLFTGL IGGTNKRAPGVPARFSGSLIGDKAALTITGAQTEDEAIYFCALWYSNLW VFGGGTKLTVL | anti-CD3 VL1 |
| 67 | QAVVTQEPSLTVSPGGTVTLTCGSSTGAVTTSNYANWVQQKPGKSPRGL IGGTNKRAPGVPARFSGSLLGGKAALTISGAQPEDEADYYCALWYSNH WVFGCGTKLEIK | anti-CD3 VL2 |
| 68 | QAVVTQEPSLTVSPGGTVTLTCRSSTGAVTTSNYANWVQQKPGQAPRG LIGGTNKRAPWTPARFSGSLLGGKAALTITGAQAEDEADYYCALWYSN LWVFGGGTKLTVL | anti-CD3 VL3 |
| 69 | QAVVTQEPSFSVSPGGTVTLTCRSSTGAVTTSNYANWVQQTPGQAFRGL IGGTNKRAPGVPARFSGSLIGDKAALTITGAQADDESIYFCALWYSNLW VFGGGTKLTVL | anti-CD3 VL4 |
| 70 | QAVVTQEPSFSVSPGGTVTLTCRSSTGAVTTSNYANWVQQTPGQAFRGL IGGTNKRAPGVPARFSGSILGNKAALTITGAQADDESIYFCALWYSNLW VFGGGTKLTVL | anti-CD3 VL5 |
| 71 | QAVVTQEPSFSVSPGGTVTLTCRSSTGAVTTSNYANWVQQTPGQAFRGL IGGTNKRAPGVPARFSGSILGNKAALTITGAQADDESDYYCALWYSNLW VFGGGTKLTVL | anti-CD3 VL6 |
| 72 | QAVVTQEPSLTVSPGGTVTLTCGSSTGAVTTSNYANWVQEKPGQAFRG LIGGTNKRAPGTPARFSGSLLGGKAALTLSGAQPEDEAEYYCALWYSNL WVFGGGTKLTVL | anti-CD3 VL7 |
| 73 | QTVVTQEPSLTVSPGGTVTLTCGSSTGAVTSGNYPNWVQQKPGQAPRGL IGGTKFLAPGTPARFSGSLLGGKAALTLSGVQPEDEAEYYCVLWYSNRW VFGGGTKLTVL | anti-CD3 VL8 |
| 74 | QAVVTQEPSLTVSPGGTVTLTCGSSTGAVTTSNYANWVQQKPGQAFRG LIGGTNKRAPGVPARFSGSLLGGKAALTISGAQPEDEADYYCALWYSNH WVFGGGTKLEIK | anti-CD3 VL9 |
| 75 | QAVVTQEPSLTVSPGGTVTLTCGSSTGAVTTSNYANWVQQKPGQAFRG LIGGTNKRAPGVPARFSGSLLGGKAALTISGAQPEDEADYYCALWYSNH WVFGCGTKLEIK | anti-CD3 VL10 |
| 76 | QAVVTQEPSLTVSPGGTVTLTCGSSTGAVTTSNYANWVQQKPGQCFRG LIGGTNKRAPGVPARFSGSLLGGKAALTISGAQPEDEADYYCALWYSNH WVFGEGTKLEIK | anti-CD3 VL11 |
| 77 | QAVVTQESALTTSPGETVTLTCRSSTGAVTTSNYANWVQEKPDHLFTGL IGGTNKRAPGVPARFSGSLIGDKAALTITGAQTEDEAIYFCALWYSNLW VFGCGTKLTVL | anti-CD3 VL12 |
| 78 | QAVVTQEPSLTVSPGGTVTLTCGSSTGAVTTSNYANWVQQKPGKSPRGL IGGTNKRAPGVPARFSGSLLGGKAALTISGAQPEDEADYYCALWYSNH WVFGGGTKLEIK | anti-CD3 VL13 |

| # | SEQUENCE | ANNOTATION |
|---|---|---|
| 79 | QAVVTQEPSLTVSPGGTVTLTCRSSTGAVTTSNYANWVQQKPGQAPRG LIGGTNKRAPWTPARFSGSLLGGKAALTITGAQAEDEADYYCALWYSN LWVFGCGTKLTVL | anti-CD3 VL14 |
| 80 | QAVVTQEPSFSVSPGGTVTLTCRSSTGAVTTSNYANWVQQTPGQAFRGL IGGTNKRAPGVPARFSGSLIGDKAALTITGAQADDESIYFCALWYSNLW VFGGGTKLTVL | anti-CD3 VL15 |
| 81 | QAVVTQEPSFSVSPGGTVTLTCRSSTGAVTTSNYANWVQQTPGQAFRGL IGGTNKRAPGVPARFSGSILGNKAALTITGAQADDESIYFCALWYSNLW VFGCGTKLTVL | anti-CD3 VL16 |
| 82 | QAVVTQEPSFSVSPGGTVTLTCRSSTGAVTTSNYANWVQQTPGQAFRGL IGGTNKRAPGVPARFSGSILGNKAALTITGAQADDESDYYCALWYSNLW VFGCGTKLTVL | anti-CD3 VL17 |
| 83 | QAVVTQEPSLTVSPGGTVTLTCGSSTGAVTTSNYANWVQEKPGQAFRG LIGGTNKRAPGTPARFSGSLLGGKAALTLSGAQPEDEAEYYCALWYSNL WVFGCGTKLTVL | anti-CD3 VL18 |
| 84 | QTVVTQEPSLTVSPGGTVTLTCGSSTGAVTSGNYPNWVQQKPGQAPRGL IGGTKFLAPGTPARFSGSLLGGKAALTLSGVQPEDEAEYYCVLWYSNRW VFGCGTKLTVL | anti-CD3 VL19 |
| 85 | QVQLQESGGG LVQAGGSLRL SCAASGRTFS NYHMGWFRQA PGKERELVAA ISGSGGSTYY TDSVKGRFTI SRNNAKNTMS LQMSNLKPED TGVYYCTTPT EKGSSIDYWG QGTQVTVSSG RYPYDVPDY | anti-CD3 VHH |
| 86 | QLQLQESGGGLVQPGGSLRLSCAASGFTLDNYAIGWFRQAPGKEREGVS CISSSDGSTYYADSVKGRFTISRNNAKGTVYLLMNSLKPEDTAVYYCAT ELVPACTYSNGRGPLDGMDYWGKGTQVTVKP | FR alpha sdAb |
| 87 | EVQLLESGGGEVQPGGSLRLSCAASGSIFSIDATAWYRQAPGKQRELVAI ITSSGSTNYPESVKGRFTISRDNAKNTVYLQMSSLRAEDTAVYYCNAITR YGGSTYDFWGQGTLVTVKP | FR alpha sdAb |
| 88 | EVQPGGSLRLSCAASETFGVVFTLGWYRQAPGKGREFVARVTGTDTVD YAESVKGRFTISSDFARNTVYLQMNSLRAEDTAVYYCNTGAYWGQGTL VTVKP | FR alpha sdAb |
| 89 | EVQLVESGGGLVQPGGSLRLSCAASGFILDYYAIGWFRQAPGKEREGVL CIDASDDITYYADSVKGRFTISRDNAKNTVYLQMNSLKPEDTGVYYCAT PIGLSSSCLLEYDYDWGQGTLVTVKP | cMET sdAb |
| 90 | QVQLVQSGAEVKKPGSSVKVSCKASGYAFSYSWINWVRQAPGQGLEW MGRIFPGDGDTDYNGKFKGRVTITADKSTSTAYMELSSLRSEDTAVYYC ARNVFDGYWLVYWGQGTLVTVSGSGGGGSGGGGTGGGGSDIVMTQTP LSLPVTPGEPASISCRSSKSLLHSNGITYLYWYLQKPGQSPQLLIYQMSNL VSGVPDRFSGSGSGTDFTLKISRVEAEDVGVYYCAQNLELPYTFGGGTK VEIK | CD20 scFv |
| 91 | QVQLVQSGAE VKKPGSSVKV SCKASGYAFS YSWINWVRQA PGQGLEWMGR IFPGDGDTDY NGKFKGRVTI TADKSTSTAY MELSSLRSED TAVYYCARNV FDGYWLVYWG QGTLVTVSS | CD20 VH |
| 92 | DIVMTQTPLS LPVTPGEPAS ISCRSSKSLL HSNGITYLYW YLQKPGQSPQLLIYQMSNLV SGVPDRFSGS GSGTDFTLKI SRVEAEDVGV YYCAQNLELPYTFGGGTKVE IKRTV | CD20 VL |
| 93 | QVQLQESGPGLVKPSETLSLTCTVSGGSISSYYWSWIRQPPGKGLEWIGY VYYSGTTNYNPSLKSRVTISVDTSKNQFSLKLSSVTAADTAVYYCASIAV TGFYFDYWGQGTLVTVSSGGGGSGGGGSGGGGSEIVLTQSPGTLSLSPG ERVTLSCRASQRVNNNYLAWYQQRPGQAPRLLIYGASSRATGIPDRFSG SGSGTDFTLTISRLEPEDFAVYYCQQYDRSPLTFGGGTKLEIK | DLL3 scFv |
| 94 | QVQLQESGPG LVKPSETLSL TCTVSGGSIS SYYWSWIRQP PGKGLEWIGY VYYSGTTNYN PSLKSRVTIS VDTSKNQFSL KLSSVTAADT AVYYCASIAV TGFYFDYWGQ GTLVTVSSGG GGSGGGGSGG GGSEIVLTQS PGTLSLSPGERVTLSCRASQ RVNNNYLAWY QQRPGQAPRL LIYGASSRAT GIPDRFSGSG SGTDFTLTIS RLEPEDFAVY YCQQYDRSPL TFGGGTKLEI K | DLL3 scFv |

| # | SEQUENCE | ANNOTATION |
|---|---|---|
| 95 | QIQLVQSGPELKKPGETVKISCKASGYTFTNYGMNWVKQAPGKGLKW MAWINTYTGEPTYADDFKGRFAFSLETSASTASLQIINLKNEDTATYFCA RIGDSSPSDYWGQGTTLTVSSSSASTKGPSVFPLAPSSKSTSGGTAALGCL VKDYFPEPVTVSWNSGALTSGVHTFPAVLQSSGLYSLSSVVTVPSSSLGT QTYICNVNHKPSNTKVDKKVEPKSC | DLL3 Fd |
| 96 | SIVMTQTPKFLLVSAGDRVTITCKASQSVSNDVVWYQQKPGQSPKLLIY YASNRYTGVPDRFAGSGYGTDFSFTISTVQAEDLAVYFCQQDYTSPWTF GGGTKLEIRRTVAAPSVFIFPPSDEQLKSGTASVVCLLNNFYPREAKVQW KVDNALQSGNSQESVTEQDSKDSTYSLSSTLTLSKADYEKHKVYACEVT HQGLSSPVTKSFNRGEC | DLL3 LC |
| 97 | EVQLVESGGGLVQPKGSLKLSCAASGFTFNTYAMNWVRQAPGKGLEW VARIRSKSNNYATYYADSVKDRFTISRDDSQSMLYLQMNNLKTEDTAM YYCVRQWDYDVRAMNYWGQGTSVTVSSASTKGPSVFPLAPSSKSTSGG TAALGCLVKDYFPEPVTVSWNSGALTSGVHTFPAVLQSSGLYSLSSVVT VPSSSLGTQTYICNVNHKPSNTKVDKKVEPKSC | 5T4 Fd |
| 98 | DIVMTQSHIFMSTSVGDRVSITCKASQDVDTAVAWYQQKPGQSPKLLIY WASTRLTGVPDRFTGSGSGTDFTLTISNVQSEDLADYFCQQYSSYPYTFG GGTKLEIKRTVAAPSVFIFPPSDEQLKSGTASVVCLLNNFYPREAKVQWK VDNALQSGNSQESVTEQDSKDSTYSLSSTLTLSKADYEKHKVYACEVTH QGLSSPVTKSFNRGEC | 5T4 LC |
| 99 | EVQLVESGGGL VQPKGSLKLS CAASGFTFNT YAMNWVRQAP GKGLEWVARI RSKSNNYATY YADSVKDRFT ISRDDSQSML YLQMNNLKTE DTAMYXCVRQ WDYDVRAMNY WGQGTSVTVS S | anti-5T4 VH |
| 100 | DIVMTQSHIF MSTSVGDRVS ITCKASQDVDTAVAWYQQKP GQSPKLLIYW ASTRLTGVPD RFTGSGSGTD FTLTISNVQSEDLADYFCQQ YSSYPYTFGG GTKLEIK | anti-5T4 VL |
| 101 | QVQLQESGPGLVKPSQTLSLTCTVSGGSISSFNYYWSWIRHHPGKGLEWI GYIYYSGSTYSNPSLKSRVTISVDTSKNQFSLTLSSVTAADTAVYYCARG YNWNYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKKVEPKSC | gpNMB Fd |
| 102 | EIVMTQSPATLSVSPGERATLSCRASQSVDNNLVWYQQKPGQAPRLLIY GASTRATGIPARFSGSGSGTEFTLTISSLQSEDFAVYYCQQYNNWPPWTF GQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACE VTHQGLSSPVTKSFNRGEC | gpNMB LC |
| 103 | DKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGK EYKCKVSNKALPAPIEKTISKAKGQPREPQVYTLPPCRDELTKNQVSLW CLVKGFYPSDIAVEWESNGQPENNYKTTPPVLDSDGSFFLYSKLTVDKS RWQQGNVFSCSVMHEALHNHYTQKSLSLSPT | Knob Fc |
| 104 | DKTHTCPPCPAPELLGGPSVFLFPPKPKDTLMRSRTPEVTCVVVDVSHED PEVKFNWYVDGVEVHNAKTKPREEQYNSTYRVVSVLTVLHQDWLNGK EYKCKVSNKALPAPIEKTISKAKGQPREPQVCTLPPSRDELTKNQVSLSC AVKGFYPSDIAVEWESNGQPENNYKTTPPVLDSDGSFFLVSKLTVDKSR WQQGNVFSCSVMHEALHNHYTQKSLSLSPT | Hole Fc |
| 105 | DKTHTCPPCPAPGGPSVFLFPPKPKDTLMISRTPEVTCVVVDVSHEDPEV KFNWYVDGVEVHNAKTKPREEQYNSTYRVVSVLTVLHQDWLNGKEYK CKVSNKALPAPIEKTISKAKGQPREPQVYTLPPCRDELTKNQVSLWCLV KGFYPSDIAVEWESNGQPENNYKTTPPVLDSDGSFFLYSKLTVDKSRWQ QGNVFSCSVMHEALHNHYTQKSLSLSPT | Knob Fc |
| 106 | DKTHTCPPCPAPGGPSVFLFPPKPKDTLMRSRTPEVTCVVVDVSHEDPEV KFNWYVDGVEVHNAKTKPREEQYNSTYRVVSVLTVLHQDWLNGKEYK CKVSNKALPAPIEKTISKAKGQPREPQVCTLPPSRDELTKNQVSLSCAVK GFYPSDIAVEWESNGQPENNYKTTPPVLDSDGSFFLVSKLTVDKSRWQQ GNVFSCSVMHEALHNHYTQKSLSLSPT | Hole Fc |
| 107 | DKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGK EYKCKVSNKALPAPIEKTISKAKGQPREPQVYTLPPCRDELTKNQVSLW CLVKGFYPSDIAVEWESNGQPENNYKTTPPVLDSDGSFFLYSKLTVDKS RWQQGNVFSCSVMHEALHNHYTQKSLSLSPG | Knob Fc |

| # | SEQUENCE | ANNOTATION |
|---|---|---|
| 108 | DKTHTCPPCPAPELLGGPSVFLFPPKPKDTLMRSRTPEVTCVVVDVSHED PEVKFNWYVDGVEVHNAKTKPREEQYNSTYRVVSVLTVLHQDWLNGK EYKCKVSNKALPAPIEKTISKAKGQPREPQVCTLPPSRDELTKNQVSLSC AVKGFYPSDIAVEWESNGQPENNYKTTPPVLDSDGSFFLVSKLTVDKSR WQQGNVFSCSVMHEALHNHYTQKSLSLSPG | Hole Fc |
| 109 | DKTHTCPPCPAPGGPSVFLFPPKPKDTLMISRTPEVTCVVVDVSHEDPEV KFNWYVDGVEVHNAKTKPREEQYNSTYRVVSVLTVLHQDWLNGKEYK CKVSNKALPAPIEKTISKAKGQPREPQVYTLPPCRDELTKNQVSLWCLV KGFYPSDIAVEWESNGQPENNYKTTPPVLDSDGSFFLYSKLTVDKSRWQ QGNVFSCSVMHEALHNHYTQKSLSLSPG | Knob Fc |
| 110 | DKTHTCPPCPAPGGPSVFLFPPKPKDTLMRSRTPEVTCVVVDVSHEDPEV KFNWYVDGVEVHNAKTKPREEQYNSTYRVVSVLTVLHQDWLNGKEYK CKVSNKALPAPIEKTISKAKGQPREPQVCTLPPSRDELTKNQVSLSCAVK GFYPSDIAVEWESNGQPENNYKTTPPVLDSDGSFFLVSKLTVDKSRWQQ GNVFSCSVMHEALHNHYTQKSLSLSPG | Hole Fc |
| 111 | DKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGK EYKCKVSNKALPAPIEKTISKAKGQPREPQVCTLPPSRDELTKNQVSLSC AVKGFYPSDIAVEWESNGQPENNYKTTPPVLDSDGSFFLVSKLTVDKSR WQQGNVFSCSVMHEALHNRYTQKSLSLSPT | Hole Fc |
| 112 | DKTHTCPPCPAPGGPSVFLFPPKPKDTLMISRTPEVTCVVVDVSHEDPEV KFNWYVDGVEVHNAKTKPREEQYNSTYRVVSVLTVLHQDWLNGKEYK CKVSNKALPAPIEKTISKAKGQPREPQVCTLPPSRDELTKNQVSLSCAVK GFYPSDIAVEWESNGQPENNYKTTPPVLDSDGSFFLVSKLTVDKSRWQQ GNVFSCSVMHEALHNRYTQKSLSLSPT | Hole Fc |
| 113 | DKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGK EYKCKVSNKALPAPIEKTISKAKGQPREPQVCTLPPSRDELTKNQVSLSC AVKGFYPSDIAVEWESNGQPENNYKTTPPVLDSDGSFFLVSKLTVDKSR WQQGNVFSCSVMHEALHNRYTQKSLSLSPG | Hole Fc |
| 114 | DKTHTCPPCPAPGGPSVFLFPPKPKDTLMISRTPEVTCVVVDVSHEDPEV KFNWYVDGVEVHNAKTKPREEQYNSTYRVVSVLTVLHQDWLNGKEYK CKVSNKALPAPIEKTISKAKGQPREPQVCTLPPSRDELTKNQVSLSCAVK GFYPSDIAVEWESNGQPENNYKTTPPVLDSDGSFFLVSKLTVDKSRWQQ GNVFSCSVMHEALHNRYTQKSLSLSPG | Hole Fc |
| 115 | DKTHTCPPCPAPELLGGPSVFLFPPKPKDTLYISRTPEVTCVVVDVSHEDP EVKFNWYVDGVEVHNAKTKPREEQYNSTYRVVSVLTVLHQDWLNGKE YKCKVSNKALPAPIEKTISKAKGQPREPQVYTLPPCRDELTKNQVSLWC LVKGFYPSDIAVEWESNGQPENNYKTTPPVLDSDGSFFLYSKLTVDKSR WQQGNVFSCSVVHEALHNHYTQKSLSLSPT | Knob Fc |
| 116 | DKTHTCPPCPAPGGPSVFLFPPKPKDTLYISRTPEVTCVVVDVSHEDPEV KFNWYVDGVEVHNAKTKPREEQYNSTYRVVSVLTVLHQDWLNGKEYK CKVSNKALPAPIEKTISKAKGQPREPQVYTLPPCRDELTKNQVSLWCLV KGFYPSDIAVEWESNGQPENNYKTTPPVLDSDGSFFLYSKLTVDKSRWQ QGNVFSCSVVHEALHNHYTQKSLSLSPT | Knob Fc |
| 117 | DKTHTCPPCPAPELLGGPSVFLFPPKPKDTLYISRTPEVTCVVVDVSHEDP EVKFNWYVDGVEVHNAKTKPREEQYNSTYRVVSVLTVLHQDWLNGKE YKCKVSNKALPAPIEKTISKAKGQPREPQVYTLPPCRDELTKNQVSLWC LVKGFYPSDIAVEWESNGQPENNYKTTPPVLDSDGSFFLYSKLTVDKSR WQQGNVFSCSVVHEALHNHYTQKSLSLSPG | Knob Fc |
| 118 | DKTHTCPPCPAPGGPSVFLFPPKPKDTLYISRTPEVTCVVVDVSHEDPEV KFNWYVDGVEVHNAKTKPREEQYNSTYRVVSVLTVLHQDWLNGKEYK CKVSNKALPAPIEKTISKAKGQPREPQVYTLPPCRDELTKNQVSLWCLV KGFYPSDIAVEWESNGQPENNYKTTPPVLDSDGSFFLYSKLVDKSRWQ QGNVFSCSVVHEALHNHYTQKSLSLSPG | Knob Fc |
| 119 | DKTHTCPPCPAPELLGGPSVFLFPPKPKDTLYISRTPEVTCVVVDVSHEDP EVKFNWYVDGVEVHNAKTKPREEQYNSTYRVVSVLTVLHQDWLNGKE YKCKVSNKALPAPIEKTISKAKGQPREPQVCTLPPSRDELTKNQVSLSCA VKGFYPSDIAVEWESNGQPENNYKTTPPVLDSDGSFFLVSKLTVDKSRW QQGNVFSCSVVHEALHNRYTQKSLSLSPT | Hole Fc |
| 120 | DKTHTCPPCPAPGGPSVFLFPPKPKDTLYISRTPEVTCVVVDVSHEDPEV KFNWYVDGVEVHNAKTKPREEQYNSTYRVVSVLTVLHQDWLNGKEYK CKVSNKALPAPIEKTISKAKGQPREPQVCTLPPSRDELTKNQVSLSCAVK | Hole Fc |

| # | SEQUENCE | ANNOTATION |
|---|---|---|
| | GFYPSDIAVEWESNGQPENNYKTTPPVLDSDGSFFLVSKLTVDKSRWQQ<br>GNVFSCSVVHEALHNRYTQKSLSLSPT | |
| 121 | DKTHTCPPCPAPELLGGPSVFLFPPKPKDTLYISRTPEVTCVVVDVSHEDP<br>EVKFNWYVDGVEVHNAKTKPREEQYNSTYRVVSVLTVLHQDWLNGKE<br>YKCKVSNKALPAPIEKTISKAKGQPREPQVCTLPPSRDELTKNQVSLSCA<br>VKGFYPSDIAVEWESNGQPENNYKTTPPVLDSDGSFFLVSKLTVDKSRW<br>QQGNVFSCSVVHEALHNRYTQKSLSLSPG | Hole Fc |
| 122 | DKTHTCPPCPAPGGPSVFLFPPKPKDTLYISRTPEVTCVVVDVSHEDPEV<br>KFNWYVDGVEVHNAKTKPREEQYNSTYRVVSVLTVLHQDWLNGKEYK<br>CKVSNKALPAPIEKTISKAKGQPREPQVCTLPPSRDELTKNQVSLSCAVK<br>GFYPSDIAVEWESNGQPENNYKTTPPVLDSDGSFFLVSKLTVDKSRWQQ<br>GNVFSCSVVHEALHNRYTQKSLSLSPG | Hole Fc |
| 123 | (GGGGS)n, wherein n is 1 to 5 | Linker |
| 124 | (GGGGGS)n, wherein n is 1 to 4 | linker |
| 125 | GGGGS | Linker |
| 126 | GGGGGS | Linker |
| 127 | GGGGGSGGGGGSGGGGGS | Linker |
| 128 | GGGGSGGGGSGGGGS | Linker |
| 129 | GGSGGGGSGGGGSGGGGS | Linker |
| 130 | GlyxXaa-Glyy-Xaa-Glyz<br>Xaa is independently selected from A, V, L, I, M, F, W, P,<br>G, S, T, C, Y, N, Q, K, R, H, D, or E<br>x, y, and z are each integers in the range from 1-5 | Linker |
| 131 | Gly-Gly-Gly-Xaa-Gly-Gly-Gly-Xaa-Gly-Gly-Gly<br>Xaa is independently selected from A, V, L, I, M, F, W, P,<br>G, S, T, C, Y, N, Q, K, R, H, D, or E | Linker |
| 132 | (SSSSG)n<br>n = 1-9 | Linker |
| 133 | GGGGG-C-GGGGG | Linker |
| 134 | (EAAAK)n | Linker |
| 135 | AS-(AP)n-GT<br>n = 2-20 | Linker |
| 136 | AS-(EAAAK)n-GT<br>n = 2-20 | Linker |
| 137 | (GGGGA)n<br>n = 2-20 | Linker |
| 138 | (PGGGS)n<br>n = 2-20 | Linker |
| 139 | (AGGGS)n<br>n = 2-20 | Linker |
| 140 | GGS-(EGKSSGSGSESKST)n-GGS<br>n = 2-20 | Linker |
| 141 | SSSASASSA | Linker |
| 142 | GSPGSPG | Linker |
| 143 | ATTTGSSPGPT | Linker |
| 144 | X1 X2 X3 X4 X5 (P4 P3 P2 P1 ↓ P1')<br>X1 = I, L, Y, M, F, V, or A; (P4 = I, L, Y, M, F, V, or A)<br>X2 = A, G, S, V, E, D, Q, N, or Y; (P3 = A, G, S, V, E, D, Q, N, or Y)<br>X3 = H, P, A, V, G, S, or T; (P2 = H, P, A, V, G, S, or T)<br>X4 = D or E; (P1 = D or E)<br>X5 = I, L, Y, M, F, V, T, S, G or A (P1' = I, L, Y, M, F, V, T, S, G or A) | Linker consensus |

-continued

| # | SEQUENCE | ANNOTATION |
|---|---|---|
| 145 | X1 E X3 D X5 (P4 P3 P2 P1 ↓ P1')<br>X1 = I or L; (P4 = I or L)<br>(P3 = E)<br>X3 = P or A; (P2 = P or A)<br>X5 = I, V, T, S, or G (P1' = I, V, T, S, or G) | Linker consensus |
| 146 | LEAD | granzyme B substrate |
| 147 | LEPD | Linker |
| 148 | LEAE | Linker |
| 149 | IEPDI | Linker |
| 150 | LEPDG | Linker |
| 151 | LEADT | Linker |
| 152 | IEPDG | Linker |
| 153 | IEPDV | Linker |
| 154 | IEPDS | Linker |
| 155 | IEPDT | Linker |
| 156 | X1QARX5 (P1QAR↓(A/V))<br>X1 = any amino acid; (P1 is any amino acid)<br>X5 = A or V | Linker consensus |
| 157 | RQARX5(RQAR(A/V))<br>X5 = A or V | Linker |
| 158 | RQAR | matriptase substrate |
| 159 | RQARV | linker |
| 160 | X1X2 X3 X4 (P3 P2 P1 ↓ P1')<br>X1 = P, V or A; (P3 = P, V or A)<br>X2 = Q or D; (P2 = Q or D)<br>X3 = A or N; (P1 = A or N)<br>X4 = L, I or M (P1' = L, I or M) | Linker consensus |
| 161 | PX2X3X4 (P3 P2 P1 ↓ P1')<br>(P3 = P)<br>X2 = Q or D; (P2 = Q or D)<br>X3 = A or N; (P1 is A or N)<br>X4 = L or I (P1' is L or I) | Linker consensus |
| 162 | PAGL | MMP substrate |
| 163 | TGLEADGSPAGLGRQARVG | Linker |
| 164 | TGLEADGSRQARVGPAGLG | Linker |
| 165 | TGSPAGLEADGSRQARVGS | Linker |
| 166 | TGPAGLGLEADGSRQARVG | Linker |
| 167 | TGRQARVGLEADGSPAGLG | Linker |
| 168 | TGSRQARVGPAGLEADGS | Linker |
| 169 | TGPAGLGSRQARVGLEADGS | Linker |
| 170 | GPAGLGLEPDGSRQARVG | Linker |
| 171 | GGSGGGGIEPDIGGSGGS | Linker |
| 172 | GGSGGGGLEADTGGSGGS | Linker |
| 173 | GSIEPDIGS | Linker |
| 174 | GSLEADTGS | Linker |

-continued

| # | SEQUENCE | ANNOTATION |
|---|---|---|
| 175 | GGSGGGGIEPDGGGSGGS | Linker |
| 176 | GGSGGGGIEPDVGGSGGS | Linker |
| 177 | GGSGGGGIEPDSGGSGGS | Linker |
| 178 | GGSGGGGIEPDTGGSGGS | Linker |
| 179 | GGGSLEPDGSGS | Linker |
| 180 | GPAGLGLEADGSRQARVG | Linker |
| 181 | GGEGGGGSGGSGGGS | Linker |
| 182 | GSSAGSEAGGSGQAGVGS | Linker |
| 183 | GGSGGGGLEAEGSGGGGS | Linker |
| 184 | GGSGGGGIEPDPGGSGGS | Linker |
| 185 | TGGSGGGGIEPDIGGSGGS | Linker |
| 186 | ACPWAVSGARASPGSAASPRLREGPELSPDDPAGLLDLRQGMFAQLVA QNVLLIDGPLSWYSDPGLAGVSLTGGLSYKEDTKELVVAKAGVYYVFF QLELRRVVAGEGSGSVSLALHLQPLRSAAGAAALALTVDLPPASSEANS AFGFQGRLLHLSAGQRLGVHLHTEARARHAWQLTQGATVLGLFRVTPE IPAGLPSPRSE | 41BBL |
| 187 | EVQLVQSGAEVKKPGESLRISCKGSGYSFSTYWISWVRQMPGKGLEWM GKIYPGDSYTNYSPSFQGQVTISADKSISTAYLQWSSLKASDTAMYYCA RGYGIFDYWGQGTLVTVSS | 41BB VH |
| 188 | SYELTQPPSVSVSPGQTASITCSGDNIGDQYAHWYQQKPGQSPVLVIYQD KNRPSGIPERFSGSNSGNTATLTISGTQAMDEADYYCATYTGFGSLAVFG GGTKLTVL | 41BB VL |
| 189 | QVQLQQWGAGLLKPSETLSLTCAVYGGSFSGYYWSWIRQSPEKGLEWI GEINHGGYVTYNPSLESRVTISVDTSKNQFSLKLSSVTAADTAVYYCAR DYGPGNYDWYFDLWGRGTLVTVSS | 41BB VH |
| 190 | EIVLTQSPATLSLSPGERATLSCRASQSVSSYLAWYQQKPGQAPRLLIYD ASNRATGIPARFSGSGSGTDFTLTISSLEPEDFAVYYCQQRSNWPPALTFG GGTKVEIK | 41BB VL |
| 191 | QMQLVQSGAEVKKPGASVKVSCKASGYSFSGYYMHWVRQAPGQGLE WMGWVNPMSGGTNYAQKFQGRVTITRDTSASTAYMELSSLRSEDTAV YYCAREGMAMRLELDKWGQGTLVTVSS | 41BB VH |
| 192 | SYELTQPPSVSVAPGKTARITCGGNNIGSKSVHWYQQKPGQAPVLVIYY DSDRPSGIPERFSGSNSGNTATLTISRVEAGDEADYYCQVWDSSSVVFGG GTQLTVL | 41BB VL |
| 193 | QDSTSDLIPAPPLSKVPLQQNFQDNQFHGKWYVVGQAGNIKLREDKDPN KMMATIYELKEDKSYNVTGVTFDDKKCTYAISTFVPGSQPGEFTLGKIKS FPGHTSSLVRVVSTNYNQHAMVFFKFVFQNREEFYITLYGRTKELTSELK ENFIRFSKSLGLPENHIVFPVPIDQCIDG | 41BB Anticalin |
| 194 | QDSTSDLIPAPPLSKVPLQQNFQDNQFHGKWYVVGQAGNIRLREDKDPI KMMATIYELKEDKSYDVTMVKFDDKKCMYDIWTFVPGSQPGEFTLGKI KSFPGHTSSLVRVVSTNYNQHAMVFFKFVFQNREEFYITLYGRTKELTSE LKENFIRFSKSLGLPENHIVFPVPIDQCIDG | 41BB Anticalin |
| 195 | QDSTSDLIPAPPLSKVPLQQNFQDNQFHGKWYVVGQAGNIRLREDKDPN KMMATIYELKEDKSYDVTAVAFDDKKCTYDIWTFVPGSQPGEFTLGKIK SFPGHTSSLVRVVSTNYNQHAMVFFKFVFQNREEFYITLYGRTKELTSEL KENFIRFSKSLGLPENHIVFPVPIDQCIDG | 41BB Anticalin |
| 196 | QDSTSDLIPAPPLSKVPLQQNFQDNQFHGKWYVVGQAGNIKLREDKDPN KMMATIYELKEDKSYDVTAVAFDDKKCTYDIWTFVPGSQPGEFTLGKIK SFPGHTSSLVRVVSTNYNQHAMVFFKFVFQNREEFYITLYGRTKELTSEL KENFIRFSKSLGLPENHIVFPVPIDQCIDG | 41BB Anticalin |
| 197 | QDSTSDLIPA PPLSKVPLQQ NFQDNQFHGK WYVVGQAGNI KLREDSKMMA TIYELKEDKS YDVTGVSFDD KKCTYAIMTF | 41BB Anticalin |

-continued

| # | SEQUENCE | ANNOTATION |
|---|---|---|
| | VPGSQPGEFT LGKIKSFPGH TSSLVRVVST NYNQHAMVFF KFVFQNREEF YITLYGRTKE LTSELKENFI RFSKSLGLPE NHIVFPVPID QCIDG | |
| 198 | QDSTSDLIPA PPLSKVPLQQ NFQDNQFHGK WYVVGQAGNI KLREDKDPVK MMATIYELKE DKSYDVTGVT FDDKKCRYDI STFVPGSQPG EFTFGKIKSF PGHTSSLVRV VSTNYNQHAM VFFKFVFQNR EEFYITLYGR TKELTSELKE NFIRFSKSLG LPENHIVFPV PIDQCIDG | 41BB Anticalin |
| 199 | QDSTSDLIPAPPLSKVPLQQNFQDNQFHGKWYVVGQAGNIRLREDKDPH KMMATIYELKEDKSYDVTGVTFDDKKCTYAISTFVPGSQPGEFTLGKIKS FPGHTSSLVRVVSTNYNQHAMVFFKFVFQNREEFYITLYGRTKELTSELK ENFIRFSKSLGLPENHIVFPVPIDQCIDG | 41BB Anticalin |
| 200 | QDSTSDLIPAPPLSKVPLQQNFQDNQFHGKWYVVGQAGNIKLREDKDPN KMMATIYELKEDKSYDVTGVTFDDKKCTYAISTLVPGSQPGEFTFGKIKS FPGHTSSLVRVVSTNYNQHAMVFFKFVFQNREEFYITLYGRTKELTSELK ENFIRFSKSLGLPENHIVFPVPIDQCIDG | 41BB Anticalin |
| 201 | QDSTSDLIPAPPLSKVPLQQNFQDNQFHGKWYVVGQAGNIRLREDKDPS KMMATIYELKEDKSYDVTAVTFDDKKCNYAISTFVPGSQPGEFTLGKIK SFPGHTSSLVRVVSTNYNQHAMVFFKFVFQNREEFYITLYGRTKELTSEL KENFIRFSKSLGLPENHIVFPVPIDQCIDG | 41BB Anticalin |
| 202 | REGPELSPDDPAGLLDLRQGMFAQLVAQNVLLIDGPLSWYSDPGLAGVS LTGGLSYKEDTKELVVAKAGVYYVFFQLELRRVVAGEGSGSVSLALHL QPLRSAAGAAALALTVDLPPASSEARNSAFGFQGRLLHLSAGQRLGVHL HTEARARHAWQLTQGATVLGLFRVTPEIPAGLPSPRSE | 71-254 of human 41BBL |
| 203 | LDLRQGMFAQLVAQNVLLIDGPLSWYSDPGLAGVSLTGGLSYKEDTKE LVVAKAGVYYVFFQLELRRVVAGEGSGSVSLALHLQPLRSAAGAAALA LTVDLPPASSEARNSAFGFQGRLLHLSAGQRLGVHLHTEARARHAWQL TQGATVLGLFRVTPEIPAGLPSPRSE | 85-254 of human 41BBL |
| 204 | DPAGLLDLRQGMFAQLVAQNVLLIDGPLSWYSDPGLAGVSLTGGLSYK EDTKELVVAKAGVYYVFFQLELRRVVAGEGSGSVSLALHLQPLRSAAG AAALALTVDLPPASSEARNSAFGFQGRLLHLSAGQRLGVHLHTEARARH AWQLTQGATVLGLFRVTPEIPAGLPSPRSE | 80-254 of human 41BBL |
| 205 | PWAVSGARASPGSAASPRLREGPELSPDDPAGLLDLRQGMFAQLVAQN VLLIDGPLSWYSDPGLAGVSLTGGLSYKEDTKELVVAKAGVYYVFFQLE LRRVVAGEGSGSVSLALHLQPLRSAAGAAALALTVDLPPASSEARNSAF GFQGRLLHLSAGQRLGVHLHTEARARHAWQLTQGATVLGLFRVTPEIP AGLPSPRSE | 52-254 of human 4-1BBL |
| 206 | REGPELSPDDPAGLLDLRQGMFAQLVAQNVLLIDGPLSWYSDPGLAGVS LTGGLSYKEDTKELVVAKAGVYYVFFQLELRRVVAGEGSGSVSLALHL QPLRSAAGAAALALTVDLPPASSEARNSAFGFQGRLLHLSAGQRLGVHL HTEARARHAWQLTQGATVLGLFRVTPEIPAGL | 71-248 of human 41BBL |
| 207 | LDLRQGMFAQLVAQNVLLIDGPLSWYSDPGLAGVSLTGGLSYKEDTKE LVVAKAGVYYVFFQLELRRVVAGEGSGSVSLALHLQPLRSAAGAAALA LTVDLPPASSEARNSAFGFQGRLLHLSAGQRLGVHLHTEARARHAWQL TQGATVLGLFRVTPEIPAGL | 85-248 of human 41BBL |
| 208 | DPAGLLDLRQGMFAQLVAQNVLLIDGPLSWYSDPGLAGVSLTGGLSYK EDTKELVVAKAGVYYVFFQLELRRVVAGEGSGSVSLALHLQPLRSAAG AAALALTVDLPPASSEARNSAFGFQGRLLHLSAGQRLGVHLHTEARARH AWQLTQGATVLGLFRVTPEIPAGL | 80-248 of human 41BBL |
| 209 | PWAVSGARASPGSAASPRLREGPELSPDDPAGLLDLRQGMFAQLVAQN VLLIDGPLSWYSDPGLAGVSLTGGLSYKEDTKELVVAKAGVYYVFFQLE LRRVVAGEGSGSVSLALHLQPLRSAAGAAALALTVDLPPASSEARNSAF GFQGRLLHLSAGQRLGVHLHTEARARHAWQLTQGATVLGLFRVTPEIP AGL | 52-248 of human 41BBL |
| 210 | EVQLLESGGGEVQPGGSLRLSCAASGFSFSINAMGWYRQAPGKRREFVA AIESGRNTVYAESVKGRFTISRDNAKNTVYLQMSSLRAEDTAVYYCGLL KGNRVVSPSVAYWGQGTLVTVKP | 41BB sdAb |
| 211 | QVSHRYPRIQSIKVQFTEYKKEKGFILTSQKEDEIMKVQNNSVIINCDGFY LISLKGYFSQEVNISLHYQKDEEPLFQLKKVRSVNSLMVASLTYKDKVY LNVTTDNTSLDDFHVNGGELILIHQNPGEFCVL | OX40 ligand |

| # | SEQUENCE | ANNOTATION |
|---|---|---|
| 212 | QVSHRYPRFQ SIKVQFTEYK KEKGFILTSQ KEDEIMKVQN NSVIINCDGF YLISLKGYFS QEVNISLHYQ KDEEPLFQLK KVRSVNSLMV ASLTYKDKVY LNVTTDNTSL DDFHVNGGEL ILIHQNPGEFCVL | OX40 ligand |
| 213 | QVSHRYPRIQSIKVQFTEYKKEKGFILTSQKEDEIMKVQNNSVIINCDGFY LISLKGYFSQEVNISLHYQKDEEPLFQLKKVRSVNSLMVASLTYKDKVY LNVTTDNTSLDDFHVNGGELILIHQNPGEFCVL | OX40 ligand |
| 214 | QVSHRYPRIQ SIKVQFTEYK KEKGFILTSQ KEDEIMKVQN NSVIINCDGF YLISLKGYFS QEVNISLHYQ KDEEPLFQLK KVRSVNSLMV ASLTYKDKVY LNVTTDNTSL DDFHVNGGEL ILIHQNPGEF CVL | OX40 ligand |
| 215 | VSHRYPRIQSIKVQFTEYKKEKGFILTSQKEDEIMKVQNNSVIINCDGFYL ISLKGYFSQEVNISLHYQKDEEPLFQLKKVRSVNSLMVASLTYKDKVYL NVTTDNTSLDDFHVNGGELILIHQNPGEFCVL | OX40 ligand |
| 216 | EVQLVQSGAEVKKPGASVKVSCKASGYTFTDSYMSWVRQAPGQGLEWI GDMYPDNGDSSYNQKFRERVTITRDTSTSTAYLELSSLRSEDTAVYYCV LAPRWYFSVWGQGTLVTVSS | OX40 VH |
| 217 | DIQMTQSPSSLSASVGDRVTITCRASQDISNYLNWYQQKPGKAPKLLIYY TSRLRSGVPSRFSGSGSGTDFTLTISSLQPEDFATYYCQQGHTLPPTFGQG TKVEIKRT | OX40 VL |
| 218 | EVQLVESGGGLVQPGGSLKLSCAASGFTFSGSAMHWVRQASGKGLEWV GRIRSKANSYATAYAASVKGRFTISRDDSKNTAYLQMNSLKTEDTAVYY CTSGIYDSSGYDYWGQGTLVTVSS | OX40 VH |
| 219 | DIVMTQSPLSLPVTPGEPASISCRSSQSLLHSNGYNYLDWYLQKPGQSPQ LLIYLGSNRASGVPDRFSGSGSGTDFTLKISRVEAEDVGVYYCMQALQTP LTFGGGTKVEIK | OX40 VL |
| 220 | EVQLLESGGGEVQPGGSLRLSCAASGFTFSDAFMYWVRQAPGKGLEWV SSISNRGLKTAYAESVKGRFTISRDNAKNTLYLQMSSLRAEDTAVYYCS RDVDGDFRGQGTLVTVKP | OX40 sdAb |
| 221 | QLETAKEPCMAKFGPLPSKWQMASSEPPCVNKVSDWKLEILQNGLYLIY GQVAPNANYNDVAPFEVRLYKNKDMIQTLTNKSKIQNVGGTYELHVGD TIDLIFNSEHQVLKNNTYWGIILLANPQFIS | GITR ligand |
| 222 | QVQLVESGGGVVQPGRSLRLSCAASGFTFSSYAMSWVRQAPGKGLEWV ASISSGGTTYYPDSVKGRFTISRDNSKNTLYLQMNSLRAEDTAVYYCAR VGGYYDSMDYWGQGTLVTVSS | GITR VH |
| 223 | EIVLTQSPGTLSLSPGERATLSCRASESVDNYGVSFMNWYQQKPGQAPR LLIYAASNQGSGIPDRFSGSGSGTDFTLTISRLEPEDFAVYYCQQTKEVT WTFGQGTKVEIK | GITR VL |
| 224 | QVTLRESGPALVKPTQTLTLTCTFSGFSLSTSGMGVGWIRQPPGKALEW LAHIWWDDDKYYQPSLKSRLTISKDTSKNQVVLTMTNMDPVDTATYYC ARTRRYFPFAYWGQGTLVTVSS | GITR VH |
| 225 | EIVMTQSPATLSVSPGERATLSCKASQNVGTNVAWYQQKPGQAPRLLIY SASYRYSGIPARFSGSGSGTEFTLTISSLQSEDFAVYYCQQYNTDPLTFGG GTKVEIK | GITR VL |
| 226 | QVQLQESGPGLVKPSETLSLTCTVSGGSISSGGYFWSWIRQPPGKGLEWI GYIYYSGTTYYNPSLKSRVTISDTSKNQFSLKLSSVTAADTAVYYCARD LFYYDTSGPRGFDPWGQGTLVTVSS | GITR VH |
| 227 | EIVLTQSPGTLSLSPGERATLSCRASQTVSSNYLAWYQQKPGQAPRLLIY GSSTRATGIPDRFSGSGSGTDFTLTISRLEPEDFAVYYCQQYDSSPWTFGQ GTKVEIK | GITR VL |
| 228 | QVQLVESGGGVVQPGRSLRLSCAASGFTFSSYGMHWVRQAPGKGLEW VAVIWYPGSNKYYAESVKGRFTISRDNSKNTLYLQMNSLRAEDTAVYY CARGGELGRYYYYGMDVWGQGTTVTVSS | GITR VH |
| 229 | DIQMTQSPSSLSASVGDRVTVTCRASQGIRNDLGWYQQKPGKAPKRLIY AASSLQSGVPSRFSGSGSGTEFTLTISSLQPEDFATYYCLHHNNYPWTFG QGTKVDIK | GITR VL |

| # | SEQUENCE | ANNOTATION |
|---|---|---|
| 230 | EVQLLESGGGEVQPGGSLRLSCAASGSVFSIDAMGWYRQAPGKQRELV AVLSGISSAKYAASAPGRFTISRDNAKNTVYLQMSSLRAEDTAVYYCYA DVSTGWGRDAHGYWGQGTLVTV | GITR sdAb |
| 231 | UniProt no. P32970 | CD70-ECD |
| 232 | QVQLVESGGGVVQPGRSLRLSCAASGFTFSSYDMHWVRQAPGKGLEW VAVIWYDGSNKYYADSVKGRFTISRDNSKNTLYLQMNSLRAEDTAVYY CARGSGNWGFFDYWGQGTLVTVSS | CD70 VH |
| 233 | DIQMTQSPSSLSASVGDRVTITCRASQGISRWLAWYQQKPEKAPKSLIYA ASSLQSGVPSRFSGSGSGTDFTLTISSLQPEDFATYYCQQYNTYPRTFGQG TKVEIK | CD70 VL |
| 234 | QVQLQQSGGGLVQPGGSLRLSCAASGSIFSINGMGWYRQAPGKERELVA GLTSGGSVTNYADSVKGRFTISRDNAKNTVYLQMNSLKPEDTAVYYCR AEIFTRTGENYYGMDYWGKGTQVTVKP | ICOS sdAb |
| 235 | EVQLVESGGGEVQPGGSLRLSCAASGRMFSNYAMGWFRQAPGKEREFV AAINYRRDAADYAESVKGRFTISRDNAKNTVYLQMNSLRAEDTAVYYC GFTYAGWASSRRDDYNYWGQGTLVTVKP | CD28 sdAb |
| 236 | RVKFSRSADAPAYQQGQNQLYNELNLGRREEYDVLDKRRGRDPEMGG KPRRKNPQEGLYNELQKDKMAEAYSEIGMKGERRRGKGHDGLYQGLS TATKDTYDALHMQALPPR | CD3zeta signaling domain |
| 237 | KRGRKKLLYIFKQPFMRPVQTTQEEDGCSCRFPEEEEGGCEL | 4-1BB -derived costimulatory domain |
| 238 | SKRSRLLHSDYMNMTPRRPGPTRKHYQPYAPPRDFAAYRS | CD28-derived costimulatory domain |
| 239 | RSKRSRLLHSDYMNMTPRRPGPTRKHYQPYAPPRDFAAYRS | CD28-derived costimulatory domain 2 |
| 240 | FWVRSKRSRLLHSDYMNMTPRRPGPTRKHYQPYAPPRDFAAYRS | CD2 8-derived costimulatory domain 3 |
| 241 | KPTTTPAPRPPTPAPTIASQPLSLRPEASRPAAGGAVHTRGLDFASDIYIW APLAGTCGVLLLSLVITLYC | CD8-derived hinge and transmembrane domain |
| 242 | AKPTTTPAPRPPTPAPTIASQPLSLRPEACRPAAGGAVHTRGLDFACDIYI WAPLAGTCG VLLLSLVIT | CD8-derived hinge and transmembrane domain |
| 243 | KPTTTPAPRPPTPAPTIASQPLSLRPEACRPAAGGAVHTRGLDFACDIYIW APLAGTCGVLLLSLVIT | CD8 hinge and transmembrane domain |
| 244 | GGSGGS | (GGS)2 linker |
| 245 | GGSGGSGGS | (GGS)3 linker |
| 246 | GGSGGSGGSGGS | (GGS)4 linker |
| 247 | GGSGGSGGSGGSGGS | (GGS)5 linker |
| 248 | GGGG | glycine linker |
| 249 | GGGGG | glycine linker |
| 250 | GGSGGS | (GGS)2 linker |
| 251 | EVQLVESGGGEVQPGGSLRLSCAASGSMTGANTMGWYRQAPGKGRDL VSLIGNYVTHYAESVKGRFTISRDNAKNTLYLQMSSLRAEDTAVYYCYL YTDNLGTSWGQGTLVTVKP | hz18H10v1 |
| 252 | EVQLVESGGGEVQPGGSLRLSCAASGSMTGANTMGWYRQAPGKQRDL VSLIGNYVTHYAESVKGRFTISRDNAKNTLYLQMSSLRAEDTAVYYCYL YTDNLGTSWGQGTLVTVKP | hz18H10v2 |

-continued

| # | SEQUENCE | ANNOTATION |
|---|---|---|
| 253 | EVQLVESGGGEVQPGGSLRLSCAASGSMTGANTMGWYRQAPGKQRDLVSLIGNYVTHYAESVKGRFTISRDNAKNTVYLQMSSLRAEDTAVYYCYLYTDNLGTSWGQGTLVTVKP | hz18H10v3 |
| 254 | EVQLVESGGGEVQPGGSLRLSCAASGSMTGANTMGWYRQAPGKQRDLVALIGNYVTHYAESVKGRFTISRDNAKNTVYLQMSSLRAEDTAVYYCYLYTDNLGTSWGQGTLVTVKP | hz18H10v4 |
| 255 | EVQLVESGGGEVQPGGSLRLSCAASGSMTGANTMGWYRQAPGKQRDLVALIGNYVTHYAESVKGRFTISRENAKNTVYLQMSSLRAEDTAVYYCYLYTDNLGTSWGQGTLVTVKP | hz18H10v5 |
| 256 | EVQLVESGGGEVQPGGSLRLSCAASGSVTGANTMGWYRQAPGKQRDLVALIGNYVTHYAESVKGRFTISRDNAKNTVYLQMSSLRAEDTAVYYCYLYTDNLGTSWGQGTLVTVKP | hz18H10v6 |
| 257 | EVQLVESGGGEVQPGGSLRLSCAASGSITGANTMGWYRQAPGKQRDLVALIGNYVTHYAESVKGRFTISRDNAKNTVYLQMSSLRAEDTAVYYCYLYTDNLGTSWGQGTLVTVKP | hz18H10v7 |
| 258 | EVQLVESGGGEVQPGGSLRLSCAASGSVTGANTMGWYRQAPGKQRDLVSLIGNYVTHYAESVKGRFTISRDNAKNTLYLQMSSLRAEDTAVYYCYLYTDNLGTSWGQGTLVTVKP | hz18H10v8 |
| 259 | EVQLVESGGGEVQPGGSLRLSCAASGSVTGANTMGWYRQAPGKQRDLVSLIGNYVTHYAESVKGRFTISRDNAKNTVYLQMSSLRAEDTAVYYCYLYTDNLGTSWGQGTLVTVKP | hz18H10v9 |
| 260 | EVQLVESGGGEVQPGGSLRLSCAASGSMTGANTMGWYRQAPGKQRDLVSLIGNYVTHYAESVKGRFTISRENAKNTVYLQMSSLRAEDTAVYYCYLYTDNLGTSWGQGTLVTVKP | hz18H10v10 |
| 261 | EVQLVESGGGEVQPGGSLRLSCAASGSVTGANTMGWYRQAPGKQRDLVSLIGNYVTHYAESVKGRFTISRENAKNTVYLQMSSLRAEDTAVYYCYLYTDNLGTSWGQGTLVTVKP | hz18H10v11 |
| 262 | EVQLVESGGGEVQPGGSLRLSCAASGSVTGANTMGWYRQAPGKQRDLVALIGNYVTHYAESVKGRFTISRENAKNTVYLQMSSLRAEDTAVYYCYLYTDNLGTSWGQGTLVTVKP | hz18H10v12 |
| 263 | EVQLVESGGGEVQPGGSLRLSCAASGSMTGANTMGWYRQAPGKQRELVALIGNYVTHYAESVKGRFTISRENAKNTVYLQMSSLRAEDTAVYYCYLYTDNLGTSWGQGTLVTVKP | hz18H10v13 |
| 264 | EVQLVESGGGEVQPGGSLRLSCAASGSVTGANTMGWYRQAPGKQRDLVALIGNYVTHYAESVKGRFTISRDNAKNTLYLQMSSLRAEDTAVYYCYLYTDNLGTSWGQGTLVTVKP | hz18H10v14 |
| 265 | EVQLVESGGGEVQPGGSLRLSCAASGSITGANTMGWYRQAPGKQRDLVALIGNYVTHYAESVKGRFTISRDNAKNTLYLQMSSLRAEDTAVYYCYLYTDNLGTSWGQGTLVTVKP | hz18H10v15 |
| 266 | EVQLVESGGGEVQPGGSLRLSCAASGSITGANTMGWYRQAPGKQRDLVALIGNYVTHYAESVKGRFTISRENAKNTVYLQMSSLRAEDTAVYYCYLYTDNLGTSWGQGTLVTVKP | hz18H10v16 |
| 267 | EVQLVESGGGEVQPGGSLRLSCAASGSITGANTMGWYRQAPGKQRDLVALIGNYVTHYAESVKGRFTISRDNAKNTVYLQMNSLRAEDTAVYYCYLYTDNLGTSWGQGTLVTVKP | hz18H10v17 |
| 268 | GSMTGANTMG | CDR1 |
| 269 | GGSGGSGGS | (GGS)3 linker |
| 270 | GGSGGSGGSGGS | (GGS)4 linker |
| 271 | GGSGGSGGSGGSGGS | (GGS)5 linker |
| 272 | GSVTGANTMG | CDR1 |
| 273 | GSITGANTMG | CDR1 |
| 274 | GGSGGS | (GGS)2 linker |
| 275 | GGSGGSGGS | (GGS)3 linker |

| # | SEQUENCE | ANNOTATION |
|---|---|---|
| 276 | GGSGGSGGSGGS | (GGS)4 linker |
| 277 | GGSGGSGGSGGSGGS | (GGS)5 linker |
| 278 | LIGNYVTH | CDR2 |
| 279 | GGSGGS | (GGS)2 linker |
| 280 | GGSGGSGGS | (GGS)3 linker |
| 281 | GGSGGSGGSGGS | (GGS)4 linker |
| 282 | GGSGGSGGSGGSGGS | (GGS)5 linker |
| 283 | YTDNLGTS | CDR3 |
| 284 | QVQLVQSGGGLVQPGGSLRLSCVASGSMTGANTMGWYRQAPGKQRDL VALIGNYHYADSVKGRFTISRENAKNTVILQMNSLNPEDTAVYYCYLYT DNLGTSWGQGTLVTVKP | 18H10 |
| 285 | QAVVTQEPSLTVSPGGTVTLTCGSSTGAVTTSNYANWVQQKPGQAFRG LIGGTNKRAPGVPARFSGSLLGGKAALTISGAQPEDEADYYCALWYSNH WVFGCGTKLTVL | anti-CD3 VL (CON) |
| 286 | MQIPQAPWPVVWAVLQLGWRPGWFLDSPDRPWNPPTFSPALLVVTEGD NATFTCSFSNTSESFVLNWYRMSPSNQTDKLAAFPEDRSQPGQDCRFRV TQLPNGRDFHMSVVRARRNDSGTYLCGAISLAPKAQIKESLRAELRVTE RRAEVPTAHPSPSPRPAGQFQTLVVGVVGGLLGSLVLLVWVLAVICSRA ARGTIGARRTGQPLKEDPSAVPVFSVDYGELDFQWREKTPEPPVPCVPE QTEYATIVFPSGMGTSSPARRGSADGPRSAQPLRPEDGHCSWPL | PD-1 |
| 296 | QVQLQQSGGGLVQAGGSLRVSCAASGRTFSSYGMGWFRQAPGKEREFV AAISWSGGTQYYADSAKGRFTISRDNAKNTVYLQMNSLKPEDTAVYYC ADYTDYVVYRPQEIGYWGQGTQVTVKP | cPD1-8 |
| 297 | QLQLQQSGGGLAQAGGSLRLSCAASGRTVSIYAMGWFRQAPGKEREFV AGIGWNGGTTYYADSVEGRFTISRDHAKNTAYLQMNSLKPEDTAVYYC AAQESAAGTLGDYWGRGTQVTVKP | cPD1-14 |
| 298 | QVTLKESGGGLVQAGGSLRLSCAASGRTEIIYAMGWFRQAPGKEREFVA GIGWSGGTTYYADSVEGRFTISRDSAKNTVYLQMRSLKPEDTAVYYCA AQDSVAGTLGDYWGQGTQVTVKP | cPD1-13 |
| 299 | QVTLRESGGGLVQPGGSLRLSCAASGLTFGLYAMTWFRQAPGKDREGIS CISSSDGSTIYADSVKGRFTASRDNAKDTMYLQMNNLNPEDTAVYYCAT DYETRCDYGLRLRDRTAYWGPGTQVTVKP | cPD1-5 |
| 300 | GRTFSSY | cPD1-8 CDR1 |
| 301 | GRTVSIY | cPD1-14 CDR1 |
| 302 | GRTEIIY | cPD1-13 CDR2 |
| 303 | GLTFGLY | cPD1-5 CDR1 |
| 304 | SWSGGT | cPD1-8 CDR2 |
| 305 | GWNGGT | cPD1-14 CDR2 |
| 306 | GWSGGT | cPD1-13 CDR2 |
| 307 | SDGST | cPD1-5 CDR2 |
| 308 | YTDYVVYRPQEIGY | cPD1-8 CDR3 |
| 309 | QESAAGTLGDY | cPD1-14 CDR3 |
| 310 | QDSVAGTLGDY | cPD1-13 CDR3 |
| 311 | DYETRCDYGLRLRDRTAY | cPD1-5 CDR3 |
| 312 | QVQLQQSGGGLAQAGGSLRLSCAASGRTVSIYAMGWFRQAPGKEREFV AGIGWNGGTTYYADSVEGRFTISRDHAKNTAYLQMNSLKPEDTAVYYC AAQESAAGTLGDYWGRGTQVTVKPGG | 1-14 |

| # | SEQUENCE | ANNOTATION |
|---|---|---|
| 316 | EVQLVESGGGLVQPGRSLRLSCAASGFTFDDYAMHWVRQAPGKGLEW VSGISWNSGSIGYADSVKGFTISRDNAKNSLYLQMNSLRAEDTALYYCA KDSRGYGDYRLGGAYWGQGTLVTVSS | Anti-CD3 VH 312557 |
| 317 | EVQLVESGGGLVQPGRSLRLSCAASGFTFDDYAMHWVRQAPGKCLEW VSGISWNSGSIGYADSVKGFTISRDNAKNSLYLQMNSLRAEDTALYYCA KDSRGYGDYRLGGAYWGQGTLVTVSS | Anti-CD3 VH 312557 G44C |
| 318 | EIVMTQSPATLSVSPGERATLSCRASQSVSSNLAWYQQKPGQAPRLLIYG ASTRATGIPARFSGSGSGTEFTLTISSLQSEDFAVYYCQQYNNWPWTFGQ GTKVEIK | Anti-CD3 VL 312557 |
| 319 | EIVMTQSPATLSVSPGERATLSCRASQSVSSNLAWYQQKPGQAPRLLIYG ASTRATGIPARFSGSGSGTEFTLTISSLQSEDFAVYYCQQYNNWPWTFGC GTKVEIK | Anti-CD3 VL 312557 Q100C |
| 320 | EVQLVESGGGLVQPGRSLRLSCVASGFTFDDYSMHWVRQAPGKGLEW VSGISWNSGSKDYADSVKGRFTISRDNAKNSLYLQMNSLRAEDTALYYC AKYGSGYGKFYHYGLDVWGQGTTVTVSS | CD3-VH-G |
| 321 | EVQLVESGGGLVQPGRSLRLSCVASGFTFDDYSMHWVRQAPGKCLEWV SGISWNSGSKDYADSVKGRFTISRDNAKNSLYLQMNSLRAEDTALYYCA KYGSGYGKFYHYGLDVWGQGTTVTVSS | CD3-VH-G G44C |
| 322 | DIQMTQSPSSLSASVGDRVTITCRASQSISSYLNWYQQKPGKAPKLLIYA ASSLQSGVPSRFSGSGSGTDFTLTISSLQPEDFATYYCQQSYSTPPITFGQG TRLEIK | $V_{K1}$-39Jκ5 |
| 323 | DIQMTQSPSSLSASVGDRVTITCRASQSISSYLNWYQQKPGKAPKLLIYA ASSLQSGVPSRFSGSGSGTDFTLTISSLQPEDFATYYCQQSYSTPPITFGCG TRLEIK | $V_{K1}$-39Jκ5 Q100C |

The invention claimed is:

1. A PD-1-binding polypeptide construct, comprising at least one heavy chain only variable domain (PD-1 VHH domain) that specifically binds PD-1, wherein the at least one VHH domain comprises a CDR1, CDR 2 and CDR 3 comprising:
  the amino acid sequence set forth in SEQ ID NOs: 268, 278 and 283, respectively;
  the amino acid sequence set forth in SEQ ID NOs: 272, 278 and 283, respectively;
  the amino acid sequence set forth in SEQ ID NOs: 313, 314 and 315, respectively; or
  the amino acid sequence set forth in SEQ ID NOs: 273, 278 and 283, respectively.

2. The PD-1-binding polypeptide construct of claim 1, comprising at least one heavy chain only variable domain (PD-1 VHH domain) that specifically binds PD-1 and comprises one or more additional binding domain that binds to a target other than PD-1.

3. The PD-1-binding polypeptide construct of any of claim 1 or 2, wherein the PD-1 VHH domain that specifically binds PD-1, blocks the interaction of PD-1 and PD-L1.

4. The PD-1-binding polypeptide construct of claim 2, wherein the one or more additional binding domain binds a co-stimulatory molecule.

5. The PD-1-binding polypeptide construct of claim 2, wherein the one or more additional binding domain binds a T-cell surface marker.

6. The PD-1-binding polypeptide construct of claim 5, wherein the T-cell surface marker is CD8.

7. The PD-1-binding polypeptide construct of claim 5, wherein the T-cell surface marker is CD4.

8. The PD-1-binding polypeptide construct of claim 2, wherein the one or more additional binding domain binds an immune checkpoint other than PD1.

9. The PD-1-binding polypeptide construct of claim 2, wherein the one or more additional binding domains binds to an activating receptor on an immune cell.

10. The PD-1-binding polypeptide construct of claim 2, wherein the one or more additional domains binds to a tumor associated antigen (TAA).

11. The PD-1-binding polypeptide construct of claim 2, wherein the one or more additional binding domain binds to a cytokine receptor.

12. The PD-1-binding polypeptide construct of any of claims 1 or 2 wherein the polypeptide comprises an immunoglobulin Fc region.

13. The PD-1-binding polypeptide construct of any of claims 1 or 2 wherein the at least one PD-1 VHH domain comprises the amino acid sequence set forth in any of SEQ ID NOS: 251-267, 284 or 312, or a sequence of amino acids that exhibits at least 85%, 86%, 87%, 88%, 89%, 90%, 91%, 92%, 93%, 94%, 95%, 96%, 97%, 98%, or 99% sequence identity to amino acid sequence set forth in any of SEQ ID NOS: 251-267, 284 or 312 and binds PD-1.

14. An isolated single domain antibody that binds PD-1, comprising a complementarity determining region 1 (CDR1); a complementarity determining region 2 (CDR2); and a complementarity determining region 3 (CDR3) comprising:
   the amino acid sequence set forth in SEQ ID NOs: 268, 278 and 283, respectively;
   the amino acid sequence set forth in SEQ ID NOs: 272, 278 and 283, respectively;
   the amino acid sequence set forth in SEQ ID NOs: 313, 314 and 315, respectively; or
   the amino acid sequence set forth in SEQ ID NOs: 273, 278 and 283, respectively.

15. The isolated single domain antibody of claim 14, comprising the amino acid sequence set forth in any of SEQ ID NOS: 251-267 or 284, or a sequence of amino acids that exhibits at least 85%, 86%, 87%, 88%, 89%, 90%, 91%, 92%, 93%, 94%, 95%, 96%, 97%, 98%, or 99% sequence identity to amino acid sequence set forth in any of SEQ ID NO: 251-267, 284 or 312 and binds PD-1.

16. The isolated single domain antibody of claim 15, wherein the sdAb comprises the sequence of amino acid sequence set forth in any of SEQ ID NO: 251, 252, 253, 254, 255, 256, 257, 258, 259, 260, 261, 262, 263, 264, 265, 266, 267, 284 or 312.

17. A polynucleotide encoding the PD-1-binding polypeptide of claim 1.

18. A polynucleotide encoding the single domain antibody of claim 14.

19. A vector, comprising the polynucleotide of claim 17.

20. A cell, comprising a polynucleotide of claim 17.

21. A method of producing a polypeptide construct, the method comprising introducing into a cell a polynucleotide of claim 17 and culturing the cell under conditions to produce the polypeptide construct.

22. An engineered immune cell, comprising a binding molecule comprising the PD-1-binding polypeptide construct binding molecule of claim 1, optionally wherein the binding molecule is secretable from the cell.

23. A pharmaceutical composition comprising the PD-1-binding polypeptide construct of claim 1.

24. A cell, comprising a vector of claim 19.

25. A method of producing a polypeptide, the method comprising introducing into a cell a vector of claim 19 and culturing the cell under conditions to produce the polypeptide.

26. An engineered immune cell, comprising a binding molecule comprising the single domain antibody of claim 14, optionally wherein the binding molecule is secretable from the cell.

27. A pharmaceutical composition comprising the single domain antibody of claim 14.

28. A pharmaceutical composition comprising the engineered immune cell of claim 22.

\* \* \* \* \*